United States Patent
Anderberg et al.

(10) Patent No.: US 11,454,635 B2
(45) Date of Patent: *Sep. 27, 2022

(54) METHODS AND COMPOSITIONS FOR DIAGNOSIS AND PROGNOSIS OF RENAL INJURY AND RENAL FAILURE

(75) Inventors: Joseph Anderberg, Encinitas, CA (US); Jeff Gray, Solana Beach, CA (US); Paul McPherson, Encinitas, CA (US); Kevin Nakamura, Cardiff by the Sea, CA (US); James Patrick Kampf, San Diego, CA (US)

(73) Assignee: Astute Medical, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/577,242

(22) PCT Filed: Feb. 4, 2011

(86) PCT No.: PCT/US2011/023830
§ 371 (c)(1),
(2), (4) Date: Oct. 26, 2012

(87) PCT Pub. No.: WO2011/097539
PCT Pub. Date: Aug. 11, 2011

(65) Prior Publication Data
US 2013/0157881 A1 Jun. 20, 2013

Related U.S. Application Data

(60) Provisional application No. 61/302,021, filed on Feb. 5, 2010, provisional application No. 61/302,026, filed on Feb. 5, 2010, provisional application No. 61/302,025, filed on Feb. 5, 2010, provisional application No. 61/302,027, filed on Feb. 5, 2010, provisional application No. 61/302,036, filed on Feb. 5, 2010, provisional application No. 61/374,060, filed on Aug. 16, 2010.

(51) Int. Cl.
*G01N 33/68* (2006.01)
*G01N 33/86* (2006.01)

(52) U.S. Cl.
CPC ..... *G01N 33/6893* (2013.01); *G01N 33/6863* (2013.01); *G01N 33/86* (2013.01); *G01N 2333/4745* (2013.01); *G01N 2333/522* (2013.01); *G01N 2333/96447* (2013.01); *G01N 2800/347* (2013.01); *G01N 2800/50* (2013.01); *G01N 2800/52* (2013.01)

(58) Field of Classification Search
CPC .............. G01N 33/6863; G01N 33/86; G01N 2333/96447; G01N 2800/52; G01N 2333/4745; G01N 2333/522; G01N 2800/347; G01N 2800/50
See application file for complete search history.

(56) References Cited

U.S. PATENT DOCUMENTS

| | | | |
|---|---|---|---|
| 6,218,122 B1 | 4/2001 | Friend et al. | |
| 6,664,385 B1 | 12/2003 | Sanicola-Nadel et al. | |
| 6,709,855 B1 * | 3/2004 | Stanton ................ | C12Q 1/6876 435/283.1 |
| 6,784,154 B2 | 8/2004 | Westenfelder | |
| 6,861,404 B1 | 3/2005 | Cohen et al. | |
| 6,941,172 B2 | 9/2005 | Nachum | |
| 7,138,230 B2 | 11/2006 | Hu et al. | |
| 7,141,382 B1 | 11/2006 | Parikh et al. | |
| 7,235,358 B2 * | 6/2007 | Wohlgemuth et al. ...... | 435/6.18 |
| 7,608,413 B1 | 10/2009 | Joseloff et al. | |
| 7,662,578 B2 | 2/2010 | Devarajan | |
| 7,981,684 B2 | 7/2011 | Levin et al. | |
| 7,998,744 B2 | 8/2011 | Stevenson et al. | |
| 8,008,008 B2 | 8/2011 | Parr et al. | |
| 8,071,293 B2 | 12/2011 | High et al. | |
| 8,080,394 B2 | 12/2011 | Levy et al. | |
| 8,241,861 B1 | 8/2012 | Heinecke et al. | |
| 2003/0003588 A1 | 1/2003 | Comper | |
| 2003/0186308 A1 * | 10/2003 | Young ................ | C07K 14/4743 435/6.14 |
| 2004/0053309 A1 | 3/2004 | Holt et al. | |
| 2004/0072238 A1 | 4/2004 | Yamano et al. | |
| 2004/0106155 A1 | 6/2004 | Comper | |

(Continued)

FOREIGN PATENT DOCUMENTS

| | | |
|---|---|---|
| CA | 2699440 | 2/2009 |
| CA | 2740134 | 4/2010 |

(Continued)

OTHER PUBLICATIONS

Hoste et al. Crit Care. 2006;1 0(3):R73. Epub May 12, 2006.*
Cutillas et al.( Am J Physiol Renal Physiol 287: F353-F364, 2004).*
Lopez-Bermejo J.Clin endocrinol Metab 2003,88:3401-3408.*
Ronco et al. (J Am Coll Cardiol, 2008 52:1527-1539).*
Hix et al (Crit Care Med 2006;vol. 34,No. 2, pp. 2979-2983.*
Kimmel et al., Association of Renal Stress/Damage and Filtration Biomarkers with Subsequent AKI during Hospitalization among Patients Presenting to the Emergency Department, Clin. J. Am. Soc. Nephrol., (2016), 11(6), p. 938-946. (Year: 2016).*
Aregger et al., Identification of IGFBP-7 by urinary proteomics as a novel prognostic marker in early acute kidney injury, 85, (2014), p. 909-919. (Year: 2014).*

(Continued)

*Primary Examiner* — Ellen J Marcsisin
(74) *Attorney, Agent, or Firm* — Womble Bond Dickinson (US) LLP

(57) ABSTRACT

The present invention relates to methods and compositions for monitoring, diagnosis, prognosis, and determination of treatment regimens in subjects suffering from or suspected of having a renal injury. In particular, the invention relates to using a one or more assays configured to detect a kidney injury marker selected from the group consisting of Coagulation factor VII, CA19-9, Insulin-like growth factor-binding protein 7, C—X—C motif chemokine 6, and C—C motif chemokine 13 as diagnostic and prognostic biomarkers in renal injuries.

16 Claims, No Drawings

Specification includes a Sequence Listing.

(56) References Cited

U.S. PATENT DOCUMENTS

| | | |
|---|---|---|
| 2005/0002934 A1 | 1/2005 | Reed |
| 2005/0048033 A1 | 3/2005 | Fraser et al. |
| 2005/0112688 A1 | 5/2005 | Hu et al. |
| 2005/0137481 A1 | 6/2005 | Sheard et al. |
| 2005/0148029 A1 | 7/2005 | Buechler et al. |
| 2005/0158801 A1 | 7/2005 | Hu et al. |
| 2005/0256075 A1 | 11/2005 | Alitalo et al. |
| 2005/0272101 A1 | 12/2005 | Devarajan et al. |
| 2006/0003327 A1 | 1/2006 | Achiron et al. |
| 2006/0057066 A1 | 3/2006 | Natsoulis et al. |
| 2006/0088823 A1 | 4/2006 | Haab et al. |
| 2006/0204951 A1 | 9/2006 | Folkman et al. |
| 2006/0223077 A1 | 10/2006 | Ni et al. |
| 2006/0240437 A1 | 10/2006 | Krolewski et al. |
| 2006/0246485 A1 | 11/2006 | Sarwal et al. |
| 2007/0031905 A1 | 2/2007 | Shariat |
| 2007/0087387 A1* | 4/2007 | Devarajan ............... 435/7.1 |
| 2007/0093969 A1 | 4/2007 | Mendrick et al. |
| 2007/0105142 A1 | 5/2007 | Wilhelm |
| 2007/0112327 A1 | 5/2007 | Yun et al. |
| 2007/0154897 A1 | 7/2007 | Yen et al. |
| 2007/0184439 A1* | 8/2007 | Guilford ............ C12Q 1/6886 435/6.12 |
| 2007/0248989 A1 | 10/2007 | Devarajan |
| 2007/0249002 A1 | 10/2007 | Hu et al. |
| 2008/0014644 A1 | 1/2008 | Barasch et al. |
| 2008/0038192 A1 | 2/2008 | Gervais |
| 2008/0038269 A1 | 2/2008 | Susan |
| 2008/0090304 A1 | 4/2008 | Barasch et al. |
| 2008/0133141 A1 | 6/2008 | Frost |
| 2008/0153092 A1 | 6/2008 | Kienle et al. |
| 2008/0206794 A1 | 8/2008 | Hu et al. |
| 2008/0254483 A1 | 10/2008 | Darbouret et al. |
| 2008/0254485 A1 | 10/2008 | Valkirs et al. |
| 2009/0022730 A1 | 1/2009 | Raulf et al. |
| 2009/0047689 A1 | 2/2009 | Kolman et al. |
| 2009/0081713 A1 | 3/2009 | Klein et al. |
| 2009/0088409 A1 | 4/2009 | Charlton |
| 2009/0090856 A1 | 4/2009 | Grant et al. |
| 2009/0148539 A1 | 6/2009 | Elias et al. |
| 2009/0176656 A1 | 7/2009 | Halloran |
| 2009/0197287 A1* | 8/2009 | Hu et al. ............ 435/7.92 |
| 2009/0203588 A1 | 8/2009 | Willman et al. |
| 2009/0220526 A1 | 9/2009 | Hamid |
| 2009/0258002 A1 | 10/2009 | Barrett et al. |
| 2009/0298073 A1 | 12/2009 | Gerhold et al. |
| 2009/0298106 A1 | 12/2009 | Hooper |
| 2010/0022627 A1 | 1/2010 | Scherer |
| 2010/0081148 A1 | 4/2010 | Singbartl et al. |
| 2010/0190164 A1 | 7/2010 | Tammen et al. |
| 2010/0240078 A1 | 9/2010 | Lee et al. |
| 2010/0267041 A1 | 10/2010 | Shuber et al. |
| 2010/0285491 A1 | 11/2010 | Wienhues-Thelen et al. |
| 2011/0065608 A1 | 3/2011 | Labrie et al. |
| 2011/0104726 A1 | 5/2011 | Valkirs et al. |
| 2011/0174062 A1 | 7/2011 | Anderberg et al. |
| 2011/0195429 A1 | 8/2011 | Anderberg et al. |
| 2011/0201038 A1 | 8/2011 | Anderberg et al. |
| 2011/0207161 A1 | 8/2011 | Anderberg et al. |
| 2012/0190044 A1 | 7/2012 | Anderberg et al. |
| 2012/0190051 A1 | 7/2012 | Anderberg et al. |
| 2013/0035290 A1 | 2/2013 | Elias et al. |

FOREIGN PATENT DOCUMENTS

| | | |
|---|---|---|
| CN | 1791797 A | 6/2006 |
| CN | 102725636 A | 10/2012 |
| EP | 0828159 A1 | 3/1998 |
| EP | 1905846 A2 | 4/2008 |
| EP | 2261660 A1 | 12/2010 |
| EP | 2480882 A1 | 8/2012 |
| EP | 2513649 A1 | 10/2012 |
| JP | H01294697 A | 11/1989 |
| JP | 2011-506941 A | 3/2011 |
| RU | 2180965 C1 | 3/2002 |
| SU | 1429031 A1 | 10/1988 |
| WO | 1998055508 A2 | 12/1998 |
| WO | 0198493 A1 | 12/2001 |
| WO | 2003054004 A2 | 7/2003 |
| WO | WO2003054004 * | 7/2003 |
| WO | 2003075016 A1 | 9/2003 |
| WO | 2004005934 A2 | 1/2004 |
| WO | WO2004059293 * | 7/2004 |
| WO | 2005087264 A1 | 9/2005 |
| WO | 2006083986 A2 | 8/2006 |
| WO | 2007013919 A2 | 2/2007 |
| WO | 2007041623 A2 | 4/2007 |
| WO | WO2007041623 A1 * | 4/2007 |
| WO | 2008060607 A2 | 5/2008 |
| WO | 2008084331 A2 | 7/2008 |
| WO | WO 2008/089994 | 7/2008 |
| WO | WO2008089994 * | 7/2008 ............. G01N 33/68 |
| WO | 2008104804 A2 | 9/2008 |
| WO | 2008116867 A1 | 10/2008 |
| WO | 2008122670 A2 | 10/2008 |
| WO | 2008154238 A1 | 12/2008 |
| WO | 2009038742 A2 | 3/2009 |
| WO | 2010025424 A1 | 3/2010 |
| WO | 2010025434 A1 | 3/2010 |
| WO | 2010048346 A1 | 4/2010 |
| WO | 2010048347 A2 | 4/2010 |
| WO | 2010054389 A1 | 5/2010 |
| WO | 2010091236 A1 | 8/2010 |
| WO | 2010111746 A1 | 10/2010 |
| WO | 2010128158 A1 | 11/2010 |
| WO | 2011025917 A1 | 3/2011 |
| WO | 2011035323 A1 | 3/2011 |
| WO | 2011075744 A1 | 6/2011 |

OTHER PUBLICATIONS

FDA, European Medicines Agency to Consider Additional Test Results When Assessing New Drug Safety—Collaborative effort by FDA and EMEA expected to yield additional safety data. http://www.natap.org/2008/newsUpdates/071608_01.htm dated Jun. 12, 2008.

Harpur et al., Biological Qualification of Biomarkers of Chemical-Induced Renal Toxicity in Two Strains of Male Rat. Toxicol Sci. Aug. 2011;122(2):235-252.

Final Office Action issued by the United States Patent and Trademark Office in U.S. Appl. No. 13/061,446 dated Jun. 7, 2013.

Non Final Office Action issued by the United States Patent and Trademark Office in U.S. Appl. No. 13/125,454 dated Mar. 5, 2013.

Thaker et al., Identification of thrombospondin 1 (TSP-1) as a novel mediator of cell injury in kidney ischemia. J Clin Invest. Dec. 2005;115(12):3451-3458.

Restriction Requirement issued by the United States Patent and Trademark Office in U.S. Appl. No. 13/061,413 dated Sep. 5, 2012.

Response to Restriction Requirement in U.S. Appl. No. 13/061,413 dated Oct. 16, 2012.

Response to Non Final Office Action issued in U.S. Appl. No. 13/061,413 dated Jul. 2, 2013.

Final Office Action issued by the United States Patent and Trademark Office in U.S. Appl. No. 13/061,413 dated Aug. 23, 2013.

Restriction Requirement issued by the United States Patent and Trademark Office in U.S. Appl. No. 13/148,031 dated Mar. 20, 2013.

Mast et al., Clinical utility of the soluble transferrin receptor and comparison with serum ferritin in several populations. Clin Chem. Jan. 1998;44(1):45-51.

Non Final Office Action issued by the United States Patent and Trademark Office in U.S. Appl. No. 13/389,363 dated Apr. 18, 2013.

Iglesias et al., Thyroid Dysfunction and Kidney Disease (Revised version). Eur J Endocrinol. Dec. 18, 2008:32 pages retrieved from URL://www.eje.org/content!early/2008/12/18/EJE-08-0837.full.pdf.

Rajashekar et al., Systemic diseases with renal manifestations. Prim Care. Jun. 2008;35(2):297-328.abstract retrieved from URL:www.ncbi.nlm.nih.gov/pubmed/18486717.

(56) References Cited

OTHER PUBLICATIONS

Rini et al., Renal cell carcinoma. Lancet. Mar. 28, 2009;373(9669):1119-1132.
Non Final Office Action issued by the United States Patent and Trademark Office in U.S. Appl. No. 13/125,360 dated Aug. 27, 2013.
Sharma et al. Two-dimensional fluorescence difference gel electrophoresis analysis of the urine proteome in human diabetic nephropathy. Proteomics. Jul. 2005;5(10):2648-2655.
Non Final Office Action issued by the United States Patent and Trademark Office in U.S. Appl. No. 13/130,474 dated Nov. 27, 2012.
Non Final Office Action issued by the United States Patent and Trademark Office in U.S. Appl. No. 13/148,030 dated May 1, 2013.
Malm et al., Changes in the plasma levels of vitamin K-dependent proteins C and S and of C4b-binding protein during pregnancy and oral contraception. Br J Haematol. Apr. 1988;68(4):437-443.
Matsuzaka et al., Relationship between vitamin K dependent coagulation factors and anticoagulants (protein C and protein S) in neonatal vitamin K deficiency. Arch Dis Child. Mar. 1993;68(3 Spec No):297-302.
International Search Report and Written Opinion issued in PCT/US2013/028005 dated Jun. 18, 2013.
Maddens et al., Chitinase-like Proteins are Candidate Biomarkers for Sepsis-induced Acute Kidney Injury. Mol Cell Proteomics. Jan. 10, 2012;11(6):1-13.
Restriction Requirement issued by the United States Patent and Trademark Office in U.S. Appl. No. 13/517,244 dated Jul. 1, 2013.
Extended European Search Report and Written Opinion issued in EP 11751238 dated Aug. 13, 2013.
Haase et al., A comparison of the RIFLE and Acute Kidney Injury Network classifications for cardiac surgery-associated acute kidney injury: A prospective cohort study. J Thorac Cardiovasc Surg. Dec. 2009;138(6):1370-1376.
Zaffanello M et al., Early diagnosis of acute kidney injury with urinary biomarkers in the newborn. J Matern Fetal Neonatal Med. 2009;22 Suppl 3:62-66.
Extended European Search Report and Written Opinion issued in EP 11748210 dated Aug. 16, 2013.
Calabrese et al., Oxidative stress and cellular stress response in diabetic nephropathy. Database Biosis [Online]. Biosciences Information Service Jan. 2007; XP002705326. Database accession No. PREV200800097004 (abstract):3 pages & Cell Stress Chaperones. 2007 Winter;12(4):299-306.
Musial et al., The Heat Shock Protein Profile in Children with Chronic Kidney Disease. Perit Dial Int. Mar.-Apr. 2010;30(2):227-232.
Tao et al., Expression of 60-kDa and Inducible 70-kDa Stress Proteins in Gentamicin-Induced Acute Renal Failure. Clin Exp Nephrol. Jul. 1997;1:254-260.
Response dated May 16, 2012 to Extended European Search Report and Written Opinion in PCT/US2009/055449.
Extended European Search Report and Written Opinion dated Feb. 23, 2012 in PCT/US2009/065419.
Extended European Search Report and Written Opinion dated Jul. 27, 2012 in PCT/US2010/023294.
Extended European Search Report and Written Opinion dated Oct. 24, 2011 in PCT/US2009/055449.
Extended European Search Report and Written Opinion dated Feb. 22, 2012 in PCT/US2009/055460.
Extended European Search Report and Written Opinion dated Jul. 9, 2012 in PCT/US2009/061561.
Extended European Search Report and Written Opinion dated Aug. 23, 2012 in PCT/US2009/061562.
Extended European Search Report and Written Opinion dated Jul. 9, 2012 in PCT/US2010/023292.
Extended European Search Report and Written Opinion dated Aug. 23, 2012 in PCT/US2010/023297.
Extended European Search Report and Written Opinion dated Jun. 8, 2012 in PCT/US2009/063906.
International Preliminary Report on Patentability dated Oct. 21, 2011 in PCT/US2010/023297.
International Preliminary Report on Patentability dated Mar. 29, 2011 in PCT/US2010/049234.
International Preliminary Report on Patentability dated May 18, 2012 in PCT/US2010/055730.
International Preliminary Report on Patentability dated Mar. 10, 2011 in PCT/US2009/055449.
International Preliminary Report on Patentability dated Mar. 10, 2011 in PCT/US2009/055460.
International Preliminary Report on Patentability dated Aug. 16, 2012 in PCT/US2011/023830.
International Preliminary Report on Patentability dated Aug. 16, 2012 in PCT/US2011/023831.
International Preliminary Report on Patentability dated Aug. 16, 2012 in PCT/US2011/023832.
International Preliminary Report on Patentability dated Apr. 5, 2012 in PCT/US2010/049695.
International Preliminary Report on Patentability dated May 5, 2011 in PCT/US2009/061561.
International Preliminary Report on Patentability dated May 5, 2011 in PCT/US2009/061562.
International Preliminary Report on Patentability dated Jun. 3, 2011 in PCT/US2009/065419.
International Preliminary Report on Patentability dated Jul. 5, 2012 in PCT/US2010/061377.
International Preliminary Report on Patentability dated Aug. 18, 2011 in PCT/US2010/023292.
International Preliminary Report on Patentability dated Aug. 18, 2011 in PCT/US2010/023294.
International Preliminary Report on Patentability dated May 10, 2011 in PCT/US2009/063906.
International Search Report and Written Opinion dated Dec. 3, 2010 in PCT/US2010/049234.
International Search Report and Written Opinion dated Feb. 8, 2011 in PCT/US2010/055730.
International Search Report and Written Opinion dated Oct. 28, 2010 in PCT/US2010/044772.
International Search Report and Written Opinion dated Oct. 8, 2010 in PCT/US2010/044708.
International Search Report and Written Opinion dated Dec. 10, 2009 in PCT/US2009/055449.
International Search Report and Written Opinion dated Dec. 31, 2009 in PCT/US2009/055460.
International Search Report and Written Opinion dated Dec. 3, 2010 in PCT/US2010/049695.
International Search Report and Written Opinion dated Jan. 20, 2010 in PCT/US2009/061561.
International Search Report and Written Opinion dated Apr. 13, 2010 in PCT/US2009/061562.
International Search Report and Written Opinion dated Mar. 30, 2010 in PCT/US2009/065419.
International Search Report and Written Opinion dated Mar. 8, 2011 in PCT/US2010/061377.
International Search Report and Written Opinion dated Apr. 30, 2010 in PCT/US2010/023292.
International Search Report and Written Opinion dated Apr. 22, 2010 in PCT/US2010/023294.
International Search Report and Written Opinion dated Jun. 3, 2010 in PCT/US2010/023297.
International Search Report and Written Opinion dated Jan. 15, 2010 in PCT/US2009/063906.
International Search Report and Written Opinion dated Nov. 18, 2010 in PCT/US2010/046910.
International Search Report and Written Opinion dated Jan. 18, 2012 in PCT/US2011/053015.
International Search Report and Written Opinion dated Feb. 24, 2012 in PCT/US2011/055055.
International Search Report and Written Opinion dated Jan. 19, 2011 in PCT/US2010/055721.
International Search Report and Written Opinion dated May 10, 2012 in PCT/US2012/020571.

(56) References Cited

OTHER PUBLICATIONS

International Search Report and Written Opinion dated Apr. 27, 2011 in PCT/US2011/023830.
International Search Report and Written Opinion dated Apr. 27, 2011 in PCT/US2011/023831.
International Search Report and Written Opinion dated Apr. 29, 2011 in PCT/US2011/023832.
International Search Report and Written Opinion dated May 17, 2011 in PCT/US2011/026384.
Yuen et al., Ischemic and Nephrotoxic Acute Renal Failure are Distinguished by their Broad Transcriptomic Responses. Physiol Genomics. May 16, 2006;25(3):375-386.
Zager et al. Proximal tubular cytochrome c efflux: Determinant, and potential marker, of mitochondrial injury. Kidney Int. Jun. 2004;65(6):2123-2134.
International Preliminary Report on Patentability dated Sep. 7, 2012 in PCT/US2011/026384.
Non-Final Office Action issued by the US Patent and Trademark Office dated Nov. 16, 2012 in U.S. Appl. No. 13/389,351.
Non-Final Office Action issued by the US Patent and Trademark Office dated Nov. 27, 2012 in U.S. Appl. No. 13/130,474.
Flynn et al., Urinary excretion of beta2-glycoprotein-1 (apolipoprotein H) and other markers of tubular malfunction in "non-tubular" renal disease J Clin Pathol. Jul. 1992;45(7):561-567.
Kasahara et al Clinical Significance of Serum Oxidized Low-Density Lipoprotein/beta2-Giycoprotein I Complexes in Patients with Chronic Renal Diseases. Nephron Clin Pract. 2004;98(1):15-24.
Lapsley et al., Beta 2-glycoprotein-1 (apolipoprotein H) excretion in chronic renal tubular disorders: Comparison with other protein markers of tubular malfunction. J Clin Pathol. Oct. 1991;44(10):812-816.
Matsuda et al., Beta 2-Glycoprotein I-Dependent and -Independent Anticardiolipin Antibody in Patients with End-Stage Renal Disease. Thromb Res. Oct. 15, 1993;72(2):109-117.
Ramirez et al., Prospective Study on Autoantibodies Against Apolipoprotein H (beta2GPI) in Several Clinical Parameters From Patients With Terminal Renal Failure and Functioning Renal Transplants. Transplant Proc. Jul.-Aug. 2009;41(6):2370-2.
Zheng et al., Antiphospholipid antibody profiles in lupus nephritis with glomerular microthrombosis: a prospective study of 124 cases. Arthritis Res Ther. 2009;11(3):1-9.
Extended European Search Report and Written Opinion issued in PCT/US2010044772 dated Dec. 3, 2012.
Voshol et al., Evaluation of Biomarker Discovery Approaches to Detect Protein Biomarkers of Acute Renal Allograft Rejection. J Proteome Res. Jul.-Aug. 2005;4(4):1192-1199.
Extended European Search Report and Written Opinion issued in PCT/US2010044708 dated Dec. 3, 2012.
Neziri et al., Cloning and molecular characterization of Dashurin encoded by C20orf116, a PCI-domain containing protein. Biochim Biophys Acta. Apr. 2010;1800(4):430-438.
Non Final Office Action issued by the US Patent and Trademark Office in U.S. Appl. No. 13/164,768 dated Dec. 18, 2012.
Non Final Office Action issued by the US Patent and Trademark Office in U.S. Appl. No. 13/061,413 dated Jan. 2, 2013.
Norman et al., Progressive Renal Disease: Fibroblasts, Extracellular Matrix, and Integrins. Exp Nephrol. Mar.-Apr. 1999;7(2):167-177.
International Search Report and Written Opinion issued in 200980154224.5 dated Nov. 23, 2012.
English Translation of International Search Report and Written Opinion issued in 200980154224.5 dated Nov. 23, 2012.
Zhu et al., Expression of Urinary Epidermal Growth Factor and Renal Function. J Clin Urol Dec. 31, 1998;13(8):374-379.
Zhu et al., Expression of Urinary Epidermal Growth Factor and Renal Function. J Clin Urol Dec. 31, 1998;13(8):374-379 (abstract English translation).
Sun et al., A Survey on the Relationship between the Epidermal Growth Factor and Renal Function. Int J Transpl Hemopurific Dec. 31, 2006;4(1):41-44.
Sun et al., A Survey on the Relationship between the Epidermal Growth Factor and Renal Function. Int J Transpl Hemopurific Dec. 31, 2006;4(1):41-44 (abstract English translation).
Non Final Office Action issued in 2009801542245 dated Dec. 17, 2012.
Non Final Office Action issued by the US Patent and Trademark Office in U.S. Appl. No. 13/125,360 dated Jan. 24, 2013.
Caron et al. Ischemic injury alters endothelial cell properties of kidney cortex:stimulation of MMP-9. Exp Cell Res. Oct. 15, 2005;301(1):105-116.
Non Final Office Action issued by the US Patent and Trademark Office in U.S. Appl. No. 13/508,363 dated Feb. 1, 2013.
Non Final Office Action issued by the US Patent and Trademark Office in U.S. Appl. No. 13/577,243 dated Feb. 14, 2013.
Non Final Office Action issued in Japanese Patent Application No. 2011-525262 dated Feb. 5, 2013.
Non Final Office Action issued in Japanese Patent Application No. 2011-525262 dated Feb. 5, 2013 (English translation).
International Search Report and Written Opinion issued in PCT/US2012/066152 dated Mar. 15, 2013.
Extended European Search Report and Written Opinion issued in EP 18817878 dated Apr. 5, 2013.
Mezzano et al., Endothelial Cell Markers in Chronic Uremia: Relationship with Hemostatic Defects and Severity of Renal Failure. Thromb Res. Dec. 15, 1997;88(6):465-472.
Tan et al., The level of urinary secretory immunoglobulin A (sIgA) of patients with IgA nephropathy is elevated and associated with pathological phenotypes. Clin Exp Immunol. Apr. 2009;156(1):111-116.
Zhang et al., The level of serum secretory IgA of patients with IgA nephropathy is elevated and associated with pathological phenotypes. Nephrol Dial Transplant. Jan. 2008;23(1):207-212.
Search Report and Written Opinion issued by SIPO in 2009801406946 dated Apr. 15, 2013—includes English translation.
Office Action issued by SIPO in 2009801406946 dated May 29, 2013—includes English translation.
Search Report and Written Opinion issued in PCT/US2013/023479 dated May 15, 2013.
Choi et al., Expression Of Vascular Endothelial Growth Factor-C And Its Receptor mRNA In The Rat Kidney With Ischemia-Reperfusion Injury. Clinical Kidney J. Jun. 2, 2011;4(Suppl 2):2 pages.
Cooper, Effect Of Tobacco Smoking On Renal Function. Indian J Med Res Sep. 2006;124(3):261-268.
Extended European Search Report and Written Opinion issued in EP 10829198 dated May 21, 2013.
Senatorski et al., Urine activity of cathepsin B, collagenase and urine excretion of TGF-beta1 and fibronectin in membranous glomerulonephritis. Res Exp Med (Berl). Dec. 1998;198(4):199-206.
Schaefer et al., Urinary excretion of cathepsin B and cystatins as parameters of tubular damage. Kidney Int Suppl. Nov. 1994;47:S64-S67.
Kos et al., Cathepsins B,H and L and Their Inhibitors Stefin A and Cystatin C in Sera of Melanoma Patients. Clin Cancer Res. Oct. 1997;3(10):1815-1822.
Nambi et al., Down regulation of kidney neutral endopeptidase mRNA, protein and activity during acute renal failure: possible mechanism for ischemia-induced acute renal failure in rats? Mol Cell Biochem. Jul. 1999;197(1-2):53-59.
Li et al., Predictive value of RIFLE classification on prognosis of critically ill patients with acute kidney injury treated with continuous renal replacement therapy. Chin Med J (Engl). May 5, 2009;122(9):1020-1025.
Extended European Search Report and Written Opinion issued in EP 10829191 dated May 24, 2013.
Berahovich et al., Proteolytic activation of alternative CCR1 ligands in inflammation. J Immunol. Jun. 1, 2005;174(11):7341-7351.
Hatta et al., Cytokine Array Comparisons of Plasma from Cycling Fertile Women on Cycle Day 5 and Ovulation. Am J Reprod Immunol. Sep. 2009;62(3):158-164.

(56) References Cited

OTHER PUBLICATIONS

Grigoryev et al., The Local and Systemic Inflammatory Transcriptome after Acute Kidney Injury. J Am Soc Nephrol. Mar. 2008;19(3):547-558.
Gümüs et al., Serum Levels of Total Acid Phosphatase, Prostatic Acid Phosphatase, Total and Free Prostate-Specific Antigen in Patients Within Chronic Hemodialysis Program. Braz J Urol, Mar.-Apr. 2001;27(2):133-135.
Gupta et al., Role of Protein C in Renal Dysfunction after Polymicrobial Sepsis. J Am Soc Nephrol. Mar. 2007;18(3):860-867.
Han et al., Urinary biomarkers in the early diagnosis of acute kidney injury, Kidney Int. Apr. 2008;73(7):863-869.
Han et al., Upregulation of hyaluronan and its binding receptors in an experimental model of chronic cyclosporine nephropathy. Nephrology (Carlton). Mar. 2010;15(2):216-224.
Han, Biomarkers for Early Detection of Acute Kidney Injury. Nephrology Rounds Apr. 2008;6(4):6 pp.
Harris et al., Growth Factors and Cytokines in Acute Renal Failure. Adv Ren Replace Ther. Apr. 1997;4(2 Suppl):43-53.
He et al., Interleukin-18 binding protein transgenic mice are protected against ischemic acute kidney injury. Am J Physiol Renal Physiol. Nov. 2008;295(5):F1414 F1421.
Herget-Rosenthal et al., Early detection of acute renal failure by serum cystatin C. Kidney Int. Sep. 2004;66(3):1115-1122.
Hidaka et al., Urinary clusterin levels in the rat correlate with the severity of tubular damage and may help to differentiate between glomerular and tubular injuries. Cell Tissue Res. Dec. 2002;310(3):289-296.
Hirschberg et al. Factors Predicting Poor Outcome In Patients with Acute Renal Failure (ARF). J. Am. Soc. Nephrol. Sep. 1, 1996;7(9):1374.
Hoste et al., RIFLE criteria for acute kidney injury are associated with hospital mortality in critically ill patients: a cohort analysis. Crit Care, 2006;10(3):R73 (10 pages).
Hugo and Daniel, Thrombospondin in Renal Disease. Nephron Exp Nephrol. 2009;111(3):e61-e66.
Hugo et al. ,Thrombospondin 1 precedes and predicts the development of tubulointerstitial fibrosis in glomerular disease in the rat. Kidney Int. Feb. 1998;53(2):302-311.
Jang and Rabb, The innate immune response in ischemic acute kidney injury. Clin Immunol. Jan. 2009;130(1):41-50.
Jonsson, The role of fibroblast growth factor 23 in renal disease. Nephrol. Dial. Transplant Mar. 2005;20(3):479-482.
Julian et al., Sources of Urinary Proteins and their Analysis by Urinary Proteomics for the Detection of Biomarkers of Disease. Proteomics Clin Appl., 2009;3(9):1029-1043.
Kadiroglu et al., The Evaluation of Effects of Demographic Features, Biochemical Parameters, and Cytokines on Clinical Outcomes in Patients with Acute Renal Failure. Ren Fail. 2007;29(4):503-508.
Kalousova et al., Soluble Receptor for Advanced Glycation End Products in Patients With Decreased Renal Function. Am. J. Kidney Dis.Mar. 2006;47(3): 406-411.
Kamata et al., Up-regulation of glomerular extracellular matrix and transforming growth factor-beta expression in RF/J mice. Kidney Int. Mar. 1999;55(3):864-876.
Kehoe et al. Elevated Plasma Renin Activity Associated with Renal Dysfunction. Nephron 1986;44:51-57 (abstract only).
Kellum et al. Definition and Classification of Acute Kidney Injury. Nephron Clin Pract 2008;109(4):c182-c187.
Kellum., Acute kidney injury, Crit Care Med, 2008;36(4):S141-S145.
Keyes and Bagshaw, Early diagnosis of acute kidney injury in critically ill patients. Expert Rev Mol Diagn. Jul. 2008;8(4):455-464.
Khanna et al., Expression of TGF-beta and fibrogenic genes in transplant recipients with tacrolimus and cyclosporine nephrotoxicity. Kidney Int. Dec. 2002;62(6):2257-2263.
Kharasch et al., Gene Expression Profiling of Nephrotoxicity from the Sevoflurane Degradation Product Fluoromethyl-2,2-difluoro-1-(trifluoromethyl)vinyl Ether ("Compound A") in Rats. Toxicol Sci. Apr. 2006;90(2):419-431.
Kiley and Chevalier, Urinary biomarkers: The future looks promising. Kidney Int. Jul. 2009;76( 2): 133-134.
Kilis-Pstrusinska et al., [Levels of selected soluble adhesion molecules in blood serum of children with chronic glomerulonephritis]. Pol Merkur Lekarski. Apr. 2001;10(58):247-249.
Kilis-Pstrusinska et al., Serum levels of soluble adhesion molecules in children with glomerulonephritis (GN). Nephrol Dialysis Transplant. Jun. 2001;16(6):A62.
Kinsey et al., Inflammation in Acute Kidney Injury. Nephron Exp Nephrol. 2008; 109(4):e102-e107.
Koo et al., Cadaver versus living donor kidneys: Impact of donor factors on antigen induction before transplantation. Kidney Int. Oct. 1999;56(4):1551-1559.
Landray et al., Inflammation, Endothelial Dysfunction, and Platelet Activation in Patients With Chronic Kidney Disease: The Chronic Renal Impairment in Birmingham (CRIB) Study. Am J Kidney Dis. Feb. 2004;43(2):244-253.
Lang et al., Heat Shock Protein 60 Is Released in Immune-Mediated Glomerulonephritis and Aggravates Disease: In Vivo Evidence for an Immunologic Danger Signal. J Am Soc Nephrol. Feb. 2005;16(2):383-391.
Larsson et al., Circulating concentration of FGF-23 increases as renal function declines in patients with chronic kidney disease, but does not change in response to variation in Phosphate intake in healthy volunteers. Kidney Int.Dec. 2003,64(6):2272-2279.
Liu et al., Predictive and pathogenetic value of plasma biomarkers for acute kidney injury in patients with acute lung injury. Crit Care Med Dec. 2007;35(12):2755-2761.
Liu et al., Serum Interleukin-6 and interleukin-8 are early biomarkers of acute kidney injury and predict prolonged mechanical ventilation in children undergoing cardiac surgery: a case-control study. Critical Care 2009;13(4):R104 (9 pp.).
Lopes-Virella et al., Urinary high density lipoprotein in minimal change glomerular disease and chronic glomerulopathies. Clin Chim Acta. May 16, 1979;94(1):73-81.
Lu et al., Increased Macrophage Infiltration and Fractalkine Expression in Cisplatin-Induced Acute Renal Failure in Mice. J Pharmacol Exp Ther. Jan. 2008;324(1):111-117.
Malyszko et al., Visfatin and apelin, new adipocytokines, and their relation to endothelial function in patients with chronic renal failure. Adv Med Sci. 2008;53(1):32-36.
Matousovic et al., IgA-containing immune complexes in the urine of IgA nephropathy patients. Nephrol Dial Transplant Sep. 2006;21(9):2478-2484.
Mattes, Experience With a Biomarker Consortium. CPath Predictive Safety Training Consortium, Critical Path Institute:48 pp., (Fall 2007).
Melnikov et al., Impaired IL-18 processing protects caspase-1-deficient mice from ischemic acute renal failure. J Clin Invest, May 2001;107(9):1145-1152.
Milford et al., Prognostic Markers in Diarrhoea-Associated Haemolytic-Uraemic Syndrome: Initial Neutrophil Count, Human Neutrophil Elastase and Von Willebrand Factor Antigen. Nephrol Dial Transplant 1991;6(4):232-237.
Montagna et al., Impairment of cellular redox status and membrane protein activities in kidneys from rats with ischemic acute renal failure. Biochim Biophys Acta Aug. 14, 1998;1407(2):99-108.
Musial et al., Soluble adhesion molecules in chronic renal failure (CRF) children treated conservatively. Nephrol Dialysis Transplant. 2002;17(Abstracts Suppl 1):232.
Nguyen et al., Heparin-Binding EGF-Like Growth Factor Is Up-Regulated in the Obstructed Kidney in a Cell- and Region-Specific Manner and Acts to Inhibit Apoptosis. Am J Pathol. Mar. 2000;156(3):889-898.
Nishiyama et al., Up-Regulation of Galectin-3 in Acute Renal Failure of the Rat. Am J Pathol. Sep. 2000;157(3):815-823.
Ohno et al., Prognostic significance of tenascin-C expression in clear cell renal cell carcinoma. Oncol Rep. 2008;20(3):511-516.

(56) References Cited

OTHER PUBLICATIONS

Ozer et al., A panel of urinary biomarkers to monitor reversibility of renal injury and a serum marker with improved potential to assess renal function. Nat Biotechnol. May 2010;28(5):486-494.
Extended European Search Report and Written Opinion issued in EP 10817878 dated Apr. 15, 2013.
Office Action and Search Report issued by SIPO in Application No. 200980140805.3 dated Apr. 23, 2013—includes English Translation.
Mishra et al.. Neutrophil gelatinase-associated lipocalin (NGAL) as a biomarker for acute renal injury after cardiac surgery. Lancet. Apr. 2-8, 2005;365(9466):1231-1238.
International Preliminary Report on Patentability issued in PCT/US2011/055055 dated May 24, 2013.
Extended European Search Report and Written Opinion issued in EP 10838357 dated Jun. 3, 2013.
Stenvinkel et al., High Serum Hyaluronan Indicates Poor Survival in Renal Replacement Therapy. Am J Kidney Dis. Dec. 1999;34(6):1083-1088.
Non-Final Office Action issued by the United States Patent and Trade Office in U.S. Appl. No. 13/577,242 dated Jun. 20, 2013.
Extended European Search Report and Written Opinion issued in EP 10818036 dated Jun. 6, 2013.
Extended European Search Report and Written Opinion issued in EP 11740470 dated Jun. 18, 2013.
Tary-Lehmann et al., Enzyme-Linked Immunosorbent Assay Spot Detection of Interferon-Gamma and Interleukin 5-Producing Cells as a Predictive Marker for Renal Allograft Failure. Transplantation. Jul. 27, 1998;66(2):219-224.
Kimmel et al., Immunologic function and survival in hemodialysis patients. Kidney Int. Jul. 1998;54(1):236-244.
Simmons et al., Plasma cytokine levels predict mortality in patients with acute renal failure. Kidney Int. Apr. 2004;65(4):1357-1365.
Search Report issued by SIPO in Application No. 200980149555.X dated May 23, 2013—includes English translation.
Cai, Detection and Application for the biomarker of Rental Injury in Early Stage. Laboratory Med Clinic. Jun. 2005;2(3):124-127—incl Engl transl abstract only.
Office Action issued by SIPO in Application No. 200980149555.X dated Jul. 1, 2013—includes English translation.
Search Report issued by SIPO in Application No. 201080014932.1 dated Jun. 9, 2013—includes English translation.
Office Action issued by SIPO in Application No. 201080014932.1 dated Jun. 25, 2013—includes English translation.
Jung et al., Diagnostic significance of urinary enzymes in detecting acute rejection crises in renal transplant recipients depending on expression of results illustrated through the example of alanine aminopeptidase. Clin Biochem. Aug. 1985;18(4):257-260.
Search Report issued by SIPO in Application No. 200980149636.X dated Jun. 17, 2013—includes English translation.
Office Action issued by SIPO in Application No. 200980149636.X dated Jul. 1, 2013—includes English translation.
Extended European Search Report and Written Opinion issued in EP 11740468 dated Jun. 13, 2013.
Fried et al., Inflammatory and Prothrombotic Markers and the Progression of Renal Disease in Elderly Individuals. J Am Soc Nephrol. Dec. 2004;15(12):3184-3191.
Edelstein, Biomarkers of Acute Kidney Injury. Adv Chronic Kidney Dis.Jul. 2008;15(3)222-234.
Extended European Search Report and Written Opinion issued in EP 11740469 dated Jun. 3, 2013.
Fujisaki et al., Infusion of radiocontrast agents induces exaggerated release of urinary endothelin in patients with impaired renal function. Clin Exp Nephrol. Dec. 2003;7(4):279-283.
Hirai et al., Plasma endothelin-1(ET-1) is a useful marker for renal dysfunction. Atheroscler Suppl. Jun. 19, 2006;7(3):60[Mo-P1:65].
Cottone et al., Endothelin-1 and F2-isoprostane relate to and predict renal dysfunction in hypertensive patients. Nephrol Dial Transpl. Feb. 2009;24(2):497-503.

Schulz et al., Endothelin-1 as an early prognostic marker in acute renal failure (ARF) and sepsis. Kidney Blood Press Res. 2000;23(3-5):341-342.
Search Report issued by SIPO in Application No. 201080057014.7 dated Jul. 8, 2013—includes English translation.
Office Action issued by SIPO in Application No. 201080057014.7 dated Jul. 18, 2013—includes English translation.
Extended European Search Report and Written Opinion issued in EP 10812639 dated Jul. 16, 2013.
Song et al., Expression of TRAIL, DR4, and DR5 in kidney and serum from patients receiving renal transplantation. Transplant Proc. Jun. 2004;36(5):1340-1343.
International Search Report and Written Opinion dated Jun. 3, 2011 in PCT/US2011/026759.
International Search Report and Written Opinion dated Sep. 7, 2012 in PCT/US2012/043279.
International Search Report and Written Opinion dated Dec. 15, 2011 in PCT/US2011/001126.
International Search Report and Written Opinion dated Nov. 25, 2011 in PCT/US2011/001127.
International Search Report and Written Opinion dated Nov. 25, 2011 in PCT/US2011/001128.
International Search Report and Written Opinion dated Nov. 25, 2011 in PCT/US2011/001125.
International Search Report and Written Opinion dated Jun. 20, 2012 in PCT/US2012/020572.
International Search Report and Written Opinion dated May 2, 2012 in PCT/US2012/022926.
International Search Report and Written Opinion dated Sep. 21, 2012 in PCT/US2012/045583.
Non Final Office Action issued by the USPTO in U.S. Appl. No. 13/061,446 dated Oct. 12, 2012.
Abd El Latif et al., Urinary epidermal growth factor excretion: A useful prognostic marker for progression of renal damage in children. J Med Sci Oct. 2007; 7(7): 1171-1176.
Abou-Shousha and Youssef, Interleukin-2 Regulatory Effect on P-Selectin and Interleukin-8 Production in Patients with Chronic Renal Failure. Egypt J Immunol. 2006;13(1):11-18.
Akcay et al., Mediators of Inflammation in Acute Kidney Injury. Mediators Inflamm. 2009;2009:137072 (12 pp).
Albright, Acute Renal Failure: A Practical Update. Mayo Clin. Proc. Jan. 2001;76(1):67-74.
Anders et al., Chemokines and chemokine receptors are involved in the resolution or progression of renal disease. Kidney Int. Feb. 2003;63(2):401-415.
Anilkumar et al., Trimeric assembly of the C-terminal region of Thrombospondin-1 or Thrombospondin-2 is necessary for cell spreading and fascin spike organisation. J Cell Sci. Jun. 1, 2002;115(Pt 11):2357-2366.
Arribas and Esselens, ADAM17 as a Therapeutic Target in Multiple Diseases. Curr Pharm Des. 2009;15(20):2319-2335.
Arrizabalaga et al., Tubular and Interstitial Expression of ICAM-1 as a Marker of Renal Injury in IgA Nephropathy. Am J Nephrol May-Jun. 2003;23(3):121-128.
Bagshaw et al., Urinary biomarkers in septic acute kidney injury. Intensive Care Med. Jul. 2007;33(7):1285-1296.
Bajwa et al., Immune Mechanisms and Novel Pharmacological Therapies of Acute Kidney Injury. Curr Drug Targets Dec. 2009;10(12):1196-1204.
Barrera-Chimal et al., Hsp72 is an early and sensitive biomarker to detect acute kidney injury. EMBO Mol Med. Jan. 2011;3(1):5-20.
Beushausen, NWG Biomarker Objectives. ILSI Health and Environmental Sciences Institute, ILSI-HESI Annual Meeting 2006:17 pp.
Bicik et al., Role of Transforming Growth Factor-.beta.2 in, and a Possible Transforming Growth Factor-beta2 Gene Polymorphism as a Marker of, Renal Dysfunction in Essential Hypertension: A Study in Turkish Patients, Current Therapeutic Research, 2005;44(4):266-278.
Biotrin International, Biotrin Biomarkers: How late do you want to detect preclinical kidney damage? Biotrin's acute kidney injury test (AKI Test). Biotrin's Preclinical Kidney Biomarkers: 8 pp.

(56) References Cited

OTHER PUBLICATIONS

Bonomini et al., Serum Levels of Soluble Adhesion Molecules in Chronic Renal Failure and Dialysis Patients. Nephron. Aug. 1998;79(4):399-407.
Bonventre and Zuk, Ischemic acute renal failure: An inflammatory disease? Kidney Int. Aug. 2004;66(2):480-485.
Bonventre, Dedifferentiation and Proliferation of Surviving Epithelial Cells in Acute Renal Failure. J Am Soc Nephrol Jun. 2003;14 Suppl 1:S55-S61.
Bonventre, Pathophysiology of Acute Kidney Injury: Roles of Potential Inhibitors of Inflammation. Contrib Nephrol. 2007; 156: 39-46.
Burne et al., IL-1 and TNF independent pathways mediate ICAM-1/VCAM-1 up-regulation in ischemia reperfusion injury. J Leukoc Biol. Aug. 2001;70(2):192-198.
Burne-Taney and Rabb, The role of adhesion molecules and T cells in ischemic renal injury. Curr Opin Nephrol Hypertens. Jan. 2003;12(1):85-90.
Canani et al., The Fatty Acid-Binding Protein-2 A54T Polymorphism Is Associated With Renal Disease in Patients With Type 2 Diabetes. Diabetes Nov. 2005;54(11):3326-3330.
Catania et al., Role of matrix metalloproteinases in renal pathophysiologies. Am J Physiol Renal Physiol Mar. 2007;292(3):F905-F911.
Coca et al., Biomarkers for the diagnosis and risk stratification of acute kidney injury: A systematic review. Kidney Int May 2008;73(9):1008-1016.
Cruz et al., North East Italian Prospective Hospital Renal Outcome Survey on Acute Kidney Injury (NEiPHROS-AKI) Targeting the Problem with the RIFLE Criteria. Clin J Amer. Soc. Nephrol. May 2007;2(3):418-425.
Daha and Van Kooten, Is the proximal tubular cell a proinflammatory cell? Nephrol Dial Transplant 2000;15 Suppl 6:41-43.
De Sa et al., Leukocyte, platelet and endothelial activation in patients with acute renal failure treated by intermittent hemodialysis. Am J Nephrol. Jul.-Aug. 2001;21(4):264-273.
Devarajan and Williams, Proteomics for Biomarker Discovery in Acute Kidney Injury. Semin Nephrol. Nov. 2007;27(6):637-651.
Devarajan, Cellular and molecular derangements in acute tubular necrosis. Curr Opin Pediatr. Apr. 2005;17(2):193-199.
Devarajan, Novel biomarkers for the early prediction of acute kidney injury. Cancer Therapy Sep. 2005;3:477-488.
Devarajan, Update on Mechanisms of Ischemic Acute Kidney Injury. J Am Soc Nephrol. Jun. 2006;17(6):1503-1520.
Domanski et al., Purine and Cytokine Concentrations in the Renal Vein of the Allograft During Reperfusion. Transplant Proc. Jun. 2007;39(5):1319-1322.
FDA, European Medicines Agency to Consider Additional Test Results When Assessing New Drug Safety—Collaborative effort by FDA and EMEA expected to yield additional safety data. http://www.natap.org/2008/newsUpdates/071608_01.htm, (2008).
Ferguson et al., Biomarkers of nephrotoxic acute kidney injury. Toxicology Mar. 20, 2008;245(3):182-193
Frangogiannis, Chemokines in ischemia and reperfusion. Thromb Haemost May 2007;97(5):738-747.
Furuichi et al., Chemokine/chemokine receptor-mediated inflammation regulates pathologic changes from acute kidney injury to chronic kidney disease. Clin Exp Nephrol Feb. 2009;13(1):9-14.
Furuichi et al., Roles of chemokines in renal ischemia/reperfusion injury. Front Biosci. May 1, 2008;13:4021-4028.
Galkina and Ley, Leukocyte Recruitment and Vascular Injury in Diabetic Nephropathy. J Am Soc Nephrol. Feb. 2006;17(2):368-377.
Garcia et al., Adenosine A2A receptor activation and macrophagemediated experimental glomerulonephritis. FASEB J. Feb. 2008;22(2):445-454.
Gbadegesin et al., Plasma and urinary soluble adhesion molecule expression is increased during first documented acute pyelonephritis. Arch Dis Child. Mar. 2002;86(3):218-221.
Goes et al., Effect of Recombinant Human Insulin-Like Growth Factor-1 on the Inflammatory Response to Acute Renal Injury. J Am Soc Nephrol. May 1996;7(5):710-720.
Parikh and Devarajan, New biomarkers of acute kidney injury. Crit Care Med 2008;36(4 Suppl):S159-S165.
Parikh et al., Urinary IL-18 is an early predictive biomarker of acute kidney injury after cardiac surgery. Kidney Int, 2006;70(1):199-203.
Perco et al., Protein biomarkers associated with acute renal failure and chronic kidney disease. Eur J Clin Invest. Nov. 2006;36(11):753-763.
Picard et al., Origin of renal myofibroblasts in the model of unilateral ureter obstruction in the rat. Histochem Cell Biol. Jul. 2008;130(1):141-155.
Price, Abrupt Changes In Prostate-Specific Antigen Concentration in Acute Renal Failure. Clin Chem. Jan. 1993;39(1):161-162.
Prozialeck and Edwards, Cell Adhesion Molecules in Chemically-Induced Renal Injury. Pharmacol Ther. Apr. 2007;114(1):74-93.
Radford et al. Predicting renal outcome in IgA nephropathy. J Am Soc Nephrol Feb. 1997;8(2):199-207.
Ramesh and Reeves, TNF-α mediates chemokine and cytokine expression and renal injury in cisplatin nephrotoxicity. J. Clin. Invest. Sep. 2002;110(6):835-842.
Ramesh et al., Endotoxin and cisplatin synergistically induce renal dysfunction and cytokine production in mice. Am J Physiol Renal Physiol. Jul. 2007;293(1):F325-F332.
Ramirez et al., Prospective Study on Autoantibodies Against Apolipoprotein H ( B2GPI) in Several Clinical Parameters From Patients With Terminal Renal Failure and Functioning Renal Transplants. Transplantation Proceedings Jul. 2009;41(6):2370-2372.
Ricci et al., The RIFLE criteria and mortality in acute kidney injury: A systematic review. Kidney Int Mar. 2008;73(5):538-546.
Rosenkranz et al., P-selectin deficiency exacerbates experimental glomerulonephritis: a protective role for endothelial P-selectin in inflammation. J Clin Invest. Mar. 1999;103(5):649-659.
Rouschop et al., Pre-transplant plasma and cellular levels of CD44 correlate with acute renal allograft rejection. Nephrol Dial Transplant Oct. 2005;20(10):2248-2254.
Rouschop et al., Renal expression of CD44 correlates with acute renal allograft rejection. Kidney Int. Sep. 2006;70(6):1127-1134.
Schena et al., EGF and MCP-1 Urinary Excretion Is a Suitable Prognostic Marker in Iga Nephropathy. J Am Soc Of Nephrology; Meeting of The American Society of Nephrology. Sep. 1, 2002;13(Program and Abstracts Issue): 458A.
Schiffer et al., Activated Renal Macrophages Are Markers of Disease Onset and Disease Remission in Lupus Nephritis, J Immunol Feb. 1, 2008;180(3):1938-1947.
Schmaldienst et al., Angiogenin: a novel inhibitor of neutrophil-lactoferrin release during extracorporeal circulation. Kidney Blood Press Res. 2003;26(2):107-112.
Schmidt et al., Sexual hormone abnormalities in male patients with renal failure. Nephrol Dial Transplant. Mar. 2002;17(3):368-371.
Segawa et al., In situ expression and soluble form of P-selectin in human glomerulonephritis. Kidney Int. Oct. 1997;52(4):1054-1063.
Segerer et al., Chemokines, Chemokine Receptors, and Renal Disease: From Basic Science To Pathophysiologic and Therapeutic Studies. J Am Soc Nephrol Jan. 2000;11(1):152-176.
Severini and Aliberti, Diagnostic significance of urinary enzymes: Development of a high performance liquid chromatographic method for the measurement of urinary lysozyme. Clin Chim Acta Feb. 27, 1987;163(1):97-103.
Shlipak et al., Elevations of Inflammatory and Procoagulant Biomarkers in Elderly Persons With Renal Insufficiency. Circulation Jan. 2003;107(1):87-92.
Shoji et al., Plasma angiopoietin-like protein 3 (ANGPTL3) concentration is associated with uremic dyslipidemia. Atherosclerosis. Dec. 2009;207(2):579-584.
Stafford-Smith et al., Acute Kidney Injury and Chronic Kidney Disease After Cardiac Surgery. Adv Chronic Kidney Dis. Jul. 2008;15(3):257-277.
Stasko et al., Soluble P-Selectin During a Single Hemodialysis Session in Patients With Chronic Renal Failure and Erythropoietin Treatment. Clin Appl Thromb Hemost. Oct. 2007;13(4):410-415.

(56) References Cited

OTHER PUBLICATIONS

Stuard et al., Soluble adhesion molecules in chronic renal failure patients. Nephrol Dialysis Transplant. 1997;12(9):A100.
Supavekin et al., Differential gene expression following early renal ischemia/reperfusion. Kidney Int. May 2003;63(5):1714-1724.
Sutton et al., Injury of the renal microvascular endothelium alters barrier function after ischemia. Am J Physiol Renal Physiol Aug. 2003;285(2):F191-F198.
Sutton et al., Microvascular endothelial injury and dysfunction during ischemic acute renal failure. Kidney Int. Nov. 2002;62(5):1539-1549.
Sutton, Alteration of microvascular permeability in acute kidney injury. Microvasc Res. Jan. 2009;77(1):4-7.
Symon et al., The endogenous insulin-like growth factor system in radiocontrast nephropathy. Am. J. Physiol. Renal Physiol. Mar. 1998;274(3 Pt2):F490-497.
Takada et al., The Cytokine-adhesion Molecule Cascade in Ischemia/Reperfusion Injury of the Rat Kidney. Inhibition by a Soluble P-selectin Ligand. J. Clin. Invest. Jun. 1997; 99(11):2682-2690.
Taulan et al., Comprehensive analysis of the renal transcriptional response to acute uranyl nitrate exposure. BMC Genomics Jan. 11, 2006;7(2) 14 pages.
Teppo et al., Soluble Intercellular Adhesion Molecule-1 (Sicam-1) after Kidney Transplantation: The Origin and Role of Urinary Sicam-1? Transplantation Apr. 27, 2001;71(8):1113-1119.
Thorburn et al., CXC and CC chemokines induced in human renal epithelial cells by inflammatory cytokines. APMIS Jul. 2009;117(7):477-487.
Timoshanko et al., Interleukin-12 from Intrinsic Cells Is an Effector of Renal Injury in Crescentic Glomerulonephritis. J. Am. Soc. Nephrol. Mar. 2001;12(3):464-471.
Torres et al., The ratio of epidermal growth factor to monocyte chemotactic peptide-1 in the urine predicts renal prognosis in IgA nephropathy. Kidney Int. Feb. 2008;73(3):327-333.
Vaidya and Bonventre, Mechanistic biomarkers for cytotoxic acute kidney injury. Expert Opin Drug Metab Toxicol. Oct. 2006;2(5):697-713.
Vaidya et al., Biomarkers of Acute Kidney Injury. Annu Rev Pharmacol Toxicol. Feb. 2008;48:463-493.
Vanhoutte et al., Biomarker discovery with SELDI-TOF MS in human urine associated with early renal injury evaluation with computational analytical tools. Nephrol Dial Transplant Oct. 2007;22(10):2932-2943.
Villanueva et al., Ischemic acute renal failure induces the expression of a wide range of nephrogenic proteins. Am J Physiol Regul Integr Comp Physiol Apr. 2006;290(4):R861-R870.
Vonderscher, Biomarker of Drug Induced Kidney Injury Qualification for Regulatory Decision Making (CRADA). IOM/FDA, Silver Spring, MD Apr. 23, 2007:31 pp.
Waikar et al., Diagnosis, Epidemiology and Outcomes of Acute Kidney Injury. Clin J Am Soc Nephrol. May 2008;3(3):844-861.
Wan et al., The pathogenesis of septic acute renal failure. Curr Opin Crit Care Dec. 2003;9(6):496-502.
Wang et al., Netrin-1 and kidney injury. I. Netrin-1 protects against ischemia-reperfusion injury of the kidney. Am J Physiol Renal Physiol. Apr. 2008;294(4):F739-F747.
Wang et al., Validation of putative genomic biomarkers of nephrotoxicity in rats. Toxicology Apr. 18, 2008;246(2-3):91-100.
Wilson and Hadley, Urinary lysozyme. J Pediatr. Feb. 1950;36(2):199-211.
Winchester et al., Sorbents in Acute Renal Failure and End-Stage Renal Disease: Middle Molecule and Cytokine Removal. Blood Purif. 2004;22(1):73-77.
Yang et al. Frequency of anti-bactericidal/permeability-increasing protein (BPI) and anti-azurocidin in patients with renal disease. Clin. Exp. Immunol. Jul. 1996;105(1):125-131.
Yu et al., Urinary biomarkers trefoil factor 3 and albumin enable early detection of kidney tubular injury. Nat Biotechnol May 2010;128(5):470-477.

Office Action and Search Report issued by the JPO in Japanese application No. 2012-552128 dated Sep. 2, 2014—incl Engl language translation.
Extended European Search Report and Written Opinion issued in EP 13177829.2 dated Oct. 30, 2013.
Office Action and Search Report issued by SIPO in Chinese application No. 201180013356.3 dated Sep. 5, 2013—incl Engl language translation.
Office Action and Search Report issued by SIPO in Chinese application No. 201180013356.3 dated May 19, 2014—incl Engl language translation.
Youngman Oh, "The insulin-like growth factor system in chronic kidney disease: Pathophysiology and therapeutic opportunities", 2012, Kidney Res Clin Pract, 31:26-37.
Franz Schaefer and Ralph Rabkin, "Insulin-like Growth Factor-I and the Kidney", Insulin-like Growth Factors, Kluwer Academic/Plenum Publishers, New York, 2003, pp. 244-261.
"Dent Disease." Genetics Home Reference. National Library of Medicine, Jan. 18, 2016. Web. Jan. 22, 2016. http://ghr.nlm.nih.gov/condition/dent-disease.
Office Action issued by the JPO in Japanese Application No. 2012-552128 dated Jun. 23, 2015—incl Engl lang translation.
Han et al., Urinary Biomarkers in the Early Detection of Acute Kidney Injury after Cardiac Surgery. Clin J Am Soc Nephrol. May 2009;4(5):873-882.
Office Action issued by the JPO in Japanese application No. 2016-232017 dated Sep. 19, 2017—incl Engl lang transl.
D'Elia et al., "Risk factors for thromboembolic events in renal failure," International Journal of Cardiology, 2005, 101:19-25; Abstract Only.
Devarajan, "Emerging urinary biomarkers in the diagnosis of acute kidney injury," Expert Opinion on Medical Diagnostics, 2008, 2(4):387-398.
Gris et al., "Increased cardiovascular risk factors and features of endothelial activation and dysfunction in dialyzed uremic patients," Kidney International, 1994, 46:807-813.
Kutsukake et al., "Circulating IGF-binding protein 7 (IGFBP7) levels are elevated in patients with endometriosis or undergoing diabetic hemodialysis," Reproductive Biology and Endocrinology, Nov. 19, 2008, 6(54):1-6.
Shudo et al., "Giant hydronephrosis due to a uretal stone, and elevated serum levels of CA 19-9," Internal Medicine, 1999, 38(11):887-891.
Vaziri et al., "Blood coagulation, fibrinolytic, and inhibitory proteins in end-stage renal disease: effect of hemodialysis," American Journal of Kidney Diseases, 1994, 23(6):828-835; Abstract Only.
Wilson et al., "Generation and Characterization of an IGFBP-7 Antibody: Identification of 31kD IGFBP-7 in Human Biological Fluids and Hs578T Human Breast Cancer Conditioned Media," Journal of Clinical Endocrinology and Metabolism, Jan. 1, 1997, 82(4):1301-1303.
Xiaofang et al., "Serum tumour markers in patients with chronic kidney disease," Scadinavian Journal of Clinical & Labroratory Investigation, 2007, 67:661-667; Abstract Only.
Official action dated May 6, 2013, issued in Australian application (No. 2011213684).
Official action dated Jan. 7, 2019, issued in Brazilian application (No. BR112012019542-5).
Official action dated Mar. 17, 2017, issued in Canadian application (No. 2,788,826).
Official action dated Jan. 11, 2018, issued in Canadian application (No. 2,788,826).
Official action dated Dec. 27, 2018, issued in Canadian application (No. 2,788,826).
Official action dated Dec. 12, 2018, issued in Eurasian application (No. 201290629).
Official action dated Jul. 27, 2018, issued in Indian application (No. 1886/MUMNP/2012).
Office action dated Nov. 27, 2018, issued in Mexican application (No. MX/a/2016/010109).
Official action dated Jan. 22, 2020, issued in Indian application (No. 1886/MUMNP/2012).

(56) References Cited

OTHER PUBLICATIONS

Official action dated Feb. 22, 2021, issued in Canadian application (No. 2,788,826).
Office Action and Search Report issued by SIPO in Chinese patent application No. 201510522677.6 dated Mar. 2, 2017—incl Engl language translation, (17 pages).
Hawn et al., Genetic Variation of the Human Urinary Tract Innate Immune Response and Asymptomatic Bacteriuria in Women. PLoS One. Dec. 15, 2009;4(12):e8300 (12 pages).

* cited by examiner

METHODS AND COMPOSITIONS FOR DIAGNOSIS AND PROGNOSIS OF RENAL INJURY AND RENAL FAILURE

CROSS REFERENCE TO RELATED APPLICATIONS

The present invention is filed under 35 U.S.C. § 371 as the U.S. national phase of International Application No. PCT/US2011/023830, filed Feb. 4, 2011, which designated the U.S. and claims the benefit of priority to U.S. Provisional Patent Application 61/302,021 filed Feb. 5, 2010; U.S. Provisional Patent Application No. 61/302,025 filed Feb. 5, 2010; U.S. Provisional Patent Application No. 61/302,026 filed Feb. 5, 2010; U.S. Provisional Patent Application No. 61/302,027 filed Feb. 5, 2010; U.S. Provisional Patent Application No. 61/302,036 filed Feb. 5, 2010; and U.S. Provisional Patent Application No. 61/374,060 filed Aug. 16, 2010, each of which is hereby incorporated in its entirety including all tables, figures, and claims.

SEQUENCE LISTING

The instant application contains a Sequence Listing which has been submitted in ASCII format via EFS-Web and is hereby incorporated by reference in its entirety. Said ASCII copy, created on Aug. 4, 2012, is named AST1610US_SeqList_txt.txt and is 8,958 bytes in size.

BACKGROUND OF THE INVENTION

The following discussion of the background of the invention is merely provided to aid the reader in understanding the invention and is not admitted to describe or constitute prior art to the present invention.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, $17^{th}$ Ed., McGraw Hill, New York, pages 1741-1830, which are hereby incorporated by reference in their entirety. Renal disease and/or injury may be acute or chronic. Acute and chronic kidney disease are described as follows (from Current Medical Diagnosis & Treatment 2008, $47^{th}$ Ed, McGraw Hill, New York, pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week)reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in the following table, which is adapted from the Merck Manual, $17^{th}$ ed., Chapter 222, and which is hereby incorporated by reference in their entirety:

| Type | Risk Factors |
| --- | --- |
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GFR from reduced glomerular transcapillary pressure, especially in patients with bilateral renal artery stenosis) | ACE inhibitors or angiotensin II receptor blockers |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |
| Acute glomerulonephritis | ANCA-associated: Crescentic glomerulonephritis, polyarteritis nodosa, Wegener's granulomatosis; Anti-GBM glomerulonephritis: Goodpasture's syndrome; |

-continued

| Type | Risk Factors |
| --- | --- |
| | Immune-complex: Lupus glomerulonephritis, postinfectious glomerulonephritis, cryoglobulinemic glomerulonephritis |
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |
| Acute vascular nephropathy | Vasculitis, malignant hypertension, thrombotic microangiopathies, scleroderma, atheroembolism |
| Infiltrative diseases | Lymphoma, sarcoidosis, leukemia |
| Postrenal | |
| Tubular precipitation | Uric acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of subjects with ARF may be as low as about 60%.

Acute kidney injury caused by radiocontrast agents (also called contrast media) and other nephrotoxins such as cyclosporine, antibiotics including aminoglycosides and anticancer drugs such as cisplatin manifests over a period of days to about a week. Contrast induced nephropathy (CIN, which is AKI caused by radiocontrast agents) is thought to be caused by intrarenal vasoconstriction (leading to ischemic injury) and from the generation of reactive oxygen species that are directly toxic to renal tubular epithelial cells. CIN classically presents as an acute (onset within 24-48h) but reversible (peak 3-5 days, resolution within 1 week) rise in blood urea nitrogen and serum creatinine.

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, *Curr Opin Nephrol Hypertens* 14:265-270, 2005 and Chertow et al, *J Am Soc Nephrol* 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

One study (Lassnigg et all, J Am Soc Nephrol 15:1597-1605, 2004, hereby incorporated by reference in its entirety) investigated both increases and decreases in serum creatinine. Patients with a mild fall in serum creatinine of −0.1 to −0.3 mg/dL following heart surgery had the lowest mortality rate. Patients with a larger fall in serum creatinine (more than or equal to −0.4 mg/dL) or any increase in serum creatinine had a larger mortality rate. These findings caused the authors to conclude that even very subtle changes in renal function (as detected by small creatinine changes within 48 hours of surgery) seriously effect patient's outcomes. In an effort to reach consensus on a unified classification system for using serum creatinine to define AKI in clinical trials and in clinical practice, Bellomo et al., *Crit. Care.* 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;

"Injury": serum creatinine increased 2.0 fold from baseline OR urine production <0.5 ml/kg/hr for 12 h;

"Failure": serum creatinine increased 3.0 fold from baseline OR creatinine >355 μmol/l (with a rise of >44) or urine output below 0.3 ml/kg/hr for 24 h or anuria for at least 12 hours;

And included two clinical outcomes:

"Loss": persistent need for renal replacement therapy for more than four weeks.

"ESRD": end stage renal disease—the need for dialysis for more than 3 months.

These criteria are called the RIFLE criteria, which provide a useful clinical tool to classify renal status. As discussed in Kellum, *Crit. Care Med.* 36: S141-45, 2008 and Ricci et al., *Kidney Int.* 73, 538-546, 2008, each hereby incorporated by reference in its entirety, the RIFLE criteria provide a uniform definition of AKI which has been validated in numerous studies.

More recently, Mehta et al., *Crit. Care* 11:R31 (doi: 10.1186.cc5713), 2007, hereby incorporated by reference in its entirety, proposes the following similar classifications for stratifying AKI patients, which have been modified from RIFLE:

"Stage I": increase in serum creatinine of more than or equal to 0.3 mg/dL (≥26.4 μmol/L) or increase to more than or equal to 150% (1.5-fold) from baseline OR urine output less than 0.5 mL/kg per hour for more than 6 hours;

"Stage II": increase in serum creatinine to more than 200% (>2-fold) from baseline OR urine output less than 0.5 mL/kg per hour for more than 12 hours;

"Stage III": increase in serum creatinine to more than 300% (>3-fold) from baseline OR serum creatinine ≥354 μmol/L accompanied by an acute increase of at least 44 μmol/L OR urine output less than 0.3 mL/kg per hour for 24 hours or anuria for 12 hours.

The CIN Consensus Working Panel (McCollough et al, Rev Cardiovasc Med. 2006; 7(4): 177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

Although serial measurement of serum creatinine over a period of days is an accepted method of detecting and diagnosing AKI and is considered one of the most important tools to evaluate AKI patients, serum creatinine is generally regarded to have several limitations in the diagnosis, assessment and monitoring of AKI patients. The time period for serum creatinine to rise to values (e.g., a 0.3 mg/dL or 25% rise) considered diagnostic for AKI can be 48 hours or longer depending on the definition used. Since cellular injury in AKI can occur over a period of hours, serum creatinine elevations detected at 48 hours or longer can be a late indicator of injury, and relying on serum creatinine can thus delay diagnosis of AKI. Furthermore, serum creatinine is not a good indicator of the exact kidney status and treatment needs during the most acute phases of AKI when kidney function is changing rapidly. Some patients with AKI will recover fully, some will need dialysis (either short term or long term) and some will have other detrimental outcomes including death, major adverse cardiac events and chronic kidney disease. Because serum creatinine is a marker of filtration rate, it does not differentiate between the causes of AKI (pre-renal, intrinsic renal, post-renal obstruction, atheroembolic, etc) or the category or location of injury in intrinsic renal disease (for example, tubular, glomerular or interstitial in origin). Urine output is similarly limited, Knowing these things can be of vital importance in managing and treating patients with AKI.

These limitations underscore the need for better methods to detect and assess AKI, particularly in the early and subclinical stages, but also in later stages when recovery and repair of the kidney can occur. Furthermore, there is a need to better identify patients who are at risk of having an AKI.

BRIEF SUMMARY OF THE INVENTION

It is an object of the invention to provide methods and compositions for evaluating renal function in a subject. As described herein, measurement of one or more biomarkers selected from the group consisting of Coagulation factor VII, CA19-9, Insulin-like growth factor-binding protein 7, C—X—C motif chemokine 6, and C—C motif chemokine 13 (each referred to herein as a "kidney injury marker") can be used for diagnosis, prognosis, risk stratification, staging, monitoring, categorizing and determination of further diagnosis and treatment regimens in subjects suffering or at risk of suffering from an injury to renal function, reduced renal function, and/or acute renal failure (also called acute kidney injury).

The kidney injury markers of the present invention may be used, individually or in panels comprising a plurality of kidney injury markers, for risk stratification (that is, to identify subjects at risk for a future injury to renal function, for future progression to reduced renal function, for future progression to ARF, for future improvement in renal function, etc.); for diagnosis of existing disease (that is, to identify subjects who have suffered an injury to renal function, who have progressed to reduced renal function, who have progressed to ARF, etc.); for monitoring for deterioration or improvement of renal function; and for predicting a future medical outcome, such as improved or worsening renal function, a decreased or increased mortality risk, a decreased or increased risk that a subject will require renal replacement therapy (i.e., hemodialysis, peritoneal dialysis, hemofiltration, and/or renal transplantation, a decreased or increased risk that a subject will recover from an injury to renal function, a decreased or increased risk that a subject will recover from ARF, a decreased or increased risk that a subject will progress to end stage renal disease, a decreased or increased risk that a subject will progress to chronic renal failure, a decreased or increased risk that a subject will suffer rejection of a transplanted kidney, etc.

In a first aspect, the present invention relates to methods for evaluating renal status in a subject. These methods comprise performing an assay method that is configured to detect one or more biomarkers selected from the group consisting of Coagulation factor VII, CA19-9, Insulin-like growth factor-binding protein 7, C—X—C motif chemokine 6, and C—C motif chemokine 13 is/are then correlated to the renal status of the subject. This correlation to renal status may include correlating the assay result(s) to one or more of risk stratification, diagnosis, prognosis, staging, classifying and monitoring of the subject as described herein. Thus, the present invention utilizes one or more kidney injury markers of the present invention for the evaluation of renal injury.

In certain embodiments, the methods for evaluating renal status described herein are methods for risk stratification of the subject; that is, assigning a likelihood of one or more future changes in renal status to the subject. In these embodiments, the assay result(s) is/are correlated to one or more such future changes. The following are preferred risk stratification embodiments.

In preferred risk stratification embodiments, these methods comprise determining a subject's risk for a future injury to renal function, and the assay result(s) is/are correlated to a likelihood of such a future injury to renal function. For example, the measured concentration(s) may each be compared to a threshold value. For a "positive going" kidney injury marker, an increased likelihood of suffering a future injury to renal function is assigned to the subject when the measured concentration is above the threshold, relative to a likelihood assigned when the measured concentration is below the threshold. For a "negative going" kidney injury marker, an increased likelihood of suffering a future injury to renal function is assigned to the subject when the measured concentration is below the threshold, relative to a likelihood assigned when the measured concentration is above the threshold.

In other preferred risk stratification embodiments, these methods comprise determining a subject's risk for future reduced renal function, and the assay result(s) is/are correlated to a likelihood of such reduced renal function. For example, the measured concentrations may each be compared to a threshold value. For a "positive going" kidney injury marker, an increased likelihood of suffering a future reduced renal function is assigned to the subject when the measured concentration is above the threshold, relative to a likelihood assigned when the measured concentration is below the threshold. For a "negative going" kidney injury marker, an increased likelihood of future reduced renal function is assigned to the subject when the measured concentration is below the threshold, relative to a likelihood assigned when the measured concentration is above the threshold.

In still other preferred risk stratification embodiments, these methods comprise determining a subject's likelihood for a future improvement in renal function, and the assay result(s) is/are correlated to a likelihood of such a future improvement in renal function. For example, the measured concentration(s) may each be compared to a threshold value. For a "positive going" kidney injury marker, an increased likelihood of a future improvement in renal function is assigned to the subject when the measured concentration is below the threshold, relative to a likelihood assigned when the measured concentration is above the threshold. For a "negative going" kidney injury marker, an increased likelihood of a future improvement in renal function is assigned to the subject when the measured concentration is above the threshold, relative to a likelihood assigned when the measured concentration is below the threshold.

In yet other preferred risk stratification embodiments, these methods comprise determining a subject's risk for progression to ARF, and the result(s) is/are correlated to a likelihood of such progression to ARF. For example, the measured concentration(s) may each be compared to a threshold value. For a "positive going" kidney injury marker, an increased likelihood of progression to ARF is assigned to the subject when the measured concentration is above the threshold, relative to a likelihood assigned when the measured concentration is below the threshold. For a "negative going" kidney injury marker, an increased likelihood of progression to ARF is assigned to the subject when the measured concentration is below the threshold, relative to a likelihood assigned when the measured concentration is above the threshold.

And in other preferred risk stratification embodiments, these methods comprise determining a subject's outcome risk, and the assay result(s) is/are correlated to a likelihood of the occurrence of a clinical outcome related to a renal injury suffered by the subject. For example, the measured concentration(s) may each be compared to a threshold value. For a "positive going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is above the threshold, relative to a likelihood assigned when the measured concentration is below the threshold. For a "negative going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is below the threshold, relative to a likelihood assigned when the measured concentration is above the threshold.

In such risk stratification embodiments, preferably the likelihood or risk assigned is that an event of interest is more or less likely to occur within 180 days of the time at which the body fluid sample is obtained from the subject. In particularly preferred embodiments, the likelihood or risk assigned relates to an event of interest occurring within a shorter time period such as 18 months, 120 days, 90 days, 60 days, 45 days, 30 days, 21 days, 14 days, 7 days, 5 days, 96 hours, 72 hours, 48 hours, 36 hours, 24 hours, 12 hours, or less. A risk at 0 hours of the time at which the body fluid sample is obtained from the subject is equivalent to diagnosis of a current condition.

In preferred risk stratification embodiments, the subject is selected for risk stratification based on the pre-existence in the subject of one or more known risk factors for prerenal, intrinsic renal, or postrenal ARF. For example, a subject undergoing or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin are all preferred subjects for monitoring risks according to the methods described herein. This list is not meant to be limiting. By "pre-existence" in this context is meant that the risk factor exists at the time the body fluid sample is obtained from the subject. In particularly preferred embodiments, a subject is chosen for risk stratification based on an existing diagnosis of injury to renal function, reduced renal function, or ARF.

In other embodiments, the methods for evaluating renal status described herein are methods for diagnosing a renal injury in the subject; that is, assessing whether or not a subject has suffered from an injury to renal function, reduced renal function, or ARF. In these embodiments, the assay result(s), for example measured concentration(s) of one or more biomarkers selected from the group consisting of Coagulation factor VII, CA19-9, Insulin-like growth factor-binding protein 7, C—X—C motif chemokine 6, and C—C motif chemokine 13 is/are correlated to the occurrence or nonoccurrence of a change in renal status. The following are preferred diagnostic embodiments.

In preferred diagnostic embodiments, these methods comprise diagnosing the occurrence or nonoccurrence of an injury to renal function, and the assay result(s) is/are correlated to the occurrence or nonoccurrence of such an injury. For example, each of the measured concentration(s) may be compared to a threshold value. For a positive going marker, an increased likelihood of the occurrence of an injury to renal function is assigned to the subject when the measured concentration is above the threshold (relative to the likelihood assigned when the measured concentration is below the threshold); alternatively, when the measured concentration is below the threshold, an increased likelihood of the nonoccurrence of an injury to renal function may be assigned to the subject (relative to the likelihood assigned when the measured concentration is above the threshold). For a negative going marker, an increased likelihood of the occurrence of an injury to renal function is assigned to the subject when the measured concentration is below the threshold (relative to the likelihood assigned when the measured concentration is above the threshold); alternatively, when the measured concentration is above the threshold, an increased likelihood of the nonoccurrence of an injury to renal function may be assigned to the subject (relative to the likelihood assigned when the measured concentration is below the threshold).

In other preferred diagnostic embodiments, these methods comprise diagnosing the occurrence or nonoccurrence of reduced renal function, and the assay result(s) is/are correlated to the occurrence or nonoccurrence of an injury causing reduced renal function. For example, each of the measured concentration(s) may be compared to a threshold value. For a positive going marker, an increased likelihood of the occurrence of an injury causing reduced renal function is assigned to the subject when the measured concentration is above the threshold (relative to the likelihood assigned when the measured concentration is below the threshold); alternatively, when the measured concentration is below the threshold, an increased likelihood of the nonoccurrence of an injury causing reduced renal function may be assigned to the subject (relative to the likelihood assigned when the measured concentration is above the threshold). For a negative going marker, an increased likelihood of the occurrence of an injury causing reduced renal function is assigned to the subject when the measured concentration is below the threshold (relative to the likelihood assigned when the measured concentration is above the threshold); alternatively, when the measured concentration is above the threshold, an increased likelihood of the nonoccurrence of an injury causing reduced renal function may be assigned to the subject (relative to the likelihood assigned when the measured concentration is below the threshold).

In yet other preferred diagnostic embodiments, these methods comprise diagnosing the occurrence or nonoccurrence of ARF, and the assay result(s) is/are correlated to the occurrence or nonoccurrence of an injury causing ARF. For example, each of the measured concentration(s) may be compared to a threshold value. For a positive going marker, an increased likelihood of the occurrence of ARF is assigned to the subject when the measured concentration is above the threshold (relative to the likelihood assigned when the measured concentration is below the threshold); alternatively, when the measured concentration is below the threshold, an increased likelihood of the nonoccurrence of ARF may be assigned to the subject (relative to the likelihood assigned when the measured concentration is above the threshold). For a negative going marker, an increased likelihood of the occurrence of ARF is assigned to the subject when the measured concentration is below the threshold (relative to the likelihood assigned when the measured concentration is above the threshold); alternatively, when the measured concentration is above the threshold, an increased likelihood of the nonoccurrence of ARF may be assigned to the subject (relative to the likelihood assigned when the measured concentration is below the threshold).

In still other preferred diagnostic embodiments, these methods comprise diagnosing a subject as being in need of renal replacement therapy, and the assay result(s) is/are correlated to a need for renal replacement therapy. For example, each of the measured concentration(s) may be compared to a threshold value. For a positive going marker, an increased likelihood of the occurrence of an injury creating a need for renal replacement therapy is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal replacement therapy may be assigned to the subject (relative to the likelihood assigned when the measured concentration is above the threshold). For a negative going marker, an increased likelihood of the occurrence of an injury creating a need for renal replacement therapy is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal replacement therapy may be assigned to the subject (relative to the likelihood assigned when the measured concentration is below the threshold).

In still other preferred diagnostic embodiments, these methods comprise diagnosing a subject as being in need of renal transplantation, and the assay result (s0 is/are correlated to a need for renal transplantation. For example, each of the measured concentration(s) may be compared to a threshold value. For a positive going marker, an increased likelihood of the occurrence of an injury creating a need for renal transplantation is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal transplantation may be assigned to the subject (relative to the likelihood assigned when the measured concentration is above the threshold). For a negative going marker, an increased likelihood of the occurrence of an injury creating a need for renal transplantation is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal transplantation may be assigned to the subject (relative to the likelihood assigned when the measured concentration is below the threshold).

In still other embodiments, the methods for evaluating renal status described herein are methods for monitoring a renal injury in the subject; that is, assessing whether or not renal function is improving or worsening in a subject who has suffered from an injury to renal function, reduced renal function, or ARF. In these embodiments, the assay result(s), for example measured concentration(s) of one or more biomarkers selected from the group consisting of Coagulation factor VII, CA19-9, Insulin-like growth factor-binding protein 7, C—X—C motif chemokine 6, and C—C motif chemokine 13 is/are correlated to the occurrence or nonoccurrence of a change in renal status. The following are preferred monitoring embodiments.

In preferred monitoring embodiments, these methods comprise monitoring renal status in a subject suffering from an injury to renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other preferred monitoring embodiments, these methods comprise monitoring renal status in a subject suffering from reduced renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In yet other preferred monitoring embodiments, these methods comprise monitoring renal status in a subject suffering from acute renal failure, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other additional preferred monitoring embodiments, these methods comprise monitoring renal status in a subject at risk of an injury to renal function due to the pre-existence of one or more known risk factors for prerenal, intrinsic renal, or postrenal ARF, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In still other embodiments, the methods for evaluating renal status described herein are methods for classifying a renal injury in the subject; that is, determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage. In these embodiments, the assay result(s), for example measured concentration(s) of one or more biomarkers selected from the group consisting of Coagulation factor VII, CA19-9, Insulin-like growth factor-binding protein 7, C—X—C motif chemokine 6, and C—C motif chemokine 13 is/are correlated to a particular class and/or subclass. The following are preferred classification embodiments.

In preferred classification embodiments, these methods comprise determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage, and the assay result(s) is/are correlated to the injury classification for the subject. For example, the measured concentration may be compared to a threshold value, and when the measured concentration is above the threshold, a particular classification is assigned; alternatively, when the measured concentration is below the threshold, a different classification may be assigned to the subject.

A variety of methods may be used by the skilled artisan to arrive at a desired threshold value for use in these methods. For example, the threshold value may be determined from a population of normal subjects by selecting a concentration representing the $75^{th}$, $85^{th}$, $90^{th}$, $95^{th}$, or $99^{th}$ percentile of a kidney injury marker measured in such normal subjects. Alternatively, the threshold value may be determined from a "diseased" population of subjects, e.g., those suffering from an injury or having a predisposition for an injury (e.g., progression to ARF or some other clinical outcome such as death, dialysis, renal transplantation, etc.), by selecting a concentration representing the $75^{th}$, $85^{th}$, $90^{th}$, $95^{th}$, or $99^{th}$ percentile of a kidney injury marker measured in such subjects. In another alternative, the threshold value may be determined from a prior measurement of a kidney injury marker in the same subject; that is, a temporal change in the level of a kidney injury marker in the subject may be used to assign risk to the subject.

The foregoing discussion is not meant to imply, however, that the kidney injury markers of the present invention must be compared to corresponding individual thresholds. Methods for combining assay results can comprise the use of multivariate logistical regression, loglinear modeling, neural network analysis, n-of-m analysis, decision tree analysis, calculating ratios of markers, etc. This list is not meant to be limiting. In these methods, a composite result which is determined by combining individual markers may be treated as if it is itself a marker; that is, a threshold may be determined for the composite result as described herein for individual markers, and the composite result for an individual patient compared to this threshold.

The ability of a particular test to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured concentration of one or more kidney injury markers, or a composite of such markers, may be treated as continuous variables. For example, any particular concentration can be converted into a corresponding probability of a future reduction in renal function for the subject, the occurrence of an injury, a classification, etc. In yet another alternative, a threshold that can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

at least about 75% sensitivity, combined with at least about 75% specificity;

a positive likelihood ratio (calculated as sensitivity/(1-specificity)) of greater than 1, at least about 2, more preferably at least about 3, still more preferably at least about 5, and most preferably at least about 10; or a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess renal status in a subject. For example, a "first" subpopulation which is predisposed to one or more future changes in renal status, the occurrence of an injury, a classification, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

In certain embodiments, the assay method is an immunoassay. Antibodies for use in such assays will specifically bind a full length kidney injury marker of interest, and may also bind one or more polypeptides that are "related" thereto, as that term is defined hereinafter. Numerous immunoassay formats are known to those of skill in the art. Preferred body fluid samples are selected from the group consisting of urine, blood, serum, saliva, tears, and plasma.

The foregoing method steps should not be interpreted to mean that the kidney injury marker assay result(s) is/are used in isolation in the methods described herein. Rather, additional variables or other clinical indicia may be included in the methods described herein. For example, a risk stratification, diagnostic, classification, monitoring, etc. method may combine the assay result(s) with one or more variables measured for the subject selected from the group consisting of demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score, risk scores of Thakar et al. (J. Am. Soc. Nephrol. 16: 162-68, 2005), Mehran et al. (J. Am. Coll. Cardiol. 44: 1393-99, 2004), Wijeysundera et al. (JAMA 297: 1801-9, 2007), Goldstein and Chawla (Clin. J. Am. Soc. Nephrol. 5: 943-49, 2010), or Chawla et al. (Kidney Intl. 68: 2274-80, 2005)), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with one or more kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

When more than one marker is measured, the individual markers may be measured in samples obtained at the same time, or may be determined from samples obtained at different (e.g., an earlier or later) times. The individual markers may also be measured on the same or different body fluid samples. For example, one kidney injury marker may be measured in a serum or plasma sample and another kidney injury marker may be measured in a urine sample. In addition, assignment of a likelihood may combine an individual kidney injury marker assay result with temporal changes in one or more additional variables.

In various related aspects, the present invention also relates to devices and kits for performing the methods described herein. Suitable kits comprise reagents sufficient for performing an assay for at least one of the described kidney injury markers, together with instructions for performing the described threshold comparisons.

In certain embodiments, reagents for performing such assays are provided in an assay device, and such assay devices may be included in such a kit. Preferred reagents can comprise one or more solid phase antibodies, the solid phase antibody comprising antibody that detects the intended biomarker target(s) bound to a solid support. In the case of sandwich immunoassays, such reagents can also include one or more detectably labeled antibodies, the detectably labeled antibody comprising antibody that detects the intended biomarker target(s) bound to a detectable label. Additional optional elements that may be provided as part of an assay device are described hereinafter.

Detectable labels may include molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labeled antibody that binds to the second antibody, biotin, digoxigenin, maltose, oligohistidine, 2,4-dintrobenzene, phenylarsenate, ssDNA, dsDNA, etc.).

Generation of a signal from the signal development element can be performed using various optical, acoustical, and electrochemical methods well known in the art. Examples of detection modes include fluorescence, radiochemical detection, reflectance, absorbance, amperometry, conductance, impedance, interferometry, ellipsometry, etc. In certain of these methods, the solid phase antibody is coupled to a transducer (e.g., a diffraction grating, electrochemical sensor, etc) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labeled molecule.

DETAILED DESCRIPTION OF THE INVENTION

The present invention relates to methods and compositions for diagnosis, differential diagnosis, risk stratification, monitoring, classifying and determination of treatment regimens in subjects suffering or at risk of suffering from injury to renal function, reduced renal function and/or acute renal failure through measurement of one or more kidney injury markers. In various embodiments, a measured concentration of one or more biomarkers selected from the group consisting of Coagulation factor VII, CA19-9, Insulin-like growth factor-binding protein 7, C—X—C motif chemokine 6, and C—C motif chemokine 13 or one or more markers related thereto, are correlated to the renal status of the subject.

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc. "Improvement in Renal Function" is an abrupt (within 14 days, preferably within 7 days, more preferably within 72 hours, and still more preferably within 48 hours) measurable increase in a measure of renal function. Preferred methods for measuring and/or estimating GFR are described hereinafter.

As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL (≥8.8 μmol/L), a percentage increase in serum creatinine of greater than or equal to 20% (1.2-fold from baseline), or a reduction in urine output (documented oliguria of less than 0.5 ml/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl (≥26.4 μmol/L), a percentage increase in serum creatinine of greater than or equal to 50% (1. 5-fold from baseline), or a reduction in urine output (documented oliguria of less than 0.5 ml/kg per hour for at least 6 hours). This term is synonymous with "acute kidney injury" or "AKI."

As used herein, the term "Coagulation factor VII" refers to one or more polypeptides present in a biological sample that are derived from the Coagulation factor VII precursor (human precursor: Swiss-Prot P08709 (SEQ ID NO: 1))

```
        10         20         30         40         50         60
MVSQALRLLC LLLGLQGCLA AGGVAKASGG ETRDMPWKPG PHRVFVTQEE AHGVLHRRRR 70         80         90        100        110        120
ANAFLEELRP GSLERECKEE QCSFEEAREI FKDAERTKLF WISYSDGDQC ASSPCQNGGS 130        140        150        160        170        180
CKDQLQSYIC FCLPAFEGRN CETHKDDQLI CVNENGGCEQ YCSDHTGTKR SCRCHEGYSL 190        200        210        220        230        240
LADGVSCTPT VEYPCGKIPI LEKRNASKPQ GRIVGGKVCP KGECPWQVLL LVNGAQLCGG 250        260        270        280        290        300
TLINTIWVVS AAHCFDKIKN WRNLIAVLGE HDLSEHDGDE QSRRVAQVII PSTYVPGTTN 310        320        330        340        350        360
HDIALLRLHQ PVVLTDHVVP LCLPERTFSE RTLAFVRFSL VSGWGQLLDR GATALELMVL 370        380        390        400        410        420
NVPRLMTQDC LQQSRKVGDS PNITEYMFCA GYSDGSKDSC KGDSGGPHAT HYRGTWYLTG 430        440        450        460
IVSWGQGCAT VGHFGVYTRV SQYIEWLQKL MRSEPRPGVL LRAPFP
```

The following domains have been identified in Coagulation factor VII:

| Residues | Length | Domain ID |
|---|---|---|
| 1-20 | 20 | Signal peptide |
| 21-60 | 40 | Propeptide |
| 61-212 | 152 | Coagulation factor VII, light chain |
| 213-466 | 254 | Coagulation factor VII, heavy chain |
| 22-43 | 22 | Missing in Coagulation factor VII isoform B |

As used herein, the term "CA19-9" (also called carbohydrate antigen 19-9 or sialylated Lewis (a) antigen) is a monosialoganglioside antigen found in patients with gastrointestinal adenocarcinoma. It is reportedly elevated in 21 to 42 percent of cases of gastric cancer, 20 to 40 percent of colon cancer, and 71 to 93 percent of pancreatic cancer. The main clinical use of CA19-9 is to see whether a pancreatic tumor is secreting it; if that is the case, then the levels should fall when the tumor is treated, and they may rise again if the disease recurs. In 5% of patients who lack the Lewis antigen, CA19-9 is not elevated in pancreatic cancer even with large tumors because they have a deficiency of a fucosyltransferase enzyme that is needed to produce CA19-9 as well as the Lewis antigen.

As used herein, the term "Insulin-like growth factor-binding protein 7" refers to one or more polypeptides present in a biological sample that are derived from the Insulin-like growth factor-binding protein 7 precursor (human precursor: Swiss-Prot Q16270 (SEQ ID NO: 2))

```
        10         20         30         40         50         60
MERPSLRALL LGAAGLLLLL LPLSSSSSSD TCGPCEPASC PPLPPLGCLL GETRDACGCC 70         80         90        100        110        120
PMCARGEGEP CGGGGAGRGY CAPGMECVKS RKRRKGKAGA AAGGPGVSGV CVCKSRYPVC 130        140        150        160        170        180
GSDGTTYPSG CQLRAASQRA ESRGEKAITQ VSKGTCEQGP SIVTPPKDIW NVTGAQVYLS 190        200        210        220        230        240
CEVIGIPTPV LIWNKVKRGH YGVQRTELLP GDRDNLAIQT RGGPEKHEVT GWVLVSPLSK 250        260        270        280
EDAGEYECHA SNSQGQASAS AKITVVDALH EIPVKKGEGA EL
```

The following domains have been identified in Insulin-like growth factor-binding protein 7:

| Residues | Length | Domain ID |
|---|---|---|
| 1-26 | 26 | Signal peptide |
| 27-282 | 256 | Insulin-like growth factor-binding protein 7 |

As used herein, the term "C—X—C motif chemokine 6" refers to one or more polypeptides present in a biological sample that are derived from the C—X—C motif chemokine 6 precursor (human precursor: Swiss-Prot P80162 (SEQ ID NO: 3))

```
        10         20         30         40         50         60
MSLPSSRAAR VPGPSGSLCA LLALLLLLTP PGPLASAGPV SAVLTELRCT CLRVTLRVNP 70         80         90        100        110
KTIGKLQVFP AGPQCSKVEV VASLKNGKQV CLDPEAPFLK KVIQKILDSG NKKN
```

The following domains have been identified in C—X—C motif chemokine 6:

| Residues | Length | Domain ID |
| --- | --- | --- |
| 1-37 | 37 | Signal peptide |
| 38-114 | 77 | C-X-C motif chemokine 6 |
| 40-114 | 75 | C-X-C motif chemokine 6 (N-processed variant 1) |
| 43-114 | 72 | C-X-C motif chemokine 6 (N-processed variant 2) |
| 46-114 | 69 | C-X-C motif chemokine 6 (N-processed variant 3) |

As used herein, the term "C—C motif chemokine 13" refers to one or more polypeptides present in a biological sample that are derived from the C—C motif chemokine 13 precursor (human precursor: Swiss-Prot Q99616 (SEQ ID NO: 4))

```
        10         20         30         40         50         60
MKVSAVLLCL LLMTAAFNPQ GLAQPDALNV PSTCCFTFSS KKISLQRLKS YVITTSRCPQ 70         80         90
KAVIFRTKLG KEICADPKEK WVQNYMKHLG RKAHTLKT
```

The following domains have been identified in C—C motif chemokine 13:

| Residues | Length | Domain ID |
| --- | --- | --- |
| 1-16 | 16 | Signal peptide |
| 17-98 | 82 | C-C motif chemokine 13, long chain |
| 22-98 | 82 | C-C motif chemokine 13, medium chain |
| 24-98 | 82 | C-C motif chemokine 13, short chain |

As used herein, the term "relating a signal to the presence or amount" of an analyte reflects the following understanding. Assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay. The term "related marker" as used herein with regard to a biomarker such as one of the kidney injury markers described herein refers to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

In this regard, the skilled artisan will understand that the signals obtained from an immunoassay are a direct result of complexes formed between one or more antibodies and the target biomolecule (i.e., the analyte) and polypeptides containing the necessary epitope(s) to which the antibodies bind. While such assays may detect the full length biomarker and the assay result be expressed as a concentration of a biomarker of interest, the signal from the assay is actually a result of all such "immunoreactive" polypeptides present in the sample. Expression of biomarkers may also be determined by means other than immunoassays, including protein measurements (such as dot blots, western blots, chromatographic methods, mass spectrometry, etc.) and nucleic acid measurements (mRNA quatitation). This list is not meant to be limiting.

The term "positive going" marker as that term is used herein refer to a marker that is determined to be elevated in subjects suffering from a disease or condition, relative to subjects not suffering from that disease or condition. The term "negative going" marker as that term is used herein refer to a marker that is determined to be reduced in subjects suffering from a disease or condition, relative to subjects not suffering from that disease or condition.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described kidney injury markers. The kit comprises reagents for the analysis of at least one test sample which comprise at least one antibody that a kidney injury marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ M$^{-1}$, and preferably between about $10^8$ M$^{-1}$ to about $10^9$ M$^{-1}$, about $10^9$ M$^{-1}$ to about $10^{10}$ M$^{-1}$, or about $10^{10}$ m$^{-1}$ to about $10^{12}$ M$^{-1}$.

Affinity is calculated as $K_d = k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: $r/c = K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

While the present application describes antibody-based binding assays in detail, alternatives to antibodies as binding species in assays are well known in the art. These include receptors for a particular target, aptamers, etc. Aptamers are oligonucleic acid or peptide molecules that bind to a specific target molecule. Aptamers are usually created by selecting them from a large random sequence pool, but natural aptamers also exist. High-affinity aptamers containing modified nucleotides conferring improved characteristics on the ligand, such as improved in vivo stability or improved delivery characteristics. Examples of such modifications include chemical substitutions at the ribose and/or phosphate and/or base positions, and may include amino acid side chain functionalities.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the 97.5th percentile of the concentration seen in a normal population. Another method may be to look at serial samples from the same patient, where a prior "baseline" result is used to monitor for temporal changes in a biomarker level.

Population studies may also be used to select a decision threshold. Reciever Operating Characteristic ("ROC") arose from the field of signal dectection therory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1-specificity, the ROC graph is sometimes called the sensitivity vs (1-specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

Additional clinical indicia may be combined with the kidney injury marker assay result(s) of the present invention. These include other biomarkers related to renal status. Examples include the following, which recite the common biomarker name, followed by the Swiss-Prot entry number for that biomarker or its parent: Actin (P68133); Adenosine deaminase binding protein (DPP4, P27487); Alpha-1-acid glycoprotein 1 (P02763); Alpha-1-microglobulin (P02760); Albumin (P02768); Angiotensinogenase (Renin, P00797); Annexin A2 (P07355); Beta-glucuronidase (P08236); B-2- microglobulin (P61679); Beta-galactosidase (P16278); BMP-7 (P18075); Brain natriuretic peptide (proBNP, BNP-32, NTproBNP; P16860); Calcium-binding protein Beta (S100-beta, P04271); Carbonic anhydrase (Q16790); Casein Kinase 2 (P68400); Ceruloplasmin (P00450); Clusterin (P10909); Complement C3 (P01024); Cysteine-rich protein (CYR61, O00622); Cytochrome C(P99999); Epidermal growth factor (EGF, P01133); Endothelin-1 (P05305); Exosomal Fetuin-A (P02765); Fatty acid-binding protein, heart (FABP3, P05413); Fatty acid-binding protein, liver (P07148); Ferritin (light chain, P02793; heavy chain P02794); Fructose-1,6-biphosphatase (P09467); GRO-alpha (CXCL1, (P09341); Growth Hormone (P01241); Hepatocyte growth factor (P14210); Insulin-like growth factor I (P01343); Immunoglobulin G; Immunoglobulin Light Chains (Kappa and Lambda); Interferon gamma (P01308); Lysozyme (P61626); Interleukin-1alpha (P01583); Interleukin-2 (P60568); Interleukin-4 (P60568); Interleukin-9 (P15248); Interleukin-12p40 (P29460); Interleukin-13 (P35225); Interleukin-16 (Q14005); L1 cell adhesion molecule (P32004); Lactate dehydrogenase (P00338); Leucine Aminopeptidase (P28838); Meprin A-alpha subunit (Q16819); Meprin A-beta subunit (Q16820); Midkine (P21741); MIP2-alpha (CXCL2, P19875); MMP-2 (P08253); MMP-9 (P14780); Netrin-1 (O95631); Neutral endopeptidase (P08473); Osteopontin (P10451); Renal papillary antigen 1 (RPA1); Renal papillary antigen 2 (RPA2); Retinol binding protein (P09455); Ribonuclease; S100 calcium-binding protein A6 (P06703); Serum Amyloid P Component (P02743); Sodium/Hydrogen exchanger isoform 3 (NHE3, P48764); Spermidine/spermine N1-acetyltransferase (P21673); TGF-Beta1 (P01137); Transferrin (P02787); Trefoil factor 3 (TFF3, Q07654); Toll-Like protein 4 (O00206); Total protein; Tubulointerstitial nephritis antigen (Q9UJW2); Uromodulin (Tamm-Horsfall protein, P07911).

For purposes of risk stratification, Adiponectin (Q15848); Alkaline phosphatase (P05186); Aminopeptidase N(P15144); CalbindinD28k (P05937); Cystatin C(P01034); 8 subunit of FIFO ATPase (P03928); Gamma-glutamyltransferase (P19440); GSTa (alpha-glutathione-S-transferase, P08263); GSTpi (Glutathione-S-transferase P; GST class-pi; P09211); IGFBP-1 (P08833); IGFBP-2 (P18065); IGFBP-6 (P24592); Integral membrane protein 1 (Itml, P46977); Interleukin-6 (P05231); Interleukin-8 (P10145); Interleukin-18 (Q14116); IP-10 (10 kDa interferon-gamma-induced protein, P02778); IRPR (IFRD1, O00458); Isovaleryl-CoA dehydrogenase (IVD, P26440); I-TAC/CXCL11 (O14625); Keratin 19 (P08727); Kim-1 (Hepatitis A virus cellular receptor 1, O43656); L-arginine:glycine amidinotransferase (P50440); Leptin (P41159); Lipocalin2 (NGAL, P80188); MCP-1 (P13500); MIG (Gamma-interferon-induced monokine Q07325); MIP-1a (P10147); MIP-3a (P78556); MIP-1beta (P13236); MIP-1d (Q16663); NAG (N-acetyl-beta-D-glucosaminidase, P54802); Organic ion transporter (OCT2, O15244); Osteoprotegerin (O14788); P8 protein (O60356); Plasminogen activator inhibitor 1 (PAI-1, P05121); ProANP (1-98) (P01160); Protein phosphatase 1-beta (PPI-beta, P62140); Rab GDI-beta (P50395); Renal kallikrein (Q86U61); RT1.B-1 (alpha) chain of the integral membrane protein (Q5Y7A8); Soluble tumor necrosis factor receptor superfamily member 1A (sTNFR-I, P19438); Soluble tumor necrosis factor receptor superfamily member 1B (sTNFR-II, P20333); Tissue inhibitor of metalloproteinases 3 (TIMP-3, P35625); uPAR (Q03405) may be combined with the kidney injury marker assay result(s) of the present invention.

Other clinical indicia which may be combined with the kidney injury marker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, and/or a renal failure index calculated as urine sodium/(urine creatinine/plasma creatinine). Other measures of renal function which may be combined with the kidney injury marker assay result(s) are described hereinafter and in Harrison's Principles of Internal Medicine, 17$^{th}$ Ed., McGraw Hill, New York, pages 1741-1830, and Current Medical Diagnosis & Treatment 2008, 47$^{th}$ Ed, McGraw Hill, New York, pages 785-815, each of which are hereby incorporated by reference in their entirety.

Combining assay results/clinical indicia in this manner can comprise the use of multivariate logistical regression, loglinear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney) glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma Concentration}}$$

By normalizing the GFR to the body surface area, a GFR of approximately 75-100 ml/min per 1.73 m$^2$ can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{Cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{Cr} \times V$) divided by its plasma concentration. This is commonly represented mathematically as:

$$C_{Cr} = \frac{U_{Cr} - V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{-hour volume}}{P_{Cr} \times 24 \times 60 \text{ mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr-corrected} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection and measurement is adequate. In the case where, for example, only a cumulative 24-h output was available and no patient weights are provided, minor modifications of the RIFLE urine output criteria have been described. For example, Bagshaw et al., Nephrol. Dial. Transplant. 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N.J., 1999. In addition, since the methods and compositions described herein provide prognostic information, the markers of the present invention may be used to monitor a course of treatment. For example, improved or worsened prognostic state may indicate that a particular treatment is or is not efficacious.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1

Contrast-Induced Nephropathy Sample Collection

The objective of this sample collection study is to collect samples of plasma and urine and clinical data from patients before and after receiving intravascular contrast media. Approximately 250 adults undergoing radiographic/angiographic procedures involving intravascular administration of iodinated contrast media are enrolled. To be enrolled in the study, each patient must meet all of the following inclusion criteria and none of the following exclusion criteria:

Inclusion Criteria males and females 18 years of age or older;

undergoing a radiographic/angiographic procedure (such as a CT scan or coronary intervention) involving the intravascular administration of contrast media;

expected to be hospitalized for at least 48 hours after contrast administration.

able and willing to provide written informed consent for study participation and to comply with all study procedures.

Exclusion Criteria renal transplant recipients;

acutely worsening renal function prior to the contrast procedure;

already receiving dialysis (either acute or chronic) or in imminent need of dialysis at enrollment;

expected to undergo a major surgical procedure (such as involving cardiopulmonary bypass) or an additional imaging procedure with contrast media with significant risk for further renal insult within the 48 hrs following contrast administration;

participation in an interventional clinical study with an experimental therapy within the previous 30 days;

known infection with human immunodeficiency virus (HIV) or a hepatitis virus.

Immediately prior to the first contrast administration (and after any pre-procedure hydration), an EDTA anti-coagulated blood sample (10 mL) and a urine sample (10 mL) are collected from each patient. Blood and urine samples are then collected at 4 (±0.5), 8 (±1), 24 (±2) 48 (±2), and 72 (±2) hrs following the last administration of contrast media during the index contrast procedure. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Serum creatinine is assessed at the site immediately prior to the first contrast administration (after any pre-procedure hydration) and at 4 (±0.5), 8 (±1), 24 (±2) and 48 (±2)), and 72 (±2) hours following the last administration of contrast (ideally at the same time as the study samples are obtained). In addition, each patient's status is evaluated through day 30 with regard to additional serum and urine creatinine measurements, a need for dialysis, hospitalization status, and adverse clinical outcomes (including mortality).

Prior to contrast administration, each patient is assigned a risk based on the following assessment: systolic blood pressure <80 mm Hg=5 points; intra-arterial balloon pump=5 points; congestive heart failure (Class III-IV or history of pulmonary edema)=5 points; age >75 yrs=4 points; hematocrit level <39% for men, <35% for women=3 points; diabetes=3 points; contrast media volume=1 point for each 100 mL; serum creatinine level >1.5 g/dL=4 points OR estimated GFR 40-60 mL/min/1.73 m$^2$=2 points, 20-40 mL/min/1.73 m$^2$=4 points, <20 mL/min/1.73 m$^2$=6 points. The risks assigned are as follows: risk for CIN and dialysis: 5 or less total points=risk of CIN-7.5%, risk of dialysis-0.04%; 6-10 total points=risk of CIN-14%, risk of dialysis-0.12%; 11-16 total points=risk of CIN-26.1%, risk of dialysis-1.09%; >16 total points=risk of CIN-57.3%, risk of dialysis-12.8%.

Example 2

Cardiac Surgery Sample Collection

The objective of this sample collection study is to collect samples of plasma and urine and clinical data from patients before and after undergoing cardiovascular surgery, a procedure known to be potentially damaging to kidney function. Approximately 900 adults undergoing such surgery are enrolled. To be enrolled in the study, each patient must meet all of the following inclusion criteria and none of the following exclusion criteria:
Inclusion Criteria
males and females 18 years of age or older;
undergoing cardiovascular surgery;
Toronto/Ottawa Predictive Risk Index for Renal Replacement risk score of at least 2 (Wijeysundera et al., *JAMA* 297: 1801-9, 2007); and
able and willing to provide written informed consent for study participation and to comply with all study procedures.
Exclusion Criteria
known pregnancy;
previous renal transplantation;
acutely worsening renal function prior to enrollment (e.g., any category of RIFLE criteria);
already receiving dialysis (either acute or chronic) or in imminent need of dialysis at enrollment;
currently enrolled in another clinical study or expected to be enrolled in another clinical study within 7 days of cardiac surgery that involves drug infusion or a therapeutic intervention for AKI;
known infection with human immunodeficiency virus (HIV) or a hepatitis virus.

Within 3 hours prior to the first incision (and after any pre-procedure hydration), an EDTA anti-coagulated blood sample (10 mL), whole blood (3 mL), and a urine sample (35 mL) are collected from each patient. Blood and urine samples are then collected at 3 (±0.5), 6 (±0.5), 12 (±1), 24 (±2) and 48 (±2) hrs following the procedure and then daily on days 3 through 7 if the subject remains in the hospital. Blood is collected via direct venipuncture or via other available venous access, such as an existing femoral sheath, central venous line, peripheral intravenous line or hep-lock. These study blood samples are frozen and shipped to Astute Medical, Inc., San Diego, Calif. The study urine samples are frozen and shipped to Astute Medical, Inc.

Example 3

Acutely Ill Subject Sample Collection

The objective of this study is to collect samples from acutely ill patients. Approximately 900 adults expected to be in the ICU for at least 48 hours will be enrolled. To be enrolled in the study, each patient must meet all of the following inclusion criteria and none of the following exclusion criteria:
Inclusion Criteria
males and females 18 years of age or older;
Study population 1: approximately 300 patients that have at least one of:
shock (SBP <90 mmHg and/or need for vasopressor support to maintain MAP >60 mmHg and/or documented drop in SBP of at least 40 mmHg); and sepsis;
Study population 2: approximately 300 patients that have at least one of:
IV antibiotics ordered in computerized physician order entry (CPOE) within 24 hours of enrollment;
contrast media exposure within 24 hours of enrollment;
increased Intra-Abdominal Pressure with acute decompensated heart failure; and
severe trauma as the primary reason for ICU admission and likely to be hospitalized in the ICU for 48 hours after enrollment;
Study population 3: approximately 300 patients expected to be hospitalized through acute care setting (ICU or ED) with a known risk factor for acute renal injury (e.g. sepsis, hypotension/shock (Shock=systolic BP<90 mmHg and/or the need for vasopressor support to maintain a MAP >60 mmHg and/or a documented drop in SBP >40 mmHg), major trauma, hemorrhage, or major surgery); and/or expected to be hospitalized to the ICU for at least 24 hours after enrollment.
Exclusion Criteria
known pregnancy;
institutionalized individuals;
previous renal transplantation;
known acutely worsening renal function prior to enrollment (e.g., any category of RIFLE criteria);
received dialysis (either acute or chronic) within 5 days prior to enrollment or in imminent need of dialysis at the time of enrollment;
known infection with human immunodeficiency virus (HIV) or a hepatitis virus;

meets only the SBP <90 mmHg inclusion criterion set forth above, and does not have shock in the attending physician's or principal investigator's opinion.

After providing informed consent, an EDTA anti-coagulated blood sample (10 mL) and a urine sample (25-30 mL) are collected from each patient. Blood and urine samples are then collected at 4 (±0.5) and 8 (±1) hours after contrast administration (if applicable); at 12 (±1), 24 (±2), and 48 (±2) hours after enrollment, and thereafter daily up to day 7 to day 14 while the subject is hospitalized. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Example 4

Immunoassay Format

Analytes are measured using standard sandwich enzyme immunoassay techniques. A first antibody which binds the analyte is immobilized in wells of a 96 well polystyrene microplate. Analyte standards and test samples are pipetted into the appropriate wells and any analyte present is bound by the immobilized antibody. After washing away any unbound substances, a horseradish peroxidase-conjugated second antibody which binds the analyte is added to the wells, thereby forming sandwich complexes with the analyte (if present) and the first antibody. Following a wash to remove any unbound antibody-enzyme reagent, a substrate solution comprising tetramethylbenzidine and hydrogen peroxide is added to the wells. Color develops in proportion to the amount of analyte present in the sample. The color development is stopped and the intensity of the color is measured at 540 nm or 570 nm. An analyte concentration is assigned to the test sample by comparison to a standard curve determined from the analyte standards. Concentrations reported below are as follows: Coagulation factor VII-ng/mL, CA19-9-U/mL, Insulin-like growth factor-binding protein 7 ng/mL, C—X—C motif chemokine 6-pg/mL, and C—C motif chemokine 13-pg/mL.

Example 5

Apparently Healthy Donor and Chronic Disease Patient Samples

Human urine samples from donors with no known chronic or acute disease ("Apparently Healthy Donors") were purchased from two vendors (Golden West Biologicals, Inc., 27625 Commerce Center Dr., Temecula, Calif. 92590 and Virginia Medical Research, Inc., 915 First Colonial Rd., Virginia Beach, Va. 23454). The urine samples were shipped and stored frozen at less than −20° C. The vendors supplied demographic information for the individual donors including gender, race (Black/White), smoking status and age.

Human urine samples from donors with various chronic diseases ("Chronic Disease Patients") including congestive heart failure, coronary artery disease, chronic kidney disease, chronic obstructive pulmonary disease, diabetes mellitus and hypertension were purchased from Virginia Medical Research, Inc., 915 First Colonial Rd., Virginia Beach, Va. 23454. The urine samples were shipped and stored frozen at less than −20 degrees centigrade. The vendor provided a case report form for each individual donor with age, gender, race (Black/White), smoking status and alcohol use, height, weight, chronic disease(s) diagnosis, current medications and previous surgeries.

Example 6

Use of Kidney Injury Markers for Evaluating Renal Status in Patients

Patients from the intensive care unit (ICU) were enrolled in the following study. Each patient was classified by kidney status as non-injury (O), risk of injury (R), injury (I), and failure (F) according to the maximum stage reached within 7 days of enrollment as determined by the RIFLE criteria. EDTA anti-coagulated blood samples (10 mL) and a urine samples (25-30 mL) were collected from each patient at enrollment, 4 (±0.5) and 8 (±1) hours after contrast administration (if applicable); at 12 (±1), 24 (±2), and 48 (±2) hours after enrollment, and thereafter daily up to day 7 to day 14 while the subject is hospitalized. Markers were each measured by standard immunoassay methods using commercially available assay reagents in the urine samples and the plasma component of the blood samples collected.

Two cohorts were defined to represent a "diseased" and a "normal" population. While these terms are used for convenience, "diseased" and "normal" simply represent two cohorts for comparison (say RIFLE 0 vs RIFLE R, I and F; RIFLE 0 vs RIFLE R; RIFLE 0 and R vs RIFLE I and F; etc.). The time "prior max stage" represents the time at which a sample is collected, relative to the time a particular patient reaches the lowest disease stage as defined for that cohort, binned into three groups which are +/−12 hours. For example, "24 hr prior" which uses 0 vs R, I, F as the two cohorts would mean 24 hr (+/−12 hours) prior to reaching stage R (or I if no sample at R, or F if no sample at R or I).

A receiver operating characteristic (ROC) curve was generated for each biomarker measured and the area under each ROC curve (AUC) is determined. Patients in Cohort 2 were also separated according to the reason for adjudication to cohort 2 as being based on serum creatinine measurements (sCr), being based on urine output (UO), or being based on either serum creatinine measurements or urine output. Using the same example discussed above (0 vs R, I, F), for those patients adjudicated to stage R, I, or F on the basis of serum creatinine measurements alone, the stage 0 cohort may include patients adjudicated to stage R, I, or F on the basis of urine output; for those patients adjudicated to stage R, I, or F on the basis of urine output alone, the stage 0 cohort may include patients adjudicated to stage R, I, or F on the basis of serum creatinine measurements; and for those patients adjudicated to stage R, I, or F on the basis of serum creatinine measurements or urine output, the stage 0 cohort contains only patients in stage 0 for both serum creatinine measurements and urine output. Also, in the data for patients adjudicated on the basis of serum creatinine measurements or urine output, the adjudication method which yielded the most severe RIFLE stage is used.

The ability to distinguish cohort 1 from Cohort 2 was determined using ROC analysis. SE is the standard error of the AUC, n is the number of sample or individual patients ("pts," as indicated). Standard errors are calculated as described in Hanley, J. A., and McNeil, B. J., The meaning and use of the area under a receiver operating characteristic (ROC) curve. Radiology (1982) 143: 29-36; p values are calculated with a two-tailed Z-test. An AUC <0.5 is indicative of a negative going marker for the comparison, and an AUC >0.5 is indicative of a positive going marker for the comparison.

Various threshold (or "cutoff") concentrations were selected, and the associated sensitivity and specificity for distinguishing cohort 1 from cohort 2 are determined. OR is the odds ratio calculated for the particular cutoff concentration, and 95% CI is the confidence interval for the odds ratio.

TABLE 1

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | Cancer Antigen 19-9 | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 14.7 | 27.5 | 14.7 | 29.5 | 14.7 | 37.5 |
| Average | 194 | 160 | 194 | 138 | 194 | 79.7 |
| Stdev | 1100 | 432 | 1100 | 429 | 1100 | 127 |
| p(t-test) | | 0.84 | | 0.72 | | 0.61 |
| Min | 1.00E−9 | 1.00E−9 | 1.00E−9 | 1.00E−9 | 1.00E−9 | 1.00E−9 |
| Max | 11900 | 2270 | 11900 | 2940 | 11900 | 590 |
| n (Samp) | 122 | 45 | 122 | 51 | 122 | 24 |
| n (Patient) | 99 | 45 | 99 | 51 | 99 | 24 |
| sCr only | | | | | | |
| Median | 21.9 | 37.2 | 21.9 | 35.1 | 21.9 | 26.5 |
| Average | 168 | 68.7 | 168 | 122 | 168 | 97.2 |
| Stdev | 807 | 102 | 807 | 213 | 807 | 172 |
| p(t-test) | | 0.67 | | 0.80 | | 0.76 |
| Min | 1.00E−9 | 4.38 | 1.00E−9 | 3.94 | 1.00E−9 | 3.60 |
| Max | 11900 | 380 | 11900 | 758 | 11900 | 590 |
| n (Samp) | 259 | 12 | 259 | 19 | 259 | 12 |
| n (Patient) | 159 | 12 | 159 | 19 | 159 | 12 |
| UO only | | | | | | |
| Median | 15.5 | 27.5 | 15.5 | 27.9 | 15.5 | 30.3 |
| Average | 228 | 166 | 228 | 134 | 228 | 53.6 |
| Stdev | 1160 | 442 | 1160 | 442 | 1160 | 57.8 |
| p(t-test) | | 0.74 | | 0.60 | | 0.49 |
| Min | 1.00E−9 | 1.00E−9 | 1.00E−9 | 1.00E−9 | 1.00E−9 | 1.00E−9 |
| Max | 11900 | 2270 | 11900 | 2940 | 11900 | 187 |
| n (Samp) | 109 | 43 | 109 | 46 | 109 | 22 |
| n (Patient) | 85 | 43 | 85 | 46 | 85 | 22 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.58 | 0.58 | 0.55 | 0.60 | 0.61 | 0.55 | 0.60 | 0.57 | 0.54 |
| SE | 0.051 | 0.088 | 0.053 | 0.048 | 0.071 | 0.051 | 0.066 | 0.088 | 0.069 |
| p | 0.12 | 0.34 | 0.34 | 0.038 | 0.13 | 0.30 | 0.12 | 0.43 | 0.53 |
| nCohort 1 | 122 | 259 | 109 | 122 | 259 | 109 | 122 | 259 | 109 |
| nCohort 2 | 45 | 12 | 43 | 51 | 19 | 46 | 24 | 12 | 22 |
| Cutoff 1 | 13.1 | 13.7 | 13.4 | 17.3 | 17.3 | 17.5 | 12.5 | 18.5 | 9.76 |
| Sens 1 | 71% | 75% | 72% | 71% | 74% | 72% | 71% | 75% | 73% |
| Spec 1 | 48% | 39% | 44% | 56% | 44% | 53% | 47% | 46% | 30% |
| Cutoff 2 | 7.31 | 13.1 | 6.81 | 10.2 | 10.2 | 7.89 | 6.42 | 13.7 | 7.31 |
| Sens 2 | 80% | 83% | 81% | 80% | 84% | 80% | 83% | 83% | 82% |
| Spec 2 | 26% | 38% | 22% | 37% | 32% | 25% | 25% | 39% | 23% |
| Cutoff 3 | 0 | 7.31 | 0 | 2.28 | 6.42 | 0.389 | 3.42 | 8.65 | 3.42 |
| Sens 3 | 100% | 92% | 100% | 90% | 95% | 91% | 92% | 92% | 91% |
| Spec 3 | 0% | 24% | 0% | 17% | 22% | 9% | 18% | 29% | 13% |
| Cutoff 4 | 31.3 | 57.3 | 53.0 | 31.3 | 57.3 | 53.0 | 31.3 | 57.3 | 53.0 |
| Sens 4 | 47% | 42% | 30% | 49% | 37% | 28% | 54% | 25% | 41% |
| Spec 4 | 70% | 70% | 71% | 70% | 70% | 71% | 70% | 70% | 71% |
| Cutoff 5 | 69.9 | 109 | 90.2 | 69.9 | 109 | 90.2 | 69.9 | 109 | 90.2 |
| Sens 5 | 20% | 8% | 19% | 24% | 16% | 20% | 25% | 17% | 23% |
| Spec 5 | 80% | 80% | 81% | 80% | 80% | 81% | 80% | 80% | 81% |
| Cutoff 6 | 215 | 289 | 504 | 215 | 289 | 504 | 215 | 289 | 504 |
| Sens 6 | 13% | 8% | 7% | 10% | 11% | 4% | 8% | 8% | 0% |
| Spec 6 | 90% | 90% | 91% | 90% | 90% | 91% | 90% | 90% | 91% |
| OR Quart 2 | 0.97 | 0.98 | 0.42 | 0.86 | 2.0 | 0.51 | 0.55 | 4.1 | 0.74 |
| p Value | 0.95 | 0.99 | 0.16 | 0.79 | 0.42 | 0.24 | 0.43 | 0.21 | 0.68 |
| 95% CI of | 0.34 | 0.13 | 0.13 | 0.30 | 0.36 | 0.16 | 0.12 | 0.45 | 0.18 |
| OR Quart2 | 2.8 | 7.2 | 1.4 | 2.5 | 11 | 1.6 | 2.5 | 38 | 3.1 |
| OR Quart 3 | 2.0 | 2.0 | 2.8 | 3.0 | 3.2 | 2.4 | 1.8 | 4.1 | 1.2 |
| p Value | 0.17 | 0.42 | 0.036 | 0.024 | 0.16 | 0.073 | 0.36 | 0.21 | 0.78 |
| 95% CI of | 0.75 | 0.36 | 1.1 | 1.2 | 0.62 | 0.92 | 0.52 | 0.45 | 0.33 |
| OR Quart3 | 5.2 | 11 | 7.3 | 7.7 | 16 | 6.3 | 6.1 | 38 | 4.4 |
| OR Quart 4 | 1.4 | 2.0 | 0.87 | 2.0 | 3.7 | 1.2 | 1.7 | 3.0 | 1.5 |
| p Value | 0.49 | 0.42 | 0.79 | 0.17 | 0.11 | 0.67 | 0.39 | 0.34 | 0.56 |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| 95% CI of | 0.52 | 0.36 | 0.31 | 0.75 | 0.74 | 0.46 | 0.50 | 0.31 | 0.41 |
| OR Quart4 | 3.9 | 11 | 2.5 | 5.1 | 19 | 3.4 | 5.8 | 30 | 5.2 |

C-C motif chemokine 13

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 1.00E−9 | 1.00E−9 | 1.00E−9 | 1.00E−9 | 1.00E−9 | 1.00E−9 |
| Average | 2.84 | 4.72 | 2.84 | 5.68 | 2.84 | 4.14 |
| Stdev | 17.0 | 16.7 | 17.0 | 18.7 | 17.0 | 15.4 |
| p(t-test) | | 0.38 | | 0.16 | | 0.63 |
| Min | 1.00E−9 | 1.00E−9 | 1.00E−9 | 1.00E−9 | 1.00E−9 | 1.00E−9 |
| Max | 214 | 106 | 214 | 101 | 214 | 65.2 |
| n (Samp) | 360 | 76 | 360 | 92 | 360 | 43 |
| n (Patient) | 190 | 76 | 190 | 92 | 190 | 43 |
| sCr only | | | | | | |
| Median | 1.00E−9 | 1.00E−9 | 1.00E−9 | 1.00E−9 | 1.00E−9 | 1.00E−9 |
| Average | 2.76 | 9.67 | 2.76 | 6.17 | 2.76 | 4.11 |
| Stdev | 15.7 | 32.6 | 15.7 | 17.9 | 15.7 | 12.8 |
| p(t-test) | | 0.028 | | 0.20 | | 0.68 |
| Min | 1.00E−9 | 1.00E−9 | 1.00E−9 | 1.00E−9 | 1.00E−9 | 1.00E−9 |
| Max | 214 | 143 | 214 | 86.2 | 214 | 51.0 |
| n (Samp) | 760 | 29 | 760 | 37 | 760 | 23 |
| n (Patient) | 297 | 29 | 297 | 37 | 297 | 23 |
| UO only | | | | | | |
| Median | 1.00E−9 | 1.00E−9 | 1.00E−9 | 1.00E−9 | 1.00E−9 | 1.00E−9 |
| Average | 2.93 | 5.27 | 2.93 | 6.34 | 2.93 | 4.38 |
| Stdev | 17.7 | 18.9 | 17.7 | 19.8 | 17.7 | 15.1 |
| p(t-test) | | 0.34 | | 0.14 | | 0.64 |
| Min | 1.00E−9 | 1.00E−9 | 1.00E−9 | 1.00E−9 | 1.00E−9 | 1.00E−9 |
| Max | 214 | 119 | 214 | 101 | 214 | 65.2 |
| n (Samp) | 317 | 66 | 317 | 79 | 317 | 36 |
| n (Patient) | 136 | 66 | 136 | 79 | 136 | 36 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.53 | 0.54 | 0.53 | 0.54 | 0.55 | 0.54 | 0.50 | 0.53 | 0.52 |
| SE | 0.037 | 0.056 | 0.040 | 0.034 | 0.050 | 0.037 | 0.047 | 0.062 | 0.051 |
| p | 0.41 | 0.50 | 0.39 | 0.30 | 0.33 | 0.25 | 1.00 | 0.60 | 0.67 |
| nCohort 1 | 360 | 760 | 317 | 360 | 760 | 317 | 360 | 760 | 317 |
| nCohort 2 | 76 | 29 | 66 | 92 | 37 | 79 | 43 | 23 | 36 |
| Cutoff 1 | 0 | 0 | 0 | 0 | 0 | 0 | 0 | 0 | 0 |
| Sens 1 | 100% | 100% | 100% | 100% | 100% | 100% | 100% | 100% | 100% |
| Spec 1 | 0% | 0% | 0% | 0% | 0% | 0% | 0% | 0% | 0% |
| Cutoff 2 | 0 | 0 | 0 | 0 | 0 | 0 | 0 | 0 | 0 |
| Sens 2 | 100% | 100% | 100% | 100% | 100% | 100% | 100% | 100% | 100% |
| Spec 2 | 0% | 0% | 0% | 0% | 0% | 0% | 0% | 0% | 0% |
| Cutoff 3 | 0 | 0 | 0 | 0 | 0 | 0 | 0 | 0 | 0 |
| Sens 3 | 100% | 100% | 100% | 100% | 100% | 100% | 100% | 100% | 100% |
| Spec 3 | 0% | 0% | 0% | 0% | 0% | 0% | 0% | 0% | 0% |
| Cutoff 4 | 1.00E−9 | 1.00E−9 | 1.00E−9 | 1.00E−9 | 1.00E−9 | 1.00E−9 | 1.00E−9 | 1.00E−9 | 1.00E−9 |
| Sens 4 | 13% | 14% | 14% | 14% | 16% | 15% | 7% | 13% | 11% |
| Spec 4 | 93% | 93% | 93% | 93% | 93% | 93% | 93% | 93% | 93% |
| Cutoff 5 | 1.00E−9 | 1.00E−9 | 1.00E−9 | 1.00E−9 | 1.00E−9 | 1.00E−9 | 1.00E−9 | 1.00E−9 | 1.00E−9 |
| Sens 5 | 13% | 14% | 14% | 14% | 16% | 15% | 7% | 13% | 11% |
| Spec 5 | 93% | 93% | 93% | 93% | 93% | 93% | 93% | 93% | 93% |
| Cutoff 6 | 1.00E−9 | 1.00E−9 | 1.00E−9 | 1.00E−9 | 1.00E−9 | 1.00E−9 | 1.00E−9 | 1.00E−9 | 1.00E−9 |
| Sens 6 | 13% | 14% | 14% | 14% | 16% | 15% | 7% | 13% | 11% |
| Spec 6 | 93% | 93% | 93% | 93% | 93% | 93% | 93% | 93% | 93% |
| OR Quart 2 | 26 | >29 | 39 | 41 | >37 | 32 | 30 | >22 | 22 |
| p Value | 4.4E−11 | <0.0011 | 3.4E−9 | 9.3E−14 | <4.2E−4 | 7.5E−12 | 5.2E−6 | <0.0026 | 3.5E−5 |
| 95% CI of | 10.0 | >3.8 | 12 | 15 | >5.0 | 12 | 6.9 | >2.9 | 5.1 |
| OR Quart2 | 70 | na | 130 | 110 | na | 85 | 130 | na | 97 |
| OR Quart 3 | 0 | >0 | 0 | 0 | >0 | 0 | 0 | >0 | 0 |
| p Value | na | <na | na | na | <na | na | na | <na | na |
| 95% CI of | na | >na | na | na | >na | na | na | >na | na |
| OR Quart3 | na | na | na | na | na | na | na | na | na |
| OR Quart 4 | 2.1 | >4.1 | 3.2 | 2.8 | >6.2 | 2.6 | 1.5 | >3.0 | 2.0 |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| p Value | 0.19 | <0.21 | 0.091 | 0.058 | <0.094 | 0.085 | 0.66 | <0.34 | 0.42 |
| 95% CI of | 0.69 | >0.45 | 0.83 | 0.97 | >0.73 | 0.88 | 0.25 | >0.31 | 0.36 |
| OR Quart4 | 6.4 | na | 12 | 8.2 | na | 7.7 | 9.2 | na | 11 |

C-X-C motif chemokine 6

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 13.2 | 24.1 | 13.2 | 19.1 | 13.2 | 8.72 |
| Average | 27.1 | 52.2 | 27.1 | 56.8 | 27.1 | 24.5 |
| Stdev | 59.3 | 169 | 59.3 | 127 | 59.3 | 34.7 |
| p(t-test) | | 0.026 | | 0.0012 | | 0.78 |
| Min | 1.00E−9 | 0.240 | 1.00E−9 | 1.00E−9 | 1.00E−9 | 1.00E−9 |
| Max | 593 | 1450 | 593 | 769 | 593 | 140 |
| n (Samp) | 358 | 75 | 358 | 92 | 358 | 43 |
| n (Patient) | 190 | 75 | 190 | 92 | 190 | 43 |
| sCr only | | | | | | |
| Median | 15.2 | 28.4 | 15.2 | 19.3 | 15.2 | 9.05 |
| Average | 39.5 | 117 | 39.5 | 85.7 | 39.5 | 22.7 |
| Stdev | 122 | 310 | 122 | 182 | 122 | 26.1 |
| p(t-test) | | 0.0023 | | 0.028 | | 0.51 |
| Min | 1.00E−9 | 0.240 | 1.00E−9 | 1.00E−9 | 1.00E−9 | 1.00E−9 |
| Max | 2500 | 1450 | 2500 | 769 | 2500 | 78.5 |
| n (Samp) | 758 | 29 | 758 | 37 | 758 | 23 |
| n (Patient) | 297 | 29 | 297 | 37 | 297 | 23 |
| UO only | | | | | | |
| Median | 13.9 | 28.7 | 13.9 | 21.4 | 13.9 | 10.0 |
| Average | 27.3 | 56.2 | 27.3 | 63.0 | 27.3 | 28.4 |
| Stdev | 56.5 | 180 | 56.5 | 136 | 56.5 | 39.2 |
| p(t-test) | | 0.019 | | 3.7E−4 | | 0.91 |
| Min | 1.00E−9 | 0.324 | 1.00E−9 | 0.324 | 1.00E−9 | 1.00E−9 |
| Max | 593 | 1450 | 593 | 769 | 593 | 140 |
| n (Samp) | 315 | 65 | 315 | 79 | 315 | 36 |
| n (Patient) | 136 | 65 | 136 | 79 | 136 | 36 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.59 | 0.55 | 0.62 | 0.59 | 0.57 | 0.59 | 0.46 | 0.44 | 0.46 |
| SE | 0.037 | 0.056 | 0.040 | 0.034 | 0.050 | 0.037 | 0.047 | 0.063 | 0.052 |
| p | 0.014 | 0.38 | 0.0032 | 0.013 | 0.19 | 0.010 | 0.40 | 0.35 | 0.49 |
| nCohort 1 | 358 | 758 | 315 | 358 | 758 | 315 | 358 | 758 | 315 |
| nCohort 2 | 75 | 29 | 65 | 92 | 37 | 79 | 43 | 23 | 36 |
| Cutoff 1 | 7.26 | 5.99 | 9.02 | 7.68 | 9.65 | 10.2 | 4.01 | 5.34 | 4.01 |
| Sens 1 | 71% | 72% | 71% | 71% | 70% | 71% | 72% | 74% | 72% |
| Spec 1 | 33% | 23% | 36% | 35% | 35% | 38% | 22% | 22% | 18% |
| Cutoff 2 | 4.82 | 2.65 | 6.71 | 5.34 | 5.99 | 5.40 | 3.11 | 4.50 | 3.11 |
| Sens 2 | 81% | 83% | 80% | 80% | 81% | 82% | 81% | 83% | 81% |
| Spec 2 | 24% | 11% | 27% | 28% | 23% | 23% | 16% | 18% | 13% |
| Cutoff 3 | 2.31 | 1.16 | 3.83 | 2.46 | 2.38 | 2.82 | 1.36 | 2.81 | 1.41 |
| Sens 3 | 91% | 93% | 91% | 90% | 92% | 91% | 91% | 91% | 92% |
| Spec 3 | 13% | 6% | 17% | 14% | 11% | 12% | 9% | 12% | 7% |
| Cutoff 4 | 22.6 | 28.7 | 25.5 | 22.6 | 28.7 | 25.5 | 22.6 | 28.7 | 25.5 |
| Sens 4 | 51% | 48% | 54% | 45% | 46% | 42% | 30% | 30% | 36% |
| Spec 4 | 70% | 70% | 70% | 70% | 70% | 70% | 70% | 70% | 70% |
| Cutoff 5 | 31.4 | 39.8 | 32.1 | 31.4 | 39.8 | 32.1 | 31.4 | 39.8 | 32.1 |
| Sens 5 | 40% | 38% | 45% | 34% | 32% | 35% | 28% | 26% | 33% |
| Spec 5 | 80% | 80% | 80% | 80% | 80% | 80% | 80% | 80% | 80% |
| Cutoff 6 | 51.6 | 64.0 | 53.8 | 51.6 | 64.0 | 53.8 | 51.6 | 64.0 | 53.8 |
| Sens 6 | 20% | 31% | 15% | 18% | 22% | 20% | 16% | 13% | 14% |
| Spec 6 | 90% | 90% | 90% | 90% | 90% | 90% | 90% | 90% | 90% |
| OR Quart 2 | 0.86 | 0.43 | 0.83 | 1.1 | 0.87 | 0.66 | 0.14 | 0.33 | 0.066 |
| p Value | 0.69 | 0.17 | 0.66 | 0.88 | 0.78 | 0.30 | 0.011 | 0.18 | 0.0097 |
| 95% CI of | 0.40 | 0.13 | 0.35 | 0.52 | 0.31 | 0.30 | 0.030 | 0.065 | 0.0085 |
| OR Quart2 | 1.9 | 1.4 | 1.9 | 2.1 | 2.4 | 1.5 | 0.63 | 1.6 | 0.52 |
| OR Quart 3 | 0.79 | 0.54 | 0.91 | 1.1 | 1.1 | 1.2 | 1.0 | 1.2 | 0.58 |
| p Value | 0.55 | 0.28 | 0.83 | 0.72 | 0.81 | 0.58 | 0.98 | 0.77 | 0.25 |
| 95% CI of | 0.36 | 0.18 | 0.39 | 0.56 | 0.43 | 0.60 | 0.44 | 0.39 | 0.23 |
| OR Quart3 | 1.7 | 1.6 | 2.1 | 2.3 | 3.0 | 2.5 | 2.3 | 3.6 | 1.5 |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| OR Quart 4 | 2.4 | 1.2 | 2.8 | 2.3 | 1.7 | 2.1 | 1.2 | 1.4 | 1.1 |
| p Value | 0.011 | 0.66 | 0.0062 | 0.0094 | 0.27 | 0.035 | 0.66 | 0.58 | 0.81 |
| 95% CI of | 1.2 | 0.50 | 1.3 | 1.2 | 0.67 | 1.1 | 0.54 | 0.46 | 0.49 |
| OR Quart4 | 4.7 | 3.0 | 5.8 | 4.5 | 4.1 | 4.1 | 2.7 | 4.0 | 2.5 |

Coagulation factor VII

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 2.63 | 4.77 | 2.63 | 5.05 | 2.63 | 3.72 |
| Average | 5.27 | 6.37 | 5.27 | 8.73 | 5.27 | 14.0 |
| Stdev | 8.53 | 5.43 | 8.53 | 11.0 | 8.53 | 47.2 |
| p(t-test) | | 0.39 | | 0.0093 | | 0.0097 |
| Min | 0.00408 | 0.00408 | 0.00408 | 0.00408 | 0.00408 | 0.00408 |
| Max | 65.5 | 20.4 | 65.5 | 63.6 | 65.5 | 249 |
| n (Samp) | 255 | 48 | 255 | 57 | 255 | 27 |
| n (Patient) | 103 | 48 | 103 | 57 | 103 | 27 |
| sCr only | | | | | | |
| Median | 3.35 | 2.46 | 3.35 | 6.36 | 3.35 | 3.86 |
| Average | 6.76 | 7.40 | 6.76 | 9.71 | 6.76 | 6.19 |
| Stdev | 14.4 | 12.1 | 14.4 | 10.0 | 14.4 | 6.27 |
| p(t-test) | | 0.86 | | 0.35 | | 0.89 |
| Min | 0.00408 | 0.00408 | 0.00408 | 0.00408 | 0.00408 | 0.00408 |
| Max | 249 | 48.8 | 249 | 32.3 | 249 | 23.5 |
| n (Samp) | 447 | 16 | 447 | 21 | 447 | 13 |
| n (Patient) | 170 | 16 | 170 | 21 | 170 | 13 |
| UO only | | | | | | |
| Median | 2.34 | 5.38 | 2.34 | 4.65 | 2.34 | 3.77 |
| Average | 4.84 | 6.59 | 4.84 | 8.10 | 4.84 | 14.0 |
| Stdev | 8.24 | 5.17 | 8.24 | 10.8 | 8.24 | 49.1 |
| p(t-test) | | 0.17 | | 0.017 | | 0.013 |
| Min | 0.00408 | 0.409 | 0.00408 | 0.384 | 0.00408 | 0.303 |
| Max | 65.5 | 20.4 | 65.5 | 63.6 | 65.5 | 249 |
| n (Samp) | 218 | 46 | 218 | 51 | 218 | 25 |
| n (Patient) | 87 | 46 | 87 | 51 | 87 | 25 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.62 | 0.48 | 0.67 | 0.65 | 0.61 | 0.66 | 0.58 | 0.56 | 0.60 |
| SE | 0.046 | 0.074 | 0.047 | 0.043 | 0.067 | 0.045 | 0.060 | 0.084 | 0.063 |
| p | 0.012 | 0.83 | 2.3E−4 | 5.7E−4 | 0.097 | 3.6E−4 | 0.16 | 0.49 | 0.10 |
| nCohort 1 | 255 | 447 | 218 | 255 | 447 | 218 | 255 | 447 | 218 |
| nCohort 2 | 48 | 16 | 46 | 57 | 21 | 51 | 27 | 13 | 25 |
| Cutoff 1 | 1.70 | 1.23 | 3.00 | 2.64 | 3.00 | 2.42 | 2.06 | 2.06 | 1.88 |
| Sens 1 | 71% | 75% | 72% | 72% | 71% | 71% | 70% | 77% | 72% |
| Spec 1 | 39% | 26% | 57% | 51% | 47% | 52% | 43% | 37% | 46% |
| Cutoff 2 | 1.24 | 0.952 | 1.72 | 2.09 | 2.42 | 1.79 | 1.70 | 1.81 | 1.67 |
| Sens 2 | 81% | 81% | 80% | 81% | 81% | 80% | 81% | 85% | 80% |
| Spec 2 | 31% | 19% | 43% | 43% | 41% | 44% | 39% | 35% | 41% |
| Cutoff 3 | 0.564 | 0 | 0.704 | 0.906 | 0.692 | 1.23 | 1.10 | 1.72 | 0.952 |
| Sens 3 | 92% | 100% | 91% | 91% | 90% | 90% | 93% | 92% | 92% |
| Spec 3 | 15% | 0% | 20% | 22% | 14% | 32% | 28% | 33% | 24% |
| Cutoff 4 | 5.19 | 6.42 | 4.32 | 5.19 | 6.42 | 4.32 | 5.19 | 6.42 | 4.32 |
| Sens 4 | 48% | 38% | 59% | 47% | 48% | 53% | 33% | 38% | 32% |
| Spec 4 | 70% | 70% | 70% | 70% | 70% | 70% | 70% | 70% | 70% |
| Cutoff 5 | 7.42 | 9.53 | 7.01 | 7.42 | 9.53 | 7.01 | 7.42 | 9.53 | 7.01 |
| Sens 5 | 35% | 19% | 41% | 35% | 33% | 35% | 26% | 23% | 20% |
| Spec 5 | 80% | 80% | 80% | 80% | 80% | 80% | 80% | 80% | 80% |
| Cutoff 6 | 11.5 | 15.3 | 10.1 | 11.5 | 15.3 | 10.1 | 11.5 | 15.3 | 10.1 |
| Sens 6 | 19% | 12% | 24% | 23% | 24% | 24% | 11% | 8% | 16% |
| Spec 6 | 90% | 90% | 90% | 90% | 90% | 90% | 90% | 90% | 90% |
| OR Quart 2 | 1.1 | 0.74 | 1.4 | 1.6 | 1.3 | 2.4 | 4.9 | 5.2 | 1.7 |
| p Value | 0.82 | 0.70 | 0.55 | 0.34 | 0.73 | 0.12 | 0.046 | 0.14 | 0.48 |
| 95% CI of | 0.41 | 0.16 | 0.44 | 0.61 | 0.33 | 0.80 | 1.0 | 0.60 | 0.39 |
| OR Quart2 | 3.1 | 3.4 | 4.8 | 4.1 | 4.8 | 7.4 | 24 | 45 | 7.4 |
| OR Quart 3 | 1.6 | 1.3 | 3.0 | 2.1 | 1.3 | 3.6 | 4.4 | 4.1 | 4.2 |
| p Value | 0.36 | 0.73 | 0.050 | 0.12 | 0.73 | 0.020 | 0.068 | 0.21 | 0.035 |
| 95% CI of | 0.60 | 0.33 | 1.0 | 0.83 | 0.33 | 1.2 | 0.90 | 0.45 | 1.1 |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| OR Quart3 | 4.1 | 4.8 | 8.9 | 5.2 | 4.8 | 11 | 21 | 37 | 16 |
| OR Quart 4 | 2.8 | 1.0 | 5.7 | 3.4 | 1.8 | 5.2 | 4.3 | 3.1 | 2.1 |
| p Value | 0.025 | 0.99 | 0.0012 | 0.0061 | 0.36 | 0.0022 | 0.071 | 0.34 | 0.32 |
| 95% CI of | 1.1 | 0.25 | 2.0 | 1.4 | 0.51 | 1.8 | 0.88 | 0.31 | 0.49 |
| OR Quart4 | 6.9 | 4.1 | 16 | 8.3 | 6.3 | 15 | 21 | 30 | 8.7 |

Insulin-like growth factor-binding protein 7

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 45.5 | 70.2 | 45.5 | 72.8 | 45.5 | 42.8 |
| Average | 66.2 | 111 | 66.2 | 127 | 66.2 | 76.9 |
| Stdev | 69.6 | 104 | 69.6 | 176 | 69.6 | 76.2 |
| p(t-test) | | 5.0E−6 | | 3.1E−7 | | 0.35 |
| Min | 1.06 | 8.34 | 1.06 | 5.23 | 1.06 | 4.58 |
| Max | 533 | 594 | 533 | 1250 | 533 | 382 |
| n (Samp) | 360 | 75 | 360 | 90 | 360 | 43 |
| n (Patient) | 190 | 75 | 190 | 90 | 190 | 43 |
| sCr only | | | | | | |
| Median | 51.8 | 61.7 | 51.8 | 106 | 51.8 | 80.7 |
| Average | 77.0 | 179 | 77.0 | 167 | 77.0 | 94.5 |
| Stdev | 89.0 | 343 | 89.0 | 163 | 89.0 | 82.8 |
| p(t-test) | | 9.0E−7 | | 1.6E−8 | | 0.35 |
| Min | 1.00E−9 | 8.34 | 1.00E−9 | 8.49 | 1.00E−9 | 4.58 |
| Max | 1250 | 1830 | 1250 | 674 | 1250 | 344 |
| n (Samp) | 756 | 29 | 756 | 37 | 756 | 23 |
| n (Patient) | 296 | 29 | 296 | 37 | 296 | 23 |
| UO only | | | | | | |
| Median | 45.9 | 79.3 | 45.9 | 71.5 | 45.9 | 44.2 |
| Average | 67.4 | 120 | 67.4 | 135 | 67.4 | 80.6 |
| Stdev | 68.6 | 103 | 68.6 | 187 | 68.6 | 80.9 |
| p(t-test) | | 3.9E−7 | | 3.8E−7 | | 0.28 |
| Min | 1.06 | 13.5 | 1.06 | 5.23 | 1.06 | 5.13 |
| Max | 533 | 594 | 533 | 1250 | 533 | 382 |
| n (Samp) | 317 | 65 | 317 | 77 | 317 | 36 |
| n (Patient) | 136 | 65 | 136 | 77 | 136 | 36 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.67 | 0.61 | 0.71 | 0.65 | 0.71 | 0.64 | 0.54 | 0.59 | 0.54 |
| SE | 0.037 | 0.057 | 0.038 | 0.034 | 0.049 | 0.037 | 0.047 | 0.063 | 0.052 |
| p | 3.0E−6 | 0.049 | 2.3E−8 | 1.7E−5 | 1.9E−5 | 9.5E−5 | 0.41 | 0.18 | 0.49 |
| nCohort 1 | 360 | 756 | 317 | 360 | 756 | 317 | 360 | 756 | 317 |
| nCohort 2 | 75 | 29 | 65 | 90 | 37 | 77 | 43 | 23 | 36 |
| Cutoff 1 | 48.2 | 45.6 | 58.0 | 51.2 | 62.6 | 51.1 | 32.4 | 34.7 | 32.4 |
| Sens 1 | 71% | 72% | 71% | 70% | 70% | 70% | 72% | 74% | 72% |
| Spec 1 | 52% | 44% | 61% | 56% | 59% | 55% | 36% | 32% | 33% |
| Cutoff 2 | 37.2 | 24.8 | 45.6 | 28.5 | 49.1 | 28.5 | 23.0 | 29.9 | 23.0 |
| Sens 2 | 80% | 83% | 80% | 80% | 81% | 81% | 81% | 83% | 81% |
| Spec 2 | 41% | 23% | 49% | 32% | 47% | 29% | 25% | 28% | 22% |
| Cutoff 3 | 24.6 | 18.2 | 36.9 | 17.8 | 27.7 | 19.9 | 11.9 | 25.3 | 11.9 |
| Sens 3 | 91% | 93% | 91% | 90% | 92% | 91% | 91% | 91% | 92% |
| Spec 3 | 27% | 16% | 39% | 18% | 26% | 16% | 9% | 24% | 7% |
| Cutoff 4 | 69.8 | 79.3 | 73.1 | 69.8 | 79.3 | 73.1 | 69.8 | 79.3 | 73.1 |
| Sens 4 | 52% | 48% | 52% | 52% | 59% | 49% | 40% | 52% | 39% |
| Spec 4 | 70% | 70% | 70% | 70% | 70% | 70% | 70% | 70% | 70% |
| Cutoff 5 | 93.6 | 105 | 94.7 | 93.6 | 105 | 94.7 | 93.6 | 105 | 94.7 |
| Sens 5 | 40% | 41% | 46% | 41% | 51% | 43% | 33% | 35% | 33% |
| Spec 5 | 80% | 80% | 80% | 80% | 80% | 80% | 80% | 80% | 80% |
| Cutoff 6 | 139 | 160 | 140 | 139 | 160 | 140 | 139 | 160 | 140 |
| Sens 6 | 27% | 31% | 32% | 24% | 30% | 25% | 14% | 13% | 14% |
| Spec 6 | 90% | 90% | 90% | 90% | 90% | 90% | 90% | 90% | 90% |
| OR Quart 2 | 1.8 | 0.83 | 4.8 | 0.77 | 2.0 | 0.99 | 1.5 | 1.5 | 1.1 |
| p Value | 0.21 | 0.76 | 0.017 | 0.52 | 0.32 | 0.98 | 0.38 | 0.53 | 0.81 |
| 95% CI of | 0.73 | 0.25 | 1.3 | 0.34 | 0.50 | 0.42 | 0.61 | 0.42 | 0.43 |
| OR Quart2 | 4.2 | 2.8 | 17 | 1.7 | 8.2 | 2.3 | 3.7 | 5.4 | 2.9 |
| OR Quart 3 | 2.6 | 1.0 | 7.7 | 2.0 | 3.1 | 1.8 | 0.64 | 0.74 | 0.42 |
| p Value | 0.023 | 1.0 | 0.0015 | 0.060 | 0.094 | 0.13 | 0.41 | 0.70 | 0.16 |

TABLE 1-continued

Comparison of marker levels in urine samples collected from Cohort 1 (patients that did not progress beyond RIFLE stage 0) and in urine samples collected from subjects at 0, 24 hours, and 48 hours prior to reaching stage R, I or F in Cohort 2.

| | | | | | | | | | |
|---|---|---|---|---|---|---|---|---|---|
| 95% CI of | 1.1 | 0.32 | 2.2 | 0.97 | 0.83 | 0.84 | 0.22 | 0.16 | 0.12 |
| OR Quart3 | 6.0 | 3.2 | 27 | 3.9 | 12 | 4.0 | 1.9 | 3.4 | 1.4 |
| OR Quart 4 | 4.2 | 2.1 | 14 | 3.1 | 6.9 | 3.6 | 1.8 | 2.6 | 1.5 |
| p Value | 4.7E−4 | 0.16 | 2.6E−5 | 8.1E−4 | 0.0022 | 6.6E−4 | 0.21 | 0.12 | 0.38 |
| 95% CI of | 1.9 | 0.76 | 4.1 | 1.6 | 2.0 | 1.7 | 0.73 | 0.79 | 0.61 |
| OR Quart4 | 9.3 | 5.6 | 48 | 6.2 | 24 | 7.5 | 4.2 | 8.3 | 3.7 |

TABLE 2

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

Cancer Antigen 19-9

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 21.9 | 38.2 | 21.9 | 28.5 | 21.9 | 17.7 |
| Average | 154 | 148 | 154 | 233 | 154 | 91.3 |
| Stdev | 810 | 279 | 810 | 592 | 810 | 125 |
| p(t-test) | | 0.97 | | 0.60 | | 0.76 |
| Min | 1.00E−9 | 1.00E−9 | 1.00E−9 | 1.00E−9 | 1.00E−9 | 1.00E−9 |
| Max | 11900 | 1070 | 11900 | 2940 | 11900 | 371 |
| n (Samp) | 241 | 22 | 241 | 32 | 241 | 16 |
| n (Patient) | 159 | 22 | 159 | 32 | 159 | 16 |
| sCr only | | | | | | |
| Median | nd | nd | 22.9 | 44.1 | 22.9 | 75.0 |
| Average | nd | nd | 160 | 46.8 | 160 | 140 |
| Stdev | nd | nd | 746 | 31.4 | 746 | 225 |
| p(t-test) | nd | nd | | 0.71 | | 0.94 |
| Min | nd | nd | 1.00E−9 | 3.94 | 1.00E−9 | 3.60 |
| Max | nd | nd | 11900 | 90.5 | 11900 | 645 |
| n (Samp) | nd | nd | 307 | 6 | 307 | 7 |
| n (Patient) | nd | nd | 186 | 6 | 186 | 7 |
| UO only | | | | | | |
| Median | 23.1 | 38.2 | 23.1 | 29.3 | 23.1 | 34.8 |
| Average | 165 | 149 | 165 | 252 | 165 | 95.1 |
| Stdev | 863 | 279 | 863 | 620 | 863 | 127 |
| p(t-test) | | 0.93 | | 0.60 | | 0.76 |
| Min | 1.00E−9 | 1.00E−9 | 1.00E−9 | 1.00E−9 | 1.00E−9 | 1.00E−9 |
| Max | 11900 | 1070 | 11900 | 2940 | 11900 | 371 |
| n (Samp) | 210 | 22 | 210 | 29 | 210 | 15 |
| n (Patient) | 132 | 22 | 132 | 29 | 132 | 15 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.59 | nd | 0.58 | 0.59 | 0.59 | 0.58 | 0.51 | 0.64 | 0.53 |
| SE | 0.066 | nd | 0.066 | 0.056 | 0.12 | 0.059 | 0.075 | 0.11 | 0.079 |
| p | 0.18 | nd | 0.25 | 0.097 | 0.48 | 0.15 | 0.87 | 0.22 | 0.67 |
| nCohort 1 | 241 | nd | 210 | 241 | 307 | 210 | 241 | 307 | 210 |
| nCohort 2 | 22 | nd | 22 | 32 | 6 | 29 | 16 | 7 | 15 |
| Cutoff 1 | 22.6 | nd | 22.6 | 20.7 | 26.6 | 20.7 | 6.23 | 57.7 | 9.76 |
| Sens 1 | 73% | nd | 73% | 72% | 83% | 72% | 75% | 71% | 73% |
| Spec 1 | 51% | nd | 48% | 49% | 55% | 46% | 20% | 71% | 28% |
| Cutoff 2 | 6.42 | nd | 6.42 | 18.5 | 26.6 | 18.5 | 4.76 | 14.2 | 6.23 |
| Sens 2 | 82% | nd | 82% | 81% | 83% | 83% | 81% | 86% | 80% |
| Spec 2 | 21% | nd | 19% | 47% | 55% | 45% | 17% | 38% | 18% |
| Cutoff 3 | 0 | nd | 0 | 3.42 | 3.42 | 1.00E−9 | 0 | 3.42 | 0 |
| Sens 3 | 100% | nd | 100% | 91% | 100% | 93% | 100% | 100% | 100% |
| Spec 3 | 0% | nd | 0% | 15% | 15% | 5% | 0% | 15% | 0% |
| Cutoff 4 | 50.1 | nd | 54.2 | 50.1 | 57.3 | 54.2 | 50.1 | 57.3 | 54.2 |
| Sens 4 | 36% | nd | 36% | 38% | 33% | 34% | 44% | 71% | 40% |
| Spec 4 | 70% | nd | 70% | 70% | 70% | 70% | 70% | 70% | 70% |
| Cutoff 5 | 86.3 | nd | 90.2 | 86.3 | 115 | 90.2 | 86.3 | 115 | 90.2 |
| Sens 5 | 27% | nd | 27% | 28% | 0% | 28% | 38% | 14% | 33% |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | | | | |
|---|---|---|---|---|---|---|---|---|---|
| Spec 5 | 80% | nd | 80% | 80% | 80% | 80% | 80% | 80% | 80% |
| Cutoff 6 | 227 | nd | 239 | 227 | 289 | 239 | 227 | 289 | 239 |
| Sens 6 | 18% | nd | 18% | 16% | 0% | 17% | 12% | 14% | 13% |
| Spec 6 | 90% | nd | 90% | 90% | 90% | 90% | 90% | 90% | 90% |
| OR Quart 2 | 0.38 | nd | 0.38 | 1.4 | 0 | 2.1 | 0.79 | 0.99 | 0.74 |
| p Value | 0.25 | nd | 0.26 | 0.55 | na | 0.24 | 0.73 | 0.99 | 0.70 |
| 95% CI of | 0.070 | nd | 0.070 | 0.44 | na | 0.60 | 0.20 | 0.061 | 0.16 |
| OR Quart2 | 2.0 | nd | 2.0 | 4.8 | na | 7.4 | 3.1 | 16 | 3.4 |
| OR Quart 3 | 1.7 | nd | 1.7 | 1.9 | 3.1 | 2.1 | 0.19 | 1.0 | 0.74 |
| p Value | 0.40 | nd | 0.38 | 0.27 | 0.33 | 0.24 | 0.13 | 1.0 | 0.70 |
| 95% CI of | 0.51 | nd | 0.52 | 0.61 | 0.31 | 0.60 | 0.021 | 0.061 | 0.16 |
| OR Quart3 | 5.4 | nd | 5.5 | 6.1 | 30 | 7.4 | 1.7 | 16 | 3.4 |
| OR Quart 4 | 1.4 | nd | 1.5 | 2.4 | 2.0 | 2.4 | 1.2 | 4.1 | 1.2 |
| p Value | 0.56 | nd | 0.54 | 0.13 | 0.57 | 0.16 | 0.77 | 0.21 | 0.75 |
| 95% CI of | 0.43 | nd | 0.43 | 0.78 | 0.18 | 0.70 | 0.35 | 0.45 | 0.32 |
| OR Quart4 | 4.7 | nd | 4.9 | 7.3 | 23 | 8.4 | 4.1 | 38 | 4.9 |

C-C motif chemokine 13

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 1.00E−9 | 1.00E−9 | 1.00E−9 | 1.00E−9 | 1.00E−9 | 1.00E−9 |
| Average | 2.76 | 7.45 | 2.76 | 9.69 | 2.76 | 3.39 |
| Stdev | 16.1 | 29.1 | 16.1 | 22.8 | 16.1 | 12.5 |
| p(t-test) | | 0.10 | | 0.0053 | | 0.84 |
| Min | 1.00E−9 | 1.00E−9 | 1.00E−9 | 1.00E−9 | 1.00E−9 | 1.00E−9 |
| Max | 214 | 143 | 214 | 101 | 214 | 61.9 |
| n (Samp) | 694 | 37 | 694 | 48 | 694 | 28 |
| n (Patient) | 281 | 37 | 281 | 48 | 281 | 28 |
| sCr only | | | | | | |
| Median | 1.00E−9 | 1.00E−9 | 1.00E−9 | 1.00E−9 | 1.00E−9 | 1.00E−9 |
| Average | 2.95 | 11.8 | 2.95 | 18.4 | 2.95 | 9.44 |
| Stdev | 17.0 | 35.5 | 17.0 | 41.2 | 17.0 | 25.2 |
| p(t-test) | | 0.13 | | 0.0017 | | 0.18 |
| Min | 1.00E−9 | 1.00E−9 | 1.00E−9 | 1.00E−9 | 1.00E−9 | 1.00E−9 |
| Max | 241 | 106 | 241 | 143 | 241 | 86.2 |
| n (Samp) | 904 | 9 | 904 | 13 | 904 | 13 |
| n (Patient) | 337 | 9 | 337 | 13 | 337 | 13 |
| UO only | | | | | | |
| Median | 1.00E−9 | 1.00E−9 | 1.00E−9 | 1.00E−9 | 1.00E−9 | 1.00E−9 |
| Average | 2.93 | 4.84 | 2.93 | 10.6 | 2.93 | 3.80 |
| Stdev | 17.1 | 24.5 | 17.1 | 24.0 | 17.1 | 13.2 |
| p(t-test) | | 0.53 | | 0.0058 | | 0.80 |
| Min | 1.00E−9 | 1.00E−9 | 1.00E−9 | 1.00E−9 | 1.00E−9 | 1.00E−9 |
| Max | 214 | 143 | 214 | 101 | 214 | 61.9 |
| n (Samp) | 584 | 35 | 584 | 43 | 584 | 25 |
| n (Patient) | 209 | 35 | 209 | 43 | 209 | 25 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.51 | 0.52 | 0.50 | 0.61 | 0.62 | 0.62 | 0.52 | 0.54 | 0.53 |
| SE | 0.049 | 0.098 | 0.050 | 0.044 | 0.084 | 0.047 | 0.056 | 0.083 | 0.060 |
| p | 0.86 | 0.81 | 0.95 | 0.012 | 0.15 | 0.012 | 0.73 | 0.59 | 0.65 |
| nCohort 1 | 694 | 904 | 584 | 694 | 904 | 584 | 694 | 904 | 584 |
| nCohort 2 | 37 | 9 | 35 | 48 | 13 | 43 | 28 | 13 | 25 |
| Cutoff 1 | 0 | 0 | 0 | 0 | 0 | 0 | 0 | 0 | 0 |
| Sens 1 | 100% | 100% | 100% | 100% | 100% | 100% | 100% | 100% | 100% |
| Spec 1 | 0% | 0% | 0% | 0% | 0% | 0% | 0% | 0% | 0% |
| Cutoff 2 | 0 | 0 | 0 | 0 | 0 | 0 | 0 | 0 | 0 |
| Sens 2 | 100% | 100% | 100% | 100% | 100% | 100% | 100% | 100% | 100% |
| Spec 2 | 0% | 0% | 0% | 0% | 0% | 0% | 0% | 0% | 0% |
| Cutoff 3 | 0 | 0 | 0 | 0 | 0 | 0 | 0 | 0 | 0 |
| Sens 3 | 100% | 100% | 100% | 100% | 100% | 100% | 100% | 100% | 100% |
| Spec 3 | 0% | 0% | 0% | 0% | 0% | 0% | 0% | 0% | 0% |
| Cutoff 4 | 1.00E−9 | 1.00E−9 | 1.00E−9 | 1.00E−9 | 1.00E−9 | 1.00E−9 | 1.00E−9 | 1.00E−9 | 1.00E−9 |
| Sens 4 | 8% | 11% | 6% | 29% | 31% | 30% | 11% | 15% | 12% |
| Spec 4 | 93% | 93% | 93% | 93% | 93% | 93% | 93% | 93% | 93% |
| Cutoff 5 | 1.00E−9 | 1.00E−9 | 1.00E−9 | 1.00E−9 | 1.00E−9 | 1.00E−9 | 1.00E−9 | 1.00E−9 | 1.00E−9 |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | | | | |
|---|---|---|---|---|---|---|---|---|---|
| Sens 5 | 8% | 11% | 6% | 29% | 31% | 30% | 11% | 15% | 12% |
| Spec 5 | 93% | 93% | 93% | 93% | 93% | 93% | 93% | 93% | 93% |
| Cutoff 6 | 1.00E−9 | 1.00E−9 | 1.00E−9 | 1.00E−9 | 1.00E−9 | 1.00E−9 | 1.00E−9 | 1.00E−9 | 1.00E−9 |
| Sens 6 | 8% | 11% | 6% | 29% | 31% | 30% | 11% | 15% | 12% |
| Spec 6 | 93% | 93% | 93% | 93% | 93% | 93% | 93% | 93% | 93% |
| OR Quart 2 | >42 | >8.3 | 0 | >41 | >9.4 | 35 | >29 | >12 | >26 |
| p Value | <2.6E−4 | <0.047 | na | <2.6E−4 | <0.035 | 5.1E−4 | <0.0010 | <0.020 | <0.0016 |
| 95% CI of | >5.6 | >1.0 | na | >5.6 | >1.2 | 4.7 | >3.9 | >1.5 | >3.4 |
| OR Quart2 | na | na | na | na | na | 260 | na | na | na |
| OR Quart 3 | >0 | >0 | 21 | >0 | >0 | 0 | >0 | >0 | >0 |
| p Value | <na | <na | 4.1E−5 | <na | <na | na | <na | <na | <na |
| 95% CI of | >na | >na | 4.9 | >na | >na | na | >na | >na | >na |
| OR Quart3 | na | na | 88 | na | na | na | na | na | na |
| OR Quart 4 | >3.0 | >1.0 | 0 | >15 | >4.1 | 14 | >3.0 | >2.0 | >3.0 |
| p Value | <0.34 | <1.0 | na | <0.0092 | <0.21 | 0.012 | <0.34 | <0.57 | <0.34 |
| 95% CI of | >0.31 | >0.062 | na | >2.0 | >0.45 | 1.8 | >0.31 | >0.18 | >0.31 |
| OR Quart4 | na | na | na | na | na | 110 | na | na | na |

C-X-C motif chemokine 6

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 13.9 | 34.6 | 13.9 | 41.8 | 13.9 | 13.0 |
| Average | 35.3 | 102 | 35.3 | 102 | 35.3 | 26.7 |
| Stdev | 119 | 279 | 119 | 172 | 119 | 35.5 |
| p(t-test) | | 0.0028 | | 3.3E−4 | | 0.70 |
| Min | 1.00E−9 | 1.00E−9 | 1.00E−9 | 1.00E−9 | 1.00E−9 | 1.00E−9 |
| Max | 2500 | 1450 | 2500 | 769 | 2500 | 140 |
| n (Samp) | 693 | 37 | 693 | 48 | 693 | 28 |
| n (Patient) | 281 | 37 | 281 | 48 | 281 | 28 |
| sCr only | | | | | | |
| Median | 15.6 | 66.7 | 15.6 | 51.3 | 15.6 | 15.0 |
| Average | 38.5 | 239 | 38.5 | 168 | 38.5 | 97.8 |
| Stdev | 114 | 466 | 114 | 300 | 114 | 209 |
| p(t-test) | | 9.4E−7 | | 9.5E−5 | | 0.066 |
| Min | 1.00E−9 | 4.70 | 1.00E−9 | 1.00E−9 | 1.00E−9 | 0.641 |
| Max | 2500 | 1450 | 2500 | 955 | 2500 | 769 |
| n (Samp) | 902 | 9 | 902 | 13 | 902 | 13 |
| n (Patient) | 337 | 9 | 337 | 13 | 337 | 13 |
| UO only | | | | | | |
| Median | 14.9 | 28.4 | 14.9 | 40.8 | 14.9 | 21.2 |
| Average | 37.4 | 104 | 37.4 | 106 | 37.4 | 30.0 |
| Stdev | 128 | 287 | 128 | 180 | 128 | 37.1 |
| p(t-test) | | 0.0067 | | 1.0E−3 | | 0.77 |
| Min | 1.00E−9 | 1.00E−9 | 1.00E−9 | 1.65 | 1.00E−9 | 1.00E−9 |
| Max | 2500 | 1450 | 2500 | 769 | 2500 | 140 |
| n (Samp) | 583 | 35 | 583 | 43 | 583 | 25 |
| n (Patient) | 209 | 35 | 209 | 43 | 209 | 25 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.64 | 0.75 | 0.63 | 0.72 | 0.70 | 0.71 | 0.49 | 0.53 | 0.52 |
| SE | 0.050 | 0.095 | 0.052 | 0.043 | 0.082 | 0.045 | 0.056 | 0.082 | 0.060 |
| p | 0.0042 | 0.0078 | 0.016 | 4.3E−7 | 0.017 | 3.1E−6 | 0.90 | 0.71 | 0.77 |
| nCohort 1 | 693 | 902 | 583 | 693 | 902 | 583 | 693 | 902 | 583 |
| nCohort 2 | 37 | 9 | 35 | 48 | 13 | 43 | 28 | 13 | 25 |
| Cutoff 1 | 14.8 | 25.3 | 14.8 | 22.7 | 22.0 | 22.7 | 4.83 | 5.34 | 5.40 |
| Sens 1 | 70% | 78% | 71% | 71% | 77% | 72% | 71% | 77% | 72% |
| Spec 1 | 53% | 64% | 50% | 67% | 60% | 65% | 21% | 21% | 22% |
| Cutoff 2 | 7.91 | 7.91 | 11.8 | 9.65 | 6.00 | 9.65 | 3.84 | 4.01 | 4.82 |
| Sens 2 | 81% | 89% | 80% | 81% | 85% | 81% | 82% | 85% | 80% |
| Spec 2 | 34% | 30% | 40% | 39% | 23% | 35% | 18% | 16% | 18% |
| Cutoff 3 | 3.84 | 4.67 | 3.83 | 7.26 | 3.84 | 8.50 | 0.534 | 2.81 | 0.506 |
| Sens 3 | 92% | 100% | 91% | 92% | 92% | 91% | 93% | 92% | 92% |
| Spec 3 | 18% | 18% | 16% | 30% | 15% | 33% | 5% | 12% | 4% |
| Cutoff 4 | 26.1 | 29.5 | 27.3 | 26.1 | 29.5 | 27.3 | 26.1 | 29.5 | 27.3 |
| Sens 4 | 54% | 67% | 51% | 58% | 69% | 58% | 36% | 38% | 36% |
| Spec 4 | 70% | 70% | 70% | 70% | 70% | 70% | 70% | 70% | 70% |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | | | | |
|---|---|---|---|---|---|---|---|---|---|
| Cutoff 5 | 35.9 | 41.2 | 36.6 | 35.9 | 41.2 | 36.6 | 35.9 | 41.2 | 36.6 |
| Sens 5 | 46% | 67% | 40% | 54% | 62% | 53% | 29% | 38% | 32% |
| Spec 5 | 80% | 80% | 80% | 80% | 80% | 80% | 80% | 80% | 80% |
| Cutoff 6 | 58.1 | 64.7 | 60.3 | 58.1 | 64.7 | 60.3 | 58.1 | 64.7 | 60.3 |
| Sens 6 | 22% | 56% | 17% | 38% | 31% | 37% | 7% | 31% | 12% |
| Spec 6 | 90% | 90% | 90% | 90% | 90% | 90% | 90% | 90% | 90% |
| OR Quart 2 | 0.82 | 1.00 | 1.2 | 3.1 | 0 | 12 | 0.55 | 0.39 | 0.49 |
| p Value | 0.75 | 1.00 | 0.77 | 0.093 | na | 0.019 | 0.29 | 0.27 | 0.25 |
| 95% CI of | 0.25 | 0.062 | 0.36 | 0.83 | na | 1.5 | 0.18 | 0.075 | 0.14 |
| OR Quart2 | 2.7 | 16 | 4.0 | 12 | na | 92 | 1.7 | 2.0 | 1.7 |
| OR Quart 3 | 1.2 | 1.00 | 1.4 | 3.1 | 0.66 | 7.3 | 0.43 | 0.20 | 0.49 |
| p Value | 0.78 | 1.00 | 0.56 | 0.093 | 0.65 | 0.065 | 0.17 | 0.14 | 0.25 |
| 95% CI of | 0.39 | 0.062 | 0.44 | 0.83 | 0.11 | 0.89 | 0.13 | 0.023 | 0.14 |
| OR Quart3 | 3.6 | 16 | 4.6 | 12 | 4.0 | 60 | 1.4 | 1.7 | 1.7 |
| OR Quart 4 | 3.4 | 6.1 | 3.7 | 10 | 2.7 | 28 | 1.1 | 1.00 | 1.1 |
| p Value | 0.011 | 0.095 | 0.013 | 1.6E−4 | 0.14 | 0.0012 | 0.80 | 0.99 | 0.80 |
| 95% CI of | 1.3 | 0.73 | 1.3 | 3.1 | 0.71 | 3.7 | 0.45 | 0.28 | 0.43 |
| OR Quart4 | 8.7 | 51 | 10 | 35 | 10 | 210 | 2.8 | 3.5 | 3.0 |

| | Coagulation factor VII | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 2.91 | 4.90 | 2.91 | 4.98 | 2.91 | 3.79 |
| Average | 6.32 | 5.78 | 6.32 | 7.80 | 6.32 | 4.26 |
| Stdev | 14.6 | 4.33 | 14.6 | 6.92 | 14.6 | 3.96 |
| p(t-test) | | 0.85 | | 0.56 | | 0.56 |
| Min | 0.00408 | 0.423 | 0.00408 | 0.262 | 0.00408 | 0.00408 |
| Max | 249 | 16.3 | 249 | 24.9 | 249 | 11.9 |
| n (Samp) | 421 | 25 | 421 | 33 | 421 | 17 |
| n (Patient) | 165 | 25 | 165 | 33 | 165 | 17 |
| sCr only | | | | | | |
| Median | nd | nd | 3.24 | 4.20 | 3.24 | 6.27 |
| Average | nd | nd | 6.60 | 9.15 | 6.60 | 6.89 |
| Stdev | nd | nd | 13.7 | 8.82 | 13.7 | 6.55 |
| p(t-test) | nd | nd | | 0.60 | | 0.96 |
| Min | nd | nd | 0.00408 | 2.19 | 0.00408 | 0.00408 |
| Max | nd | nd | 249 | 24.9 | 249 | 19.4 |
| n (Samp) | nd | nd | 511 | 8 | 511 | 7 |
| n (Patient) | nd | nd | 198 | 8 | 198 | 7 |
| UO only | | | | | | |
| Median | 2.79 | 5.21 | 2.79 | 4.98 | 2.79 | 3.79 |
| Average | 6.14 | 6.06 | 6.14 | 7.51 | 6.14 | 4.39 |
| Stdev | 15.3 | 4.18 | 15.3 | 6.49 | 15.3 | 3.79 |
| p(t-test) | | 0.98 | | 0.63 | | 0.64 |
| Min | 0.00408 | 0.550 | 0.00408 | 0.262 | 0.00408 | 0.517 |
| Max | 249 | 16.3 | 249 | 19.4 | 249 | 11.9 |
| n (Samp) | 357 | 25 | 357 | 29 | 357 | 17 |
| n (Patient) | 135 | 25 | 135 | 29 | 135 | 17 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.60 | nd | 0.64 | 0.63 | 0.65 | 0.63 | 0.48 | 0.58 | 0.51 |
| SE | 0.061 | nd | 0.061 | 0.054 | 0.11 | 0.057 | 0.072 | 0.11 | 0.072 |
| p | 0.100 | nd | 0.022 | 0.015 | 0.16 | 0.028 | 0.79 | 0.48 | 0.84 |
| nCohort 1 | 421 | nd | 357 | 421 | 511 | 357 | 421 | 511 | 357 |
| nCohort 2 | 25 | nd | 25 | 33 | 8 | 29 | 17 | 7 | 17 |
| Cutoff 1 | 3.28 | nd | 4.12 | 2.73 | 3.00 | 2.73 | 1.04 | 3.28 | 1.28 |
| Sens 1 | 72% | nd | 72% | 73% | 75% | 72% | 71% | 71% | 71% |
| Spec 1 | 53% | nd | 63% | 48% | 48% | 50% | 22% | 50% | 28% |
| Cutoff 2 | 2.54 | nd | 3.28 | 2.16 | 2.42 | 1.43 | 0.837 | 1.81 | 0.906 |
| Sens 2 | 80% | nd | 80% | 82% | 88% | 83% | 82% | 86% | 82% |
| Spec 2 | 47% | nd | 55% | 42% | 42% | 32% | 18% | 36% | 19% |
| Cutoff 3 | 0.762 | nd | 0.940 | 1.32 | 2.16 | 0.539 | 0.513 | 0 | 0.760 |
| Sens 3 | 92% | nd | 92% | 91% | 100% | 93% | 94% | 100% | 94% |
| Spec 3 | 17% | nd | 19% | 30% | 39% | 11% | 11% | 0% | 16% |
| Cutoff 4 | 5.99 | nd | 5.61 | 5.99 | 6.42 | 5.61 | 5.99 | 6.42 | 5.61 |
| Sens 4 | 36% | nd | 48% | 45% | 38% | 48% | 29% | 43% | 24% |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | | | | |
|---|---|---|---|---|---|---|---|---|---|
| Spec 4 | 70% | nd | 70% | 70% | 70% | 70% | 70% | 70% | 70% |
| Cutoff 5 | 8.32 | nd | 8.12 | 8.32 | 9.31 | 8.12 | 8.32 | 9.31 | 8.12 |
| Sens 5 | 16% | nd | 20% | 36% | 38% | 41% | 18% | 29% | 18% |
| Spec 5 | 80% | nd | 80% | 80% | 80% | 80% | 80% | 80% | 80% |
| Cutoff 6 | 13.6 | nd | 12.2 | 13.6 | 14.8 | 12.2 | 13.6 | 14.8 | 12.2 |
| Sens 6 | 8% | nd | 12% | 21% | 25% | 28% | 0% | 14% | 0% |
| Spec 6 | 90% | nd | 90% | 90% | 90% | 90% | 90% | 90% | 90% |
| OR Quart 2 | 0.74 | nd | 0.65 | 3.1 | >4.1 | 1.5 | 1.3 | 0.99 | 0.58 |
| p Value | 0.69 | nd | 0.64 | 0.092 | <0.21 | 0.53 | 0.72 | 1.00 | 0.47 |
| 95% CI of | 0.16 | nd | 0.11 | 0.83 | >0.45 | 0.41 | 0.33 | 0.061 | 0.13 |
| OR Quart2 | 3.4 | nd | 4.0 | 12 | na | 5.6 | 4.9 | 16 | 2.5 |
| OR Quart 3 | 2.6 | nd | 4.4 | 2.4 | >1.0 | 1.5 | 0.49 | 3.0 | 1.0 |
| p Value | 0.11 | nd | 0.025 | 0.21 | <1.0 | 0.52 | 0.42 | 0.34 | 1.0 |
| 95% CI of | 0.80 | nd | 1.2 | 0.61 | >0.062 | 0.42 | 0.088 | 0.31 | 0.28 |
| OR Quart3 | 8.7 | nd | 16 | 9.6 | na | 5.6 | 2.7 | 30 | 3.6 |
| OR Quart 4 | 2.1 | nd | 2.8 | 5.1 | >3.0 | 3.6 | 1.5 | 2.0 | 0.78 |
| p Value | 0.25 | nd | 0.14 | 0.012 | <0.34 | 0.032 | 0.51 | 0.57 | 0.72 |
| 95% CI of | 0.60 | nd | 0.72 | 1.4 | >0.31 | 1.1 | 0.42 | 0.18 | 0.20 |
| OR Quart4 | 7.0 | nd | 11 | 18 | na | 11 | 5.6 | 22 | 3.0 |

Insulin-like growth factor-binding protein 7

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 49.6 | 73.9 | 49.6 | 121 | 49.6 | 76.1 |
| Average | 70.0 | 177 | 70.0 | 203 | 70.0 | 114 |
| Stdev | 68.7 | 304 | 68.7 | 224 | 68.7 | 96.5 |
| p(t-test) | | 5.5E−11 | | 5.8E−23 | | 0.0012 |
| Min | 1.00E−9 | 10.3 | 1.00E−9 | 13.1 | 1.00E−9 | 8.47 |
| Max | 533 | 1830 | 533 | 1250 | 533 | 382 |
| n (Samp) | 691 | 37 | 691 | 48 | 691 | 28 |
| n (Patient) | 280 | 37 | 280 | 48 | 280 | 28 |
| sCr only | | | | | | |
| Median | 52.7 | 195 | 52.7 | 204 | 52.7 | 89.5 |
| Average | 79.1 | 241 | 79.1 | 343 | 79.1 | 160 |
| Stdev | 90.5 | 170 | 90.5 | 473 | 90.5 | 144 |
| p(t-test) | | 1.5E−7 | | 1.1E−18 | | 0.0016 |
| Min | 1.00E−9 | 54.6 | 1.00E−9 | 17.1 | 1.00E−9 | 26.6 |
| Max | 1250 | 594 | 1250 | 1830 | 1250 | 458 |
| n (Samp) | 900 | 9 | 900 | 13 | 900 | 13 |
| n (Patient) | 336 | 9 | 336 | 13 | 336 | 13 |
| UO only | | | | | | |
| Median | 50.1 | 73.9 | 50.1 | 119 | 50.1 | 85.5 |
| Average | 71.2 | 173 | 71.2 | 202 | 71.2 | 122 |
| Stdev | 70.0 | 311 | 70.0 | 230 | 70.0 | 97.4 |
| p(t-test) | | 9.2E−9 | | 7.8E−19 | | 5.1E−4 |
| Min | 1.00E−9 | 10.3 | 1.00E−9 | 13.1 | 1.00E−9 | 8.47 |
| Max | 533 | 1830 | 533 | 1250 | 533 | 382 |
| n (Samp) | 581 | 35 | 581 | 43 | 581 | 25 |
| n (Patient) | 208 | 35 | 208 | 43 | 208 | 25 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.69 | 0.86 | 0.67 | 0.78 | 0.82 | 0.77 | 0.65 | 0.72 | 0.68 |
| SE | 0.049 | 0.079 | 0.051 | 0.040 | 0.072 | 0.043 | 0.057 | 0.081 | 0.060 |
| p | 1.1E−4 | 6.1E−6 | 9.0E−4 | 2.2E−12 | 1.2E−5 | 5.3E−10 | 0.0088 | 0.0063 | 0.0035 |
| nCohort 1 | 691 | 900 | 581 | 691 | 900 | 581 | 691 | 900 | 581 |
| nCohort 2 | 37 | 9 | 35 | 48 | 13 | 43 | 28 | 13 | 25 |
| Cutoff 1 | 57.5 | 133 | 55.1 | 83.2 | 85.6 | 79.0 | 51.2 | 69.9 | 51.8 |
| Sens 1 | 70% | 78% | 71% | 71% | 77% | 72% | 71% | 77% | 72% |
| Spec 1 | 58% | 85% | 55% | 73% | 72% | 71% | 51% | 64% | 52% |
| Cutoff 2 | 46.5 | 68.6 | 39.6 | 65.8 | 73.9 | 65.8 | 34.6 | 54.9 | 47.0 |
| Sens 2 | 81% | 89% | 80% | 81% | 85% | 81% | 82% | 85% | 80% |

TABLE 2-continued

Comparison of marker levels in urine samples collected from Cohort 1 (patients that did not progress beyond RIFLE stage 0 or R) and in urine samples collected from subjects at 0, 24 hours, and 48 hours prior to reaching stage I or F in Cohort 2.

| | | | | | | | | | |
|---|---|---|---|---|---|---|---|---|---|
| Spec 2 | 47% | 62% | 38% | 63% | 67% | 63% | 33% | 52% | 47% |
| Cutoff 3 | 33.6 | 54.4 | 33.2 | 41.6 | 62.3 | 41.6 | 26.4 | 34.7 | 28.2 |
| Sens 3 | 92% | 100% | 91% | 92% | 92% | 91% | 93% | 92% | 92% |
| Spec 3 | 32% | 52% | 30% | 41% | 58% | 40% | 26% | 31% | 27% |
| Cutoff 4 | 76.2 | 82.2 | 77.2 | 76.2 | 82.2 | 77.2 | 76.2 | 82.2 | 77.2 |
| Sens 4 | 49% | 78% | 49% | 73% | 77% | 72% | 50% | 54% | 52% |
| Spec 4 | 70% | 70% | 70% | 70% | 70% | 70% | 70% | 70% | 70% |
| Cutoff 5 | 99.9 | 112 | 99.6 | 99.9 | 112 | 99.6 | 99.9 | 112 | 99.6 |
| Sens 5 | 49% | 78% | 46% | 65% | 69% | 63% | 36% | 38% | 44% |
| Spec 5 | 80% | 80% | 80% | 80% | 80% | 80% | 80% | 80% | 80% |
| Cutoff 6 | 146 | 163 | 147 | 146 | 163 | 147 | 146 | 163 | 147 |
| Sens 6 | 41% | 56% | 37% | 40% | 54% | 37% | 29% | 38% | 32% |
| Spec 6 | 90% | 90% | 90% | 90% | 90% | 90% | 90% | 90% | 90% |
| OR Quart 2 | 2.0 | >0 | 2.4 | 1.7 | 0 | 1.0 | 3.1 | 1.0 | 2.5 |
| p Value | 0.32 | <na | 0.21 | 0.48 | na | 1.0 | 0.18 | 1.0 | 0.27 |
| 95% CI of | 0.50 | >na | 0.61 | 0.39 | na | 0.25 | 0.61 | 0.062 | 0.48 |
| OR Quart2 | 8.3 | na | 9.4 | 7.1 | na | 4.1 | 15 | 16 | 13 |
| OR Quart 3 | 3.5 | >2.0 | 2.8 | 2.7 | 3.0 | 1.8 | 4.1 | 5.1 | 3.1 |
| p Value | 0.062 | <0.57 | 0.14 | 0.14 | 0.34 | 0.36 | 0.076 | 0.14 | 0.17 |
| 95% CI of | 0.94 | >0.18 | 0.72 | 0.71 | 0.31 | 0.51 | 0.86 | 0.59 | 0.61 |
| OR Quart3 | 13 | na | 11 | 10 | 29 | 6.2 | 20 | 44 | 16 |
| OR Quart 4 | 6.5 | >7.2 | 6.2 | 13 | 9.3 | 8.3 | 6.3 | 6.1 | 6.4 |
| p Value | 0.0030 | <0.066 | 0.0040 | 3.6E-5 | 0.035 | 1.1E-4 | 0.017 | 0.095 | 0.016 |
| 95% CI of | 1.9 | >0.88 | 1.8 | 3.8 | 1.2 | 2.8 | 1.4 | 0.73 | 1.4 |
| OR Quart4 | 23 | na | 22 | 42 | 74 | 24 | 29 | 51 | 29 |

TABLE 3

Comparison of marker levels in urine samples collected within 12 hours of reaching stage R from Cohort 1 (patients that reached, but did not progress beyond, RIFLE stage R) and from Cohort 2 (patients that reached RIFLE stage I or F).

Coagulation factor VII

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 4.15 | 4.98 | 1.42 | 2.19 | 5.74 | 6.35 |
| Average | 5.72 | 6.64 | 3.27 | 4.92 | 6.37 | 8.23 |
| Stdev | 5.41 | 6.33 | 3.88 | 5.72 | 5.35 | 6.91 |
| p(t-test) | | 0.52 | | 0.41 | | 0.28 |
| Min | 0.00408 | 0.535 | 0.00408 | 0.842 | 0.409 | 0.423 |
| Max | 20.4 | 19.1 | 14.7 | 16.8 | 20.4 | 19.1 |
| n (Samp) | 52 | 23 | 18 | 7 | 43 | 16 |
| n (Patient) | 52 | 23 | 18 | 7 | 43 | 16 |

At Enrollment

| | sCr or UO | sCr only | UO only |
|---|---|---|---|
| AUC | 0.53 | 0.60 | 0.56 |
| SE | 0.073 | 0.13 | 0.086 |
| p | 0.66 | 0.43 | 0.48 |
| nCohort 1 | 52 | 18 | 43 |
| nCohort 2 | 23 | 7 | 16 |
| Cutoff 1 | 1.45 | 1.45 | 2.87 |
| Sens 1 | 74% | 71% | 75% |
| Spec 1 | 31% | 56% | 37% |
| Cutoff 2 | 0.842 | 0.842 | 1.68 |
| Sens 2 | 83% | 86% | 81% |
| Spec 2 | 15% | 22% | 26% |
| Cutoff 3 | 0.837 | 0.536 | 0.423 |
| Sens 3 | 91% | 100% | 94% |
| Spec 3 | 15% | 22% | 2% |
| Cutoff 4 | 8.08 | 4.03 | 8.49 |
| Sens 4 | 30% | 43% | 38% |
| Spec 4 | 71% | 72% | 72% |
| Cutoff 5 | 10.3 | 6.57 | 10.9 |
| Sens 5 | 26% | 29% | 38% |
| Spec 5 | 81% | 83% | 81% |
| Cutoff 6 | 13.9 | 8.82 | 13.9 |
| Sens 6 | 17% | 14% | 25% |
| Spec 6 | 90% | 94% | 91% |
| OR Quart 2 | 0.93 | 0 | 1.8 |
| p Value | 0.92 | na | 0.48 |
| 95% CI of | 0.22 | na | 0.35 |
| OR Quart2 | 4.0 | na | 9.7 |
| OR Quart 3 | 1.5 | 1.0 | 0.56 |
| p Value | 0.56 | 1.0 | 0.57 |
| 95% CI of | 0.38 | 0.091 | 0.079 |
| OR Quart3 | 6.1 | 11 | 4.0 |
| OR Quart 4 | 1.2 | 1.5 | 2.4 |
| p Value | 0.80 | 0.73 | 0.29 |
| 95% CI of | 0.29 | 0.16 | 0.47 |
| OR Quart4 | 4.9 | 14 | 13 |

TABLE 4

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| | Cancer Antigen 19-9 | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 16.8 | 92.7 | 16.8 | 75.2 | 16.8 | 91.1 |
| Average | 221 | 364 | 221 | 349 | 221 | 72.0 |
| Stdev | 1220 | 831 | 1220 | 835 | 1220 | 41.9 |
| p (t-test) | | 0.69 | | 0.72 | | 0.75 |
| Min | 1.00E-9 | 6.68 | 1.00E-9 | 6.68 | 1.00E-9 | 16.2 |
| Max | 11900 | 2940 | 11900 | 2940 | 11900 | 125 |
| n (Samp) | 99 | 12 | 99 | 12 | 99 | 7 |
| n (Patient) | 99 | 12 | 99 | 12 | 99 | 7 |
| sCr only | | | | | | |
| Median | 24.5 | 95.3 | 24.5 | 72.2 | nd | nd |
| Average | 230 | 184 | 230 | 155 | nd | nd |
| Stdev | 1020 | 235 | 1020 | 242 | nd | nd |
| p (t-test) | | 0.91 | | 0.86 | nd | nd |
| Min | 1.00E-9 | 6.68 | 1.00E-9 | 6.68 | nd | nd |
| Max | 11900 | 645 | 11900 | 645 | nd | nd |
| n (Samp) | 159 | 6 | 159 | 6 | nd | nd |
| n (Patient) | 159 | 6 | 159 | 6 | nd | nd |
| UO only | | | | | | |
| Median | 18.5 | 96.9 | 18.5 | 96.9 | 18.5 | 76.8 |
| Average | 263 | 501 | 263 | 501 | 263 | 68.8 |
| Stdev | 1310 | 1010 | 1310 | 1010 | 1310 | 45.0 |
| p (t-test) | | 0.62 | | 0.62 | | 0.72 |
| Min | 1.00E-9 | 18.6 | 1.00E-9 | 18.6 | 1.00E-9 | 16.2 |
| Max | 11900 | 2940 | 11900 | 2940 | 11900 | 125 |
| n (Samp) | 85 | 8 | 85 | 8 | 85 | 6 |
| n (Patient) | 85 | 8 | 85 | 8 | 85 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.75 | 0.69 | 0.76 | 0.73 | 0.64 | 0.76 | 0.73 | nd | 0.68 |
| SE | 0.085 | 0.12 | 0.10 | 0.086 | 0.12 | 0.10 | 0.11 | nd | 0.12 |
| p | 0.0038 | 0.13 | 0.012 | 0.0079 | 0.25 | 0.012 | 0.036 | nd | 0.15 |
| nCohort 1 | 99 | 159 | 85 | 99 | 159 | 85 | 99 | nd | 85 |
| nCohort 2 | 12 | 6 | 8 | 12 | 6 | 8 | 7 | nd | 6 |
| Cutoff 1 | 50.1 | 50.8 | 57.4 | 33.3 | 33.3 | 57.4 | 57.4 | nd | 18.5 |
| Sens 1 | 75% | 83% | 75% | 75% | 83% | 75% | 71% | nd | 83% |
| Spec 1 | 73% | 65% | 72% | 69% | 59% | 72% | 75% | nd | 51% |
| Cutoff 2 | 20.4 | 50.8 | 19.7 | 20.4 | 33.3 | 19.7 | 18.5 | nd | 18.5 |
| Sens 2 | 83% | 83% | 88% | 83% | 83% | 88% | 86% | nd | 83% |
| Spec 2 | 57% | 65% | 53% | 57% | 59% | 53% | 54% | nd | 51% |
| Cutoff 3 | 18.5 | 6.42 | 18.5 | 18.5 | 6.42 | 18.5 | 16.1 | nd | 15.3 |
| Sens 3 | 92% | 100% | 100% | 92% | 100% | 100% | 100% | nd | 100% |
| Spec 3 | 54% | 18% | 51% | 54% | 18% | 51% | 49% | nd | 46% |
| Cutoff 4 | 43.0 | 66.9 | 55.3 | 43.0 | 66.9 | 55.3 | 43.0 | nd | 55.3 |
| Sens 4 | 75% | 67% | 75% | 67% | 50% | 75% | 71% | nd | 67% |
| Spec 4 | 71% | 70% | 71% | 71% | 70% | 71% | 71% | nd | 71% |
| Cutoff 5 | 76.6 | 125 | 114 | 76.6 | 125 | 114 | 76.6 | nd | 114 |
| Sens 5 | 58% | 33% | 38% | 50% | 17% | 38% | 57% | nd | 17% |
| Spec 5 | 81% | 81% | 80% | 81% | 81% | 80% | 81% | nd | 80% |
| Cutoff 6 | 227 | 396 | 504 | 227 | 396 | 504 | 227 | nd | 504 |
| Sens 6 | 17% | 17% | 25% | 17% | 17% | 25% | 0% | nd | 0% |
| Spec 6 | 91% | 91% | 91% | 91% | 91% | 91% | 91% | nd | 91% |
| OR Quart 2 | 0.96 | 0 | >1.0 | 0.96 | 0 | >1.0 | >1.0 | nd | >2.1 |
| p Value | 0.98 | na | <0.98 | 0.98 | na | <0.98 | <1.0 | nd | <0.56 |
| 95% CI of | 0.057 | na | >0.062 | 0.057 | na | >0.062 | >0.059 | nd | >0.18 |
| OR Quart 2 | 16 | na | na | 16 | na | na | na | nd | na |
| OR Quart 3 | 3.1 | 2.1 | >2.2 | 4.3 | 2.1 | >2.2 | >2.2 | nd | >1.0 |
| p Value | 0.34 | 0.56 | <0.53 | 0.20 | 0.56 | <0.53 | <0.54 | nd | <1.0 |
| 95% CI of | 0.30 | 0.18 | >0.18 | 0.45 | 0.18 | >0.18 | >0.18 | nd | >0.059 |
| OR Quart 3 | 32 | 24 | na | 42 | 24 | na | na | nd | na |
| OR Quart 4 | 8.7 | 3.1 | >6.1 | 7.1 | 3.1 | >6.1 | >4.5 | nd | >3.3 |
| p Value | 0.051 | 0.34 | <0.11 | 0.080 | 0.34 | <0.11 | <0.19 | nd | <0.32 |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| 95% CI of | 0.99 | 0.31 | >0.65 | 0.79 | 0.31 | >0.65 | >0.47 | nd | >0.32 |
|---|---|---|---|---|---|---|---|---|---|
| OR Quart 4 | 76 | 31 | na | 63 | 31 | na | na | nd | na |

C-C motif chemokine 13

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 1.00E−9 | 1.00E−9 | 1.00E−9 | 1.00E−9 | 1.00E−9 | 1.00E−9 |
| Average | 3.50 | 22.9 | 3.50 | 20.2 | 3.50 | 11.9 |
| Stdev | 19.2 | 39.5 | 19.2 | 32.1 | 19.2 | 20.8 |
| p (t-test) | | 1.6E−4 | | 5.8E−4 | | 0.16 |
| Min | 1.00E−9 | 1.00E−9 | 1.00E−9 | 1.00E−9 | 1.00E−9 | 1.00E−9 |
| Max | 214 | 143 | 214 | 101 | 214 | 64.7 |
| n (Samp) | 190 | 21 | 190 | 21 | 190 | 11 |
| n (Patient) | 190 | 21 | 190 | 21 | 190 | 11 |
| sCr only | | | | | | |
| Median | 1.00E−9 | 1.00E−9 | 1.00E−9 | 1.00E−9 | 1.00E−9 | 1.00E−9 |
| Average | 5.03 | 18.9 | 5.03 | 9.33 | 5.03 | 1.17 |
| Stdev | 21.5 | 33.8 | 21.5 | 18.1 | 21.5 | 2.87 |
| p (t-test) | | 0.041 | | 0.51 | | 0.66 |
| Min | 1.00E−9 | 1.00E−9 | 1.00E−9 | 1.00E−9 | 1.00E−9 | 1.00E−9 |
| Max | 214 | 106 | 214 | 55.1 | 214 | 7.03 |
| n (Samp) | 297 | 11 | 297 | 11 | 297 | 6 |
| n (Patient) | 297 | 11 | 297 | 11 | 297 | 6 |
| UO only | | | | | | |
| Median | 1.00E−9 | 7.03 | 1.00E−9 | 7.03 | 1.00E−9 | 7.03 |
| Average | 4.07 | 29.4 | 4.07 | 25.6 | 4.07 | 14.6 |
| Stdev | 21.9 | 44.8 | 21.9 | 36.0 | 21.9 | 22.2 |
| p (t-test) | | 2.7E−4 | | 1.0E−3 | | 0.17 |
| Min | 1.00E−9 | 1.00E−9 | 1.00E−9 | 1.00E−9 | 1.00E−9 | 1.00E−9 |
| Max | 214 | 143 | 214 | 101 | 214 | 64.7 |
| n (Samp) | 136 | 15 | 136 | 15 | 136 | 9 |
| n (Patient) | 136 | 15 | 136 | 15 | 136 | 9 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.69 | 0.67 | 0.72 | 0.69 | 0.62 | 0.72 | 0.68 | 0.51 | 0.73 |
| SE | 0.066 | 0.091 | 0.077 | 0.067 | 0.092 | 0.077 | 0.091 | 0.12 | 0.098 |
| p | 0.0034 | 0.067 | 0.0038 | 0.0035 | 0.20 | 0.0039 | 0.050 | 0.91 | 0.021 |
| nCohort 1 | 190 | 297 | 136 | 190 | 297 | 136 | 190 | 297 | 136 |
| nCohort 2 | 21 | 11 | 15 | 21 | 11 | 15 | 11 | 6 | 9 |
| Cutoff 1 | 0 | 0 | 0 | 0 | 0 | 0 | 0 | 0 | 0 |
| Sens 1 | 100% | 100% | 100% | 100% | 100% | 100% | 100% | 100% | 100% |
| Spec 1 | 0% | 0% | 0% | 0% | 0% | 0% | 0% | 0% | 0% |
| Cutoff 2 | 0 | 0 | 0 | 0 | 0 | 0 | 0 | 0 | 0 |
| Sens 2 | 100% | 100% | 100% | 100% | 100% | 100% | 100% | 100% | 100% |
| Spec 2 | 0% | 0% | 0% | 0% | 0% | 0% | 0% | 0% | 0% |
| Cutoff 3 | 0 | 0 | 0 | 0 | 0 | 0 | 0 | 0 | 0 |
| Sens 3 | 100% | 100% | 100% | 100% | 100% | 100% | 100% | 100% | 100% |
| Spec 3 | 0% | 0% | 0% | 0% | 0% | 0% | 0% | 0% | 0% |
| Cutoff 4 | 1.00E−9 | 1.00E−9 | 1.00E−9 | 1.00E−9 | 1.00E−9 | 1.00E−9 | 1.00E−9 | 1.00E−9 | 1.00E−9 |
| Sens 4 | 48% | 45% | 53% | 48% | 36% | 53% | 45% | 17% | 56% |
| Spec 4 | 90% | 88% | 90% | 90% | 88% | 90% | 90% | 88% | 90% |
| Cutoff 5 | 1.00E−9 | 1.00E−9 | 1.00E−9 | 1.00E−9 | 1.00E−9 | 1.00E−9 | 1.00E−9 | 1.00E−9 | 1.00E−9 |
| Sens 5 | 48% | 45% | 53% | 48% | 36% | 53% | 45% | 17% | 56% |
| Spec 5 | 90% | 88% | 90% | 90% | 88% | 90% | 90% | 88% | 90% |
| Cutoff 6 | 1.00E−9 | 7.03 | 4.08 | 1.00E−9 | 7.03 | 4.08 | 1.00E−9 | 7.03 | 4.08 |
| Sens 6 | 48% | 27% | 53% | 48% | 18% | 53% | 45% | 0% | 56% |
| Spec 6 | 90% | 92% | 90% | 90% | 92% | 90% | 90% | 92% | 90% |
| OR Quart 2 | 12 | 5.3 | >8.4 | 12 | 6.4 | >8.4 | 5.4 | 4.1 | >4.5 |
| p Value | 0.021 | 0.13 | <0.053 | 0.021 | 0.089 | <0.053 | 0.13 | 0.21 | <0.19 |
| 95% CI of | 1.5 | 0.60 | >0.97 | 1.5 | 0.75 | >0.97 | 0.61 | 0.45 | >0.48 |
| OR Quart 2 | 96 | 46 | na | 96 | 55 | na | 48 | 38 | na |
| OR Quart 3 | 0 | 0 | >0 | 0 | 0 | >0 | 0 | 0 | >0 |
| p Value | na | na | <na | na | na | <na | na | na | <na |
| 95% CI of | na | na | >na | na | na | >na | na | na | >na |

TABLE 4-continued

Comparison of the maximum marker levels in urine samples collected from Cohort 1
(patients that did not progress beyond RIFLE stage 0) and the maximum values in
urine samples collected from subjects between enrollment and 0, 24 hours, and 48
hours prior to reaching stage F in Cohort 2.

| | | | | | | | | | |
|---|---|---|---|---|---|---|---|---|---|
| OR Quart 3 | na | na | na | na | na | na | na | na | na |
| OR Quart 4 | 12 | 5.3 | >9.9 | 12 | 4.2 | >9.9 | 5.3 | 0.99 | >5.6 |
| p Value | 0.021 | 0.13 | <0.036 | 0.021 | 0.21 | <0.036 | 0.13 | 0.99 | <0.12 |
| 95% CI of | 1.5 | 0.60 | >1.2 | 1.5 | 0.45 | >1.2 | 0.60 | 0.061 | >0.62 |
| OR Quart 4 | 96 | 46 | na | 96 | 38 | na | 47 | 16 | na |

C—X—C motif chemokine 6

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 14.8 | 61.3 | 14.8 | 51.3 | 14.8 | 37.9 |
| Average | 34.0 | 241 | 34.0 | 163 | 34.0 | 64.9 |
| Stdev | 74.0 | 382 | 74.0 | 232 | 74.0 | 66.9 |
| p (t-test) | | 4.8E−10 | | 7.8E−8 | | 0.18 |
| Min | 1.00E−9 | 5.30 | 1.00E−9 | 1.62 | 1.00E−9 | 8.72 |
| Max | 593 | 1450 | 593 | 769 | 593 | 172 |
| n (Samp) | 190 | 21 | 190 | 21 | 190 | 11 |
| n (Patient) | 190 | 21 | 190 | 21 | 190 | 11 |
| sCr only | | | | | | |
| Median | 21.0 | 53.8 | 21.0 | 51.3 | 21.0 | 52.6 |
| Average | 57.2 | 253 | 57.2 | 171 | 57.2 | 182 |
| Stdev | 172 | 452 | 172 | 282 | 172 | 292 |
| p (t-test) | | 7.5E−4 | | 0.036 | | 0.083 |
| Min | 1.00E−9 | 5.30 | 1.00E−9 | 1.62 | 1.00E−9 | 17.6 |
| Max | 2500 | 1450 | 2500 | 769 | 2500 | 769 |
| n (Samp) | 297 | 11 | 297 | 11 | 297 | 6 |
| n (Patient) | 297 | 11 | 297 | 11 | 297 | 6 |
| UO only | | | | | | |
| Median | 17.8 | 163 | 17.8 | 114 | 17.8 | 24.7 |
| Average | 36.8 | 323 | 36.8 | 216 | 36.8 | 69.1 |
| Stdev | 76.2 | 428 | 76.2 | 256 | 76.2 | 74.0 |
| p (t-test) | | 7.5E−11 | | 6.3E−9 | | 0.22 |
| Min | 1.00E−9 | 9.04 | 1.00E−9 | 9.04 | 1.00E−9 | 8.72 |
| Max | 593 | 1450 | 593 | 769 | 593 | 172 |
| n (Samp) | 136 | 15 | 136 | 15 | 136 | 9 |
| n (Patient) | 136 | 15 | 136 | 15 | 136 | 9 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.79 | 0.71 | 0.82 | 0.77 | 0.67 | 0.81 | 0.71 | 0.77 | 0.65 |
| SE | 0.060 | 0.089 | 0.068 | 0.062 | 0.091 | 0.069 | 0.090 | 0.11 | 0.10 |
| p | 1.3E−6 | 0.017 | 2.7E−6 | 1.8E−5 | 0.066 | 5.7E−6 | 0.018 | 0.016 | 0.14 |
| nCohort 1 | 190 | 297 | 136 | 190 | 297 | 136 | 190 | 297 | 136 |
| nCohort 2 | 21 | 11 | 15 | 21 | 11 | 15 | 11 | 6 | 9 |
| Cutoff 1 | 33.0 | 33.0 | 47.5 | 24.0 | 22.0 | 47.5 | 17.6 | 37.6 | 14.3 |
| Sens 1 | 71% | 73% | 73% | 71% | 73% | 73% | 73% | 83% | 78% |
| Spec 1 | 75% | 64% | 82% | 66% | 53% | 82% | 56% | 69% | 43% |
| Cutoff 2 | 17.6 | 17.6 | 23.5 | 17.6 | 17.6 | 23.5 | 14.3 | 37.6 | 9.02 |
| Sens 2 | 81% | 82% | 80% | 81% | 82% | 80% | 82% | 83% | 89% |
| Spec 2 | 56% | 45% | 61% | 56% | 45% | 61% | 49% | 69% | 30% |
| Cutoff 3 | 11.5 | 11.5 | 11.9 | 11.5 | 11.5 | 11.9 | 9.03 | 17.6 | 8.41 |
| Sens 3 | 90% | 91% | 93% | 90% | 91% | 93% | 91% | 100% | 100% |
| Spec 3 | 43% | 32% | 38% | 43% | 32% | 38% | 36% | 45% | 29% |
| Cutoff 4 | 27.0 | 38.6 | 30.7 | 27.0 | 38.6 | 30.7 | 27.0 | 38.6 | 30.7 |
| Sens 4 | 71% | 64% | 73% | 67% | 55% | 73% | 55% | 67% | 44% |
| Spec 4 | 70% | 70% | 71% | 70% | 70% | 71% | 70% | 70% | 71% |
| Cutoff 5 | 39.8 | 53.3 | 39.8 | 39.8 | 53.3 | 39.8 | 39.8 | 53.3 | 39.8 |
| Sens 5 | 67% | 55% | 73% | 62% | 45% | 73% | 45% | 50% | 44% |
| Spec 5 | 80% | 80% | 80% | 80% | 80% | 80% | 80% | 80% | 80% |
| Cutoff 6 | 57.9 | 111 | 68.0 | 57.9 | 111 | 68.0 | 57.9 | 111 | 68.0 |
| Sens 6 | 52% | 36% | 60% | 43% | 27% | 60% | 27% | 33% | 33% |
| Spec 6 | 90% | 90% | 90% | 90% | 90% | 90% | 90% | 90% | 90% |
| OR Quart 2 | 3.1 | 2.0 | >3.2 | 3.1 | 2.0 | >3.2 | >3.2 | >1.0 | >4.5 |
| p Value | 0.34 | 0.57 | <0.33 | 0.34 | 0.57 | <0.33 | <0.32 | <1.0 | <0.19 |
| 95% CI of | 0.31 | 0.18 | >0.31 | 0.31 | 0.18 | >0.31 | >0.32 | >0.061 | >0.48 |
| OR Quart 2 | 30 | 23 | na | 30 | 23 | na | na | na | na |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| | | | | | | | | | |
|---|---|---|---|---|---|---|---|---|---|
| OR Quart 3 | 3.1 | 2.0 | >1.0 | 4.2 | 2.0 | >1.0 | >2.1 | >1.0 | >1.0 |
| p Value | 0.34 | 0.57 | <1.0 | 0.21 | 0.57 | <1.0 | <0.55 | <1.0 | <0.98 |
| 95% CI of | 0.31 | 0.18 | >0.060 | 0.45 | 0.18 | >0.060 | >0.18 | >0.061 | >0.062 |
| OR Quart 3 | 30 | 23 | na | 39 | 23 | na | na | na | na |
| OR Quart 4 | 18 | 6.4 | >15 | 17 | 6.4 | >15 | >6.7 | >4.2 | >4.4 |
| p Value | 0.0059 | 0.089 | <0.012 | 0.0080 | 0.089 | <0.012 | <0.084 | <0.21 | <0.20 |
| 95% CI of | 2.3 | 0.75 | >1.8 | 2.1 | 0.75 | >1.8 | >0.77 | >0.45 | >0.46 |
| OR Quart 4 | 150 | 55 | na | 130 | 55 | na | na | na | na |

Coagulation factor VII

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 4.12 | 7.44 | 4.12 | 7.41 | 4.12 | 5.89 |
| Average | 8.33 | 12.6 | 8.33 | 10.3 | 8.33 | 8.14 |
| Stdev | 12.0 | 12.2 | 12.0 | 8.04 | 12.0 | 7.18 |
| p (t-test) | | 0.19 | | 0.55 | | 0.96 |
| Min | 0.00408 | 0.491 | 0.00408 | 0.348 | 0.00408 | 3.18 |
| Max | 65.5 | 48.8 | 65.5 | 24.9 | 65.5 | 24.8 |
| n (Samp) | 103 | 16 | 103 | 15 | 103 | 8 |
| n (Patient) | 103 | 16 | 103 | 15 | 103 | 8 |
| sCr only | | | | | | |
| Median | 5.99 | 13.4 | 5.99 | 13.2 | nd | nd |
| Average | 10.7 | 17.2 | 10.7 | 13.4 | nd | nd |
| Stdev | 21.3 | 15.8 | 21.3 | 9.62 | nd | nd |
| p (t-test) | | 0.40 | | 0.72 | nd | nd |
| Min | 0.00408 | 0.491 | 0.00408 | 0.348 | nd | nd |
| Max | 249 | 48.8 | 249 | 24.9 | nd | nd |
| n (Samp) | 170 | 8 | 170 | 8 | nd | nd |
| n (Patient) | 170 | 8 | 170 | 8 | nd | nd |
| UO only | | | | | | |
| Median | 3.83 | 7.44 | 3.83 | 7.41 | 3.83 | 4.54 |
| Average | 7.81 | 9.13 | 7.81 | 8.15 | 7.81 | 5.64 |
| Stdev | 11.9 | 5.61 | 11.9 | 5.33 | 11.9 | 2.93 |
| p (t-test) | | 0.73 | | 0.93 | | 0.66 |
| Min | 0.00408 | 3.48 | 0.00408 | 3.18 | 0.00408 | 3.18 |
| Max | 65.5 | 19.4 | 65.5 | 19.4 | 65.5 | 10.7 |
| n (Samp) | 87 | 10 | 87 | 9 | 87 | 6 |
| n (Patient) | 87 | 10 | 87 | 9 | 87 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.68 | 0.67 | 0.70 | 0.65 | 0.65 | 0.66 | 0.62 | nd | 0.58 |
| SE | 0.078 | 0.11 | 0.096 | 0.081 | 0.11 | 0.10 | 0.11 | nd | 0.13 |
| p | 0.020 | 0.12 | 0.039 | 0.063 | 0.16 | 0.12 | 0.29 | nd | 0.51 |
| nCohort 1 | 103 | 170 | 87 | 103 | 170 | 87 | 103 | nd | 87 |
| nCohort 2 | 16 | 8 | 10 | 15 | 8 | 9 | 8 | nd | 6 |
| Cutoff 1 | 5.28 | 6.42 | 5.28 | 5.28 | 6.42 | 3.72 | 3.72 | nd | 3.31 |
| Sens 1 | 75% | 75% | 70% | 73% | 75% | 78% | 75% | nd | 83% |
| Spec 1 | 57% | 54% | 61% | 57% | 54% | 49% | 48% | nd | 46% |
| Cutoff 2 | 4.32 | 5.29 | 4.32 | 3.72 | 5.29 | 3.31 | 3.31 | nd | 3.31 |
| Sens 2 | 81% | 88% | 80% | 80% | 88% | 89% | 88% | nd | 83% |
| Spec 2 | 53% | 46% | 56% | 48% | 46% | 46% | 43% | nd | 46% |
| Cutoff 3 | 3.31 | 0.435 | 3.72 | 3.07 | 0.313 | 3.07 | 3.07 | nd | 3.07 |
| Sens 3 | 94% | 100% | 90% | 93% | 100% | 100% | 100% | nd | 100% |
| Spec 3 | 43% | 4% | 49% | 40% | 1% | 43% | 40% | nd | 43% |
| Cutoff 4 | 7.83 | 10.3 | 7.42 | 7.83 | 10.3 | 7.42 | 7.83 | nd | 7.42 |
| Sens 4 | 44% | 50% | 50% | 40% | 50% | 44% | 25% | nd | 17% |
| Spec 4 | 71% | 71% | 70% | 71% | 71% | 70% | 71% | nd | 70% |
| Cutoff 5 | 12.8 | 14.3 | 10.1 | 12.8 | 14.3 | 10.1 | 12.8 | nd | 10.1 |
| Sens 5 | 31% | 50% | 40% | 27% | 50% | 33% | 12% | nd | 17% |
| Spec 5 | 81% | 80% | 80% | 81% | 80% | 80% | 81% | nd | 80% |
| Cutoff 6 | 19.4 | 21.0 | 17.3 | 19.4 | 21.0 | 17.3 | 19.4 | nd | 17.3 |
| Sens 6 | 19% | 38% | 10% | 13% | 25% | 11% | 12% | nd | 0% |
| Spec 6 | 90% | 90% | 91% | 90% | 90% | 91% | 90% | nd | 91% |
| OR Quart 2 | 3.1 | 0.98 | >2.2 | 3.1 | 0.98 | >3.4 | >3.2 | nd | >3.4 |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| p Value | 0.34 | 0.99 | <0.54 | 0.34 | 0.99 | <0.30 | <0.32 | nd | <0.30 |
|---|---|---|---|---|---|---|---|---|---|
| 95% CI of | 0.30 | 0.059 | >0.18 | 0.30 | 0.059 | >0.33 | >0.32 | nd | >0.33 |
| OR Quart 2 | 32 | 16 | na | 32 | 16 | na | na | nd | na |
| OR Quart 3 | 5.6 | 2.0 | >4.8 | 5.8 | 2.0 | >3.4 | >3.2 | nd | >2.2 |
| p Value | 0.13 | 0.56 | <0.18 | 0.12 | 0.56 | <0.30 | <0.32 | nd | <0.53 |
| 95% CI of | 0.61 | 0.18 | >0.50 | 0.64 | 0.18 | >0.33 | >0.32 | nd | >0.18 |
| OR Quart 3 | 51 | 23 | na | 53 | 23 | na | na | nd | na |
| OR Quart 4 | 8.5 | 4.2 | >4.6 | 7.0 | 4.2 | >3.4 | >2.1 | nd | >1.0 |
| p Value | 0.053 | 0.21 | <0.19 | 0.081 | 0.21 | <0.30 | <0.56 | nd | <1.0 |
| 95% CI of | 0.98 | 0.45 | >0.47 | 0.79 | 0.45 | >0.33 | >0.18 | nd | >0.059 |
| OR Quart 4 | 74 | 39 | na | 62 | 39 | na | na | nd | na |

Insulin-like growth factor-binding protein 7

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 54.4 | 210 | 54.4 | 206 | 54.4 | 165 |
| Average | 77.4 | 379 | 77.4 | 297 | 77.4 | 173 |
| Stdev | 79.3 | 440 | 79.3 | 285 | 79.3 | 92.7 |
| p (t-test) | | 5.8E−15 | | 1.8E−14 | | 1.7E−4 |
| Min | 1.93 | 27.2 | 1.93 | 23.1 | 1.93 | 53.6 |
| Max | 533 | 1830 | 533 | 1250 | 533 | 382 |
| n (Samp) | 190 | 21 | 190 | 21 | 190 | 11 |
| n (Patient) | 190 | 21 | 190 | 21 | 190 | 11 |
| sCr only | | | | | | |
| Median | 74.0 | 210 | 74.0 | 206 | 74.0 | 208 |
| Average | 109 | 314 | 109 | 215 | 109 | 232 |
| Stdev | 119 | 320 | 119 | 153 | 119 | 141 |
| p (t-test) | | 5.7E−7 | | 0.0044 | | 0.013 |
| Min | 1.93 | 27.2 | 1.93 | 23.1 | 1.93 | 53.6 |
| Max | 1250 | 1120 | 1250 | 458 | 1250 | 458 |
| n (Samp) | 296 | 11 | 296 | 11 | 296 | 6 |
| n (Patient) | 296 | 11 | 296 | 11 | 296 | 6 |
| UO only | | | | | | |
| Median | 61.2 | 247 | 61.2 | 247 | 61.2 | 165 |
| Average | 85.1 | 468 | 85.1 | 362 | 85.1 | 182 |
| Stdev | 81.9 | 490 | 81.9 | 308 | 81.9 | 93.3 |
| p (t-test) | | 5.3E−14 | | 5.4E−14 | | 8.9E−4 |
| Min | 1.93 | 80.7 | 1.93 | 80.7 | 1.93 | 80.7 |
| Max | 533 | 1830 | 533 | 1250 | 533 | 382 |
| n (Samp) | 136 | 15 | 136 | 15 | 136 | 9 |
| n (Patient) | 136 | 15 | 136 | 15 | 136 | 9 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.85 | 0.74 | 0.91 | 0.84 | 0.72 | 0.91 | 0.84 | 0.80 | 0.85 |
| SE | 0.054 | 0.087 | 0.051 | 0.055 | 0.089 | 0.052 | 0.076 | 0.11 | 0.082 |
| p | 1.2E−10 | 0.0065 | 1.3E−15 | 4.1E−10 | 0.013 | 2.9E−15 | 7.3E−6 | 0.0061 | 2.4E−5 |
| nCohort 1 | 190 | 296 | 136 | 190 | 296 | 136 | 190 | 296 | 136 |
| nCohort 2 | 21 | 11 | 15 | 21 | 11 | 15 | 11 | 6 | 9 |
| Cutoff 1 | 145 | 145 | 163 | 140 | 140 | 163 | 103 | 145 | 103 |
| Sens 1 | 71% | 73% | 73% | 71% | 73% | 73% | 73% | 83% | 78% |
| Spec 1 | 89% | 78% | 90% | 88% | 77% | 90% | 77% | 78% | 73% |
| Cutoff 2 | 103 | 53.2 | 145 | 103 | 53.2 | 145 | 100 | 145 | 100 |
| Sens 2 | 81% | 82% | 80% | 81% | 82% | 80% | 82% | 83% | 89% |
| Spec 2 | 77% | 36% | 87% | 77% | 36% | 87% | 75% | 78% | 71% |
| Cutoff 3 | 53.2 | 39.0 | 103 | 53.2 | 39.0 | 103 | 76.5 | 53.2 | 76.4 |
| Sens 3 | 90% | 91% | 93% | 90% | 91% | 93% | 91% | 100% | 100% |
| Spec 3 | 49% | 24% | 73% | 49% | 24% | 73% | 65% | 36% | 59% |
| Cutoff 4 | 91.1 | 114 | 99.6 | 91.1 | 114 | 99.6 | 91.1 | 114 | 99.6 |
| Sens 4 | 81% | 73% | 93% | 81% | 73% | 93% | 82% | 83% | 89% |
| Spec 4 | 70% | 70% | 71% | 70% | 70% | 71% | 70% | 70% | 71% |
| Cutoff 5 | 114 | 154 | 127 | 114 | 154 | 127 | 114 | 154 | 127 |
| Sens 5 | 76% | 64% | 80% | 76% | 55% | 80% | 64% | 67% | 67% |
| Spec 5 | 80% | 80% | 80% | 80% | 80% | 80% | 80% | 80% | 80% |
| Cutoff 6 | 151 | 257 | 172 | 151 | 257 | 172 | 151 | 257 | 172 |

TABLE 4-continued

Comparison of the maximum marker levels in urine samples collected from Cohort 1 (patients that did not progress beyond RIFLE stage 0) and the maximum values in urine samples collected from subjects between enrollment and 0, 24 hours, and 48 hours prior to reaching stage F in Cohort 2.

| | | | | | | | | | |
|---|---|---|---|---|---|---|---|---|---|
| Sens 6 | 67% | 36% | 67% | 62% | 36% | 67% | 55% | 33% | 44% |
| Spec 6 | 90% | 90% | 90% | 90% | 90% | 90% | 90% | 90% | 90% |
| OR Quart 2 | 2.0 | 0.49 | >0 | 2.0 | 0.49 | >0 | >1.0 | >1.0 | >0 |
| p Value | 0.58 | 0.56 | <na | 0.58 | 0.56 | <na | <0.99 | <1.0 | <na |
| 95% CI of | 0.18 | 0.043 | >na | 0.18 | 0.043 | >na | >0.062 | >0.061 | >na |
| OR Quart 2 | 23 | 5.5 | na | 23 | 5.5 | na | na | na | na |
| OR Quart 3 | 2.0 | 0 | >3.2 | 2.0 | 0 | >3.2 | >3.2 | >0 | >3.3 |
| p Value | 0.58 | na | <0.33 | 0.58 | na | <0.33 | <0.32 | <na | <0.31 |
| 95% CI of | 0.18 | na | >0.31 | 0.18 | na | >0.31 | >0.32 | >na | >0.32 |
| OR Quart 3 | 23 | na | na | 23 | na | na | na | na | na |
| OR Quart 4 | 22 | 4.3 | >17 | 22 | 4.3 | >17 | >8.0 | >5.3 | >7.0 |
| p Value | 0.0033 | 0.072 | <0.0081 | 0.0033 | 0.072 | <0.0081 | <0.057 | <0.13 | <0.080 |
| 95% CI of | 2.8 | 0.88 | >2.1 | 2.8 | 0.88 | >2.1 | >0.94 | >0.60 | >0.79 |
| OR Quart 4 | 170 | 21 | na | 170 | 21 | na | na | na | na |

TABLE 5

Comparison of marker levels in EDTA samples collected from Cohort 1 (patients that did not progress beyond RIFLE stage 0) and in EDTA samples collected from subjects at 0, 24 hours, and 48 hours prior to reaching stage R, I or F in Cohort 2.

| Cancer Antigen 19-9 | | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.204 | 0.311 | 0.204 | 0.316 | 0.204 | 0.205 |
| Average | 0.320 | 0.631 | 0.320 | 0.804 | 0.320 | 0.486 |
| Stdev | 0.642 | 0.759 | 0.642 | 1.07 | 0.642 | 0.749 |
| p (t-test) | | 0.023 | | 0.0019 | | 0.27 |
| Min | 1.00E−9 | 1.00E−9 | 1.00E−9 | 1.00E−9 | 1.00E−9 | 1.00E−9 |
| Max | 5.30 | 2.79 | 5.30 | 5.26 | 5.30 | 2.83 |
| n (Samp) | 81 | 37 | 81 | 45 | 81 | 26 |
| n (Patient) | 74 | 37 | 74 | 45 | 74 | 26 |
| sCr only | | | | | | |
| Median | 0.244 | 0.333 | 0.244 | 0.695 | 0.244 | 0.228 |
| Average | 0.466 | 0.735 | 0.466 | 3.65 | 0.466 | 0.763 |
| Stdev | 0.757 | 0.824 | 0.757 | 10.9 | 0.757 | 1.08 |
| p (t-test) | | 0.24 | | 6.4E−5 | | 0.26 |
| Min | 1.00E−9 | 1.00E−9 | 1.00E−9 | 1.00E−9 | 1.00E−9 | 1.00E−9 |
| Max | 5.30 | 2.77 | 5.30 | 41.6 | 5.30 | 2.83 |
| n (Samp) | 197 | 12 | 197 | 14 | 197 | 9 |
| n (Patient) | 131 | 12 | 131 | 14 | 131 | 9 |
| UO only | | | | | | |
| Median | 0.244 | 0.311 | 0.244 | 0.285 | 0.244 | 0.228 |
| Average | 0.484 | 0.563 | 0.484 | 0.738 | 0.484 | 0.334 |
| Stdev | 0.774 | 0.703 | 0.774 | 1.05 | 0.774 | 0.432 |
| p (t-test) | | 0.63 | | 0.13 | | 0.40 |
| Min | 1.00E−9 | 1.00E−9 | 1.00E−9 | 1.00E−9 | 1.00E−9 | 1.00E−9 |
| Max | 5.30 | 2.79 | 5.30 | 5.26 | 5.30 | 1.94 |
| n (Samp) | 77 | 29 | 77 | 43 | 77 | 21 |
| n (Patient) | 64 | 29 | 64 | 43 | 64 | 21 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCR only | UO only |
| AUC | 0.65 | 0.62 | 0.55 | 0.67 | 0.69 | 0.58 | 0.53 | 0.54 | 0.45 |
| SE | 0.056 | 0.089 | 0.064 | 0.052 | 0.081 | 0.055 | 0.066 | 0.10 | 0.072 |
| p | 0.0075 | 0.16 | 0.46 | 7.8E−4 | 0.018 | 0.16 | 0.62 | 0.69 | 0.48 |
| nCohort 1 | 81 | 197 | 77 | 81 | 197 | 77 | 81 | 197 | 77 |
| nCohort 2 | 37 | 12 | 29 | 45 | 14 | 43 | 26 | 9 | 21 |
| Cutoff 1 | 0.204 | 0.204 | 0.134 | 0.204 | 0.244 | 0.182 | 0.0851 | 0.134 | 0.0842 |
| Sens 1 | 70% | 75% | 72% | 71% | 71% | 72% | 73% | 78% | 71% |
| Spec 1 | 53% | 43% | 29% | 53% | 52% | 39% | 28% | 30% | 22% |

TABLE 5-continued

Comparison of marker levels in EDTA samples collected from
Cohort 1 (patients that did not progress beyond RIFLE stage 0) and in EDTA samples
collected from subjects at 0, 24 hours, and 48 hours prior to reaching stage R, I or F in
Cohort 2.

| | | | | | | | | | |
|---|---|---|---|---|---|---|---|---|---|
| Cutoff 2 | 0.124 | 0.198 | 0.0783 | 0.174 | 0.175 | 0.134 | 0.0291 | 0.124 | 0.0291 |
| Sens 2 | 81% | 83% | 83% | 80% | 93% | 81% | 85% | 89% | 86% |
| Spec 2 | 35% | 41% | 14% | 43% | 36% | 29% | 15% | 30% | 10% |
| Cutoff 3 | 1.00E−9 | 0.124 | 0 | 0.00741 | 0.175 | 1.00E−9 | 0 | 0 | 1.00E−9 |
| Sens 3 | 92% | 92% | 100% | 91% | 93% | 91% | 100% | 100% | 90% |
| Spec 3 | 10% | 30% | 0% | 14% | 36% | 9% | 0% | 0% | 9% |
| Cutoff 4 | 0.308 | 0.405 | 0.401 | 0.308 | 0.405 | 0.401 | 0.308 | 0.405 | 0.401 |
| Sens 4 | 51% | 50% | 45% | 51% | 57% | 44% | 42% | 33% | 29% |
| Spec 4 | 70% | 70% | 70% | 70% | 70% | 70% | 70% | 70% | 70% |
| Cutoff 5 | 0.357 | 0.590 | 0.633 | 0.357 | 0.590 | 0.633 | 0.357 | 0.590 | 0.633 |
| Sens 5 | 49% | 42% | 24% | 49% | 57% | 30% | 31% | 33% | 14% |
| Spec 5 | 80% | 81% | 81% | 80% | 81% | 81% | 80% | 81% | 81% |
| Cutoff 6 | 0.614 | 0.944 | 1.27 | 0.614 | 0.944 | 1.27 | 0.614 | 0.944 | 1.27 |
| Sens 6 | 27% | 33% | 14% | 40% | 29% | 19% | 19% | 22% | 5% |
| Spec 6 | 90% | 90% | 91% | 90% | 90% | 91% | 90% | 90% | 91% |
| OR Quart 2 | 1.2 | 4.2 | 0.78 | 1.9 | 3.1 | 1.8 | 0.78 | 4.2 | 1.8 |
| p Value | 0.81 | 0.20 | 0.69 | 0.28 | 0.34 | 0.28 | 0.69 | 0.21 | 0.44 |
| 95% CI of | 0.34 | 0.46 | 0.22 | 0.59 | 0.31 | 0.62 | 0.22 | 0.45 | 0.43 |
| OR Quart 2 | 4.0 | 39 | 2.7 | 6.1 | 30 | 5.5 | 2.7 | 39 | 7.2 |
| OR Quart 3 | 1.5 | 2.0 | 1.0 | 1.7 | 2.0 | 1.4 | 0.47 | 1.0 | 1.3 |
| p Value | 0.54 | 0.57 | 1.0 | 0.38 | 0.58 | 0.57 | 0.28 | 1.0 | 0.71 |
| 95% CI of | 0.43 | 0.18 | 0.29 | 0.52 | 0.18 | 0.45 | 0.12 | 0.061 | 0.31 |
| OR Quart 3 | 4.9 | 23 | 3.4 | 5.6 | 23 | 4.2 | 1.9 | 16 | 5.6 |
| OR Quart 4 | 4.4 | 5.3 | 1.4 | 6.9 | 9.1 | 2.1 | 1.4 | 3.1 | 1.8 |
| p Value | 0.012 | 0.13 | 0.61 | 8.9E−4 | 0.041 | 0.18 | 0.61 | 0.34 | 0.44 |
| 95% CI of | 1.4 | 0.60 | 0.42 | 2.2 | 1.1 | 0.71 | 0.42 | 0.31 | 0.43 |
| OR Quart 4 | 14 | 47 | 4.4 | 22 | 75 | 6.2 | 4.4 | 30 | 7.2 |

C-C motif chemokine 13

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 21.0 | 1.00E−9 | 21.0 | 22.6 | 21.0 | 49.4 |
| Average | 102 | 42.7 | 102 | 49.6 | 102 | 60.4 |
| Stdev | 364 | 79.8 | 364 | 72.1 | 364 | 63.8 |
| p (t-test) | | 0.39 | | 0.41 | | 0.64 |
| Min | 1.00E−9 | 1.00E−9 | 1.00E−9 | 1.00E−9 | 1.00E−9 | 1.00E−9 |
| Max | 2520 | 361 | 2520 | 279 | 2520 | 284 |
| n (Samp) | 52 | 29 | 52 | 34 | 52 | 18 |
| n (Patient) | 50 | 29 | 50 | 34 | 50 | 18 |
| sCr only | | | | | | |
| Median | 8.21 | 54.8 | 8.21 | 44.2 | 8.21 | 54.3 |
| Average | 58.9 | 92.4 | 58.9 | 101 | 58.9 | 76.7 |
| Stdev | 235 | 121 | 235 | 180 | 235 | 87.9 |
| p (t-test) | | 0.66 | | 0.47 | | 0.83 |
| Min | 1.00E−9 | 1.00E−9 | 1.00E−9 | 1.00E−9 | 1.00E−9 | 1.00E−9 |
| Max | 2520 | 361 | 2520 | 713 | 2520 | 284 |
| n (Samp) | 132 | 10 | 132 | 17 | 132 | 8 |
| n (Patient) | 100 | 10 | 100 | 17 | 100 | 8 |
| UO only | | | | | | |
| Median | 21.0 | 1.00E−9 | 21.0 | 1.00E−9 | 21.0 | 38.0 |
| Average | 109 | 13.6 | 109 | 33.2 | 109 | 39.5 |
| Stdev | 362 | 21.9 | 362 | 48.9 | 362 | 35.5 |
| p (t-test) | | 0.21 | | 0.26 | | 0.49 |
| Min | 1.00E−9 | 1.00E−9 | 1.00E−9 | 1.00E−9 | 1.00E−9 | 1.00E−9 |
| Max | 2520 | 62.8 | 2520 | 186 | 2520 | 96.3 |
| n (Samp) | 53 | 23 | 53 | 30 | 53 | 13 |
| n (Patient) | 46 | 23 | 46 | 30 | 46 | 13 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCR only | UO only |
| AUC | 0.44 | 0.63 | 0.32 | 0.49 | 0.59 | 0.43 | 0.64 | 0.71 | 0.54 |
| SE | 0.067 | 0.098 | 0.070 | 0.064 | 0.076 | 0.066 | 0.079 | 0.11 | 0.091 |
| p | 0.36 | 0.19 | 0.010 | 0.92 | 0.22 | 0.28 | 0.076 | 0.043 | 0.69 |
| nCohort 1 | 52 | 132 | 53 | 52 | 132 | 53 | 52 | 132 | 53 |
| nCohort 2 | 29 | 10 | 23 | 34 | 17 | 30 | 18 | 8 | 13 |

TABLE 5-continued

Comparison of marker levels in EDTA samples collected from
Cohort 1 (patients that did not progress beyond RIFLE stage 0) and in EDTA samples
collected from subjects at 0, 24 hours, and 48 hours prior to reaching stage R, I or F in
Cohort 2.

| | | | | | | | | | |
|---|---|---|---|---|---|---|---|---|---|
| Cutoff 1 | 0 | 0 | 0 | 0 | 0 | 0 | 23.9 | 38.0 | 7.19 |
| Sens 1 | 100% | 100% | 100% | 100% | 100% | 100% | 72% | 75% | 77% |
| Spec 1 | 0% | 0% | 0% | 0% | 0% | 0% | 58% | 64% | 42% |
| Cutoff 2 | 0 | 0 | 0 | 0 | 0 | 0 | 7.19 | 21.8 | 0 |
| Sens 2 | 100% | 100% | 100% | 100% | 100% | 100% | 89% | 88% | 100% |
| Spec 2 | 0% | 0% | 0% | 0% | 0% | 0% | 44% | 58% | 0% |
| Cutoff 3 | 0 | 0 | 0 | 0 | 0 | 0 | 0 | 0 | 0 |
| Sens 3 | 100% | 100% | 100% | 100% | 100% | 100% | 100% | 100% | 100% |
| Spec 3 | 0% | 0% | 0% | 0% | 0% | 0% | 0% | 0% | 0% |
| Cutoff 4 | 56.0 | 44.2 | 62.8 | 56.0 | 44.2 | 62.8 | 56.0 | 44.2 | 62.8 |
| Sens 4 | 17% | 60% | 0% | 29% | 47% | 20% | 39% | 62% | 31% |
| Spec 4 | 71% | 72% | 72% | 71% | 72% | 72% | 71% | 72% | 72% |
| Cutoff 5 | 72.2 | 59.5 | 72.2 | 72.2 | 59.5 | 72.2 | 72.2 | 59.5 | 72.2 |
| Sens 5 | 14% | 40% | 0% | 21% | 41% | 17% | 28% | 38% | 23% |
| Spec 5 | 81% | 80% | 81% | 81% | 80% | 81% | 81% | 80% | 81% |
| Cutoff 6 | 105 | 92.0 | 105 | 105 | 92.0 | 105 | 105 | 92.0 | 105 |
| Sens 6 | 10% | 40% | 0% | 15% | 24% | 13% | 6% | 12% | 0% |
| Spec 6 | 90% | 90% | 91% | 90% | 90% | 91% | 90% | 90% | 91% |
| OR Quart 2 | 1.3 | 0 | 3.0 | 0.60 | >10 | 1.2 | 4.6 | 0 | 4.6 |
| p Value | 0.66 | na | 0.22 | 0.42 | <0.033 | 0.74 | 0.20 | na | 0.20 |
| 95% CI of | 0.36 | na | 0.51 | 0.17 | >1.2 | 0.34 | 0.46 | na | 0.46 |
| OR Quart 2 | 5.0 | na | 18 | 2.1 | na | 4.6 | 46 | na | 47 |
| OR Quart 3 | 2.0 | 0.23 | 9.4 | 1.0 | >1.0 | 2.3 | 8.7 | 4.4 | 5.0 |
| p Value | 0.28 | 0.20 | 0.010 | 1.0 | <0.98 | 0.21 | 0.059 | 0.20 | 0.17 |
| 95% CI of | 0.56 | 0.024 | 1.7 | 0.31 | >0.062 | 0.63 | 0.92 | 0.46 | 0.49 |
| OR Quart 3 | 7.5 | 2.2 | 53 | 3.3 | na | 8.1 | 83 | 41 | 51 |
| OR Quart 4 | 1.3 | 1.2 | 3.9 | 0.60 | >9.9 | 1.3 | 10 | 3.2 | 4.6 |
| p Value | 0.66 | 0.76 | 0.13 | 0.42 | <0.036 | 0.66 | 0.042 | 0.33 | 0.20 |
| 95% CI of | 0.36 | 0.31 | 0.68 | 0.17 | >1.2 | 0.36 | 1.1 | 0.32 | 0.46 |
| OR Quart 4 | 5.0 | 5.1 | 23 | 2.1 | na | 5.0 | 95 | 32 | 47 |

C—X—C motif chemokine 6

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 31.8 | 31.0 | 31.8 | 36.4 | 31.8 | 17.0 |
| Average | 49.0 | 49.8 | 49.0 | 51.5 | 49.0 | 32.9 |
| Stdev | 48.9 | 51.8 | 48.9 | 61.6 | 48.9 | 36.7 |
| p (t-test) | | 0.95 | | 0.84 | | 0.21 |
| Min | 5.55 | 3.49 | 5.55 | 4.02 | 5.55 | 6.54 |
| Max | 244 | 244 | 244 | 311 | 244 | 144 |
| n (Samp) | 53 | 29 | 53 | 34 | 53 | 18 |
| n (Patient) | 51 | 29 | 51 | 34 | 51 | 18 |
| sCr only | | | | | | |
| Median | 26.4 | 31.9 | 26.4 | 44.1 | 26.4 | 28.4 |
| Average | 45.1 | 46.7 | 45.1 | 70.0 | 45.1 | 47.5 |
| Stdev | 52.8 | 41.5 | 52.8 | 79.0 | 52.8 | 48.3 |
| p (t-test) | | 0.92 | | 0.087 | | 0.90 |
| Min | 3.49 | 10.7 | 3.49 | 8.88 | 3.49 | 9.55 |
| Max | 311 | 129 | 311 | 336 | 311 | 144 |
| n (Samp) | 133 | 10 | 133 | 17 | 133 | 8 |
| n (Patient) | 101 | 10 | 101 | 17 | 101 | 8 |
| UO only | | | | | | |
| Median | 31.3 | 29.1 | 31.3 | 36.4 | 31.3 | 19.6 |
| Average | 45.1 | 46.5 | 45.1 | 52.1 | 45.1 | 25.7 |
| Stdev | 46.6 | 53.4 | 46.6 | 65.3 | 46.6 | 19.2 |
| p (t-test) | | 0.91 | | 0.57 | | 0.15 |
| Min | 5.55 | 3.49 | 5.55 | 4.02 | 5.55 | 6.54 |
| Max | 244 | 244 | 244 | 311 | 244 | 66.2 |
| n (Samp) | 54 | 23 | 54 | 30 | 54 | 13 |
| n (Patient) | 47 | 23 | 47 | 30 | 47 | 13 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCR only | UO only |
| AUC | 0.48 | 0.54 | 0.48 | 0.48 | 0.63 | 0.50 | 0.32 | 0.50 | 0.34 |
| SE | 0.067 | 0.097 | 0.073 | 0.064 | 0.076 | 0.066 | 0.078 | 0.11 | 0.090 |

TABLE 5-continued

Comparison of marker levels in EDTA samples collected from
Cohort 1 (patients that did not progress beyond RIFLE stage 0) and in EDTA samples
collected from subjects at 0, 24 hours, and 48 hours prior to reaching stage R, I or F in
Cohort 2.

| P | 0.79 | 0.70 | 0.75 | 0.81 | 0.076 | 0.96 | 0.024 | 0.98 | 0.081 |
|---|---|---|---|---|---|---|---|---|---|
| nCohort 1 | 53 | 133 | 54 | 53 | 133 | 54 | 53 | 133 | 54 |
| nCohort 2 | 29 | 10 | 23 | 34 | 17 | 30 | 18 | 8 | 13 |
| Cutoff 1 | 17.6 | 26.2 | 14.8 | 17.9 | 31.5 | 17.6 | 12.2 | 13.9 | 10.7 |
| Sens 1 | 72% | 70% | 74% | 71% | 71% | 70% | 72% | 75% | 77% |
| Spec 1 | 26% | 50% | 15% | 26% | 56% | 28% | 8% | 20% | 11% |
| Cutoff 2 | 11.0 | 13.1 | 10.7 | 15.6 | 17.9 | 13.4 | 9.82 | 11.5 | 9.82 |
| Sens 2 | 83% | 80% | 83% | 82% | 82% | 80% | 83% | 88% | 85% |
| Spec 2 | 8% | 16% | 11% | 11% | 34% | 13% | 8% | 14% | 9% |
| Cutoff 3 | 8.88 | 10.7 | 6.26 | 6.68 | 9.95 | 6.68 | 8.88 | 8.88 | 8.88 |
| Sens 3 | 93% | 90% | 91% | 91% | 94% | 90% | 94% | 100% | 92% |
| Spec 3 | 8% | 14% | 2% | 2% | 11% | 2% | 8% | 11% | 9% |
| Cutoff 4 | 46.9 | 43.7 | 43.7 | 46.9 | 43.7 | 43.7 | 46.9 | 43.7 | 43.7 |
| Sens 4 | 34% | 30% | 30% | 32% | 53% | 37% | 22% | 38% | 15% |
| Spec 4 | 72% | 71% | 70% | 72% | 71% | 70% | 72% | 71% | 70% |
| Cutoff 5 | 56.7 | 60.9 | 54.5 | 56.7 | 60.9 | 54.5 | 56.7 | 60.9 | 54.5 |
| Sens 5 | 31% | 30% | 26% | 26% | 41% | 23% | 22% | 25% | 15% |
| Spec 5 | 81% | 80% | 81% | 81% | 80% | 81% | 81% | 80% | 81% |
| Cutoff 6 | 117 | 95.2 | 94.9 | 117 | 95.2 | 94.9 | 117 | 95.2 | 94.9 |
| Sens 6 | 10% | 20% | 9% | 9% | 18% | 10% | 6% | 12% | 0% |
| Spec 6 | 91% | 90% | 91% | 91% | 90% | 91% | 91% | 90% | 91% |
| OR Quart 2 | 0.44 | 0.30 | 0.50 | 1.0 | 0.63 | 1.0 | 0.21 | 1.0 | 1.0 |
| p Value | 0.23 | 0.31 | 0.34 | 1.0 | 0.62 | 1.0 | 0.18 | 0.98 | 1.0 |
| 95% CI of | 0.12 | 0.030 | 0.12 | 0.30 | 0.099 | 0.29 | 0.021 | 0.14 | 0.12 |
| OR Quart 2 | 1.7 | 3.1 | 2.1 | 3.3 | 4.0 | 3.5 | 2.1 | 7.7 | 8.1 |
| OR Quart 3 | 0.67 | 0.97 | 0.66 | 0.67 | 1.8 | 0.65 | 1.3 | 0.50 | 2.3 |
| p Value | 0.53 | 0.97 | 0.56 | 0.53 | 0.46 | 0.51 | 0.70 | 0.58 | 0.38 |
| 95% CI of | 0.19 | 0.18 | 0.17 | 0.20 | 0.39 | 0.18 | 0.30 | 0.043 | 0.36 |
| OR Quart 3 | 2.3 | 5.2 | 2.6 | 2.3 | 8.0 | 2.4 | 6.1 | 5.8 | 15 |
| OR Quart 4 | 0.89 | 0.97 | 1.1 | 1.1 | 2.6 | 1.0 | 3.1 | 1.6 | 3.4 |
| p Value | 0.85 | 0.97 | 0.90 | 0.90 | 0.20 | 1.0 | 0.13 | 0.62 | 0.19 |
| 95% CI of | 0.26 | 0.18 | 0.29 | 0.32 | 0.61 | 0.29 | 0.72 | 0.25 | 0.56 |
| OR Quart 4 | 3.1 | 5.2 | 4.0 | 3.6 | 11 | 3.5 | 13 | 10 | 21 |

Coagulation factor VII

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 312 | 313 | 312 | 280 | 312 | 290 |
| Average | 339 | 323 | 339 | 283 | 339 | 310 |
| Stdev | 159 | 179 | 159 | 165 | 159 | 165 |
| p (t-test) | | 0.52 | | 0.017 | | 0.37 |
| Min | 2.08 | 22.9 | 2.08 | 12.2 | 2.08 | 66.4 |
| Max | 743 | 759 | 743 | 717 | 743 | 685 |
| n (Samp) | 262 | 51 | 262 | 56 | 262 | 26 |
| n (Patient) | 110 | 51 | 110 | 56 | 110 | 26 |
| sCr only | | | | | | |
| Median | 298 | 336 | 298 | 324 | 298 | 418 |
| Average | 313 | 356 | 313 | 361 | 313 | 391 |
| Stdev | 164 | 187 | 164 | 219 | 164 | 206 |
| p (t-test) | | 0.28 | | 0.20 | | 0.095 |
| Min | 2.08 | 108 | 2.08 | 66.2 | 2.08 | 62.4 |
| Max | 822 | 759 | 822 | 779 | 822 | 685 |
| n (Samp) | 466 | 18 | 466 | 21 | 466 | 13 |
| n (Patient) | 180 | 18 | 180 | 21 | 180 | 13 |
| UO only | | | | | | |
| Median | 310 | 296 | 310 | 262 | 310 | 261 |
| Average | 335 | 304 | 335 | 256 | 335 | 271 |
| Stdev | 160 | 174 | 160 | 144 | 160 | 119 |
| p (t-test) | | 0.21 | | 0.0012 | | 0.063 |
| Min | 16.0 | 22.9 | 16.0 | 12.2 | 16.0 | 66.4 |
| Max | 1020 | 722 | 1020 | 574 | 1020 | 488 |
| n (Samp) | 221 | 50 | 221 | 52 | 221 | 23 |
| n (Patient) | 91 | 50 | 91 | 52 | 91 | 23 |

TABLE 5-continued

Comparison of marker levels in EDTA samples collected from Cohort 1 (patients that did not progress beyond RIFLE stage 0) and in EDTA samples collected from subjects at 0, 24 hours, and 48 hours prior to reaching stage R, I or F in Cohort 2.

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCR only | UO only |
| AUC | 0.47 | 0.56 | 0.45 | 0.40 | 0.55 | 0.36 | 0.44 | 0.62 | 0.40 |
| SE | 0.045 | 0.071 | 0.046 | 0.043 | 0.066 | 0.045 | 0.061 | 0.084 | 0.065 |
| p | 0.43 | 0.40 | 0.23 | 0.017 | 0.45 | 0.0022 | 0.36 | 0.17 | 0.11 |
| nCohort 1 | 262 | 466 | 221 | 262 | 466 | 221 | 262 | 466 | 221 |
| nCohort 2 | 51 | 18 | 50 | 56 | 21 | 52 | 26 | 13 | 23 |
| Cutoff 1 | 193 | 225 | 176 | 165 | 190 | 156 | 220 | 187 | 220 |
| Sens 1 | 71% | 72% | 72% | 71% | 71% | 71% | 73% | 77% | 74% |
| Spec 1 | 18% | 35% | 14% | 12% | 27% | 11% | 26% | 26% | 27% |
| Cutoff 2 | 140 | 182 | 138 | 138 | 138 | 100 | 134 | 137 | 129 |
| Sens 2 | 80% | 83% | 80% | 80% | 81% | 81% | 81% | 85% | 83% |
| Spec 2 | 8% | 24% | 8% | 8% | 14% | 4% | 7% | 13% | 6% |
| Cutoff 3 | 104 | 126 | 77.8 | 80.6 | 108 | 76.2 | 116 | 124 | 116 |
| Sens 3 | 90% | 94% | 90% | 91% | 90% | 90% | 92% | 92% | 91% |
| Spec 3 | 4% | 12% | 3% | 3% | 8% | 3% | 5% | 11% | 5% |
| Cutoff 4 | 411 | 394 | 393 | 411 | 394 | 393 | 411 | 394 | 393 |
| Sens 4 | 29% | 39% | 34% | 23% | 43% | 21% | 27% | 62% | 17% |
| Spec 4 | 70% | 70% | 70% | 70% | 70% | 70% | 70% | 70% | 70% |
| Cutoff 5 | 481 | 459 | 479 | 481 | 459 | 479 | 481 | 459 | 479 |
| Sens 5 | 22% | 28% | 18% | 12% | 38% | 8% | 15% | 38% | 4% |
| Spec 5 | 80% | 80% | 80% | 80% | 80% | 80% | 80% | 80% | 80% |
| Cutoff 6 | 571 | 535 | 550 | 571 | 535 | 550 | 571 | 535 | 550 |
| Sens 6 | 10% | 22% | 10% | 5% | 24% | 2% | 8% | 31% | 0% |
| Spec 6 | 90% | 90% | 90% | 90% | 90% | 90% | 90% | 90% | 90% |
| OR Quart 2 | 1.2 | 1.0 | 1.2 | 0.91 | 0.48 | 1.3 | 1.2 | 0.32 | 2.1 |
| p Value | 0.64 | 1.0 | 0.65 | 0.84 | 0.31 | 0.60 | 0.75 | 0.33 | 0.31 |
| 95% CI of | 0.53 | 0.24 | 0.51 | 0.36 | 0.12 | 0.50 | 0.35 | 0.033 | 0.50 |
| OR Quart 2 | 2.8 | 4.1 | 3.0 | 2.3 | 2.0 | 3.3 | 4.2 | 3.2 | 8.9 |
| OR Quart 3 | 0.64 | 1.0 | 0.69 | 1.1 | 0.48 | 1.1 | 1.7 | 1.3 | 2.9 |
| p Value | 0.36 | 1.0 | 0.46 | 0.82 | 0.31 | 0.78 | 0.39 | 0.71 | 0.13 |
| 95% CI of | 0.25 | 0.24 | 0.26 | 0.46 | 0.12 | 0.44 | 0.52 | 0.29 | 0.74 |
| OR Quart 3 | 1.7 | 4.1 | 1.8 | 2.7 | 2.0 | 3.0 | 5.4 | 6.1 | 12 |
| OR Quart 4 | 1.6 | 1.5 | 1.9 | 2.6 | 1.5 | 3.2 | 1.4 | 1.7 | 2.1 |
| p Value | 0.29 | 0.52 | 0.13 | 0.020 | 0.44 | 0.0086 | 0.55 | 0.48 | 0.31 |
| 95% CI of | 0.69 | 0.42 | 0.82 | 1.2 | 0.53 | 1.3 | 0.44 | 0.39 | 0.50 |
| OR Quart 4 | 3.5 | 5.5 | 4.4 | 5.7 | 4.4 | 7.6 | 4.8 | 7.2 | 8.9 |

Insulin-like growth factor-binding protein 7

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 63.1 | 74.8 | 63.1 | 82.4 | 63.1 | 75.2 |
| Average | 68.7 | 77.4 | 68.7 | 94.1 | 68.7 | 74.1 |
| Stdev | 34.7 | 31.0 | 34.7 | 68.0 | 34.7 | 20.5 |
| p (t-test) |  | 0.19 |  | 0.0063 |  | 0.46 |
| Min | 18.6 | 35.4 | 18.6 | 30.8 | 18.6 | 28.3 |
| Max | 250 | 185 | 250 | 437 | 250 | 114 |
| n (Samp) | 81 | 37 | 81 | 45 | 81 | 26 |
| n (Patient) | 74 | 37 | 74 | 45 | 74 | 26 |
| sCr only | | | | | | |
| Median | 67.7 | 75.4 | 67.7 | 92.0 | 67.7 | 74.4 |
| Average | 75.5 | 78.1 | 75.5 | 113 | 75.5 | 74.4 |
| Stdev | 41.1 | 39.2 | 41.1 | 59.9 | 41.1 | 25.4 |
| p (t-test) |  | 0.83 |  | 0.0017 |  | 0.94 |
| Min | 18.6 | 35.4 | 18.6 | 30.8 | 18.6 | 28.3 |
| Max | 437 | 185 | 437 | 233 | 437 | 116 |
| n (Samp) | 197 | 12 | 197 | 14 | 197 | 9 |
| n (Patient) | 131 | 12 | 131 | 14 | 131 | 9 |
| UO only | | | | | | |
| Median | 69.3 | 76.7 | 69.3 | 81.8 | 69.3 | 77.9 |
| Average | 74.2 | 80.9 | 74.2 | 92.0 | 74.2 | 82.1 |
| Stdev | 33.6 | 32.7 | 33.6 | 65.1 | 33.6 | 30.6 |
| p (t-test) |  | 0.36 |  | 0.051 |  | 0.33 |
| Min | 27.8 | 39.1 | 27.8 | 36.0 | 27.8 | 39.8 |
| Max | 250 | 189 | 250 | 437 | 250 | 185 |

TABLE 5-continued

Comparison of marker levels in EDTA samples collected from Cohort 1 (patients that did not progress beyond RIFLE stage 0) and in EDTA samples collected from subjects at 0, 24 hours, and 48 hours prior to reaching stage R, I or F in Cohort 2.

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCR only | UO only |
| n (Samp) | 77 | 29 | 77 | 43 | 77 | 21 | | | |
| n (Patient) | 64 | 29 | 64 | 43 | 64 | 21 | | | |
| AUC | 0.61 | 0.52 | 0.58 | 0.65 | 0.72 | 0.60 | 0.62 | 0.54 | 0.61 |
| SE | 0.057 | 0.087 | 0.064 | 0.052 | 0.079 | 0.055 | 0.066 | 0.10 | 0.072 |
| P | 0.064 | 0.83 | 0.23 | 0.0039 | 0.0049 | 0.081 | 0.071 | 0.71 | 0.14 |
| nCohort 1 | 81 | 197 | 77 | 81 | 197 | 77 | 81 | 197 | 77 |
| nCohort 2 | 37 | 12 | 29 | 45 | 14 | 43 | 26 | 9 | 21 |
| Cutoff 1 | 56.1 | 68.2 | 56.5 | 56.3 | 82.4 | 53.8 | 58.3 | 69.0 | 62.3 |
| Sens 1 | 70% | 75% | 72% | 71% | 71% | 72% | 73% | 78% | 71% |
| Spec 1 | 44% | 51% | 36% | 44% | 66% | 31% | 47% | 51% | 42% |
| Cutoff 2 | 53.1 | 39.8 | 53.3 | 53.1 | 70.5 | 52.5 | 56.1 | 49.8 | 58.1 |
| Sens 2 | 81% | 83% | 83% | 80% | 86% | 81% | 81% | 89% | 81% |
| Spec 2 | 40% | 10% | 31% | 40% | 53% | 27% | 44% | 22% | 39% |
| Cutoff 3 | 39.4 | 36.7 | 47.5 | 42.8 | 56.5 | 42.8 | 49.8 | 27.8 | 53.3 |
| Sens 3 | 92% | 92% | 93% | 91% | 93% | 91% | 92% | 100% | 90% |
| Spec 3 | 16% | 6% | 17% | 20% | 38% | 12% | 32% | 2% | 31% |
| Cutoff 4 | 77.3 | 85.8 | 84.2 | 77.3 | 85.8 | 84.2 | 77.3 | 85.8 | 84.2 |
| Sens 4 | 46% | 17% | 38% | 53% | 64% | 49% | 42% | 22% | 38% |
| Spec 4 | 70% | 70% | 70% | 70% | 70% | 70% | 70% | 70% | 70% |
| Cutoff 5 | 85.8 | 96.3 | 87.7 | 85.8 | 96.3 | 87.7 | 85.8 | 96.3 | 87.7 |
| Sens 5 | 30% | 17% | 31% | 47% | 43% | 44% | 27% | 22% | 38% |
| Spec 5 | 80% | 80% | 81% | 80% | 80% | 81% | 80% | 80% | 81% |
| Cutoff 6 | 107 | 116 | 114 | 107 | 116 | 114 | 107 | 116 | 114 |
| Sens 6 | 11% | 8% | 14% | 18% | 29% | 19% | 4% | 11% | 10% |
| Spec 6 | 90% | 90% | 91% | 90% | 90% | 91% | 90% | 90% | 91% |
| OR Quart 2 | 1.4 | 0.32 | 3.2 | 2.5 | 0.98 | 1.2 | 4.2 | 0 | 7.3 |
| p Value | 0.59 | 0.33 | 0.082 | 0.12 | 0.99 | 0.78 | 0.094 | na | 0.078 |
| 95% CI of | 0.42 | 0.032 | 0.86 | 0.80 | 0.060 | 0.39 | 0.78 | na | 0.80 |
| OR Quart 2 | 4.7 | 3.2 | 12 | 7.8 | 16 | 3.5 | 23 | na | 66 |
| OR Quart 3 | 2.7 | 2.1 | 1.6 | 1.4 | 5.3 | 0.71 | 6.0 | 2.7 | 7.7 |
| p Value | 0.094 | 0.30 | 0.48 | 0.54 | 0.13 | 0.56 | 0.033 | 0.26 | 0.070 |
| 95% CI of | 0.85 | 0.50 | 0.41 | 0.44 | 0.60 | 0.22 | 1.2 | 0.49 | 0.85 |
| OR Quart 3 | 8.7 | 9.0 | 6.7 | 4.8 | 47 | 2.2 | 31 | 14 | 70 |
| OR Quart 4 | 2.2 | 0.64 | 2.8 | 6.1 | 7.8 | 3.1 | 5.1 | 0.98 | 11 |
| p Value | 0.18 | 0.63 | 0.14 | 0.0018 | 0.060 | 0.040 | 0.056 | 0.98 | 0.032 |
| 95% CI of | 0.69 | 0.10 | 0.73 | 2.0 | 0.92 | 1.1 | 0.96 | 0.13 | 1.2 |
| OR Quart 4 | 7.1 | 4.0 | 10 | 19 | 65 | 8.8 | 27 | 7.2 | 95 |

TABLE 6

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

| | Cancer Antigen 19-9 | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.228 | 0.629 | 0.228 | 0.536 | 0.228 | 0.489 |
| Average | 0.628 | 1.13 | 0.628 | 0.885 | 0.628 | 0.805 |
| Stdev | 3.00 | 1.07 | 3.00 | 1.17 | 3.00 | 1.05 |
| p(t-test) | | 0.66 | | 0.70 | | 0.81 |
| Min | 1.00E−9 | 0.231 | 1.00E−9 | 1.00E−9 | 1.00E−9 | 0.0291 |
| Max | 41.6 | 2.77 | 41.6 | 5.26 | 41.6 | 3.84 |
| n (Samp) | 197 | 7 | 197 | 21 | 197 | 16 |
| n (Patient) | 131 | 7 | 131 | 21 | 131 | 16 |
| UO only | | | | | | |
| Median | nd | nd | 0.244 | 0.467 | 0.244 | 0.568 |
| Average | nd | nd | 0.695 | 0.831 | 0.695 | 0.776 |
| Stdev | nd | nd | 3.19 | 1.21 | 3.19 | 1.04 |

TABLE 6-continued

Comparison of marker levels in EDTA samples collected from
Cohort 1 (patients that did not progress beyond RIFLE stage 0 or R) and in EDTA
samples collected from subjects at 0, 24 hours, and 48 hours prior to reaching stage I or F
in Cohort 2.

|  |  |  |  |  |  |  |
|---|---|---|---|---|---|---|
| p (t-test) | nd | nd | 0.86 |  | 0.93 |  |
| Min | nd | nd | 1.00E−9 | 1.00E−9 | 1.00E−9 | 0.0291 |
| Max | nd | nd | 41.6 | 5.26 | 41.6 | 3.84 |
| n (Samp) | nd | nd | 173 | 18 | 173 | 13 |
| n (Patient) | nd | nd | 111 | 18 | 111 | 13 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.79 | nd | nd | 0.71 | nd | 0.66 | 0.63 | nd | 0.62 |
| SE | 0.10 | nd | nd | 0.066 | nd | 0.073 | 0.077 | nd | 0.086 |
| p | 0.0047 | nd | nd | 0.0013 | nd | 0.031 | 0.081 | nd | 0.15 |
| nCohort 1 | 197 | nd | nd | 197 | nd | 173 | 197 | nd | 173 |
| nCohort 2 | 7 | nd | nd | 21 | nd | 18 | 16 | nd | 13 |
| Cutoff 1 | 0.401 | nd | nd | 0.259 | nd | 0.257 | 0.204 | nd | 0.204 |
| Sens 1 | 71% | nd | nd | 71% | nd | 72% | 75% | nd | 77% |
| Spec 1 | 71% | nd | nd | 55% | nd | 53% | 44% | nd | 41% |
| Cutoff 2 | 0.288 | nd | nd | 0.250 | nd | 0.228 | 0.134 | nd | 0.0842 |
| Sens 2 | 86% | nd | nd | 81% | nd | 83% | 81% | nd | 85% |
| Spec 2 | 61% | nd | nd | 55% | nd | 50% | 30% | nd | 22% |
| Cutoff 3 | 0.228 | nd | nd | 0.174 | nd | 0.134 | 0.0783 | nd | 0.0783 |
| Sens 3 | 100% | nd | nd | 90% | nd | 94% | 94% | nd | 92% |
| Spec 3 | 52% | nd | nd | 36% | nd | 29% | 20% | nd | 18% |
| Cutoff 4 | 0.361 | nd | nd | 0.361 | nd | 0.456 | 0.361 | nd | 0.456 |
| Sens 4 | 71% | nd | nd | 67% | nd | 50% | 56% | nd | 54% |
| Spec 4 | 70% | nd | nd | 70% | nd | 71% | 70% | nd | 71% |
| Cutoff 5 | 0.590 | nd | nd | 0.590 | nd | 0.633 | 0.590 | nd | 0.633 |
| Sens 5 | 57% | nd | nd | 43% | nd | 33% | 38% | nd | 23% |
| Spec 5 | 80% | nd | nd | 80% | nd | 80% | 80% | nd | 80% |
| Cutoff 6 | 0.980 | nd | nd | 0.980 | nd | 1.32 | 0.980 | nd | 1.32 |
| Sens 6 | 43% | nd | nd | 24% | nd | 11% | 19% | nd | 15% |
| Spec 6 | 90% | nd | nd | 90% | nd | 90% | 90% | nd | 90% |
| OR Quart 2 | >0 | nd | nd | 3.1 | nd | 3.1 | 0.65 | nd | 0.31 |
| p Value | <na | nd | nd | 0.34 | nd | 0.34 | 0.65 | nd | 0.32 |
| 95% CI of | >na | nd | nd | 0.31 | nd | 0.31 | 0.10 | nd | 0.031 |
| OR Quart 2 | na | nd | nd | 30 | nd | 31 | 4.1 | nd | 3.1 |
| OR Quart 3 | >3.2 | nd | nd | 6.6 | nd | 7.9 | 1.0 | nd | 1.0 |
| p Value | <0.32 | nd | nd | 0.085 | nd | 0.059 | 1.0 | nd | 1.0 |
| 95% CI of | >0.32 | nd | nd | 0.77 | nd | 0.93 | 0.19 | nd | 0.19 |
| OR Quart 3 | na | nd | nd | 57 | nd | 67 | 5.2 | nd | 5.2 |
| OR Quart 4 | >4.3 | nd | nd | 13 | nd | 7.9 | 2.9 | nd | 2.1 |
| p Value | <0.20 | nd | nd | 0.015 | nd | 0.059 | 0.13 | nd | 0.32 |
| 95% CI of | >0.47 | nd | nd | 1.6 | nd | 0.93 | 0.72 | nd | 0.49 |
| OR Quart 4 | na | nd | nd | 110 | nd | 67 | 12 | nd | 8.9 |

C-C motif chemokine 13

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 21.0 | 21.8 | 21.0 | 1.00E−9 | 21.0 | 44.5 |
| Average | 66.3 | 56.7 | 66.3 | 29.4 | 66.3 | 90.1 |
| Stdev | 235 | 86.8 | 235 | 61.3 | 235 | 140 |
| p (t-test) | | 0.92 | | 0.48 | | 0.72 |
| Min | 1.00E−9 | 1.00E−9 | 1.00E−9 | 1.00E−9 | 1.00E−9 | 1.00E−9 |
| Max | 2520 | 238 | 2520 | 279 | 2520 | 484 |
| n (Samp) | 130 | 7 | 130 | 21 | 130 | 13 |
| n (Patient) | 102 | 7 | 102 | 21 | 102 | 13 |
| UO only | | | | | | |
| Median | nd | nd | 21.0 | 1.00E−9 | 21.0 | 44.5 |
| Average | nd | nd | 70.0 | 16.9 | 70.0 | 74.5 |
| Stdev | nd | nd | 253 | 20.5 | 253 | 140 |
| p (t-test) | nd | nd | | 0.34 | | 0.95 |
| Min | nd | nd | 1.00E−9 | 1.00E−9 | 1.00E−9 | 1.00E−9 |
| Max | nd | nd | 2520 | 44.5 | 2520 | 484 |
| n (Samp) | nd | nd | 112 | 21 | 112 | 11 |
| n (Patient) | nd | nd | 87 | 21 | 87 | 11 |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.51 | nd | nd | 0.40 | nd | 0.39 | 0.59 | nd | 0.54 |
| SE | 0.11 | nd | nd | 0.070 | nd | 0.070 | 0.087 | nd | 0.093 |
| p | 0.91 | nd | nd | 0.14 | nd | 0.11 | 0.28 | nd | 0.70 |
| nCohort 1 | 130 | nd | nd | 130 | nd | 112 | 130 | nd | 112 |
| nCohort 2 | 7 | nd | nd | 21 | nd | 21 | 13 | nd | 11 |
| Cutoff 1 | 0 | nd | nd | 0 | nd | 0 | 0 | nd | 0 |
| Sens 1 | 100% | nd | nd | 100% | nd | 100% | 100% | nd | 100% |
| Spec 1 | 0% | nd | nd | 0% | nd | 0% | 0% | nd | 0% |
| Cutoff 2 | 0 | nd | nd | 0 | nd | 0 | 0 | nd | 0 |
| Sens 2 | 100% | nd | nd | 100% | nd | 100% | 100% | nd | 100% |
| Spec 2 | 0% | nd | nd | 0% | nd | 0% | 0% | nd | 0% |
| Cutoff 3 | 0 | nd | nd | 0 | nd | 0 | 0 | nd | 0 |
| Sens 3 | 100% | nd | nd | 100% | nd | 100% | 100% | nd | 100% |
| Spec 3 | 0% | nd | nd | 0% | nd | 0% | 0% | nd | 0% |
| Cutoff 4 | 56.0 | nd | nd | 56.0 | nd | 56.0 | 56.0 | nd | 56.0 |
| Sens 4 | 29% | nd | nd | 10% | nd | 0% | 38% | nd | 36% |
| Spec 4 | 73% | nd | nd | 73% | nd | 72% | 73% | nd | 72% |
| Cutoff 5 | 72.2 | nd | nd | 72.2 | nd | 72.2 | 72.2 | nd | 72.2 |
| Sens 5 | 29% | nd | nd | 5% | nd | 0% | 31% | nd | 27% |
| Spec 5 | 82% | nd | nd | 82% | nd | 81% | 82% | nd | 81% |
| Cutoff 6 | 111 | nd | nd | 111 | nd | 111 | 111 | nd | 111 |
| Sens 6 | 14% | nd | nd | 5% | nd | 0% | 15% | nd | 9% |
| Spec 6 | 90% | nd | nd | 90% | nd | 90% | 90% | nd | 90% |
| OR Quart 2 | >3.3 | nd | nd | 4.1 | nd | >13 | >4.4 | nd | >5.8 |
| p Value | <0.31 | nd | nd | 0.094 | nd | <0.019 | <0.20 | nd | <0.12 |
| 95% CI of | >0.32 | nd | nd | 0.79 | nd | >1.5 | >0.46 | nd | >0.63 |
| OR Quart 2 | na | nd | nd | 21 | nd | na | na | nd | na |
| OR Quart 3 | >2.1 | nd | nd | 8.3 | nd | >0 | >4.4 | nd | >2.1 |
| p Value | <0.55 | nd | nd | 0.0086 | nd | <na | <0.20 | nd | <0.56 |
| 95% CI of | >0.18 | nd | nd | 1.7 | nd | >na | >0.46 | nd | >0.18 |
| OR Quart 3 | na | nd | nd | 40 | nd | na | na | nd | na |
| OR Quart 4 | >2.1 | nd | nd | 0 | nd | >19 | >5.6 | nd | >4.4 |
| p Value | <0.56 | nd | nd | na | nd | <0.0059 | <0.12 | nd | <0.19 |
| 95% CI of | >0.18 | nd | nd | na | nd | >2.4 | >0.62 | nd | >0.47 |
| OR Quart 4 | na | nd | nd | na | nd | na | na | nd | na |

C—X—C motif chemokine 6

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 27.2 | 43.7 | 27.2 | 29.1 | 27.2 | 32.9 |
| Average | 42.6 | 88.3 | 42.6 | 49.9 | 42.6 | 66.7 |
| Stdev | 42.3 | 86.5 | 42.3 | 55.1 | 42.3 | 83.1 |
| p (t-test) |  | 0.0100 |  | 0.48 |  | 0.080 |
| Min | 3.49 | 8.06 | 3.49 | 9.69 | 3.49 | 9.55 |
| Max | 244 | 258 | 244 | 244 | 244 | 311 |
| n (Samp) | 131 | 7 | 131 | 21 | 131 | 13 |
| n (Patient) | 103 | 7 | 103 | 21 | 103 | 13 |
| UO only | | | | | | |
| Median | nd | nd | 25.5 | 29.1 | 25.5 | 24.0 |
| Average | nd | nd | 40.5 | 44.7 | 40.5 | 61.1 |
| Stdev | nd | nd | 42.9 | 50.5 | 42.9 | 87.4 |
| p (t-test) | nd | nd |  | 0.69 |  | 0.18 |
| Min | nd | nd | 3.49 | 8.06 | 3.49 | 9.69 |
| Max | nd | nd | 244 | 244 | 244 | 311 |
| n (Samp) | nd | nd | 113 | 21 | 113 | 11 |
| n (Patient) | nd | nd | 88 | 21 | 88 | 11 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.68 | nd | nd | 0.54 | nd | 0.55 | 0.59 | nd | 0.57 |
| SE | 0.11 | nd | nd | 0.069 | nd | 0.070 | 0.087 | nd | 0.094 |
| p | 0.11 | nd | nd | 0.55 | nd | 0.46 | 0.28 | nd | 0.48 |

TABLE 6-continued

Comparison of marker levels in EDTA samples collected from
Cohort 1 (patients that did not progress beyond RIFLE stage 0 or R) and in EDTA
samples collected from subjects at 0, 24 hours, and 48 hours prior to reaching stage I or F
in Cohort 2.

| | | | | | | | | | |
|---|---|---|---|---|---|---|---|---|---|
| nCohort 1 | 131 | nd | nd | 131 | nd | 113 | 131 | nd | 113 |
| nCohort 2 | 7 | nd | nd | 21 | nd | 21 | 13 | nd | 11 |
| Cutoff 1 | 38.9 | nd | nd | 17.6 | nd | 17.6 | 23.3 | nd | 23.3 |
| Sens 1 | 71% | nd | nd | 71% | nd | 71% | 77% | nd | 73% |
| Spec 1 | 62% | nd | nd | 34% | nd | 36% | 44% | nd | 47% |
| Cutoff 2 | 31.8 | nd | nd | 15.8 | nd | 15.8 | 17.6 | nd | 17.6 |
| Sens 2 | 86% | nd | nd | 81% | nd | 81% | 85% | nd | 82% |
| Spec 2 | 56% | nd | nd | 25% | nd | 29% | 34% | nd | 36% |
| Cutoff 3 | 6.68 | nd | nd | 13.9 | nd | 13.9 | 16.7 | nd | 16.7 |
| Sens 3 | 100% | nd | nd | 90% | nd | 90% | 92% | nd | 91% |
| Spec 3 | 5% | nd | nd | 19% | nd | 24% | 31% | nd | 34% |
| Cutoff 4 | 46.0 | nd | nd | 46.0 | nd | 43.7 | 46.0 | nd | 43.7 |
| Sens 4 | 43% | nd | nd | 33% | nd | 33% | 38% | nd | 27% |
| Spec 4 | 70% | nd | nd | 70% | nd | 72% | 70% | nd | 72% |
| Cutoff 5 | 60.9 | nd | nd | 60.9 | nd | 54.2 | 60.9 | nd | 54.2 |
| Sens 5 | 43% | nd | nd | 29% | nd | 24% | 31% | nd | 27% |
| Spec 5 | 80% | nd | nd | 80% | nd | 81% | 80% | nd | 81% |
| Cutoff 6 | 93.3 | nd | nd | 93.3 | nd | 89.9 | 93.3 | nd | 89.9 |
| Sens 6 | 43% | nd | nd | 10% | nd | 5% | 23% | nd | 18% |
| Spec 6 | 90% | nd | nd | 90% | nd | 90% | 90% | nd | 90% |
| OR Quart 2 | 0 | nd | nd | 1.6 | nd | 2.6 | 5.6 | nd | 5.8 |
| p Value | na | nd | nd | 0.50 | nd | 0.20 | 0.12 | nd | 0.12 |
| 95% CI of | na | nd | nd | 0.41 | nd | 0.61 | 0.62 | nd | 0.63 |
| OR Quart 2 | na | nd | nd | 6.2 | nd | 11 | 51 | nd | 53 |
| OR Quart 3 | 3.2 | nd | nd | 1.3 | nd | 1.8 | 3.2 | nd | 2.1 |
| p Value | 0.33 | nd | nd | 0.72 | nd | 0.46 | 0.33 | nd | 0.56 |
| 95% CI of | 0.32 | nd | nd | 0.32 | nd | 0.39 | 0.31 | nd | 0.18 |
| OR Quart 3 | 32 | nd | nd | 5.2 | nd | 8.2 | 32 | nd | 24 |
| OR Quart 4 | 3.1 | nd | nd | 1.6 | nd | 2.1 | 4.4 | nd | 3.2 |
| p Value | 0.34 | nd | nd | 0.50 | nd | 0.31 | 0.20 | nd | 0.32 |
| 95% CI of | 0.31 | nd | nd | 0.41 | nd | 0.49 | 0.46 | nd | 0.32 |
| OR Quart 4 | 31 | nd | nd | 6.2 | nd | 9.4 | 41 | nd | 33 |

Coagulation factor VII

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 310 | 281 | 310 | 235 | 310 | 221 |
| Average | 336 | 290 | 336 | 259 | 336 | 277 |
| Stdev | 172 | 149 | 172 | 173 | 172 | 188 |
| p (t-test) | | 0.19 | | 0.014 | | 0.17 |
| Min | 2.08 | 51.4 | 2.08 | 22.9 | 2.08 | 12.2 |
| Max | 1020 | 549 | 1020 | 626 | 1020 | 616 |
| n (Samp) | 437 | 26 | 437 | 33 | 437 | 17 |
| n (Patient) | 174 | 26 | 174 | 33 | 174 | 17 |
| sCr only | | | | | | |
| Median | 303 | 188 | 303 | 251 | 303 | 189 |
| Average | 323 | 244 | 323 | 296 | 323 | 317 |
| Stdev | 174 | 189 | 174 | 235 | 174 | 219 |
| p (t-test) | | 0.27 | | 0.65 | | 0.93 |
| Min | 2.08 | 77.8 | 2.08 | 66.2 | 2.08 | 110 |
| Max | 1020 | 605 | 1020 | 779 | 1020 | 622 |
| n (Samp) | 535 | 6 | 535 | 9 | 535 | 7 |
| n (Patient) | 207 | 6 | 207 | 9 | 207 | 7 |
| UO only | | | | | | |
| Median | 302 | 286 | 302 | 235 | 302 | 193 |
| Average | 321 | 310 | 321 | 253 | 321 | 247 |
| Stdev | 163 | 155 | 163 | 168 | 163 | 172 |
| p (t-test) | | 0.75 | | 0.026 | | 0.070 |
| Min | 16.0 | 51.4 | 16.0 | 22.9 | 16.0 | 12.2 |
| Max | 1020 | 611 | 1020 | 626 | 1020 | 616 |
| n (Samp) | 363 | 26 | 363 | 31 | 363 | 17 |
| n (Patient) | 141 | 26 | 141 | 31 | 141 | 17 |

TABLE 6-continued

Comparison of marker levels in EDTA samples collected from
Cohort 1 (patients that did not progress beyond RIFLE stage 0 or R) and in EDTA
samples collected from subjects at 0, 24 hours, and 48 hours prior to reaching stage I or F
in Cohort 2.

|  | 0 hr prior to AKI stage | | | 24 hr prior to AKI stage | | | 48 hr prior to AKI stage | | |
| --- | --- | --- | --- | --- | --- | --- | --- | --- | --- |
|  | sCr or UO | sCr only | UO only | sCr or UO | sCr only | UO only | sCr or UO | sCr only | UO only |
| AUC | 0.43 | 0.34 | 0.49 | 0.37 | 0.42 | 0.38 | 0.40 | 0.46 | 0.36 |
| SE | 0.060 | 0.12 | 0.059 | 0.054 | 0.10 | 0.056 | 0.074 | 0.11 | 0.074 |
| p | 0.28 | 0.19 | 0.87 | 0.017 | 0.42 | 0.028 | 0.16 | 0.71 | 0.064 |
| nCohort 1 | 437 | 535 | 363 | 437 | 535 | 363 | 437 | 535 | 363 |
| nCohort 2 | 26 | 6 | 26 | 33 | 9 | 31 | 17 | 7 | 17 |
| Cutoff 1 | 173 | 126 | 173 | 126 | 130 | 126 | 127 | 166 | 126 |
| Sens 1 | 73% | 83% | 73% | 73% | 78% | 74% | 71% | 71% | 76% |
| Spec 1 | 17% | 11% | 18% | 9% | 12% | 10% | 9% | 20% | 10% |
| Cutoff 2 | 156 | 126 | 163 | 79.5 | 74.8 | 99.7 | 116 | 156 | 116 |
| Sens 2 | 81% | 83% | 81% | 82% | 89% | 81% | 82% | 86% | 82% |
| Spec 2 | 14% | 11% | 16% | 3% | 5% | 6% | 6% | 17% | 7% |
| Cutoff 3 | 76.2 | 76.2 | 136 | 56.6 | 65.3 | 64.8 | 66.2 | 108 | 66.2 |
| Sens 3 | 92% | 100% | 92% | 91% | 100% | 90% | 94% | 100% | 94% |
| Spec 3 | 3% | 5% | 10% | 2% | 4% | 2% | 2% | 8% | 2% |
| Cutoff 4 | 405 | 403 | 387 | 405 | 403 | 387 | 405 | 403 | 387 |
| Sens 4 | 27% | 17% | 38% | 21% | 22% | 23% | 29% | 29% | 24% |
| Spec 4 | 70% | 70% | 70% | 70% | 70% | 70% | 70% | 70% | 70% |
| Cutoff 5 | 481 | 469 | 449 | 481 | 469 | 449 | 481 | 469 | 449 |
| Sens 5 | 8% | 17% | 27% | 12% | 22% | 10% | 12% | 29% | 18% |
| Spec 5 | 80% | 80% | 80% | 80% | 80% | 80% | 80% | 80% | 80% |
| Cutoff 6 | 573 | 564 | 536 | 573 | 564 | 536 | 573 | 564 | 536 |
| Sens 6 | 0% | 17% | 8% | 6% | 11% | 10% | 12% | 29% | 6% |
| Spec 6 | 90% | 90% | 90% | 90% | 90% | 90% | 90% | 90% | 90% |
| OR Quart 2 | 0.56 | 0 | 0.48 | 1.7 | 0.50 | 1.0 | 0.75 | 0.50 | 0.49 |
| p Value | 0.36 | na | 0.25 | 0.39 | 0.57 | 0.99 | 0.71 | 0.57 | 0.42 |
| 95% CI of | 0.16 | na | 0.14 | 0.53 | 0.044 | 0.31 | 0.16 | 0.045 | 0.087 |
| OR Quart 2 | 2.0 | na | 1.7 | 5.2 | 5.5 | 3.2 | 3.4 | 5.6 | 2.7 |
| OR Quart 3 | 0.70 | 2.0 | 0.61 | 1.0 | 1.5 | 0.82 | 0.49 | 0.50 | 0.49 |
| p Value | 0.56 | 0.57 | 0.40 | 1.0 | 0.65 | 0.76 | 0.42 | 0.57 | 0.42 |
| 95% CI of | 0.22 | 0.18 | 0.19 | 0.28 | 0.25 | 0.24 | 0.088 | 0.044 | 0.087 |
| OR Quart 3 | 2.3 | 23 | 1.9 | 3.5 | 9.2 | 2.8 | 2.7 | 5.5 | 2.7 |
| OR Quart 4 | 1.5 | 3.1 | 1.2 | 3.3 | 1.5 | 2.6 | 2.1 | 1.5 | 2.4 |
| p Value | 0.44 | 0.33 | 0.78 | 0.025 | 0.65 | 0.063 | 0.24 | 0.65 | 0.16 |
| 95% CI of | 0.54 | 0.32 | 0.42 | 1.2 | 0.25 | 0.95 | 0.61 | 0.25 | 0.71 |
| OR Quart 4 | 4.0 | 30 | 3.1 | 9.5 | 9.2 | 7.0 | 7.2 | 9.3 | 8.0 |

Insulin-like growth factor-binding protein 7

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| sCr or UO | | | | | | |
| Median | 68.2 | 77.5 | 68.2 | 93.6 | 68.2 | 75.4 |
| Average | 73.4 | 93.2 | 73.4 | 112 | 73.4 | 84.5 |
| Stdev | 33.2 | 49.8 | 33.2 | 89.8 | 33.2 | 34.5 |
| p (t-test) |  | 0.13 |  | 7.1E−5 |  | 0.20 |
| Min | 18.6 | 37.5 | 18.6 | 43.7 | 18.6 | 50.1 |
| Max | 250 | 189 | 250 | 437 | 250 | 176 |
| n (Samp) | 197 | 7 | 197 | 21 | 197 | 16 |
| n (Patient) | 131 | 7 | 131 | 21 | 131 | 16 |
| UO only | | | | | | |
| Median | nd | nd | 73.5 | 97.8 | 73.5 | 88.5 |
| Average | nd | nd | 76.5 | 117 | 76.5 | 92.9 |
| Stdev | nd | nd | 33.2 | 92.8 | 33.2 | 38.7 |
| p (t-test) | nd | nd |  | 1.7E−4 |  | 0.091 |
| Min | nd | nd | 27.8 | 43.7 | 27.8 | 54.2 |
| Max | nd | nd | 250 | 437 | 250 | 176 |
| n (Samp) | nd | nd | 173 | 18 | 173 | 13 |
| n (Patient) | nd | nd | 111 | 18 | 111 | 13 |

|  | 0 hr prior to AKI stage | | | 24 hr prior to AKI stage | | | 48 hr prior to AKI stage | | |
| --- | --- | --- | --- | --- | --- | --- | --- | --- | --- |
|  | sCr or UO | sCr only | UO only | sCr or UO | sCr only | UO only | sCr or UO | sCr only | UO only |
| AUC | 0.63 | nd | nd | 0.66 | nd | 0.65 | 0.61 | nd | 0.65 |
| SE | 0.12 | nd | nd | 0.068 | nd | 0.073 | 0.077 | nd | 0.085 |
| p | 0.28 | nd | nd | 0.021 | nd | 0.036 | 0.14 | nd | 0.084 |

TABLE 6-continued

Comparison of marker levels in EDTA samples collected from Cohort 1 (patients that did not progress beyond RIFLE stage 0 or R) and in EDTA samples collected from subjects at 0, 24 hours, and 48 hours prior to reaching stage I or F in Cohort 2.

| | | | | | | | | | |
|---|---|---|---|---|---|---|---|---|---|
| nCohort 1 | 197 | nd | nd | 197 | nd | 173 | 197 | nd | 173 |
| nCohort 2 | 7 | nd | nd | 21 | nd | 18 | 16 | nd | 13 |
| Cutoff 1 | 74.2 | nd | nd | 57.2 | nd | 57.2 | 58.1 | nd | 58.1 |
| Sens 1 | 71% | nd | nd | 71% | nd | 72% | 75% | nd | 77% |
| Spec 1 | 56% | nd | nd | 40% | nd | 36% | 40% | nd | 36% |
| Cutoff 2 | 57.2 | nd | nd | 53.5 | nd | 52.0 | 56.1 | nd | 56.1 |
| Sens 2 | 86% | nd | nd | 81% | nd | 83% | 81% | nd | 85% |
| Spec 2 | 40% | nd | nd | 34% | nd | 22% | 37% | nd | 33% |
| Cutoff 3 | 36.7 | nd | nd | 49.8 | nd | 49.5 | 53.9 | nd | 55.2 |
| Sens 3 | 100% | nd | nd | 90% | nd | 94% | 94% | nd | 92% |
| Spec 3 | 8% | nd | nd | 24% | nd | 18% | 34% | nd | 32% |
| Cutoff 4 | 84.3 | nd | nd | 84.3 | nd | 85.9 | 84.3 | nd | 85.9 |
| Sens 4 | 43% | nd | nd | 52% | nd | 61% | 44% | nd | 54% |
| Spec 4 | 70% | nd | nd | 70% | nd | 71% | 70% | nd | 71% |
| Cutoff 5 | 91.7 | nd | nd | 91.7 | nd | 97.1 | 91.7 | nd | 97.1 |
| Sens 5 | 43% | nd | nd | 52% | nd | 50% | 31% | nd | 38% |
| Spec 5 | 80% | nd | nd | 80% | nd | 80% | 80% | nd | 80% |
| Cutoff 6 | 114 | nd | nd | 114 | nd | 114 | 114 | nd | 114 |
| Sens 6 | 29% | nd | nd | 33% | nd | 39% | 19% | nd | 31% |
| Spec 6 | 90% | nd | nd | 90% | nd | 90% | 90% | nd | 90% |
| OR Quart 2 | 1.0 | nd | nd | 1.7 | nd | 0.72 | 5.4 | nd | >5.5 |
| p Value | 1.0 | nd | nd | 0.48 | nd | 0.67 | 0.13 | nd | <0.13 |
| 95% CI of | 0.061 | nd | nd | 0.39 | nd | 0.15 | 0.61 | nd | >0.61 |
| OR Quart 2 | 16 | nd | nd | 7.5 | nd | 3.4 | 48 | nd | na |
| OR Quart 3 | 2.0 | nd | nd | 0.65 | nd | 0 | 4.2 | nd | >2.1 |
| p Value | 0.57 | nd | nd | 0.65 | nd | na | 0.20 | nd | <0.55 |
| 95% CI of | 0.18 | nd | nd | 0.10 | nd | na | 0.46 | nd | >0.18 |
| OR Quart 3 | 23 | nd | nd | 4.1 | nd | na | 39 | nd | na |
| OR Quart 4 | 3.1 | nd | nd | 4.2 | nd | 3.2 | 6.5 | nd | >6.7 |
| p Value | 0.33 | nd | nd | 0.034 | nd | 0.063 | 0.088 | nd | <0.083 |
| 95% CI of | 0.31 | nd | nd | 1.1 | nd | 0.94 | 0.75 | nd | >0.78 |
| OR Quart 4 | 31 | nd | nd | 16 | nd | 11 | 56 | nd | na |

TABLE 7

Comparison of marker levels in EDTA samples collected within 12 hours of reaching stage R from Cohort 1 (patients that reached, but did not progress beyond, RIFLE stage R) and from Cohort 2 (patients that reached RIFLE stage I or F).
Coagulation factor VII

| | sCr or UO | | sCr only | | UO only | |
|---|---|---|---|---|---|---|
| | Cohort 1 | Cohort 2 | Cohort 1 | Cohort 2 | Cohort 1 | Cohort 2 |
| Median | 313 | 250 | 240 | 333 | 324 | 279 |
| Average | 335 | 258 | 333 | 282 | 325 | 268 |
| Stdev | 191 | 169 | 213 | 142 | 182 | 169 |
| p (t-test) | | 0.10 | | 0.57 | | 0.28 |
| Min | 35.7 | 22.9 | 65.3 | 75.6 | 35.7 | 22.9 |
| Max | 809 | 616 | 759 | 453 | 809 | 616 |
| n (Samp) | 55 | 22 | 18 | 7 | 46 | 16 |
| n (Patient) | 55 | 22 | 18 | 7 | 46 | 16 |

At Enrollment

| | sCr or UO | sCr only | UO only |
|---|---|---|---|
| AUC | 0.38 | 0.46 | 0.41 |
| SE | 0.073 | 0.13 | 0.085 |
| p | 0.100 | 0.76 | 0.28 |
| nCohort 1 | 55 | 18 | 46 |
| nCohort 2 | 22 | 7 | 16 |
| Cutoff 1 | 137 | 245 | 137 |
| Sens 1 | 73% | 71% | 81% |
| Spec 1 | 15% | 56% | 17% |
| Cutoff 2 | 95.4 | 75.6 | 137 |
| Sens 2 | 82% | 86% | 81% |
| Spec 2 | 5% | 6% | 17% |
| Cutoff 3 | 51.2 | 65.3 | 35.7 |
| Sens 3 | 91% | 100% | 94% |
| Spec 3 | 2% | 6% | 2% |
| Cutoff 4 | 446 | 415 | 446 |
| Sens 4 | 14% | 14% | 12% |
| Spec 4 | 71% | 72% | 72% |
| Cutoff 5 | 484 | 536 | 483 |
| Sens 5 | 14% | 0% | 12% |
| Spec 5 | 80% | 83% | 80% |
| Cutoff 6 | 598 | 737 | 536 |
| Sens 6 | 5% | 0% | 12% |
| Spec 6 | 91% | 94% | 91% |
| OR Quart 2 | 3.3 | 12 | 3.5 |
| p Value | 0.13 | 0.073 | 0.18 |
| 95% CI of | 0.71 | 0.80 | 0.56 |
| OR Quart 2 | 15 | 180 | 22 |
| OR Quart 3 | 1.5 | 0 | 2.3 |
| p Value | 0.62 | na | 0.37 |
| 95% CI of | 0.29 | na | 0.36 |
| OR Quart 3 | 7.9 | na | 15 |
| OR Quart 4 | 4.1 | 3.0 | 3.5 |
| p Value | 0.069 | 0.43 | 0.18 |
| 95% CI of | 0.89 | 0.20 | 0.56 |
| OR Quart 4 | 19 | 45 | 22 |

TABLE 8

Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.

| | Cancer Antigen 19-9 | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 0.204 | 0.652 | 0.204 | 0.601 | nd | nd |
| Average | 0.339 | 1.21 | 0.339 | 1.16 | nd | nd |
| Stdev | 0.668 | 1.66 | 0.668 | 1.67 | nd | nd |
| p (t-test) | | 0.0046 | | 0.0077 | nd | nd |
| Min | 1.00E−9 | 0.145 | 1.00E−9 | 0.145 | nd | nd |
| Max | 5.30 | 5.26 | 5.30 | 5.26 | nd | nd |
| n (Samp) | 74 | 8 | 74 | 8 | nd | nd |
| n (Patient) | 74 | 8 | 74 | 8 | nd | nd |
| UO only | | | | | | |
| Median | 0.258 | 0.588 | 0.258 | 0.588 | nd | nd |
| Average | 0.472 | 1.33 | 0.472 | 1.33 | nd | nd |
| Stdev | 0.791 | 1.95 | 0.791 | 1.95 | nd | nd |
| p (t-test) | | 0.034 | | 0.034 | nd | nd |
| Min | 1.00E−9 | 0.145 | 1.00E−9 | 0.145 | nd | nd |
| Max | 5.30 | 5.26 | 5.30 | 5.26 | nd | nd |
| n (Samp) | 64 | 6 | 64 | 6 | nd | nd |
| n (Patient) | 64 | 6 | 64 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.85 | nd | 0.74 | 0.84 | nd | 0.74 | nd | nd | nd |
| SE | 0.088 | nd | 0.12 | 0.090 | nd | 0.12 | nd | nd | nd |
| p | 7.4E−5 | nd | 0.045 | 2.0E−4 | nd | 0.045 | nd | nd | nd |
| nCohort 1 | 74 | nd | 64 | 74 | nd | 64 | nd | nd | nd |
| nCohort 2 | 8 | nd | 6 | 8 | nd | 6 | nd | nd | nd |
| Cutoff 1 | 0.546 | nd | 0.358 | 0.546 | nd | 0.358 | nd | nd | nd |
| Sens 1 | 75% | nd | 83% | 75% | nd | 83% | nd | nd | nd |
| Spec 1 | 88% | nd | 69% | 88% | nd | 69% | nd | nd | nd |
| Cutoff 2 | 0.358 | nd | 0.358 | 0.358 | nd | 0.358 | nd | nd | nd |
| Sens 2 | 88% | nd | 83% | 88% | nd | 83% | nd | nd | nd |
| Spec 2 | 80% | nd | 69% | 80% | nd | 69% | nd | nd | nd |
| Cutoff 3 | 0.124 | nd | 0.134 | 0.124 | nd | 0.134 | nd | nd | nd |
| Sens 3 | 100% | nd | 100% | 100% | nd | 100% | nd | nd | nd |
| Spec 3 | 34% | nd | 28% | 34% | nd | 28% | nd | nd | nd |
| Cutoff 4 | 0.311 | nd | 0.401 | 0.311 | nd | 0.401 | nd | nd | nd |
| Sens 4 | 88% | nd | 67% | 88% | nd | 67% | nd | nd | nd |
| Spec 4 | 70% | nd | 70% | 70% | nd | 70% | nd | nd | nd |
| Cutoff 5 | 0.401 | nd | 0.629 | 0.401 | nd | 0.629 | nd | nd | nd |
| Sens 5 | 75% | nd | 33% | 75% | nd | 33% | nd | nd | nd |
| Spec 5 | 81% | nd | 81% | 81% | nd | 81% | nd | nd | nd |
| Cutoff 6 | 0.629 | nd | 0.944 | 0.629 | nd | 0.944 | nd | nd | nd |
| Sens 6 | 50% | nd | 33% | 38% | nd | 33% | nd | nd | nd |
| Spec 6 | 91% | nd | 91% | 91% | nd | 91% | nd | nd | nd |
| OR Quart 2 | >1.0 | nd | >1.0 | >1.0 | nd | >1.0 | nd | nd | nd |
| p Value | <1.0 | nd | <1.0 | <1.0 | nd | <1.0 | nd | nd | nd |
| 95% CI of OR Quart 2 | >0.058 | nd | >0.058 | >0.058 | nd | >0.058 | nd | nd | nd |
| | na | nd | na | na | nd | na | nd | nd | nd |
| OR Quart 3 | >1.1 | nd | >1.1 | >1.1 | nd | >1.1 | nd | nd | nd |
| p Value | <0.97 | nd | <0.97 | <0.97 | nd | <0.97 | nd | nd | nd |
| 95% CI of OR Quart 3 | >0.061 | nd | >0.061 | >0.061 | nd | >0.061 | nd | nd | nd |
| | na | nd | na | na | nd | na | nd | nd | nd |
| OR Quart 4 | >8.0 | nd | >4.9 | >8.0 | nd | >4.9 | nd | nd | nd |
| p Value | <0.066 | nd | <0.18 | <0.066 | nd | <0.18 | nd | nd | nd |
| 95% CI of OR Quart 4 | >0.87 | nd | >0.49 | >0.87 | nd | >0.49 | nd | nd | nd |
| | na | nd | na | na | nd | na | nd | nd | nd |

TABLE 8-continued

Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.

C-C motif chemokine 13

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| sCr or UO | | | | | | |
| Median | 21.0 | 42.6 | 21.0 | 42.6 | 21.0 | 42.6 |
| Average | 104 | 90.3 | 104 | 90.3 | 104 | 42.9 |
| Stdev | 371 | 199 | 371 | 199 | 371 | 32.6 |
| p (t-test) |  | 0.90 |  | 0.90 |  | 0.69 |
| Min | 1.00E−9 | 1.00E−9 | 1.00E−9 | 1.00E−9 | 1.00E−9 | 1.00E−9 |
| Max | 2520 | 713 | 2520 | 713 | 2520 | 96.3 |
| n (Samp) | 50 | 12 | 50 | 12 | 50 | 6 |
| n (Patient) | 50 | 12 | 50 | 12 | 50 | 6 |
| sCr only | | | | | | |
| Median | 21.0 | 1.00E−9 | 21.0 | 1.00E−9 | nd | nd |
| Average | 72.5 | 20.5 | 72.5 | 20.5 | nd | nd |
| Stdev | 268 | 32.0 | 268 | 32.0 | nd | nd |
| p (t-test) |  | 0.64 |  | 0.64 | nd | nd |
| Min | 1.00E−9 | 1.00E−9 | 1.00E−9 | 1.00E−9 | nd | nd |
| Max | 2520 | 68.2 | 2520 | 68.2 | nd | nd |
| n (Samp) | 100 | 6 | 100 | 6 | nd | nd |
| n (Patient) | 100 | 6 | 100 | 6 | nd | nd |
| UO only | | | | | | |
| Median | 21.0 | 44.5 | 21.0 | 44.5 | 21.0 | 42.6 |
| Average | 115 | 127 | 115 | 127 | 115 | 42.9 |
| Stdev | 387 | 239 | 387 | 239 | 387 | 32.6 |
| p (t-test) |  | 0.93 |  | 0.93 |  | 0.65 |
| Min | 1.00E−9 | 1.00E−9 | 1.00E−9 | 1.00E−9 | 1.00E−9 | 1.00E−9 |
| Max | 2520 | 713 | 2520 | 713 | 2520 | 96.3 |
| n (Samp) | 46 | 8 | 46 | 8 | 46 | 6 |
| n (Patient) | 46 | 8 | 46 | 8 | 46 | 6 |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | 0.54 | 0.40 | 0.63 | 0.54 | 0.40 | 0.63 | 0.58 | nd | 0.58 |
| SE | 0.095 | 0.13 | 0.11 | 0.095 | 0.13 | 0.11 | 0.13 | nd | 0.13 |
| p | 0.69 | 0.41 | 0.25 | 0.69 | 0.41 | 0.25 | 0.53 | nd | 0.56 |
| nCohort 1 | 50 | 100 | 46 | 50 | 100 | 46 | 50 | nd | 46 |
| nCohort 2 | 12 | 6 | 8 | 12 | 6 | 8 | 6 | nd | 6 |
| Cutoff 1 | 0 | 0 | 38.0 | 0 | 0 | 38.0 | 7.19 | nd | 7.19 |
| Sens 1 | 100% | 100% | 75% | 100% | 100% | 75% | 83% | nd | 83% |
| Spec 1 | 0% | 0% | 61% | 0% | 0% | 61% | 44% | nd | 43% |
| Cutoff 2 | 0 | 0 | 7.19 | 0 | 0 | 7.19 | 7.19 | nd | 7.19 |
| Sens 2 | 100% | 100% | 88% | 100% | 100% | 88% | 83% | nd | 83% |
| Spec 2 | 0% | 0% | 43% | 0% | 0% | 43% | 44% | nd | 43% |
| Cutoff 3 | 0 | 0 | 0 | 0 | 0 | 0 | 0 | nd | 0 |
| Sens 3 | 100% | 100% | 100% | 100% | 100% | 100% | 100% | nd | 100% |
| Spec 3 | 0% | 0% | 0% | 0% | 0% | 0% | 0% | nd | 0% |
| Cutoff 4 | 56.0 | 44.5 | 59.5 | 56.0 | 44.5 | 59.5 | 56.0 | nd | 59.5 |
| Sens 4 | 25% | 33% | 25% | 25% | 33% | 25% | 17% | nd | 17% |
| Spec 4 | 70% | 70% | 72% | 70% | 70% | 72% | 70% | nd | 72% |
| Cutoff 5 | 72.2 | 69.2 | 69.2 | 72.2 | 69.2 | 69.2 | 72.2 | nd | 69.2 |
| Sens 5 | 17% | 0% | 25% | 17% | 0% | 25% | 17% | nd | 17% |
| Spec 5 | 80% | 81% | 80% | 80% | 81% | 80% | 80% | nd | 80% |
| Cutoff 6 | 105 | 96.3 | 105 | 105 | 96.3 | 105 | 105 | nd | 105 |
| Sens 6 | 8% | 0% | 12% | 8% | 0% | 12% | 0% | nd | 0% |
| Spec 6 | 90% | 90% | 91% | 90% | 90% | 91% | 90% | nd | 91% |
| OR Quart 2 | 0.18 | 1.0 | 0.92 | 0.18 | 1.0 | 0.92 | 1.0 | nd | 1.0 |
| p Value | 0.15 | 0.98 | 0.96 | 0.15 | 0.98 | 0.96 | 1.0 | nd | 1.0 |
| 95% CI of | 0.018 | 0.062 | 0.052 | 0.018 | 0.062 | 0.052 | 0.056 | nd | 0.056 |
| OR Quart 2 | 1.9 | 18 | 16 | 1.9 | 18 | 16 | 18 | nd | 18 |
| OR Quart 3 | 1.0 | 4.5 | 5.3 | 1.0 | 4.5 | 5.3 | 3.5 | nd | 3.6 |
| p Value | 1.0 | 0.19 | 0.16 | 1.0 | 0.19 | 0.16 | 0.30 | nd | 0.30 |
| 95% CI of | 0.20 | 0.47 | 0.51 | 0.20 | 0.47 | 0.51 | 0.32 | nd | 0.32 |
| OR Quart 3 | 5.0 | 43 | 56 | 5.0 | 43 | 56 | 39 | nd | 40 |
| OR Quart 4 | 0.63 | 0 | 2.0 | 0.63 | 0 | 2.0 | 1.0 | nd | 1.0 |
| p Value | 0.60 | na | 0.59 | 0.60 | na | 0.59 | 1.0 | nd | 1.0 |

TABLE 8-continued

Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.

| | | | | | | | | | |
|---|---|---|---|---|---|---|---|---|---|
| 95% CI of | 0.12 | na | 0.16 | 0.12 | na | 0.16 | 0.056 | nd | 0.056 |
| OR Quart 4 | 3.5 | na | 25 | 3.5 | na | 25 | 18 | nd | 18 |

C—X—C motif chemokine 6

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 34.7 | 43.2 | 34.7 | 43.2 | 34.7 | 46.7 |
| Average | 49.8 | 64.5 | 49.8 | 64.5 | 49.8 | 45.7 |
| Stdev | 49.7 | 87.6 | 49.7 | 87.6 | 49.7 | 21.8 |
| p (t-test) | | 0.44 | | 0.44 | | 0.84 |
| Min | 5.55 | 9.69 | 5.55 | 9.69 | 5.55 | 17.9 |
| Max | 244 | 336 | 244 | 336 | 244 | 72.4 |
| n (Samp) | 51 | 12 | 51 | 12 | 51 | 6 |
| n (Patient) | 51 | 12 | 51 | 12 | 51 | 6 |
| sCr only | | | | | | |
| Median | 27.2 | 33.4 | 27.2 | 33.4 | nd | nd |
| Average | 45.3 | 34.9 | 45.3 | 34.9 | nd | nd |
| Stdev | 50.5 | 22.4 | 50.5 | 22.4 | nd | nd |
| p (t-test) | | 0.62 | | 0.62 | nd | nd |
| Min | 4.02 | 9.69 | 4.02 | 9.69 | nd | nd |
| Max | 311 | 72.4 | 311 | 72.4 | nd | nd |
| n (Samp) | 101 | 6 | 101 | 6 | nd | nd |
| n (Patient) | 101 | 6 | 101 | 6 | nd | nd |
| UO only | | | | | | |
| Median | 31.0 | 46.7 | 31.0 | 46.7 | 31.0 | 46.7 |
| Average | 45.7 | 81.8 | 45.7 | 81.8 | 45.7 | 45.7 |
| Stdev | 49.1 | 105 | 49.1 | 105 | 49.1 | 21.8 |
| p (t-test) | | 0.12 | | 0.12 | | 1.00 |
| Min | 5.55 | 17.9 | 5.55 | 17.9 | 5.55 | 17.9 |
| Max | 244 | 336 | 244 | 336 | 244 | 72.4 |
| n (Samp) | 47 | 8 | 47 | 8 | 47 | 6 |
| n (Patient) | 47 | 8 | 47 | 8 | 47 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.59 | 0.51 | 0.70 | 0.59 | 0.51 | 0.70 | 0.60 | nd | 0.65 |
| SE | 0.095 | 0.12 | 0.11 | 0.095 | 0.12 | 0.11 | 0.13 | nd | 0.13 |
| p | 0.36 | 0.92 | 0.063 | 0.36 | 0.92 | 0.063 | 0.42 | nd | 0.24 |
| nCohort 1 | 51 | 101 | 47 | 51 | 101 | 47 | 51 | nd | 47 |
| nCohort 2 | 12 | 6 | 8 | 12 | 6 | 8 | 6 | nd | 6 |
| Cutoff 1 | 25.5 | 17.6 | 42.8 | 25.5 | 17.6 | 42.8 | 24.0 | nd | 24.0 |
| Sens 1 | 75% | 83% | 75% | 75% | 83% | 75% | 83% | nd | 83% |
| Spec 1 | 39% | 32% | 70% | 39% | 32% | 70% | 33% | nd | 38% |
| Cutoff 2 | 24.1 | 17.6 | 24.1 | 24.1 | 17.6 | 24.1 | 24.0 | nd | 24.0 |
| Sens 2 | 83% | 83% | 88% | 83% | 83% | 88% | 83% | nd | 83% |
| Spec 2 | 37% | 32% | 40% | 37% | 32% | 40% | 33% | nd | 38% |
| Cutoff 3 | 17.6 | 8.88 | 17.6 | 17.6 | 8.88 | 17.6 | 17.6 | nd | 17.6 |
| Sens 3 | 92% | 100% | 100% | 92% | 100% | 100% | 100% | nd | 100% |
| Spec 3 | 27% | 10% | 30% | 27% | 10% | 30% | 27% | nd | 30% |
| Cutoff 4 | 46.9 | 43.7 | 42.8 | 46.9 | 43.7 | 42.8 | 46.9 | nd | 42.8 |
| Sens 4 | 33% | 17% | 75% | 33% | 17% | 75% | 50% | nd | 67% |
| Spec 4 | 71% | 70% | 70% | 71% | 70% | 70% | 71% | nd | 70% |
| Cutoff 5 | 56.7 | 56.7 | 51.1 | 56.7 | 56.7 | 51.1 | 56.7 | nd | 51.1 |
| Sens 5 | 25% | 17% | 38% | 25% | 17% | 38% | 33% | nd | 33% |
| Spec 5 | 80% | 80% | 81% | 80% | 80% | 81% | 80% | nd | 81% |
| Cutoff 6 | 117 | 95.2 | 117 | 117 | 95.2 | 117 | 117 | nd | 117 |
| Sens 6 | 8% | 0% | 12% | 8% | 0% | 12% | 0% | nd | 0% |
| Spec 6 | 90% | 90% | 91% | 90% | 90% | 91% | 90% | nd | 91% |
| OR Quart 2 | 3.2 | 2.0 | >2.2 | 3.2 | 2.0 | >2.2 | >2.3 | nd | >2.4 |
| p Value | 0.34 | 0.58 | <0.55 | 0.34 | 0.58 | <0.55 | <0.51 | nd | <0.51 |
| 95% CI of | 0.30 | 0.17 | >0.17 | 0.30 | 0.17 | >0.17 | >0.19 | nd | >0.19 |
| OR Quart 2 | 35 | 23 | na | 35 | 23 | na | na | nd | na |
| OR Quart 3 | 6.4 | 2.0 | >2.2 | 6.4 | 2.0 | >2.2 | >2.3 | nd | >1.1 |
| p Value | 0.11 | 0.58 | <0.55 | 0.11 | 0.58 | <0.55 | <0.51 | nd | <0.96 |
| 95% CI of | 0.65 | 0.17 | >0.17 | 0.65 | 0.17 | >0.17 | >0.19 | nd | >0.061 |
| OR Quart 3 | 63 | 23 | na | 63 | 23 | na | na | nd | na |

TABLE 8-continued

Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.

| | | | | | | | | | |
|---|---|---|---|---|---|---|---|---|---|
| OR Quart 4 | 3.2 | 0.96 | >5.2 | 3.2 | 0.96 | >5.2 | >2.2 | nd | >3.5 |
| p Value | 0.34 | 0.98 | <0.17 | 0.34 | 0.98 | <0.17 | <0.55 | nd | <0.30 |
| 95% CI of | 0.30 | 0.057 | >0.50 | 0.30 | 0.057 | >0.50 | >0.17 | nd | >0.32 |
| OR Quart 4 | 35 | 16 | na | 35 | 16 | na | na | nd | na |

Coagulation factor VII

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 349 | 309 | 349 | 246 | 349 | 230 |
| Average | 382 | 318 | 382 | 274 | 382 | 298 |
| Stdev | 165 | 193 | 165 | 179 | 165 | 165 |
| p (t-test) | | 0.16 | | 0.016 | | 0.17 |
| Min | 2.33 | 32.8 | 2.33 | 32.8 | 2.33 | 139 |
| Max | 743 | 779 | 743 | 779 | 743 | 622 |
| n (Samp) | 110 | 16 | 110 | 16 | 110 | 8 |
| n (Patient) | 110 | 16 | 110 | 16 | 110 | 8 |
| sCr only | | | | | | |
| Median | 344 | 244 | 344 | 222 | nd | nd |
| Average | 368 | 261 | 368 | 231 | nd | nd |
| Stdev | 170 | 118 | 170 | 103 | nd | nd |
| p (t-test) | | 0.079 | | 0.025 | nd | nd |
| Min | 2.33 | 77.8 | 2.33 | 75.6 | nd | nd |
| Max | 822 | 430 | 822 | 386 | nd | nd |
| n (Samp) | 180 | 8 | 180 | 8 | nd | nd |
| n (Patient) | 180 | 8 | 180 | 8 | nd | nd |
| UO only | | | | | | |
| Median | 356 | 358 | 356 | 310 | 356 | 304 |
| Average | 388 | 368 | 388 | 321 | 388 | 324 |
| Stdev | 169 | 215 | 169 | 206 | 169 | 186 |
| p (t-test) | | 0.73 | | 0.25 | | 0.38 |
| Min | 119 | 32.8 | 119 | 32.8 | 119 | 139 |
| Max | 1020 | 779 | 1020 | 779 | 1020 | 622 |
| n (Samp) | 91 | 10 | 91 | 10 | 91 | 6 |
| n (Patient) | 91 | 10 | 91 | 10 | 91 | 6 |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.39 | 0.32 | 0.48 | 0.31 | 0.25 | 0.39 | 0.34 | nd | 0.40 |
| SE | 0.079 | 0.11 | 0.098 | 0.077 | 0.10 | 0.099 | 0.11 | nd | 0.13 |
| p | 0.17 | 0.086 | 0.82 | 0.011 | 0.015 | 0.28 | 0.14 | nd | 0.43 |
| nCohort 1 | 110 | 180 | 91 | 110 | 180 | 91 | 110 | nd | 91 |
| nCohort 2 | 16 | 8 | 10 | 16 | 8 | 10 | 8 | nd | 6 |
| Cutoff 1 | 185 | 190 | 283 | 151 | 190 | 246 | 195 | nd | 150 |
| Sens 1 | 75% | 75% | 70% | 75% | 75% | 70% | 75% | nd | 83% |
| Spec 1 | 11% | 15% | 26% | 9% | 15% | 19% | 13% | nd | 7% |
| Cutoff 2 | 173 | 177 | 274 | 138 | 126 | 150 | 151 | nd | 150 |
| Sens 2 | 81% | 88% | 80% | 81% | 88% | 80% | 88% | nd | 83% |
| Spec 2 | 10% | 14% | 24% | 5% | 4% | 7% | 9% | nd | 7% |
| Cutoff 3 | 32.8 | 53.5 | 138 | 32.8 | 53.5 | 138 | 138 | nd | 138 |
| Sens 3 | 94% | 100% | 90% | 94% | 100% | 90% | 100% | nd | 100% |
| Spec 3 | 1% | 2% | 4% | 1% | 2% | 4% | 5% | nd | 4% |
| Cutoff 4 | 456 | 456 | 437 | 456 | 456 | 437 | 456 | nd | 437 |
| Sens 4 | 12% | 0% | 30% | 6% | 0% | 20% | 12% | nd | 17% |
| Spec 4 | 70% | 71% | 70% | 70% | 71% | 70% | 70% | nd | 70% |
| Cutoff 5 | 533 | 510 | 549 | 533 | 510 | 549 | 533 | nd | 549 |
| Sens 5 | 12% | 0% | 20% | 6% | 0% | 10% | 12% | nd | 17% |
| Spec 5 | 80% | 80% | 80% | 80% | 80% | 80% | 80% | nd | 80% |
| Cutoff 6 | 646 | 623 | 632 | 646 | 623 | 632 | 646 | nd | 632 |
| Sens 6 | 6% | 0% | 10% | 6% | 0% | 10% | 0% | nd | 0% |
| Spec 6 | 90% | 90% | 90% | 90% | 90% | 90% | 90% | nd | 90% |
| OR Quart 2 | 2.2 | >2.1 | 1.6 | 3.3 | >1.0 | 3.4 | 2.1 | nd | 2.2 |
| p Value | 0.38 | <0.55 | 0.61 | 0.31 | <0.99 | 0.30 | 0.54 | nd | 0.54 |
| 95% CI of | 0.38 | >0.18 | 0.25 | 0.33 | >0.062 | 0.33 | 0.18 | nd | 0.18 |
| OR Quart 2 | 13 | na | 11 | 34 | na | 35 | 25 | nd | 26 |
| OR Quart 3 | 2.1 | >2.1 | 1.6 | 4.4 | >3.2 | 2.2 | 0 | nd | 0 |
| p Value | 0.40 | <0.55 | 0.61 | 0.19 | <0.32 | 0.54 | na | nd | na |

TABLE 8-continued

Comparison of the maximum marker levels in EDTA samples collected from Cohort 1 (patients that did not progress beyond RIFLE stage 0) and the maximum values in EDTA samples collected from subjects between enrollment and 0, 24 hours, and 48 hours prior to reaching stage F in Cohort 2.

| | | | | | | | | | |
|---|---|---|---|---|---|---|---|---|---|
| 95% CI of | 0.36 | >0.18 | 0.25 | 0.47 | >0.32 | 0.18 | na | nd | na |
| OR Quart 3 | 13 | na | 11 | 42 | na | 26 | na | nd | na |
| OR Quart 4 | 3.6 | >4.4 | 1.0 | 11 | >4.4 | 4.8 | 6.0 | nd | 3.4 |
| p Value | 0.14 | <0.19 | 0.97 | 0.030 | <0.19 | 0.18 | 0.11 | nd | 0.30 |
| 95% CI of | 0.67 | >0.47 | 0.14 | 1.3 | >0.47 | 0.49 | 0.66 | nd | 0.33 |
| OR Quart 4 | 19 | na | 8.0 | 92 | na | 46 | 55 | nd | 36 |

Insulin-like growth factor-binding protein 7

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 65.8 | 160 | 65.8 | 132 | nd | nd |
| Average | 70.2 | 181 | 70.2 | 174 | nd | nd |
| Stdev | 35.5 | 120 | 35.5 | 121 | nd | nd |
| p (t-test) | | 4.1E−8 | | 2.2E−7 | nd | nd |
| Min | 18.6 | 58.3 | 18.6 | 58.3 | nd | nd |
| Max | 250 | 437 | 250 | 437 | nd | nd |
| n (Samp) | 74 | 8 | 74 | 8 | nd | nd |
| n (Patient) | 74 | 8 | 74 | 8 | nd | nd |
| UO only | | | | | | |
| Median | 73.5 | 114 | 73.5 | 114 | nd | nd |
| Average | 76.8 | 171 | 76.8 | 171 | nd | nd |
| Stdev | 35.4 | 140 | 35.4 | 140 | nd | nd |
| p (t-test) | | 5.0E−5 | | 5.0E−5 | nd | nd |
| Min | 28.5 | 58.3 | 28.5 | 58.3 | nd | nd |
| Max | 250 | 437 | 250 | 437 | nd | nd |
| n (Samp) | 64 | 6 | 64 | 6 | nd | nd |
| n (Patient) | 64 | 6 | 64 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.89 | nd | 0.82 | 0.88 | nd | 0.82 | nd | nd | nd |
| SE | 0.079 | nd | 0.11 | 0.080 | nd | 0.11 | nd | nd | nd |
| p | 9.7E−7 | nd | 0.0029 | 1.6E−6 | nd | 0.0029 | nd | nd | nd |
| nCohort 1 | 74 | nd | 64 | 74 | nd | 64 | nd | nd | nd |
| nCohort 2 | 8 | nd | 6 | 8 | nd | 6 | nd | nd | nd |
| Cutoff 1 | 96.9 | nd | 91.7 | 96.9 | nd | 91.7 | nd | nd | nd |
| Sens 1 | 75% | nd | 83% | 75% | nd | 83% | nd | nd | nd |
| Spec 1 | 86% | nd | 81% | 86% | nd | 81% | nd | nd | nd |
| Cutoff 2 | 91.7 | nd | 91.7 | 91.7 | nd | 91.7 | nd | nd | nd |
| Sens 2 | 88% | nd | 83% | 88% | nd | 83% | nd | nd | nd |
| Spec 2 | 85% | nd | 81% | 85% | nd | 81% | nd | nd | nd |
| Cutoff 3 | 57.2 | nd | 58.1 | 57.2 | nd | 58.1 | nd | nd | nd |
| Sens 3 | 100% | nd | 100% | 100% | nd | 100% | nd | nd | nd |
| Spec 3 | 45% | nd | 36% | 45% | nd | 36% | nd | nd | nd |
| Cutoff 4 | 79.2 | nd | 84.3 | 79.2 | nd | 84.3 | nd | nd | nd |
| Sens 4 | 88% | nd | 83% | 88% | nd | 83% | nd | nd | nd |
| Spec 4 | 70% | nd | 70% | 70% | nd | 70% | nd | nd | nd |
| Cutoff 5 | 87.0 | nd | 91.7 | 87.0 | nd | 91.7 | nd | nd | nd |
| Sens 5 | 88% | nd | 83% | 88% | nd | 83% | nd | nd | nd |
| Spec 5 | 81% | nd | 81% | 81% | nd | 81% | nd | nd | nd |
| Cutoff 6 | 114 | nd | 115 | 114 | nd | 115 | nd | nd | nd |
| Sens 6 | 62% | nd | 50% | 62% | nd | 50% | nd | nd | nd |
| Spec 6 | 91% | nd | 91% | 91% | nd | 91% | nd | nd | nd |
| OR Quart 2 | >1.0 | nd | >1.0 | >1.0 | nd | >1.0 | nd | nd | nd |
| p Value | <1.0 | nd | <1.0 | <1.0 | nd | <1.0 | nd | nd | nd |
| 95% CI of | >0.058 | nd | >0.058 | >0.058 | nd | >0.058 | nd | nd | nd |
| OR Quart 2 | na | nd | na | na | nd | na | nd | nd | nd |
| OR Quart 3 | >0 | nd | >0 | >0 | nd | >0 | nd | nd | nd |
| p Value | <na | nd | <na | <na | nd | <na | nd | nd | nd |
| 95% CI of | >na | nd | >na | >na | nd | >na | nd | nd | nd |
| OR Quart 3 | na | nd | na | na | nd | na | nd | nd | nd |
| OR Quart 4 | >10 | nd | >6.5 | >10 | nd | >6.5 | nd | nd | nd |
| p Value | <0.041 | nd | <0.10 | <0.041 | nd | <0.10 | nd | nd | nd |
| 95% CI of | >1.1 | nd | >0.68 | >1.1 | nd | >0.68 | nd | nd | nd |
| OR Quart 4 | na | nd | na | na | nd | na | nd | nd | nd |

TABLE 9

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | Cancer Antigen 19-9 | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 22.9 | 38.8 | 22.9 | 42.2 | nd | nd |
| Average | 145 | 35.3 | 145 | 391 | nd | nd |
| Stdev | 710 | 21.1 | 710 | 917 | nd | nd |
| p(t-test) | | 0.68 | | 0.28 | nd | nd |
| Min | 1.00E−9 | 6.51 | 1.00E−9 | 18.6 | nd | nd |
| Max | 11900 | 59.3 | 11900 | 2940 | nd | nd |
| n (Samp) | 324 | 7 | 324 | 10 | nd | nd |
| n (Patient) | 190 | 7 | 190 | 10 | nd | nd |
| UO only | | | | | | |
| Median | nd | nd | 25.8 | 38.7 | nd | nd |
| Average | nd | nd | 156 | 476 | nd | nd |
| Stdev | nd | nd | 755 | 1020 | nd | nd |
| p(t-test) | nd | nd | | 0.24 | nd | nd |
| Min | nd | nd | 1.00E−9 | 18.6 | nd | nd |
| Max | nd | nd | 11900 | 2940 | nd | nd |
| n (Samp) | nd | nd | 283 | 8 | nd | nd |
| n (Patient) | nd | nd | 159 | 8 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.54 | nd | nd | 0.67 | nd | 0.65 | nd | nd | nd |
| SE | 0.11 | nd | nd | 0.095 | nd | 0.11 | nd | nd | nd |
| p | 0.71 | nd | nd | 0.068 | nd | 0.16 | nd | nd | nd |
| nCohort 1 | 324 | nd | nd | 324 | nd | 283 | nd | nd | nd |
| nCohort 2 | 7 | nd | nd | 10 | nd | 8 | nd | nd | nd |
| Cutoff 1 | 36.7 | nd | nd | 27.5 | nd | 21.8 | nd | nd | nd |
| Sens 1 | 71% | nd | nd | 70% | nd | 75% | nd | nd | nd |
| Spec 1 | 64% | nd | nd | 56% | nd | 45% | nd | nd | nd |
| Cutoff 2 | 6.59 | nd | nd | 21.9 | nd | 20.7 | nd | nd | nd |
| Sens 2 | 86% | nd | nd | 80% | nd | 88% | nd | nd | nd |
| Spec 2 | 22% | nd | nd | 48% | nd | 43% | nd | nd | nd |
| Cutoff 3 | 6.42 | nd | nd | 20.7 | nd | 18.5 | nd | nd | nd |
| Sens 3 | 100% | nd | nd | 90% | nd | 100% | nd | nd | nd |
| Spec 3 | 21% | nd | nd | 47% | nd | 41% | nd | nd | nd |
| Cutoff 4 | 54.2 | nd | nd | 54.2 | nd | 57.7 | nd | nd | nd |
| Sens 4 | 14% | nd | nd | 40% | nd | 38% | nd | nd | nd |
| Spec 4 | 70% | nd | nd | 70% | nd | 70% | nd | nd | nd |
| Cutoff 5 | 102 | nd | nd | 102 | nd | 116 | nd | nd | nd |
| Sens 5 | 0% | nd | nd | 20% | nd | 25% | nd | nd | nd |
| Spec 5 | 80% | nd | nd | 80% | nd | 80% | nd | nd | nd |
| Cutoff 6 | 240 | nd | nd | 240 | nd | 277 | nd | nd | nd |
| Sens 6 | 0% | nd | nd | 20% | nd | 25% | nd | nd | nd |
| Spec 6 | 90% | nd | nd | 90% | nd | 90% | nd | nd | nd |
| OR Quart 2 | 0 | nd | nd | >3.1 | nd | >3.1 | nd | nd | nd |
| p Value | na | nd | nd | <0.34 | nd | <0.33 | nd | nd | nd |
| 95% CI of | na | nd | nd | >0.31 | nd | >0.31 | nd | nd | nd |
| OR Quart2 | na | nd | nd | na | nd | na | nd | nd | nd |
| OR Quart 3 | 2.6 | nd | nd | >3.1 | nd | >2.0 | nd | nd | nd |
| p Value | 0.27 | nd | nd | <0.33 | nd | <0.57 | nd | nd | nd |
| 95% CI of | 0.48 | nd | nd | >0.32 | nd | >0.18 | nd | nd | nd |
| OR Quart3 | 14 | nd | nd | na | nd | na | nd | nd | nd |
| OR Quart 4 | 0 | nd | nd | >4.2 | nd | >3.1 | nd | nd | nd |
| p Value | na | nd | nd | <0.21 | nd | <0.33 | nd | nd | nd |
| 95% CI of | na | nd | nd | >0.45 | nd | >0.31 | nd | nd | nd |
| OR Quart4 | na | nd | nd | na | nd | na | nd | nd | nd |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | C-C motif chemokine 13 | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 1.00E−9 | 1.00E−9 | 1.00E−9 | 3.52 | 1.00E−9 | 1.00E−9 |
| Average | 2.67 | 13.6 | 2.67 | 22.2 | 2.67 | 8.85 |
| Stdev | 16.4 | 40.1 | 16.4 | 35.5 | 16.4 | 23.4 |
| p(t-test) | | 0.021 | | 5.2E−6 | | 0.32 |
| Min | 1.00E−9 | 1.00E−9 | 1.00E−9 | 1.00E−9 | 1.00E−9 | 1.00E−9 |
| Max | 241 | 143 | 241 | 101 | 241 | 61.9 |
| n (Samp) | 937 | 13 | 937 | 16 | 937 | 7 |
| n (Patient) | 345 | 13 | 345 | 16 | 345 | 7 |
| sCr only | | | | | | |
| Median | 1.00E−9 | 1.00E−9 | nd | nd | nd | nd |
| Average | 3.18 | 1.00E−9 | nd | nd | nd | nd |
| Stdev | 17.6 | 0 | nd | nd | nd | nd |
| p(t-test) | | 0.63 | nd | nd | nd | nd |
| Min | 1.00E−9 | 1.00E−9 | nd | nd | nd | nd |
| Max | 241 | 1.00E−9 | nd | nd | nd | nd |
| n (Samp) | 974 | 7 | nd | nd | nd | nd |
| n (Patient) | 355 | 7 | nd | nd | nd | nd |
| UO only | | | | | | |
| Median | 1.00E−9 | 1.00E−9 | 1.00E−9 | 3.52 | nd | nd |
| Average | 2.68 | 17.9 | 2.68 | 24.8 | nd | nd |
| Stdev | 17.0 | 50.7 | 17.0 | 37.3 | nd | nd |
| p(t-test) | | 0.015 | | 3.1E−6 | nd | nd |
| Min | 1.00E−9 | 1.00E−9 | 1.00E−9 | 1.00E−9 | nd | nd |
| Max | 241 | 143 | 241 | 101 | nd | nd |
| n (Samp) | 804 | 8 | 804 | 14 | nd | nd |
| n (Patient) | 264 | 8 | 264 | 14 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.55 | 0.46 | 0.53 | 0.72 | nd | 0.72 | 0.54 | nd | nd |
| SE | 0.083 | 0.11 | 0.10 | 0.073 | nd | 0.078 | 0.11 | nd | nd |
| p | 0.56 | 0.75 | 0.74 | 0.0028 | nd | 0.0046 | 0.71 | nd | nd |
| nCohort 1 | 937 | 974 | 804 | 937 | nd | 804 | 937 | nd | nd |
| nCohort 2 | 13 | 7 | 8 | 16 | nd | 14 | 7 | nd | nd |
| Cutoff 1 | 0 | 0 | 0 | 0 | nd | 0 | 0 | nd | nd |
| Sens 1 | 100% | 100% | 100% | 100% | nd | 100% | 100% | nd | nd |
| Spec 1 | 0% | 0% | 0% | 0% | nd | 0% | 0% | nd | nd |
| Cutoff 2 | 0 | 0 | 0 | 0 | nd | 0 | 0 | nd | nd |
| Sens 2 | 100% | 100% | 100% | 100% | nd | 100% | 100% | nd | nd |
| Spec 2 | 0% | 0% | 0% | 0% | nd | 0% | 0% | nd | nd |
| Cutoff 3 | 0 | 0 | 0 | 0 | nd | 0 | 0 | nd | nd |
| Sens 3 | 100% | 100% | 100% | 100% | nd | 100% | 100% | nd | nd |
| Spec 3 | 0% | 0% | 0% | 0% | nd | 0% | 0% | nd | nd |
| Cutoff 4 | 1.00E−9 | 1.00E−9 | 1.00E−9 | 1.00E−9 | nd | 1.00E−9 | 1.00E−9 | nd | nd |
| Sens 4 | 15% | 0% | 12% | 50% | nd | 50% | 14% | nd | nd |
| Spec 4 | 93% | 93% | 94% | 93% | nd | 94% | 93% | nd | nd |
| Cutoff 5 | 1.00E−9 | 1.00E−9 | 1.00E−9 | 1.00E−9 | nd | 1.00E−9 | 1.00E−9 | nd | nd |
| Sens 5 | 15% | 0% | 12% | 50% | nd | 50% | 14% | nd | nd |
| Spec 5 | 93% | 93% | 94% | 93% | nd | 94% | 93% | nd | nd |
| Cutoff 6 | 1.00E−9 | 1.00E−9 | 1.00E−9 | 1.00E−9 | nd | 1.00E−9 | 1.00E−9 | nd | nd |
| Sens 6 | 15% | 0% | 12% | 50% | nd | 50% | 14% | nd | nd |
| Spec 6 | 93% | 93% | 94% | 93% | nd | 94% | 93% | nd | nd |
| OR Quart 2 | >11 | >0 | >7.2 | >8.3 | nd | >7.2 | >6.2 | nd | nd |
| p Value | <0.020 | <na | <0.065 | <0.047 | nd | <0.066 | <0.094 | nd | nd |
| 95% CI of OR Quart2 | >1.5 | >na | >0.88 | >1.0 | nd | >0.88 | >0.74 | nd | nd |
| | na | na | na | na | nd | na | na | nd | nd |
| OR Quart 3 | >0 | >7.2 | >0 | >0 | nd | >0 | >0 | nd | nd |
| p Value | <na | <0.065 | <na | <na | nd | <na | <na | nd | nd |
| 95% CI of OR Quart3 | >na | >0.88 | >na | >na | nd | >na | >na | nd | nd |
| | na | na | na | na | nd | na | na | nd | nd |
| OR Quart 4 | >2.0 | >0 | >1.0 | >8.2 | nd | >7.2 | >1.0 | nd | nd |
| p Value | <0.57 | <na | <1.00 | <0.048 | nd | <0.066 | <1.00 | nd | nd |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | | | | | | | |
|---|---|---|---|---|---|---|---|---|---|
| 95% CI of | >0.18 | >na | >0.062 | >1.0 | nd | >0.88 | >0.062 | nd | nd |
| OR Quart4 | na | na | na | na | nd | na | na | nd | nd |

C-X-C motif chemokine 6

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 15.5 | 19.3 | 15.5 | 82.0 | 15.5 | 8.72 |
| Average | 35.9 | 206 | 35.9 | 201 | 35.9 | 26.6 |
| Stdev | 106 | 453 | 106 | 252 | 106 | 50.3 |
| p(t-test) | | 2.4E−7 | | 3.5E−9 | | 0.82 |
| Min | 1.00E−9 | 1.62 | 1.00E−9 | 9.04 | 1.00E−9 | 0.506 |
| Max | 2500 | 1450 | 2500 | 769 | 2500 | 140 |
| n (Samp) | 935 | 13 | 935 | 16 | 935 | 7 |
| n (Patient) | 345 | 13 | 345 | 16 | 345 | 7 |
| sCr only | | | | | | |
| Median | 15.9 | 61.3 | nd | nd | nd | nd |
| Average | 40.3 | 281 | nd | nd | nd | nd |
| Stdev | 116 | 530 | nd | nd | nd | nd |
| p(t-test) | | 2.8E−7 | nd | nd | nd | nd |
| Min | 1.00E−9 | 1.62 | nd | nd | nd | nd |
| Max | 2500 | 1450 | nd | nd | nd | nd |
| n (Samp) | 972 | 7 | nd | nd | nd | nd |
| n (Patient) | 355 | 7 | nd | nd | nd | nd |
| UO only | | | | | | |
| Median | 17.0 | 40.1 | 17.0 | 99.7 | nd | nd |
| Average | 37.5 | 320 | 37.5 | 225 | nd | nd |
| Stdev | 112 | 560 | 112 | 262 | nd | nd |
| p(t-test) | | 2.0E−10 | | 3.5E−9 | nd | nd |
| Min | 1.00E−9 | 3.96 | 1.00E−9 | 9.04 | nd | nd |
| Max | 2500 | 1450 | 2500 | 769 | nd | nd |
| n (Samp) | 802 | 8 | 802 | 14 | nd | nd |
| n (Patient) | 264 | 8 | 264 | 14 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.58 | 0.65 | 0.62 | 0.83 | nd | 0.84 | 0.37 | nd | nd |
| SE | 0.083 | 0.11 | 0.11 | 0.063 | nd | 0.067 | 0.11 | nd | nd |
| p | 0.36 | 0.20 | 0.28 | 2.1E−7 | nd | 4.1E−7 | 0.25 | nd | nd |
| nCohort 1 | 935 | 972 | 802 | 935 | nd | 802 | 935 | nd | nd |
| nCohort 2 | 13 | 7 | 8 | 16 | nd | 14 | 7 | nd | nd |
| Cutoff 1 | 7.87 | 11.6 | 7.87 | 48.3 | nd | 51.2 | 4.01 | nd | nd |
| Sens 1 | 77% | 71% | 75% | 75% | nd | 71% | 71% | nd | nd |
| Spec 1 | 31% | 39% | 28% | 84% | nd | 85% | 17% | nd | nd |
| Cutoff 2 | 5.34 | 7.91 | 5.34 | 24.7 | nd | 24.5 | 0.534 | nd | nd |
| Sens 2 | 85% | 86% | 88% | 81% | nd | 86% | 86% | nd | nd |
| Spec 2 | 22% | 31% | 19% | 64% | nd | 62% | 5% | nd | nd |
| Cutoff 3 | 3.84 | 1.62 | 3.83 | 12.0 | nd | 12.0 | 0.437 | nd | nd |
| Sens 3 | 92% | 100% | 100% | 94% | nd | 93% | 100% | nd | nd |
| Spec 3 | 16% | 8% | 13% | 41% | nd | 38% | 4% | nd | nd |
| Cutoff 4 | 29.2 | 30.3 | 30.1 | 29.2 | nd | 30.1 | 29.2 | nd | nd |
| Sens 4 | 46% | 57% | 50% | 75% | nd | 79% | 14% | nd | nd |
| Spec 4 | 70% | 70% | 70% | 70% | nd | 70% | 70% | nd | nd |
| Cutoff 5 | 40.3 | 43.6 | 41.1 | 40.3 | nd | 41.1 | 40.3 | nd | nd |
| Sens 5 | 38% | 57% | 50% | 75% | nd | 79% | 14% | nd | nd |
| Spec 5 | 80% | 80% | 80% | 80% | nd | 80% | 80% | nd | nd |
| Cutoff 6 | 63.9 | 69.4 | 63.9 | 63.9 | nd | 63.9 | 63.9 | nd | nd |
| Sens 6 | 23% | 29% | 25% | 56% | nd | 64% | 14% | nd | nd |
| Spec 6 | 90% | 90% | 90% | 90% | nd | 90% | 90% | nd | nd |
| OR Quart 2 | 1.0 | 2.0 | 0.50 | >2.0 | nd | >2.0 | 1.0 | nd | nd |
| p Value | 1.0 | 0.57 | 0.57 | <0.57 | nd | <0.57 | 1.00 | nd | nd |
| 95% CI of | 0.20 | 0.18 | 0.045 | >0.18 | nd | >0.18 | 0.062 | nd | nd |
| OR Quart2 | 5.0 | 22 | 5.5 | na | nd | na | 16 | nd | nd |
| OR Quart 3 | 0.66 | 0 | 0.50 | >2.0 | nd | >1.0 | 2.0 | nd | nd |
| p Value | 0.66 | na | 0.57 | <0.57 | nd | <1.00 | 0.57 | nd | nd |
| 95% CI of | 0.11 | na | 0.045 | >0.18 | nd | >0.062 | 0.18 | nd | nd |
| OR Quart3 | 4.0 | na | 5.5 | na | nd | na | 22 | nd | nd |
| OR Quart 4 | 1.7 | 4.0 | 2.0 | >13 | nd | >12 | 3.0 | nd | nd |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | | | | | | | | | |
|---|---|---|---|---|---|---|---|---|---|
| p Value | 0.48 | 0.21 | 0.42 | <0.015 | nd | <0.019 | 0.34 | nd | nd |
| 95% CI of | 0.40 | 0.45 | 0.36 | >1.6 | nd | >1.5 | 0.31 | nd | nd |
| OR Quart4 | 7.1 | 36 | 11 | na | nd | na | 29 | nd | nd |

Coagulation factor VII

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 3.14 | 3.73 | 3.14 | 2.84 | nd | nd |
| Average | 6.63 | 5.14 | 6.63 | 7.07 | nd | nd |
| Stdev | 13.6 | 5.61 | 13.6 | 8.20 | nd | nd |
| p(t-test) | | 0.73 | | 0.92 | nd | nd |
| Min | 0.00408 | 0.348 | 0.00408 | 0.682 | nd | nd |
| Max | 249 | 18.9 | 249 | 24.9 | nd | nd |
| n (Samp) | 534 | 10 | 534 | 11 | nd | nd |
| n (Patient) | 204 | 10 | 204 | 11 | nd | nd |
| UO only | | | | | | |
| Median | 3.08 | 4.33 | 3.08 | 2.79 | nd | nd |
| Average | 6.47 | 4.83 | 6.47 | 5.67 | nd | nd |
| Stdev | 14.1 | 2.60 | 14.1 | 6.68 | nd | nd |
| p(t-test) | | 0.76 | | 0.87 | nd | nd |
| Min | 0.00408 | 0.550 | 0.00408 | 0.682 | nd | nd |
| Max | 249 | 8.18 | 249 | 19.4 | nd | nd |
| n (Samp) | 454 | 7 | 454 | 8 | nd | nd |
| n (Patient) | 168 | 7 | 168 | 8 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.48 | nd | 0.57 | 0.55 | nd | 0.52 | nd | nd | nd |
| SE | 0.093 | nd | 0.11 | 0.090 | nd | 0.10 | nd | nd | nd |
| p | 0.87 | nd | 0.52 | 0.55 | nd | 0.88 | nd | nd | nd |
| nCohort 1 | 534 | nd | 454 | 534 | nd | 454 | nd | nd | nd |
| nCohort 2 | 10 | nd | 7 | 11 | nd | 8 | nd | nd | nd |
| Cutoff 1 | 2.27 | nd | 4.15 | 2.34 | nd | 2.34 | nd | nd | nd |
| Sens 1 | 70% | nd | 71% | 73% | nd | 75% | nd | nd | nd |
| Spec 1 | 40% | nd | 59% | 41% | nd | 42% | nd | nd | nd |
| Cutoff 2 | 0.539 | nd | 3.28 | 2.16 | nd | 1.50 | nd | nd | nd |
| Sens 2 | 80% | nd | 86% | 82% | nd | 88% | nd | nd | nd |
| Spec 2 | 11% | nd | 51% | 39% | nd | 31% | nd | nd | nd |
| Cutoff 3 | 0.420 | nd | 0.539 | 1.50 | nd | 0.676 | nd | nd | nd |
| Sens 3 | 90% | nd | 100% | 91% | nd | 100% | nd | nd | nd |
| Spec 3 | 7% | nd | 11% | 31% | nd | 13% | nd | nd | nd |
| Cutoff 4 | 6.36 | nd | 6.11 | 6.36 | nd | 6.11 | nd | nd | nd |
| Sens 4 | 30% | nd | 29% | 27% | nd | 25% | nd | nd | nd |
| Spec 4 | 70% | nd | 70% | 70% | nd | 70% | nd | nd | nd |
| Cutoff 5 | 9.31 | nd | 8.93 | 9.31 | nd | 8.93 | nd | nd | nd |
| Sens 5 | 10% | nd | 0% | 27% | nd | 25% | nd | nd | nd |
| Spec 5 | 80% | nd | 80% | 80% | nd | 80% | nd | nd | nd |
| Cutoff 6 | 15.0 | nd | 14.3 | 15.0 | nd | 14.3 | nd | nd | nd |
| Sens 6 | 10% | nd | 0% | 18% | nd | 12% | nd | nd | nd |
| Spec 6 | 90% | nd | 91% | 90% | nd | 91% | nd | nd | nd |
| OR Quart 2 | 2.0 | nd | 0 | 5.2 | nd | 4.1 | nd | nd | nd |
| p Value | 0.42 | nd | na | 0.14 | nd | 0.21 | nd | nd | nd |
| 95% CI of | 0.37 | nd | na | 0.59 | nd | 0.45 | nd | nd | nd |
| OR Quart2 | 11 | nd | na | 45 | nd | 37 | nd | nd | nd |
| OR Quart 3 | 0.50 | nd | 4.1 | 2.0 | nd | 1.0 | nd | nd | nd |
| p Value | 0.57 | nd | 0.21 | 0.57 | nd | 1.0 | nd | nd | nd |
| 95% CI of | 0.044 | nd | 0.45 | 0.18 | nd | 0.062 | nd | nd | nd |
| OR Quart3 | 5.5 | nd | 37 | 22 | nd | 16 | nd | nd | nd |
| OR Quart 4 | 1.5 | nd | 2.0 | 3.0 | nd | 2.0 | nd | nd | nd |
| p Value | 0.65 | nd | 0.57 | 0.34 | nd | 0.57 | nd | nd | nd |
| 95% CI of | 0.25 | nd | 0.18 | 0.31 | nd | 0.18 | nd | nd | nd |
| OR Quart4 | 9.2 | nd | 22 | 29 | nd | 22 | nd | nd | nd |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| | Insulin-like growth factor-binding protein 7 | | | | | |
|---|---|---|---|---|---|---|
| | 0 hr prior to AKI stage | | 24 hr prior to AKI stage | | 48 hr prior to AKI stage | |
| | Cohort 1 | Cohort 2 | Cohort 1 | Cohort 2 | Cohort 1 | Cohort 2 |
| sCr or UO | | | | | | |
| Median | 52.8 | 68.7 | 52.8 | 226 | 52.8 | 102 |
| Average | 76.8 | 280 | 76.8 | 332 | 76.8 | 151 |
| Stdev | 80.0 | 492 | 80.0 | 315 | 80.0 | 123 |
| p(t-test) | | 1.4E−13 | | 3.2E−28 | | 0.015 |
| Min | 1.00E−9 | 23.1 | 1.00E−9 | 20.4 | 1.00E−9 | 33.8 |
| Max | 694 | 1830 | 694 | 1250 | 694 | 382 |
| n (Samp) | 933 | 13 | 933 | 16 | 933 | 7 |
| n (Patient) | 344 | 13 | 344 | 16 | 344 | 7 |
| sCr only | | | | | | |
| Median | 54.0 | 163 | nd | nd | nd | nd |
| Average | 84.3 | 201 | nd | nd | nd | nd |
| Stdev | 111 | 203 | nd | nd | nd | nd |
| p(t-test) | | 0.0058 | nd | nd | nd | nd |
| Min | 1.00E−9 | 23.1 | nd | nd | nd | nd |
| Max | 1830 | 594 | nd | nd | nd | nd |
| n (Samp) | 970 | 7 | nd | nd | nd | nd |
| n (Patient) | 354 | 7 | nd | nd | nd | nd |
| UO only | | | | | | |
| Median | 53.6 | 114 | 53.6 | 283 | nd | nd |
| Average | 76.5 | 375 | 76.5 | 354 | nd | nd |
| Stdev | 76.0 | 615 | 76.0 | 332 | nd | nd |
| p(t-test) | | 5.7E−18 | | 2.0E−30 | nd | nd |
| Min | 1.00E−9 | 46.5 | 1.00E−9 | 20.4 | nd | nd |
| Max | 543 | 1830 | 543 | 1250 | nd | nd |
| n (Samp) | 800 | 8 | 800 | 14 | nd | nd |
| n (Patient) | 263 | 8 | 263 | 14 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.69 | 0.70 | 0.73 | 0.86 | nd | 0.85 | 0.73 | nd | nd |
| SE | 0.082 | 0.11 | 0.10 | 0.059 | nd | 0.065 | 0.11 | nd | nd |
| p | 0.023 | 0.069 | 0.024 | 1.8E−9 | nd | 5.3E−8 | 0.037 | nd | nd |
| nCohort 1 | 933 | 970 | 800 | 933 | nd | 800 | 933 | nd | nd |
| nCohort 2 | 13 | 7 | 8 | 16 | nd | 14 | 7 | nd | nd |
| Cutoff 1 | 49.1 | 68.6 | 57.5 | 118 | nd | 118 | 74.9 | nd | nd |
| Sens 1 | 77% | 71% | 75% | 75% | nd | 71% | 71% | nd | nd |
| Spec 1 | 47% | 61% | 54% | 82% | nd | 82% | 67% | nd | nd |
| Cutoff 2 | 46.5 | 39.0 | 49.1 | 104 | nd | 99.9 | 51.8 | nd | nd |
| Sens 2 | 85% | 86% | 88% | 81% | nd | 86% | 86% | nd | nd |
| Spec 2 | 45% | 35% | 46% | 79% | nd | 78% | 49% | nd | nd |
| Cutoff 3 | 39.0 | 23.1 | 46.5 | 65.8 | nd | 65.8 | 33.8 | nd | nd |
| Sens 3 | 92% | 100% | 100% | 94% | nd | 93% | 100% | nd | nd |
| Spec 3 | 36% | 19% | 44% | 61% | nd | 60% | 30% | nd | nd |
| Cutoff 4 | 82.1 | 84.7 | 82.1 | 82.1 | nd | 82.1 | 82.1 | nd | nd |
| Sens 4 | 46% | 57% | 50% | 88% | nd | 86% | 57% | nd | nd |
| Spec 4 | 70% | 70% | 70% | 70% | nd | 70% | 70% | nd | nd |
| Cutoff 5 | 110 | 118 | 110 | 110 | nd | 110 | 110 | nd | nd |
| Sens 5 | 46% | 57% | 50% | 75% | nd | 71% | 43% | nd | nd |
| Spec 5 | 80% | 80% | 80% | 80% | nd | 80% | 80% | nd | nd |
| Cutoff 6 | 159 | 175 | 159 | 159 | nd | 159 | 159 | nd | nd |
| Sens 6 | 46% | 43% | 50% | 56% | nd | 57% | 43% | nd | nd |
| Spec 6 | 90% | 90% | 90% | 90% | nd | 90% | 90% | nd | nd |
| OR Quart 2 | 3.0 | 1.0 | >2.0 | 0 | nd | 0 | >2.0 | nd | nd |
| p Value | 0.34 | 1.0 | <0.57 | na | nd | na | <0.57 | nd | nd |
| 95% CI of | 0.31 | 0.062 | >0.18 | na | nd | na | >0.18 | nd | nd |
| OR Quart2 | 29 | 16 | na | na | nd | na | na | nd | nd |
| OR Quart 3 | 3.0 | 1.0 | >2.0 | 1.0 | nd | 1.0 | >1.0 | nd | nd |
| p Value | 0.34 | 1.0 | <0.57 | 1.0 | nd | 1.0 | <1.00 | nd | nd |
| 95% CI of | 0.31 | 0.062 | >0.18 | 0.062 | nd | 0.062 | >0.062 | nd | nd |
| OR Quart3 | 29 | 16 | na | 16 | nd | 16 | na | nd | nd |
| OR Quart 4 | 6.1 | 4.0 | >4.1 | 15 | nd | 13 | >4.1 | nd | nd |

TABLE 9-continued

Comparison of marker levels in urine samples collected from Cohort 1 (patients that did not progress beyond RIFLE stage 0, R, or I) and in urine samples collected from Cohort 2 (subjects who progress to RIFLE stage F) at 0, 24 hours, and 48 hours prior to the subject reaching RIFLE stage I.

| p Value | 0.095 | 0.21 | <0.21 | 0.0096 | nd | 0.015 | <0.21 | nd | nd |
| 95% CI of | 0.73 | 0.45 | >0.45 | 1.9 | nd | 1.6 | >0.45 | nd | nd |
| OR Quart4 | 51 | 36 | na | 110 | nd | 98 | na | nd | nd |

TABLE 10

Comparison of marker levels in EDTA samples collected from Cohort 1 (patients that did not progress beyond RIFLE stage 0, R, or I) and in EDTA samples collected from Cohort 2 (subjects who progress to RIFLE stage F) at 0, 24 hours, and 48 hours prior to the subject reaching RIFLE stage I.

| | Cancer Antigen 19-9 | | | | | |
|---|---|---|---|---|---|---|
| | 0 hr prior to AKI stage | | 24 hr prior to AKI stage | | 48 hr prior to AKI stage | |
| sCr or UO | Cohort 1 | Cohort 2 | Cohort 1 | Cohort 2 | Cohort 1 | Cohort 2 |
| Median | nd | nd | 0.244 | 0.663 | nd | nd |
| Average | nd | nd | 0.645 | 1.43 | nd | nd |
| Stdev | nd | nd | 2.70 | 1.89 | nd | nd |
| p(t-test) | nd | nd | | 0.48 | nd | nd |
| Min | nd | nd | 1.00E−9 | 0.401 | nd | nd |
| Max | nd | nd | 41.6 | 5.26 | nd | nd |
| n (Samp) | nd | nd | 248 | 6 | nd | nd |
| n (Patient) | nd | nd | 158 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | nd | nd | nd | 0.82 | nd | nd | nd | nd | nd |
| SE | nd | nd | nd | 0.11 | nd | nd | nd | nd | nd |
| p | nd | nd | nd | 0.0022 | nd | nd | nd | nd | nd |
| nCohort 1 | nd | nd | nd | 248 | nd | nd | nd | nd | nd |
| nCohort 2 | nd | nd | nd | 6 | nd | nd | nd | nd | nd |
| Cutoff 1 | nd | nd | nd | 0.586 | nd | nd | nd | nd | nd |
| Sens 1 | nd | nd | nd | 83% | nd | nd | nd | nd | nd |
| Spec 1 | nd | nd | nd | 77% | nd | nd | nd | nd | nd |
| Cutoff 2 | nd | nd | nd | 0.586 | nd | nd | nd | nd | nd |
| Sens 2 | nd | nd | nd | 83% | nd | nd | nd | nd | nd |
| Spec 2 | nd | nd | nd | 77% | nd | nd | nd | nd | nd |
| Cutoff 3 | nd | nd | nd | 0.374 | nd | nd | nd | nd | nd |
| Sens 3 | nd | nd | nd | 100% | nd | nd | nd | nd | nd |
| Spec 3 | nd | nd | nd | 67% | nd | nd | nd | nd | nd |
| Cutoff 4 | nd | nd | nd | 0.452 | nd | nd | nd | nd | nd |
| Sens 4 | nd | nd | nd | 83% | nd | nd | nd | nd | nd |
| Spec 4 | nd | nd | nd | 71% | nd | nd | nd | nd | nd |
| Cutoff 5 | nd | nd | nd | 0.633 | nd | nd | nd | nd | nd |
| Sens 5 | nd | nd | nd | 50% | nd | nd | nd | nd | nd |
| Spec 5 | nd | nd | nd | 81% | nd | nd | nd | nd | nd |
| Cutoff 6 | nd | nd | nd | 1.41 | nd | nd | nd | nd | nd |
| Sens 6 | nd | nd | nd | 17% | nd | nd | nd | nd | nd |
| Spec 6 | nd | nd | nd | 90% | nd | nd | nd | nd | nd |
| OR Quart 2 | nd | nd | nd | >0 | nd | nd | nd | nd | nd |
| p Value | nd | nd | nd | <na | nd | nd | nd | nd | nd |
| 95% CI of | nd | nd | nd | >na | nd | nd | nd | nd | nd |
| OR Quart2 | nd | nd | nd | na | nd | nd | nd | nd | nd |
| OR Quart 3 | nd | nd | nd | >1.0 | nd | nd | nd | nd | nd |
| p Value | nd | nd | nd | <0.99 | nd | nd | nd | nd | nd |
| 95% CI of | nd | nd | nd | >0.062 | nd | nd | nd | nd | nd |
| OR Quart3 | nd | nd | nd | na | nd | nd | nd | nd | nd |
| OR Quart 4 | nd | nd | nd | >5.3 | nd | nd | nd | nd | nd |
| p Value | nd | nd | nd | <0.13 | nd | nd | nd | nd | nd |
| 95% CI of | nd | nd | nd | >0.61 | nd | nd | nd | nd | nd |
| OR Quart4 | nd | nd | nd | na | nd | nd | nd | nd | nd |

| | C-C motif chemokine 13 | | | | | |
|---|---|---|---|---|---|---|
| | 0 hr prior to AKI stage | | 24 hr prior to AKI stage | | 48 hr prior to AKI stage | |
| sCr or UO | Cohort 1 | Cohort 2 | Cohort 1 | Cohort 2 | Cohort 1 | Cohort 2 |
| Median | nd | nd | 21.0 | 30.9 | nd | nd |
| Average | nd | nd | 61.7 | 29.1 | nd | nd |

TABLE 10-continued

Comparison of marker levels in EDTA samples collected from Cohort 1 (patients that did not progress beyond RIFLE stage 0, R, or I) and in EDTA samples collected from Cohort 2 (subjects who progress to RIFLE stage F) at 0, 24 hours, and 48 hours prior to the subject reaching RIFLE stage I.

|  |  |  |  |  |  |  |
|---|---|---|---|---|---|---|
| Stdev | nd | nd | 207 | 27.1 | nd | nd |
| p(t-test) | nd | nd |  | 0.70 | nd | nd |
| Min | nd | nd | 1.00E−9 | 1.00E−9 | nd | nd |
| Max | nd | nd | 2520 | 68.2 | nd | nd |
| n (Samp) | nd | nd | 177 | 6 | nd | nd |
| n (Patient) | nd | nd | 126 | 6 | nd | nd |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | nd | nd | nd | 0.50 | nd | nd | nd | nd | nd |
| SE | nd | nd | nd | 0.12 | nd | nd | nd | nd | nd |
| p | nd | nd | nd | 0.99 | nd | nd | nd | nd | nd |
| nCohort 1 | nd | nd | nd | 177 | nd | nd | nd | nd | nd |
| nCohort 2 | nd | nd | nd | 6 | nd | nd | nd | nd | nd |
| Cutoff 1 | nd | nd | nd | 0 | nd | nd | nd | nd | nd |
| Sens 1 | nd | nd | nd | 100% | nd | nd | nd | nd | nd |
| Spec 1 | nd | nd | nd | 0% | nd | nd | nd | nd | nd |
| Cutoff 2 | nd | nd | nd | 0 | nd | nd | nd | nd | nd |
| Sens 2 | nd | nd | nd | 100% | nd | nd | nd | nd | nd |
| Spec 2 | nd | nd | nd | 0% | nd | nd | nd | nd | nd |
| Cutoff 3 | nd | nd | nd | 0 | nd | nd | nd | nd | nd |
| Sens 3 | nd | nd | nd | 100% | nd | nd | nd | nd | nd |
| Spec 3 | nd | nd | nd | 0% | nd | nd | nd | nd | nd |
| Cutoff 4 | nd | nd | nd | 54.3 | nd | nd | nd | nd | nd |
| Sens 4 | nd | nd | nd | 17% | nd | nd | nd | nd | nd |
| Spec 4 | nd | nd | nd | 71% | nd | nd | nd | nd | nd |
| Cutoff 5 | nd | nd | nd | 72.2 | nd | nd | nd | nd | nd |
| Sens 5 | nd | nd | nd | 0% | nd | nd | nd | nd | nd |
| Spec 5 | nd | nd | nd | 81% | nd | nd | nd | nd | nd |
| Cutoff 6 | nd | nd | nd | 111 | nd | nd | nd | nd | nd |
| Sens 6 | nd | nd | nd | 0% | nd | nd | nd | nd | nd |
| Spec 6 | nd | nd | nd | 90% | nd | nd | nd | nd | nd |
| OR Quart 2 | nd | nd | nd | 2.0 | nd | nd | nd | nd | nd |
| p Value | nd | nd | nd | 0.56 | nd | nd | nd | nd | nd |
| 95% CI of OR Quart2 | nd | nd | nd | 0.18 23 | nd | nd | nd | nd | nd |
| OR Quart 3 | nd | nd | nd | 3.1 | nd | nd | nd | nd | nd |
| p Value | nd | nd | nd | 0.33 | nd | nd | nd | nd | nd |
| 95% CI of OR Quart3 | nd | nd | nd | 0.31 31 | nd | nd | nd | nd | nd |
| OR Quart 4 | nd | nd | nd | 0 | nd | nd | nd | nd | nd |
| p Value | nd | nd | nd | na | nd | nd | nd | nd | nd |
| 95% CI of OR Quart4 | nd | nd | nd | na na | nd | nd | nd | nd | nd |

C-X-C motif chemokine 6

|  | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | nd | nd | 28.2 | 32.4 | nd | nd |
| Average | nd | nd | 45.6 | 31.0 | nd | nd |
| Stdev | nd | nd | 50.4 | 15.9 | nd | nd |
| p(t-test) | nd | nd |  | 0.48 | nd | nd |
| Min | nd | nd | 3.49 | 9.69 | nd | nd |
| Max | nd | nd | 311 | 48.8 | nd | nd |
| n (Samp) | nd | nd | 178 | 6 | nd | nd |
| n (Patient) | nd | nd | 127 | 6 | nd | nd |

|  | 0 hr prior to AKI stage | | | 24 hr prior to AKI stage | | | 48 hr prior to AKI stage | | |
|---|---|---|---|---|---|---|---|---|---|
|  | sCr or UO | sCr only | UO only | sCr or UO | sCr only | UO only | sCr or UO | sCr only | UO only |
| AUC | nd | nd | nd | 0.49 | nd | nd | nd | nd | nd |
| SE | nd | nd | nd | 0.12 | nd | nd | nd | nd | nd |
| p | nd | nd | nd | 0.96 | nd | nd | nd | nd | nd |
| nCohort 1 | nd | nd | nd | 178 | nd | nd | nd | nd | nd |
| nCohort 2 | nd | nd | nd | 6 | nd | nd | nd | nd | nd |
| Cutoff 1 | nd | nd | nd | 17.9 | nd | nd | nd | nd | nd |
| Sens 1 | nd | nd | nd | 83% | nd | nd | nd | nd | nd |
| Spec 1 | nd | nd | nd | 34% | nd | nd | nd | nd | nd |
| Cutoff 2 | nd | nd | nd | 17.9 | nd | nd | nd | nd | nd |
| Sens 2 | nd | nd | nd | 83% | nd | nd | nd | nd | nd |

TABLE 10-continued

Comparison of marker levels in EDTA samples collected from Cohort 1 (patients that did not progress beyond RIFLE stage 0, R, or I) and in EDTA samples collected from Cohort 2 (subjects who progress to RIFLE stage F) at 0, 24 hours, and 48 hours prior to the subject reaching RIFLE stage I.

| | | | | | | | | | |
|---|---|---|---|---|---|---|---|---|---|
| Spec 2 | nd | nd | nd | 34% | nd | nd | nd | nd | nd |
| Cutoff 3 | nd | nd | nd | 9.55 | nd | nd | nd | nd | nd |
| Sens 3 | nd | nd | nd | 100% | nd | nd | nd | nd | nd |
| Spec 3 | nd | nd | nd | 9% | nd | nd | nd | nd | nd |
| Cutoff 4 | nd | nd | nd | 45.4 | nd | nd | nd | nd | nd |
| Sens 4 | nd | nd | nd | 17% | nd | nd | nd | nd | nd |
| Spec 4 | nd | nd | nd | 70% | nd | nd | nd | nd | nd |
| Cutoff 5 | nd | nd | nd | 63.5 | nd | nd | nd | nd | nd |
| Sens 5 | nd | nd | nd | 0% | nd | nd | nd | nd | nd |
| Spec 5 | nd | nd | nd | 80% | nd | nd | nd | nd | nd |
| Cutoff 6 | nd | nd | nd | 107 | nd | nd | nd | nd | nd |
| Sens 6 | nd | nd | nd | 0% | nd | nd | nd | nd | nd |
| Spec 6 | nd | nd | nd | 90% | nd | nd | nd | nd | nd |
| OR Quart 2 | nd | nd | nd | >3.2 | nd | nd | nd | nd | nd |
| p Value | nd | nd | nd | <0.32 | nd | nd | nd | nd | nd |
| 95% CI of | nd | nd | nd | >0.32 | nd | nd | nd | nd | nd |
| OR Quart2 | nd | nd | nd | na | nd | nd | nd | nd | nd |
| OR Quart 3 | nd | nd | nd | >2.1 | nd | nd | nd | nd | nd |
| p Value | nd | nd | nd | <0.55 | nd | nd | nd | nd | nd |
| 95% CI of | nd | nd | nd | >0.18 | nd | nd | nd | nd | nd |
| OR Quart3 | nd | nd | nd | na | nd | nd | nd | nd | nd |
| OR Quart 4 | nd | nd | nd | >1.0 | nd | nd | nd | nd | nd |
| p Value | nd | nd | nd | <0.99 | nd | nd | nd | nd | nd |
| 95% CI of | nd | nd | nd | >0.062 | nd | nd | nd | nd | nd |
| OR Quart4 | nd | nd | nd | na | nd | nd | nd | nd | nd |

Coagulation factor VII

| | 0 hr prior to AKI stage | | 24 hr prior to AKI stage | | 48 hr prior to AKI stage | |
|---|---|---|---|---|---|---|
| | Cohort 1 | Cohort 2 | Cohort 1 | Cohort 2 | Cohort 1 | Cohort 2 |
| sCr or UO | | | | | | |
| Median | 301 | 274 | 301 | 191 | nd | nd |
| Average | 321 | 283 | 321 | 218 | nd | nd |
| Stdev | 174 | 138 | 174 | 135 | nd | nd |
| p(t-test) | | 0.45 | | 0.052 | nd | nd |
| Min | 2.08 | 77.8 | 2.08 | 32.8 | nd | nd |
| Max | 1020 | 549 | 1020 | 418 | nd | nd |
| n (Samp) | 551 | 12 | 551 | 11 | nd | nd |
| n (Patient) | 213 | 12 | 213 | 11 | nd | nd |
| UO only | | | | | | |
| Median | 289 | 379 | 289 | 286 | nd | nd |
| Average | 307 | 384 | 307 | 231 | nd | nd |
| Stdev | 165 | 151 | 165 | 138 | nd | nd |
| p(t-test) | | 0.19 | | 0.18 | nd | nd |
| Min | 8.62 | 158 | 8.62 | 32.8 | nd | nd |
| Max | 1020 | 611 | 1020 | 418 | nd | nd |
| n (Samp) | 465 | 8 | 465 | 9 | nd | nd |
| n (Patient) | 174 | 8 | 174 | 9 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | 0.45 | nd | 0.65 | 0.33 | nd | 0.38 | nd | nd | nd |
| SE | 0.087 | nd | 0.11 | 0.091 | nd | 0.10 | nd | nd | nd |
| p | 0.54 | nd | 0.16 | 0.067 | nd | 0.23 | nd | nd | nd |
| nCohort 1 | 551 | nd | 465 | 551 | nd | 465 | nd | nd | nd |
| nCohort 2 | 12 | nd | 8 | 11 | nd | 9 | nd | nd | nd |
| Cutoff 1 | 192 | nd | 283 | 101 | nd | 100 | nd | nd | nd |
| Sens 1 | 75% | nd | 75% | 73% | nd | 78% | nd | nd | nd |
| Spec 1 | 28% | nd | 49% | 8% | nd | 8% | nd | nd | nd |
| Cutoff 2 | 156 | nd | 261 | 79.5 | nd | 79.5 | nd | nd | nd |
| Sens 2 | 83% | nd | 88% | 82% | nd | 89% | nd | nd | nd |
| Spec 2 | 18% | nd | 45% | 5% | nd | 6% | nd | nd | nd |
| Cutoff 3 | 130 | nd | 156 | 74.8 | nd | 25.4 | nd | nd | nd |
| Sens 3 | 92% | nd | 100% | 91% | nd | 100% | nd | nd | nd |
| Spec 3 | 12% | nd | 19% | 5% | nd | 1% | nd | nd | nd |
| Cutoff 4 | 403 | nd | 383 | 403 | nd | 383 | nd | nd | nd |
| Sens 4 | 17% | nd | 38% | 9% | nd | 11% | nd | nd | nd |
| Spec 4 | 70% | nd | 70% | 70% | nd | 70% | nd | nd | nd |
| Cutoff 5 | 469 | nd | 448 | 469 | nd | 448 | nd | nd | nd |
| Sens 5 | 8% | nd | 38% | 0% | nd | 0% | nd | nd | nd |

TABLE 10-continued

Comparison of marker levels in EDTA samples collected from Cohort 1 (patients that did not progress beyond RIFLE stage 0, R, or I) and in EDTA samples collected from Cohort 2 (subjects who progress to RIFLE stage F) at 0, 24 hours, and 48 hours prior to the subject reaching RIFLE stage I.

| | | | | | | | | | |
|---|---|---|---|---|---|---|---|---|---|
| Spec 5 | 80% | nd | 80% | 80% | nd | 80% | nd | nd | nd |
| Cutoff 6 | 563 | nd | 530 | 563 | nd | 530 | nd | nd | nd |
| Sens 6 | 0% | nd | 25% | 0% | nd | 0% | nd | nd | nd |
| Spec 6 | 90% | nd | 90% | 90% | nd | 90% | nd | nd | nd |
| OR Quart 2 | 1.0 | nd | 2.0 | >5.2 | nd | 3.1 | nd | nd | nd |
| p Value | 1.0 | nd | 0.57 | <0.13 | nd | 0.33 | nd | nd | nd |
| 95% CI of | 0.14 | nd | 0.18 | >0.60 | nd | 0.32 | nd | nd | nd |
| OR Quart2 | 7.2 | nd | 23 | na | nd | 30 | nd | nd | nd |
| OR Quart 3 | 2.6 | nd | 2.0 | >1.0 | nd | 1.0 | nd | nd | nd |
| p Value | 0.27 | nd | 0.57 | <1.00 | nd | 1.0 | nd | nd | nd |
| 95% CI of | 0.49 | nd | 0.18 | >0.062 | nd | 0.062 | nd | nd | nd |
| OR Quart3 | 13 | nd | 23 | na | nd | 16 | nd | nd | nd |
| OR Quart 4 | 1.5 | nd | 3.0 | >5.2 | nd | 4.1 | nd | nd | nd |
| p Value | 0.65 | nd | 0.34 | <0.13 | nd | 0.21 | nd | nd | nd |
| 95% CI of | 0.25 | nd | 0.31 | >0.60 | nd | 0.46 | nd | nd | nd |
| OR Quart4 | 9.3 | nd | 30 | na | nd | 38 | nd | nd | nd | nsulin-like growth factor-binding protein 7

| | 0 hr prior to AKI stage | | 24 hr prior to AKI stage | | 48 hr prior to AKI stage | |
|---|---|---|---|---|---|---|
| sCr or UO | Cohort 1 | Cohort 2 | Cohort 1 | Cohort 2 | Cohort 1 | Cohort 2 |
| Median | nd | nd | 69.2 | 172 | nd | nd |
| Average | nd | nd | 74.9 | 194 | nd | nd |
| Stdev | nd | nd | 32.9 | 137 | nd | nd |
| p(t-test) | nd | nd | | 6.6E−13 | nd | nd |
| Min | nd | nd | 18.6 | 53.8 | nd | nd |
| Max | nd | nd | 250 | 437 | nd | nd |
| n (Samp) | nd | nd | 248 | 6 | nd | nd |
| n (Patient) | nd | nd | 158 | 6 | nd | nd |

| | 0 hr prior to AKI stage | | | 24 hr prior to AKI stage | | | 48 hr prior to AKI stage | | |
|---|---|---|---|---|---|---|---|---|---|
| | sCr or UO | sCr only | UO only | sCr or UO | sCr only | UO only | sCr or UO | sCr only | UO only |
| AUC | nd | nd | nd | 0.84 | nd | nd | nd | nd | nd |
| SE | nd | nd | nd | 0.10 | nd | nd | nd | nd | nd |
| p | nd | nd | nd | 9.7E−4 | nd | nd | nd | nd | nd |
| nCohort 1 | nd | nd | nd | 248 | nd | nd | nd | nd | nd |
| nCohort 2 | nd | nd | nd | 6 | nd | nd | nd | nd | nd |
| Cutoff 1 | nd | nd | nd | 93.0 | nd | nd | nd | nd | nd |
| Sens 1 | nd | nd | nd | 83% | nd | nd | nd | nd | nd |
| Spec 1 | nd | nd | nd | 78% | nd | nd | nd | nd | nd |
| Cutoff 2 | nd | nd | nd | 93.0 | nd | nd | nd | nd | nd |
| Sens 2 | nd | nd | nd | 83% | nd | nd | nd | nd | nd |
| Spec 2 | nd | nd | nd | 78% | nd | nd | nd | nd | nd |
| Cutoff 3 | nd | nd | nd | 53.5 | nd | nd | nd | nd | nd |
| Sens 3 | nd | nd | nd | 100% | nd | nd | nd | nd | nd |
| Spec 3 | nd | nd | nd | 30% | nd | nd | nd | nd | nd |
| Cutoff 4 | nd | nd | nd | 85.5 | nd | nd | nd | nd | nd |
| Sens 4 | nd | nd | nd | 83% | nd | nd | nd | nd | nd |
| Spec 4 | nd | nd | nd | 70% | nd | nd | nd | nd | nd |
| Cutoff 5 | nd | nd | nd | 96.3 | nd | nd | nd | nd | nd |
| Sens 5 | nd | nd | nd | 67% | nd | nd | nd | nd | nd |
| Spec 5 | nd | nd | nd | 80% | nd | nd | nd | nd | nd |
| Cutoff 6 | nd | nd | nd | 116 | nd | nd | nd | nd | nd |
| Sens 6 | nd | nd | nd | 67% | nd | nd | nd | nd | nd |
| Spec 6 | nd | nd | nd | 90% | nd | nd | nd | nd | nd |
| OR Quart 2 | nd | nd | nd | >1.0 | nd | nd | nd | nd | nd |
| p Value | nd | nd | nd | <1.0 | nd | nd | nd | nd | nd |
| 95% CI of | nd | nd | nd | >0.061 | nd | nd | nd | nd | nd |
| OR Quart2 | nd | nd | nd | na | nd | nd | nd | nd | nd |
| OR Quart 3 | nd | nd | nd | >0 | nd | nd | nd | nd | nd |
| p Value | nd | nd | nd | <na | nd | nd | nd | nd | nd |
| 95% CI of | nd | nd | nd | >na | nd | nd | nd | nd | nd |
| OR Quart3 | nd | nd | nd | na | nd | nd | nd | nd | nd |
| OR Quart 4 | nd | nd | nd | >5.3 | nd | nd | nd | nd | nd |
| p Value | nd | nd | nd | <0.13 | nd | nd | nd | nd | nd |
| 95% CI of | nd | nd | nd | >0.61 | nd | nd | nd | nd | nd |
| OR Quart4 | nd | nd | nd | na | nd | nd | nd | nd | nd |

TABLE 11

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| Cancer Antigen 19-9 | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 26.6 | 42.2 | nd | nd | 27.4 | 51.5 |
| Average | 107 | 282 | nd | nd | 106 | 305 |
| Stdev | 259 | 668 | nd | nd | 256 | 694 |
| p(t-test) | | 0.036 | nd | nd | | 0.030 |
| Min | 1.00E−9 | 1.00E−9 | nd | nd | 1.00E−9 | 1.00E−9 |
| Max | 2000 | 2940 | nd | nd | 2000 | 2940 |
| n (Samp) | 109 | 24 | nd | nd | 90 | 22 |
| n (Patient) | 109 | 24 | nd | nd | 90 | 22 |

| | At Enrollment | | |
|---|---|---|---|
| | sCr or UO | sCr only | UO only |
| AUC | 0.60 | nd | 0.60 |
| SE | 0.066 | nd | 0.070 |
| p | 0.15 | nd | 0.13 |
| nCohort 1 | 109 | nd | 90 |
| nCohort 2 | 24 | nd | 22 |
| Cutoff 1 | 23.0 | nd | 23.0 |
| Sens 1 | 71% | nd | 73% |
| Spec 1 | 46% | nd | 42% |
| Cutoff 2 | 9.92 | nd | 18.7 |
| Sens 2 | 83% | nd | 82% |
| Spec 2 | 27% | nd | 39% |
| Cutoff 3 | 5.76 | nd | 9.72 |
| Sens 3 | 92% | nd | 91% |
| Spec 3 | 20% | nd | 26% |
| Cutoff 4 | 63.8 | nd | 57.3 |
| Sens 4 | 33% | nd | 45% |
| Spec 4 | 71% | nd | 70% |
| Cutoff 5 | 117 | nd | 114 |
| Sens 5 | 33% | nd | 36% |
| Spec 5 | 81% | nd | 80% |
| Cutoff 6 | 240 | nd | 240 |
| Sens 6 | 17% | nd | 18% |
| Spec 6 | 91% | nd | 90% |
| OR Quart 2 | 1.3 | nd | 1.3 |
| p Value | 0.72 | nd | 0.72 |
| 95% CI of | 0.31 | nd | 0.31 |
| OR Quart2 | 5.3 | nd | 5.5 |
| OR Quart 3 | 2.0 | nd | 1.3 |
| p Value | 0.33 | nd | 0.72 |
| 95% CI of | 0.51 | nd | 0.31 |
| OR Quart3 | 7.4 | nd | 5.5 |
| OR Quart 4 | 2.2 | nd | 2.4 |
| p Value | 0.23 | nd | 0.20 |
| 95% CI of | 0.60 | nd | 0.63 |
| OR Quart4 | 8.3 | nd | 9.2 |

| C-X-C motif chemokine 6 | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 13.3 | 33.1 | 15.0 | 42.2 | 14.9 | 33.4 |
| Average | 27.7 | 104 | 38.1 | 120 | 28.4 | 111 |
| Stdev | 53.4 | 188 | 90.0 | 195 | 51.5 | 197 |
| p(t-test) | | 6.4E−9 | | 0.0036 | | 8.9E−8 |
| Min | 1.00E−9 | 1.62 | 1.00E−9 | 1.62 | 1.00E−9 | 3.96 |
| Max | 561 | 909 | 909 | 698 | 561 | 909 |
| n (Samp) | 296 | 61 | 342 | 12 | 217 | 55 |
| n (Patient) | 296 | 61 | 342 | 12 | 217 | 55 |

TABLE 11-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| | At Enrollment | | |
|---|---|---|---|
| | sCr or UO | sCr only | UO only |
| AUC | 0.71 | 0.70 | 0.71 |
| SE | 0.039 | 0.086 | 0.042 |
| p | 7.0E−8 | 0.017 | 8.0E−7 |
| nCohort 1 | 296 | 342 | 217 |
| nCohort 2 | 61 | 12 | 55 |
| Cutoff 1 | 17.2 | 18.8 | 17.2 |
| Sens 1 | 70% | 75% | 71% |
| Spec 1 | 58% | 58% | 55% |
| Cutoff 2 | 11.5 | 11.5 | 12.3 |
| Sens 2 | 80% | 83% | 80% |
| Spec 2 | 45% | 41% | 44% |
| Cutoff 3 | 8.44 | 10.6 | 8.22 |
| Sens 3 | 90% | 92% | 91% |
| Spec 3 | 38% | 40% | 34% |
| Cutoff 4 | 26.0 | 28.7 | 27.4 |
| Sens 4 | 57% | 58% | 58% |
| Spec 4 | 70% | 70% | 70% |
| Cutoff 5 | 37.4 | 42.2 | 37.4 |
| Sens 5 | 48% | 50% | 49% |
| Spec 5 | 80% | 80% | 80% |
| Cutoff 6 | 53.8 | 62.4 | 53.8 |
| Sens 6 | 33% | 42% | 33% |
| Spec 6 | 90% | 90% | 90% |
| OR Quart 2 | 1.8 | 2.0 | 2.4 |
| p Value | 0.30 | 0.57 | 0.12 |
| 95% CI of | 0.61 | 0.18 | 0.80 |
| OR Quart2 | 5.0 | 22 | 7.4 |
| OR Quart 3 | 3.0 | 3.1 | 3.0 |
| p Value | 0.028 | 0.34 | 0.050 |
| 95% CI of | 1.1 | 0.31 | 1.00 |
| OR Quart3 | 8.2 | 30 | 8.9 |
| OR Quart 4 | 6.6 | 6.3 | 7.8 |
| p Value | 8.5E−5 | 0.092 | 9.8E−5 |
| 95% CI of | 2.6 | 0.74 | 2.8 |
| OR Quart4 | 17 | 53 | 22 |

| Coagulation factor VII | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 3.72 | 7.55 | 4.03 | 13.2 | 3.86 | 7.85 |
| Average | 6.34 | 11.8 | 7.00 | 16.5 | 6.29 | 10.9 |
| Stdev | 7.90 | 11.2 | 8.33 | 15.3 | 7.90 | 9.42 |
| p(t-test) | | 0.0011 | | 0.0029 | | 0.0069 |
| Min | 0.00408 | 0.348 | 0.00408 | 0.348 | 0.00408 | 0.682 |
| Max | 48.9 | 47.7 | 48.9 | 47.7 | 48.9 | 36.7 |
| n (Samp) | 139 | 35 | 165 | 8 | 112 | 30 |
| n (Patient) | 139 | 35 | 165 | 8 | 112 | 30 |

| | At Enrollment | | |
|---|---|---|---|
| | sCr or UO | sCr only | UO only |
| AUC | 0.67 | 0.72 | 0.67 |
| SE | 0.054 | 0.10 | 0.059 |
| p | 0.0017 | 0.038 | 0.0031 |
| nCohort 1 | 139 | 165 | 112 |
| nCohort 2 | 35 | 8 | 30 |
| Cutoff 1 | 4.79 | 6.05 | 4.79 |
| Sens 1 | 71% | 75% | 70% |
| Spec 1 | 57% | 65% | 57% |
| Cutoff 2 | 2.33 | 5.29 | 2.33 |
| Sens 2 | 80% | 88% | 80% |
| Spec 2 | 40% | 58% | 40% |
| Cutoff 3 | 1.01 | 0.313 | 1.24 |
| Sens 3 | 91% | 100% | 90% |
| Spec 3 | 18% | 3% | 23% |
| Cutoff 4 | 7.01 | 7.52 | 7.27 |

TABLE 11-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| | | | |
|---|---|---|---|
| Sens 4 | 54% | 50% | 57% |
| Spec 4 | 71% | 70% | 71% |
| Cutoff 5 | 9.02 | 10.2 | 8.49 |
| Sens 5 | 43% | 50% | 43% |
| Spec 5 | 81% | 80% | 80% |
| Cutoff 6 | 15.7 | 18.7 | 14.3 |
| Sens 6 | 31% | 50% | 33% |
| Spec 6 | 91% | 90% | 90% |
| OR Quart 2 | 0.97 | 0 | 0.75 |
| p Value | 0.97 | na | 0.69 |
| 95% CI of | 0.26 | na | 0.18 |
| OR Quart2 | 3.6 | na | 3.1 |
| OR Quart 3 | 2.3 | 3.1 | 1.8 |
| p Value | 0.16 | 0.33 | 0.36 |
| 95% CI of | 0.71 | 0.31 | 0.52 |
| OR Quart3 | 7.4 | 32 | 6.1 |
| OR Quart 4 | 3.9 | 4.2 | 3.4 |
| p Value | 0.017 | 0.21 | 0.040 |
| 95% CI of | 1.3 | 0.45 | 1.1 |
| OR Quart4 | 12 | 39 | 11 |

| Insulin-like growth factor-binding protein 7 | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 51.1 | 131 | 57.2 | 306 | 54.4 | 131 |
| Average | 73.2 | 213 | 90.2 | 295 | 76.6 | 209 |
| Stdev | 75.7 | 221 | 115 | 240 | 78.9 | 217 |
| p(t-test) | | 1.7E−16 | | 1.7E−8 | | 3.1E−12 |
| Min | 1.06 | 20.4 | 1.06 | 23.1 | 1.06 | 20.4 |
| Max | 533 | 1250 | 1250 | 694 | 533 | 1250 |
| n (Samp) | 294 | 61 | 340 | 12 | 215 | 55 |
| n (Patient) | 294 | 61 | 340 | 12 | 215 | 55 |

| At Enrollment | | | |
|---|---|---|---|
| | sCr or UO | sCr only | UO only |
| AUC | 0.77 | 0.76 | 0.76 |
| SE | 0.037 | 0.082 | 0.040 |
| p | 1.3E−12 | 0.0015 | 3.9E−11 |
| nCohort 1 | 294 | 340 | 215 |
| nCohort 2 | 61 | 12 | 55 |
| Cutoff 1 | 73.6 | 88.9 | 73.6 |
| Sens 1 | 70% | 75% | 71% |
| Spec 1 | 67% | 69% | 64% |
| Cutoff 2 | 55.8 | 39.0 | 61.3 |
| Sens 2 | 80% | 83% | 80% |
| Spec 2 | 55% | 35% | 55% |
| Cutoff 3 | 38.2 | 23.1 | 38.4 |
| Sens 3 | 90% | 92% | 91% |
| Spec 3 | 38% | 20% | 38% |
| Cutoff 4 | 82.8 | 90.1 | 85.1 |
| Sens 4 | 67% | 67% | 65% |
| Spec 4 | 70% | 70% | 70% |
| Cutoff 5 | 102 | 120 | 104 |
| Sens 5 | 59% | 67% | 58% |
| Spec 5 | 80% | 80% | 80% |
| Cutoff 6 | 150 | 199 | 146 |
| Sens 6 | 41% | 58% | 44% |
| Spec 6 | 90% | 90% | 90% |
| OR Quart 2 | 1.6 | 0.49 | 2.4 |
| p Value | 0.40 | 0.57 | 0.16 |
| 95% CI of | 0.51 | 0.044 | 0.70 |
| OR Quart2 | 5.2 | 5.6 | 8.2 |
| OR Quart 3 | 3.1 | 0.49 | 3.8 |
| p Value | 0.038 | 0.57 | 0.027 |
| 95% CI of | 1.1 | 0.044 | 1.2 |
| OR Quart3 | 9.0 | 5.6 | 12 |

TABLE 11-continued

Comparison of marker levels in enroll urine samples collected from Cohort 1 (patients that did not progress beyond RIFLE stage 0 or R within 48 hrs) and in enroll urine samples collected from Cohort 2 (subjects reaching RIFLE stage I or F within 48 hrs). Enroll samples from patients already at RIFLE stage I or F were included in Cohort 2.

| OR Quart 4 | 10 | 4.3 | 12 |
| --- | --- | --- | --- |
| p Value | 4.9E−6 | 0.070 | 1.6E−5 |
| 95% CI of | 3.8 | 0.89 | 3.8 |
| OR Quart4 | 28 | 21 | 36 |

TABLE 12

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

| | Cancer Antigen 19-9 | | | | | |
| --- | --- | --- | --- | --- | --- | --- |
| | sCr or UO | | sCr only | | UO only | |
| | Cohort 1 | Cohort 2 | Cohort 1 | Cohort 2 | Cohort 1 | Cohort 2 |
| Median | 0.228 | 0.552 | nd | nd | 0.228 | 0.452 |
| Average | 0.462 | 0.989 | nd | nd | 0.503 | 0.942 |
| Stdev | 0.734 | 1.34 | nd | nd | 0.784 | 1.41 |
| p(t-test) | | 0.020 | nd | nd | | 0.089 |
| Min | 1.00E−9 | 0.0291 | nd | nd | 1.00E−9 | 0.0291 |
| Max | 5.30 | 5.26 | nd | nd | 5.30 | 5.26 |
| n (Samp) | 78 | 20 | nd | nd | 67 | 17 |
| n (Patient) | 78 | 20 | nd | nd | 67 | 17 |

| | At Enrollment | | |
| --- | --- | --- | --- |
| | sCr or UO | sCr only | UO only |
| AUC | 0.70 | nd | 0.65 |
| SE | 0.071 | nd | 0.079 |
| p | 0.0042 | nd | 0.054 |
| nCohort 1 | 78 | nd | 67 |
| nCohort 2 | 20 | nd | 17 |
| Cutoff 1 | 0.332 | nd | 0.259 |
| Sens 1 | 70% | nd | 71% |
| Spec 1 | 68% | nd | 54% |
| Cutoff 2 | 0.257 | nd | 0.228 |
| Sens 2 | 80% | nd | 82% |
| Spec 2 | 56% | nd | 51% |
| Cutoff 3 | 0.147 | nd | 0.134 |
| Sens 3 | 90% | nd | 94% |
| Spec 3 | 32% | nd | 28% |
| Cutoff 4 | 0.361 | nd | 0.523 |
| Sens 4 | 65% | nd | 47% |
| Spec 4 | 71% | nd | 70% |
| Cutoff 5 | 0.633 | nd | 0.652 |
| Sens 5 | 35% | nd | 29% |
| Spec 5 | 81% | nd | 81% |
| Cutoff 6 | 1.34 | nd | 1.52 |
| Sens 6 | 15% | nd | 12% |
| Spec 6 | 91% | nd | 91% |
| OR Quart 2 | 4.4 | nd | 1.6 |
| p Value | 0.20 | nd | 0.64 |
| 95% CI of | 0.45 | nd | 0.24 |
| OR Quart2 | 42 | nd | 11 |
| OR Quart 3 | 12 | nd | 4.8 |
| p Value | 0.028 | nd | 0.075 |
| 95% CI of | 1.3 | nd | 0.85 |
| OR Quart3 | 100 | nd | 26 |
| OR Quart 4 | 8.9 | nd | 3.0 |
| p Value | 0.049 | nd | 0.23 |
| 95% CI of | 1.0 | nd | 0.51 |
| OR Quart4 | 79 | nd | 17 |

TABLE 12-continued

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

| C-X-C motif chemokine 6 | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 23.9 | 29.6 | 24.0 | 42.6 | 21.8 | 28.8 |
| Average | 38.1 | 38.9 | 37.0 | 51.3 | 38.1 | 34.3 |
| Stdev | 49.2 | 32.2 | 45.9 | 43.2 | 52.2 | 20.1 |
| p(t-test) | | 0.95 | | 0.43 | | 0.79 |
| Min | 4.02 | 9.69 | 4.02 | 9.69 | 4.02 | 12.3 |
| Max | 311 | 144 | 311 | 144 | 311 | 88.5 |
| n (Samp) | 58 | 18 | 69 | 7 | 50 | 14 |
| n (Patient) | 58 | 18 | 69 | 7 | 50 | 14 |

| | At Enrollment | | |
|---|---|---|---|
| | sCr or UO | sCr only | UO only |
| AUC | 0.57 | 0.67 | 0.59 |
| SE | 0.079 | 0.12 | 0.089 |
| p | 0.35 | 0.14 | 0.30 |
| nCohort 1 | 58 | 69 | 50 |
| nCohort 2 | 18 | 7 | 14 |
| Cutoff 1 | 23.3 | 39.7 | 23.3 |
| Sens 1 | 72% | 71% | 71% |
| Spec 1 | 48% | 74% | 52% |
| Cutoff 2 | 16.7 | 26.0 | 16.7 |
| Sens 2 | 83% | 86% | 86% |
| Spec 2 | 33% | 59% | 36% |
| Cutoff 3 | 10.5 | 8.88 | 15.8 |
| Sens 3 | 94% | 100% | 93% |
| Spec 3 | 17% | 7% | 32% |
| Cutoff 4 | 38.9 | 38.9 | 38.7 |
| Sens 4 | 44% | 71% | 43% |
| Spec 4 | 71% | 71% | 70% |
| Cutoff 5 | 46.0 | 45.4 | 46.0 |
| Sens 5 | 17% | 29% | 14% |
| Spec 5 | 81% | 81% | 80% |
| Cutoff 6 | 66.6 | 66.6 | 61.7 |
| Sens 6 | 11% | 14% | 7% |
| Spec 6 | 91% | 91% | 90% |
| OR Quart 2 | 1.4 | 0 | 5.0 |
| p Value | 0.68 | na | 0.17 |
| 95% CI of | 0.27 | na | 0.49 |
| OR Quart2 | 7.4 | na | 51 |
| OR Quart 3 | 3.1 | 4.8 | 9.0 |
| p Value | 0.15 | 0.18 | 0.057 |
| 95% CI of | 0.66 | 0.48 | 0.94 |
| OR Quart3 | 15 | 48 | 87 |
| OR Quart 4 | 1.4 | 2.1 | 3.5 |
| p Value | 0.68 | 0.55 | 0.31 |
| 95% CI of | 0.27 | 0.18 | 0.32 |
| OR Quart4 | 7.4 | 26 | 37 |

| Coagulation factor VII | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 287 | 225 | 280 | 173 | 276 | 268 |
| Average | 320 | 239 | 308 | 201 | 298 | 250 |
| Stdev | 182 | 142 | 179 | 90.2 | 159 | 149 |
| p(t-test) | | 0.014 | | 0.077 | | 0.14 |
| Min | 2.08 | 12.2 | 2.08 | 75.6 | 35.7 | 12.2 |
| Max | 950 | 571 | 950 | 380 | 809 | 571 |
| n (Samp) | 140 | 36 | 166 | 9 | 112 | 31 |
| n (Patient) | 140 | 36 | 166 | 9 | 112 | 31 |

TABLE 12-continued

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

|  | At Enrollment | | |
|---|---|---|---|
|  | sCr or UO | sCr only | UO only |
| AUC | 0.37 | 0.32 | 0.42 |
| SE | 0.055 | 0.10 | 0.060 |
| p | 0.020 | 0.069 | 0.18 |
| nCohort 1 | 140 | 166 | 112 |
| nCohort 2 | 36 | 9 | 31 |
| Cutoff 1 | 153 | 158 | 153 |
| Sens 1 | 72% | 78% | 71% |
| Spec 1 | 19% | 22% | 21% |
| Cutoff 2 | 102 | 129 | 102 |
| Sens 2 | 81% | 89% | 81% |
| Spec 2 | 9% | 14% | 10% |
| Cutoff 3 | 64.8 | 74.8 | 64.8 |
| Sens 3 | 92% | 100% | 90% |
| Spec 3 | 4% | 7% | 3 % |
| Cutoff 4 | 376 | 368 | 361 |
| Sens 4 | 19% | 11% | 23% |
| Spec 4 | 71% | 71% | 71% |
| Cutoff 5 | 463 | 458 | 456 |
| Sens 5 | 6% | 0% | 6% |
| Spec 5 | 80% | 80% | 80% |
| Cutoff 6 | 574 | 537 | 526 |
| Sens 6 | 0% | 0% | 6% |
| Spec 6 | 90% | 90% | 90% |
| OR Quart 2 | 1.4 | >2.1 | 1.2 |
| p Value | 0.56 | <0.55 | 0.77 |
| 95% CI of | 0.44 | >0.18 | 0.38 |
| OR Quart2 | 4.5 | na | 3.7 |
| OR Quart 3 | 1.4 | >3.2 | 0.67 |
| p Value | 0.56 | <0.32 | 0.53 |
| 95% CI of | 0.44 | >0.32 | 0.19 |
| OR Quart3 | 4.5 | na | 2.3 |
| OR Quart 4 | 3.0 | >4.5 | 1.9 |
| p Value | 0.047 | <0.19 | 0.25 |
| 95% CI of | 1.0 | >0.48 | 0.64 |
| OR Quart4 | 8.6 | na | 5.7 |

| Insulin-like growth factor-binding protein 7 | | | | | | |
|---|---|---|---|---|---|---|
| | sCr or UO | | sCr only | | UO only | |
| | Cohort 1 | Cohort 2 | Cohort 1 | Cohort 2 | Cohort 1 | Cohort 2 |
| Median | 73.2 | 97.8 | nd | nd | 73.5 | 96.3 |
| Average | 75.2 | 124 | nd | nd | 78.8 | 120 |
| Stdev | 31.9 | 95.9 | nd | nd | 32.8 | 100.0 |
| p(t-test) |  | 2.3E-4 | nd | nd |  | 0.0049 |
| Min | 18.6 | 43.7 | nd | nd | 38.1 | 43.7 |
| Max | 188 | 437 | nd | nd | 188 | 437 |
| n (Samp) | 78 | 20 | nd | nd | 67 | 17 |
| n (Patient) | 78 | 20 | nd | nd | 67 | 17 |

|  | At Enrollment | | |
|---|---|---|---|
|  | sCr or UO | sCr only | UO only |
| AUC | 0.68 | nd | 0.63 |
| SE | 0.072 | nd | 0.079 |
| p | 0.014 | nd | 0.11 |
| nCohort 1 | 78 | nd | 67 |
| nCohort 2 | 20 | nd | 17 |
| Cutoff 1 | 66.7 | nd | 57.2 |
| Sens 1 | 70% | nd | 71% |
| Spec 1 | 46% | nd | 34% |
| Cutoff 2 | 55.2 | nd | 53.3 |
| Sens 2 | 80% | nd | 82% |
| Spec 2 | 33% | nd | 28% |
| Cutoff 3 | 52.0 | nd | 49.8 |
| Sens 3 | 90% | nd | 94% |
| Spec 3 | 23% | nd | 15% |
| Cutoff 4 | 84.3 | nd | 86.1 |

TABLE 12-continued

Comparison of marker levels in enroll EDTA samples collected from Cohort 1 (patients that did not progress beyond RIFLE stage 0 or R within 48 hrs) and in enroll EDTA samples collected from Cohort 2 (subjects reaching RIFLE stage I or F within 48 hrs). Enroll samples from patients already at stage I or F were included in Cohort 2.

| | | | |
|---|---|---|---|
| Sens 4 | 60% | nd | 59% |
| Spec 4 | 71% | nd | 70% |
| Cutoff 5 | 91.7 | nd | 97.1 |
| Sens 5 | 60% | nd | 47% |
| Spec 5 | 81% | nd | 81% |
| Cutoff 6 | 114 | nd | 128 |
| Sens 6 | 40% | nd | 24% |
| Spec 6 | 91% | nd | 91% |
| OR Quart 2 | 1.8 | nd | 1.4 |
| p Value | 0.48 | nd | 0.68 |
| 95% CI of | 0.37 | nd | 0.27 |
| OR Quart2 | 8.3 | nd | 7.3 |
| OR Quart 3 | 0.30 | nd | 0.63 |
| p Value | 0.32 | nd | 0.64 |
| 95% CI of | 0.029 | nd | 0.094 |
| OR Quart3 | 3.2 | nd | 4.2 |
| OR Quart 4 | 5.5 | nd | 3.7 |
| p Value | 0.021 | nd | 0.089 |
| 95% CI of | 1.3 | nd | 0.82 |
| OR Quart4 | 23 | nd | 17 |

Example 7

Kidney Injury Markers for Evaluating Mortality Risk in Patients

Patients from the intensive care unit (ICU) were enrolled in the following study. Each patient was classified by kidney status as non-injury (0), risk of injury (R), injury (I), and failure (F) according to the maximum stage reached within 48 hours of enrollment as determined by the RIFLE criteria. EDTA anti-coagulated blood samples (10 mL) and a urine samples (25-30 mL) were collected from each patient at the time of enrollment into the study. Markers were each measured by standard immunoassay methods using commercially available assay reagents in the urine samples and the plasma component of the blood samples collected.

The patient population was segregated based on the marker concentrations using threshold values which divided the population into thirds ("tertiles"). Patients with marker concentrations in the lower, middle, and upper third comprise the first, second, and third tertiles, respectively. The relative risk of AKI-related mortality within 7, 14, and 28 days was calculated for the second and third tertiles, relative to a value of 1 for the first tertile, as indicated in the following table. "AKI-related mortality" or "AKI-related death" was defined as death accompanied by a minimum RIFLE stage of R.

TABLE 13

Relative risk of AKI-related death within 7, 14, and 28 days from enrollment for the third tertile compared to the first tertile of marker concentrations.

| | Marker | Relative Risk for Third Tertile | p | Total Number of Patients | Total Number of AKI-related Deaths |
|---|---|---|---|---|---|
| AKI-Related Death within 7 Days after enrollment | Insulin-like growth factor-binding protein 7 | 5.5 | 0.02 | 355 | 16 |
| | C-X-C motif chemokine 6 | 3.0 | 0.09 | 356 | 16 |
| AKI-Related Death within 14 Days after enrollment | Insulin-like growth factor-binding protein 7 | 6.5 | 0.01 | 355 | 20 |
| | C-X-C motif chemokine 6 | 4.0 | 0.03 | 356 | 20 |
| AKI-Related Death within 28 Days after enrollment | Insulin-like growth factor-binding protein 7 | 4.7 | 0.01 | 355 | 22 |
| | C-X-C motif chemokine 6 | 3.0 | 0.05 | 356 | 22 |

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method of treating a subject comprising:
    (a) detecting an elevated level of insulin-like growth factor-binding protein 7 (IGFBP7) in a urine sample obtained from the subject as compared to a predetermined threshold level, wherein the threshold level is selected based on results of a population study of individuals, and wherein the results separate the population into a first subpopulation of the individuals with a level of IGFBP7 that is greater than the threshold level and a second subpopulation of the individuals with a level of IGFBP7 that is less than the threshold level;
    (b) determining that the subject is at risk of a future acute kidney injury within 48 hours of the time the urine sample is obtained from the subject based on the elevated level of insulin-like growth factor-binding protein 7 in the sample, and;
    (c) treating the subject determined to be at risk of the future acute kidney injury, wherein the treatment comprises initiating renal replacement therapy, ceasing administration of compounds to the subject that are known to be damaging to the kidney, or modifying diuretic administration of compounds,
    wherein the subject: (i) is undergoing or has undergone an acute medical event which predisposes the subject for developing the acute kidney injury; or (ii) has been exposed to an agent that predisposes the subject for developing the acute kidney injury.

2. The method of claim 1, wherein the method further comprises contacting all or a portion of the urine sample with a binding reagent which specifically binds to insulin-like growth factor-binding protein 7, and
    generating an assay result indicative of binding of insulin-like growth factor-binding protein 7 to the binding reagent.

3. The method of claim 2, wherein the assay result comprises a measured concentration of insulin-like growth factor-binding protein 7.

4. The method of claim 2, wherein the binding reagent is an antibody.

5. The method of claim 1, wherein the future acute kidney injury is a future RIFLE stage I acute kidney injury or a future RIFLE stage F acute kidney injury.

6. The method of claim 1, wherein the determining further comprises determining that the subject has an increased likelihood of a future acute kidney injury within 24 hours of the time the urine sample is obtained from the subject.

7. The method of claim 1, comprising initiating renal replacement therapy.

8. The method of claim 1, comprising ceasing administration of compounds to the subject that are damaging to the kidney.

9. The method of claim 1, comprising modifying diuretic administration of compounds used for treatment of a kidney disorder.

10. The method of claim 1, wherein the future acute kidney injury is prerenal, intrinsic renal, or postrenal acute renal failure (ARF).

11. The method of claim 1, wherein the subject is not in RIFLE stage I acute kidney injury or RIFLE stage F acute kidney injury.

12. The method of claim 1, wherein the subject is in RIFLE stage 0.

13. The method of claim 1, wherein the subject is in RIFLE stage R.

14. The method of claim 1, wherein the subject is in RIFLE stage I.

15. The method of claim 1, wherein the subject has been diagnosed with one or more of congestive heart failure, preeclampsia, eclampsia, diabetes mellitus, hypertension, coronary artery disease, proteinuria, renal insufficiency, glomerular filtration below the normal range, cirrhosis, serum creatinine above the normal range, and sepsis.

16. The method of claim 1, wherein the subject:
    (i) is undergoing or has undergone major vascular surgery, coronary artery bypass, or other cardiac surgery; or
    (ii) has been exposed to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin.

* * * * *

```
                               SEQUENCE LISTING

<160> NUMBER OF SEQ ID NOS: 4

<210> SEQ ID NO 1
<211> LENGTH: 466
<212> TYPE: PRT
<213> ORGANISM: Homo sapiens

<400> SEQUENCE: 1

Met Val Ser Gln Ala Leu Arg Leu Leu Cys Leu Leu Leu Gly Leu Gln
1               5                   10                  15

Gly Cys Leu Ala Ala Gly Gly Val Ala Lys Ala Ser Gly Gly Glu Thr
                20                  25                  30

Arg Asp Met Pro Trp Lys Pro Gly Pro His Arg Val Phe Val Thr Gln
            35                  40                  45

Glu Glu Ala His Gly Val Leu His Arg Arg Arg Ala Asn Ala Phe
    50                  55                  60

Leu Glu Glu Leu Arg Pro Gly Ser Leu Glu Arg Glu Cys Lys Glu Glu
65                  70                  75                  80

Gln Cys Ser Phe Glu Glu Ala Arg Glu Ile Phe Lys Asp Ala Glu Arg
                85                  90                  95

Thr Lys Leu Phe Trp Ile Ser Tyr Ser Asp Gly Asp Gln Cys Ala Ser
                100                 105                 110

Ser Pro Cys Gln Asn Gly Gly Ser Cys Lys Asp Gln Leu Gln Ser Tyr
            115                 120                 125

Ile Cys Phe Cys Leu Pro Ala Phe Glu Gly Arg Asn Cys Glu Thr His
    130                 135                 140

Lys Asp Asp Gln Leu Ile Cys Val Asn Glu Asn Gly Gly Cys Glu Gln
145                 150                 155                 160

Tyr Cys Ser Asp His Thr Gly Thr Lys Arg Ser Cys Arg Cys His Glu
                165                 170                 175

Gly Tyr Ser Leu Leu Ala Asp Gly Val Ser Cys Thr Pro Thr Val Glu
            180                 185                 190

Tyr Pro Cys Gly Lys Ile Pro Ile Leu Glu Lys Arg Asn Ala Ser Lys
        195                 200                 205

Pro Gln Gly Arg Ile Val Gly Gly Lys Val Cys Pro Lys Gly Glu Cys
    210                 215                 220

Pro Trp Gln Val Leu Leu Leu Val Asn Gly Ala Gln Leu Cys Gly Gly
225                 230                 235                 240

Thr Leu Ile Asn Thr Ile Trp Val Val Ser Ala Ala His Cys Phe Asp
                245                 250                 255

Lys Ile Lys Asn Trp Arg Asn Leu Ile Ala Val Leu Gly Glu His Asp
            260                 265                 270
```

```
Leu Ser Glu His Asp Gly Asp Glu Gln Ser Arg Arg Val Ala Gln Val
            275                 280                 285

Ile Ile Pro Ser Thr Tyr Val Pro Gly Thr Thr Asn His Asp Ile Ala
        290                 295                 300

Leu Leu Arg Leu His Gln Pro Val Val Leu Thr Asp His Val Val Pro
305                 310                 315                 320

Leu Cys Leu Pro Glu Arg Thr Phe Ser Glu Arg Thr Leu Ala Phe Val
                325                 330                 335

Arg Phe Ser Leu Val Ser Gly Trp Gly Gln Leu Leu Asp Arg Gly Ala
            340                 345                 350

Thr Ala Leu Glu Leu Met Val Leu Asn Val Pro Arg Leu Met Thr Gln
        355                 360                 365

Asp Cys Leu Gln Gln Ser Arg Lys Val Gly Asp Ser Pro Asn Ile Thr
370                 375                 380

Glu Tyr Met Phe Cys Ala Gly Tyr Ser Asp Gly Ser Lys Asp Ser Cys
385                 390                 395                 400

Lys Gly Asp Ser Gly Gly Pro His Ala Thr His Tyr Arg Gly Thr Trp
                405                 410                 415

Tyr Leu Thr Gly Ile Val Ser Trp Gly Gln Gly Cys Ala Thr Val Gly
            420                 425                 430

His Phe Gly Val Tyr Thr Arg Val Ser Gln Tyr Ile Glu Trp Leu Gln
        435                 440                 445

Lys Leu Met Arg Ser Glu Pro Arg Pro Gly Val Leu Leu Arg Ala Pro
450                 455                 460

Phe Pro
465

<210> SEQ ID NO 2
<211> LENGTH: 282
<212> TYPE: PRT
<213> ORGANISM: Homo sapiens

<400> SEQUENCE: 2

Met Glu Arg Pro Ser Leu Arg Ala Leu Leu Leu Gly Ala Ala Gly Leu
1               5                   10                  15

Leu Leu Leu Leu Leu Pro Leu Ser Ser Ser Ser Ser Ser Asp Thr Cys
            20                  25                  30

Gly Pro Cys Glu Pro Ala Ser Cys Pro Pro Leu Pro Pro Leu Gly Cys
        35                  40                  45

Leu Leu Gly Glu Thr Arg Asp Ala Cys Gly Cys Cys Pro Met Cys Ala
    50                  55                  60

Arg Gly Glu Gly Glu Pro Cys Gly Gly Gly Ala Gly Arg Gly Tyr
65                  70                  75                  80

Cys Ala Pro Gly Met Glu Cys Val Lys Ser Arg Lys Arg Arg Lys Gly
                85                  90                  95

Lys Ala Gly Ala Ala Ala Gly Gly Pro Gly Val Ser Gly Val Cys Val
            100                 105                 110

Cys Lys Ser Arg Tyr Pro Val Cys Gly Ser Asp Gly Thr Thr Tyr Pro
        115                 120                 125

Ser Gly Cys Gln Leu Arg Ala Ala Ser Gln Arg Ala Glu Ser Arg Gly
    130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
                165                 170                 175
```

```
Val Tyr Leu Ser Cys Glu Val Ile Gly Ile Pro Thr Pro Val Leu Ile
            180                 185                 190

Trp Asn Lys Val Lys Arg Gly His Tyr Gly Val Gln Arg Thr Glu Leu
        195                 200                 205

Leu Pro Gly Asp Arg Asp Asn Leu Ala Ile Gln Thr Arg Gly Gly Pro
    210                 215                 220

Glu Lys His Glu Val Thr Gly Trp Val Leu Val Ser Pro Leu Ser Lys
225                 230                 235                 240

Glu Asp Ala Gly Glu Tyr Glu Cys His Ala Ser Asn Ser Gln Gly Gln
                245                 250                 255

Ala Ser Ala Ser Ala Lys Ile Thr Val Val Asp Ala Leu His Glu Ile
            260                 265                 270

Pro Val Lys Lys Gly Glu Gly Ala Glu Leu
        275                 280

<210> SEQ ID NO 3
<211> LENGTH: 114
<212> TYPE: PRT
<213> ORGANISM: Homo sapiens

<400> SEQUENCE: 3

Met Ser Leu Pro Ser Ser Arg Ala Ala Arg Val Pro Gly Pro Ser Gly
1               5                   10                  15

Ser Leu Cys Ala Leu Leu Ala Leu Leu Leu Leu Thr Pro Pro Gly Gly
            20                  25                  30

Pro Leu Ala Ser Ala Gly Pro Val Ser Ala Val Leu Thr Glu Leu Arg
        35                  40                  45

Cys Thr Cys Leu Arg Val Thr Leu Arg Val Asn Pro Lys Thr Ile Gly
    50                  55                  60

Lys Leu Gln Val Phe Pro Ala Gly Pro Gln Cys Ser Lys Val Glu Val
65                  70                  75                  80

Val Ala Ser Leu Lys Asn Gly Lys Gln Val Cys Leu Asp Pro Glu Ala
                85                  90                  95

Pro Phe Leu Lys Lys Val Ile Gln Lys Ile Leu Asp Ser Gly Asn Lys
            100                 105                 110

Lys Asn

<210> SEQ ID NO 4
<211> LENGTH: 98
<212> TYPE: PRT
<213> ORGANISM: Homo sapiens

<400> SEQUENCE: 4

Met Lys Val Ser Ala Val Leu Leu Cys Leu Leu Met Thr Ala Ala
1               5                   10                  15

Phe Asn Pro Gln Gly Leu Ala Gln Pro Asp Ala Leu Asn Val Pro Ser
            20                  25                  30

Thr Cys Cys Phe Thr Phe Ser Ser Lys Lys Ile Ser Leu Gln Arg Leu
        35                  40                  45

Lys Ser Tyr Val Ile Thr Thr Ser Arg Cys Pro Gln Lys Ala Val Ile
    50                  55                  60

Phe Arg Thr Lys Leu Gly Lys Glu Ile Cys Ala Asp Pro Lys Glu Lys
65                  70                  75                  80
```

```
Trp Val Gln Asn Tyr Met Lys His Leu Gly Arg Lys Ala His Thr Leu
                 85                  90                  95
Lys Thr
```